US009487823B2

(12) United States Patent
Lasken et al.

(10) Patent No.: US 9,487,823 B2
(45) Date of Patent: Nov. 8, 2016

(54) NUCLEIC ACID AMPLIFICATION

(75) Inventors: Roger S. Lasken, New Haven, CT (US); Michael Egholm, Woodbridge, CT (US); Osama A. Alsmadi, Guilford, CT (US)

(73) Assignee: QIAGEN GMBH, Hilden (DE)

( * ) Notice: Subject to any disclaimer, the term of this patent is extended or adjusted under 35 U.S.C. 154(b) by 672 days.

(21) Appl. No.: 10/327,602

(22) Filed: Dec. 20, 2002

(65) Prior Publication Data
US 2004/0126764 A1 Jul. 1, 2004

(51) Int. Cl.
*C12Q 1/68* (2006.01)
(52) U.S. Cl.
CPC ........... *C12Q 1/6844* (2013.01); *C12Q 1/6858* (2013.01)
(58) Field of Classification Search
USPC .................... 435/6, 91.2; 536/22.1, 24.33
See application file for complete search history.

(56) References Cited

U.S. PATENT DOCUMENTS

| | | |
|---|---|---|
| 2,264,423 A | 12/1941 | Wingenroth |
| 3,395,018 A | 7/1968 | Read |
| 3,654,090 A | 4/1972 | Wilhelmus et al. |
| 3,687,808 A | 8/1972 | Merigan, Jr. et al. |
| 3,921,105 A | 11/1975 | Brgelz |
| 3,983,421 A | 9/1976 | Yogore |
| 3,995,018 A | 11/1976 | Sjoquist |
| 4,299,916 A | 11/1981 | Litman et al. |
| 4,469,863 A | 9/1984 | Ts'o et al. |
| 4,476,301 A | 10/1984 | Imbach et al. |
| 4,748,111 A | 5/1988 | Dattagupta et al. |
| 4,816,567 A | 3/1989 | Cabilly et al. |
| 4,837,003 A | 6/1989 | Nicolotti |
| 4,845,205 A | 7/1989 | Huynh Dinh et al. |
| 4,883,750 A | 11/1989 | Whiteley et al. |
| 4,937,183 A | 6/1990 | Ultee et al. |
| 4,940,670 A | 7/1990 | Rhodes |
| 4,965,188 A | 10/1990 | Mullis et al. |
| 4,981,957 A | 1/1991 | Lebleu et al. |
| 4,994,373 A | 2/1991 | Stavrianopoulos et al. |
| 4,994,557 A | 2/1991 | Kassis et al. |
| 5,001,050 A | 3/1991 | Blanco et al. |
| 5,023,243 A | 6/1991 | Tullis |
| 5,034,506 A | 7/1991 | Summerton et al. |
| 5,043,272 A | 8/1991 | Hartley |
| 5,106,727 A | 4/1992 | Hartley et al. |
| 5,118,800 A | 6/1992 | Smith et al. |
| 5,130,238 A | 7/1992 | Malek et al. |
| 5,130,302 A | 7/1992 | Spielvogel et al. |
| 5,134,066 A | 7/1992 | Rogers et al. |
| 5,137,806 A | 8/1992 | LeMaistre et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,187,060 A | 2/1993 | Cerutti et al. |
| 5,188,897 A | 2/1993 | Suhadolnik et al. |
| 5,198,543 A | 3/1993 | Blanco et al. |
| 5,214,134 A | 5/1993 | Weis et al. |
| 5,216,141 A | 6/1993 | Benner |
| 5,235,033 A | 8/1993 | Summerton et al. |
| 5,242,794 A | 9/1993 | Whiteley et al. |
| 5,262,311 A | 11/1993 | Pardee et al. |
| 5,264,423 A | 11/1993 | Cohen et al. |
| 5,264,562 A | 11/1993 | Matteucci |
| 5,264,564 A | 11/1993 | Matteucci |
| 5,264,567 A | 11/1993 | Numata et al. |
| 5,268,486 A | 12/1993 | Waggoner et al. |
| 5,273,638 A | 12/1993 | Konrad et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,328,824 A | 7/1994 | Ward et al. |
| 5,334,711 A | 8/1994 | Sproat et al. |
| 5,354,668 A | 10/1994 | Auerbach |
| 5,359,044 A | 10/1994 | Cook et al. |
| 5,367,066 A | 11/1994 | Urdea et al. |
| 5,367,069 A | 11/1994 | Beck et al. |
| 5,393,878 A | 2/1995 | Leumann |
| 5,399,676 A | 3/1995 | Froehler |

(Continued)

FOREIGN PATENT DOCUMENTS

| | | |
|---|---|---|
| AU | 84173/91 | 2/1992 |
| AU | 649066 | 5/1994 |

(Continued)

OTHER PUBLICATIONS

Lehninger (1970) Worth Publishers, Inc., New York, NY., pp. 659-675.*
Merriam-Webster (attached, available at http://www.merriam-webster.com/dictionary/substantial, accessed Feb. 1, 2016).*
Merriam-Webster (hereinafter "Merriam-Webster2"; attached, available at http://www.merriam-webster.com/dictionary/notable, accessed Feb. 1, 2016).*
Fortina et al. (DOP-PCR Amplification of Whole Genomic DNA and Microchip-Based Capillary Electrophoresis, Methods Mol Biol. 2001;163:211-9).*
Nelson et al. (Alu polymerase chain reaction: A method for rapid isolation of human-specific sequences from complex DNA sources, Proc Natl Acad Sci U S A. Sep. 1989;86(17):6686-90).*
Hawkins et al. (Whole genome amplification—applications and advances, Curr Opin Biotechnol. Feb. 2002;13(1):65-7).*

(Continued)

*Primary Examiner* — Aaron Priest
(74) *Attorney, Agent, or Firm* — Ballard Spahr LLP

(57) ABSTRACT

Disclosed are compositions and a method for amplification of nucleic acid sequences of interest. The disclosed method generally involves replication of a complex nucleic acid sample such as genomic samples using one, a few, or more primers such that, during replication, the replicated strands are displaced from the nucleic acid molecules in the sample by strand displacement replication of another replicated strand. It was discovered that highly complex nucleic acid samples can be efficiently amplified using only one or a few primers having specific nucleic acid sequences. The one or few primers are complementary to nucleic acid sequences distributed throughout nucleic acid in the sample.

98 Claims, 10 Drawing Sheets

(56) References Cited

U.S. PATENT DOCUMENTS

| | | |
|---|---|---|
| 5,405,938 A | 4/1995 | Summerton et al. |
| 5,405,939 A | 4/1995 | Suhadolnik et al. |
| 5,409,818 A | 4/1995 | Davey et al. |
| 5,412,087 A | 5/1995 | McGall et al. |
| 5,427,930 A | 6/1995 | Birkenmeyer et al. |
| 5,429,807 A | 7/1995 | Matson et al. |
| 5,432,272 A | 7/1995 | Benner |
| 5,434,257 A | 7/1995 | Matteucci et al. |
| 5,443,986 A | 8/1995 | Haughland et al. |
| 5,445,934 A | 8/1995 | Fodor et al. |
| 5,446,137 A | 8/1995 | Maag et al. |
| 5,451,067 A | 9/1995 | Pieper |
| 5,451,203 A | 9/1995 | Lamb |
| 5,453,496 A | 9/1995 | Caruthers et al. |
| 5,455,166 A | 10/1995 | Walker |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,427 A | 12/1995 | Fujima |
| 5,476,786 A | 12/1995 | Huston |
| 5,476,925 A | 12/1995 | Letsinger et al. |
| 5,484,908 A | 1/1996 | Froehler et al. |
| 5,489,677 A | 2/1996 | Sanghvi et al. |
| 5,500,341 A | 3/1996 | Spears |
| 5,502,177 A | 3/1996 | Matteucci et al. |
| 5,510,270 A | 4/1996 | Fodor et al. |
| 5,514,785 A | 5/1996 | Van Ness et al. |
| 5,516,134 A | 5/1996 | Crawford et al. |
| 5,516,663 A | 5/1996 | Backman et al. |
| 5,516,664 A | 5/1996 | Hyman |
| 5,519,126 A | 5/1996 | Hecht |
| 5,519,134 A | 5/1996 | Acevedo et al. |
| 5,521,065 A | 5/1996 | Whiteley et al. |
| 5,523,204 A | 6/1996 | Singer et al. |
| 5,525,711 A | 6/1996 | Hawkins et al. |
| 5,536,821 A | 7/1996 | Agrawal et al. |
| 5,538,871 A | 7/1996 | Nuovo et al. |
| 5,539,082 A | 7/1996 | Nielsen et al. |
| 5,541,306 A | 7/1996 | Agrawal et al. |
| 5,541,307 A | 7/1996 | Cook et al. |
| 5,547,843 A | 8/1996 | Studier et al. |
| 5,550,111 A | 8/1996 | Suhadolnik et al. |
| 5,552,540 A | 9/1996 | Haralambidis |
| 5,556,748 A | 9/1996 | Douglas |
| 5,556,771 A | 9/1996 | Shen et al. |
| 5,556,772 A | 9/1996 | Sorge et al. |
| 5,561,045 A | 10/1996 | Dorval et al. |
| 5,561,225 A | 10/1996 | Maddry et al. |
| 5,563,037 A | 10/1996 | Sutherland et al. |
| 5,563,253 A | 10/1996 | Agrawal et al. |
| 5,563,912 A | 10/1996 | Yasunaga et al. |
| 5,565,339 A | 10/1996 | Bloch et al. |
| 5,567,811 A | 10/1996 | Misiura et al. |
| 5,571,799 A | 11/1996 | Tkachuk et al. |
| 5,573,907 A | 11/1996 | Carrino et al. |
| 5,576,427 A | 11/1996 | Cook et al. |
| 5,587,361 A | 12/1996 | Cook et al. |
| 5,587,469 A | 12/1996 | Cook et al. |
| 5,591,609 A | 1/1997 | Auerbach |
| 5,591,722 A | 1/1997 | Montgomery et al. |
| 5,593,836 A | 1/1997 | Niemiec et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,599,695 A | 2/1997 | Pease et al. |
| 5,599,921 A | 2/1997 | Sorge et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,389 A | 3/1997 | Auerbach |
| 5,614,390 A | 3/1997 | McCaslin et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,629,158 A | 5/1997 | Uhlen |
| 5,629,179 A | 5/1997 | Mierendorf et al. |
| 5,633,360 A | 5/1997 | Bischofberger et al. |
| 5,635,602 A | 6/1997 | Cantor et al. |
| 5,639,599 A | 6/1997 | Ryder et al. |
| 5,639,873 A | 6/1997 | Barascut et al. |
| 5,646,265 A | 7/1997 | McGee |
| 5,648,213 A | 7/1997 | Reddy et al. |
| 5,648,245 A | 7/1997 | Fire et al. |
| 5,654,413 A | 8/1997 | Brenner |
| 5,658,873 A | 8/1997 | Bertsch-Frank et al. |
| 5,663,312 A | 9/1997 | Chaturvedula |
| 5,665,539 A | 9/1997 | Sano et al. |
| 5,670,633 A | 9/1997 | Cook et al. |
| 5,677,437 A | 10/1997 | Teng et al. |
| 5,677,439 A | 10/1997 | Weis et al. |
| 5,679,509 A | 10/1997 | Wheeler et al. |
| 5,681,941 A | 10/1997 | Cook et al. |
| 5,683,985 A | 11/1997 | Chu et al. |
| 5,691,136 A | 11/1997 | Lupski et al. |
| 5,695,933 A | 12/1997 | Schalling et al. |
| 5,700,920 A | 12/1997 | Altmann et al. |
| 5,710,028 A | 1/1998 | Eyal et al. |
| 5,712,100 A | 1/1998 | Nakahama et al. |
| 5,714,320 A | 2/1998 | Kool |
| 5,714,331 A | 2/1998 | Buchardt et al. |
| 5,719,262 A | 2/1998 | Buchardt et al. |
| 5,728,526 A | 3/1998 | George, Jr. et al. |
| 5,733,733 A | 3/1998 | Auerbach |
| 5,736,365 A | 4/1998 | Walker et al. |
| 5,744,305 A | 4/1998 | Fodor et al. |
| 5,766,891 A | 6/1998 | Shuman |
| 5,770,408 A | 6/1998 | Sato |
| 5,792,607 A | 8/1998 | Backman et al. |
| 5,795,714 A | 8/1998 | Cantor et al. |
| 5,800,992 A | 9/1998 | Fodor et al. |
| 5,800,994 A | 9/1998 | Martinelli et al. |
| 5,807,674 A | 9/1998 | Tyagi |
| 5,817,529 A | 10/1998 | Wu |
| 5,821,084 A | 10/1998 | Olmsted et al. |
| 5,824,517 A | 10/1998 | Cleuziat et al. |
| 5,830,711 A | 11/1998 | Barany et al. |
| 5,849,544 A | 12/1998 | Harris et al. |
| 5,854,033 A | 12/1998 | Lizardi |
| 5,856,096 A * | 1/1999 | Windle et al. .................. 435/6 |
| 5,866,329 A | 2/1999 | Demetriou et al. |
| 5,866,336 A | 2/1999 | Nazarenko et al. |
| 5,871,697 A | 2/1999 | Rothberg et al. |
| 5,871,914 A | 2/1999 | Nathan |
| 5,871,921 A | 2/1999 | Landegren et al. |
| 5,871,928 A | 2/1999 | Fodor et al. |
| 5,874,260 A | 2/1999 | Cleuziat et al. |
| 5,876,924 A | 3/1999 | Zhang et al. |
| 5,876,932 A | 3/1999 | Fischer |
| 5,876,992 A | 3/1999 | De Rosier et al. |
| 5,880,473 A | 3/1999 | Ginestet |
| 5,882,912 A | 3/1999 | Sandstrom et al. |
| 5,882,935 A | 3/1999 | Hirai et al. |
| 5,886,329 A | 3/1999 | Kim |
| 5,888,731 A | 3/1999 | Yager et al. |
| 5,891,636 A | 4/1999 | Van Gelder et al. |
| 5,909,132 A | 6/1999 | Trofimenkoff et al. |
| 5,912,124 A | 6/1999 | Kumar |
| 5,912,148 A | 6/1999 | Eggerding |
| 5,914,229 A | 6/1999 | Loewy |
| 5,925,517 A | 7/1999 | Tyagi et al. |
| 5,942,391 A | 8/1999 | Zhang et al. |
| 5,942,609 A | 8/1999 | Hunkapiller et al. |
| 5,945,312 A | 8/1999 | Goodman et al. |
| 5,955,933 A | 9/1999 | Nishihara et al. |
| 5,959,095 A | 9/1999 | Martinelli et al. |
| 5,962,223 A | 10/1999 | Whiteley et al. |
| 5,968,743 A | 10/1999 | Matsunaga et al. |

(56) References Cited

U.S. PATENT DOCUMENTS

| | | | |
|---|---|---|---|
| 5,976,806 A | 11/1999 | Mahajan et al. | |
| 5,985,639 A | 11/1999 | Christianson et al. | |
| 5,994,058 A * | 11/1999 | Senapathy | 435/6.18 |
| 5,998,175 A | 12/1999 | Akhavan-Tafti | |
| 6,001,611 A | 12/1999 | Will | |
| 6,007,994 A | 12/1999 | Ward et al. | |
| 6,008,373 A | 12/1999 | Waggoner et al. | |
| 6,013,431 A | 1/2000 | Soderlund et al. | |
| 6,013,444 A | 1/2000 | Dau et al. | |
| 6,017,703 A | 1/2000 | Kinders et al. | |
| 6,020,138 A | 2/2000 | Akhavan-Tafti | |
| 6,025,139 A | 2/2000 | Yager et al. | |
| 6,027,889 A | 2/2000 | Barany et al. | |
| 6,027,923 A | 2/2000 | Wallace | |
| 6,033,881 A | 3/2000 | Himmler et al. | |
| 6,037,130 A | 3/2000 | Tyagi et al. | |
| 6,054,274 A | 4/2000 | Sampson et al. | |
| 6,057,105 A | 5/2000 | Hoon et al. | |
| 6,064,274 A | 5/2000 | Nayebi et al. | |
| 6,077,668 A | 6/2000 | Kool | |
| 6,077,674 A | 6/2000 | Schleifer et al. | |
| 6,087,133 A | 7/2000 | Dattagupta et al. | |
| 6,087,476 A | 7/2000 | Kenten et al. | |
| 6,096,880 A | 8/2000 | Kool | |
| 6,117,635 A | 9/2000 | Nazarenko et al. | |
| 6,124,120 A * | 9/2000 | Lizardi | C12Q 1/6844 435/91.1 |
| 6,132,728 A | 10/2000 | Beachy et al. | |
| 6,140,055 A | 10/2000 | Todd et al. | |
| 6,143,495 A | 11/2000 | Lizardi et al. | |
| 6,169,816 B1 | 1/2001 | Ravkin | |
| 6,183,960 B1 | 2/2001 | Lizardi | |
| 6,197,533 B1 | 3/2001 | Dawkes et al. | |
| 6,203,984 B1 | 3/2001 | Hu et al. | |
| 6,210,884 B1 | 4/2001 | Lizardi | |
| 6,214,587 B1 | 4/2001 | Dattagupta et al. | |
| 6,221,603 B1 | 4/2001 | Mahtani | |
| 6,225,636 B1 | 5/2001 | Ginestet | |
| 6,235,502 B1 | 5/2001 | Weissman et al. | |
| 6,242,188 B1 | 6/2001 | Dattagupta et al. | |
| 6,248,535 B1 | 6/2001 | Danenberg et al. | |
| 6,251,639 B1 * | 6/2001 | Kurn | 435/91.2 |
| 6,255,082 B1 * | 7/2001 | Lizardi | 435/91.1 |
| 6,255,636 B1 | 7/2001 | Cochran, II et al. | |
| 6,259,807 B1 | 7/2001 | Ravkin | |
| 6,270,973 B1 * | 8/2001 | Lewis et al. | 435/6.11 |
| 6,274,320 B1 | 8/2001 | Rothberg et al. | |
| 6,277,607 B1 | 8/2001 | Tyagi et al. | |
| 6,280,949 B1 | 8/2001 | Lizardi | |
| 6,287,765 B1 | 9/2001 | Cubicciotti | |
| 6,287,768 B1 | 9/2001 | Chenchik et al. | |
| 6,287,776 B1 | 9/2001 | Hefti | |
| 6,287,824 B1 | 9/2001 | Lizardi | |
| 6,288,220 B1 | 9/2001 | Kambara et al. | |
| 6,291,183 B1 | 9/2001 | Pirrung et al. | |
| 6,291,187 B1 | 9/2001 | Kingsmore et al. | |
| 6,291,193 B1 | 9/2001 | Khodadoust | |
| 6,291,669 B1 | 9/2001 | Kwiatkowski et al. | |
| 6,294,329 B1 * | 9/2001 | Rohde | 435/6.12 |
| 6,294,664 B1 | 9/2001 | Ravikumar et al. | |
| 6,297,006 B1 | 10/2001 | Drmanac et al. | |
| 6,300,073 B1 | 10/2001 | Zhao et al. | |
| 6,312,902 B1 | 11/2001 | Shultz et al. | |
| 6,316,229 B1 | 11/2001 | Lizardi et al. | |
| 6,323,009 B1 * | 11/2001 | Lasken | C12Q 1/6844 435/91.1 |
| 6,329,150 B1 | 12/2001 | Lizardi et al. | |
| 6,344,329 B1 | 2/2002 | Lizardi | |
| 6,355,431 B1 | 3/2002 | Chee et al. | |
| 6,361,940 B1 | 3/2002 | Van Ness et al. | |
| 6,365,729 B1 | 4/2002 | Tyagi et al. | |
| 6,368,801 B1 | 4/2002 | Faruqi | |
| 6,403,319 B1 | 6/2002 | Lizardi et al. | |
| 6,417,340 B1 | 7/2002 | Mirkin et al. | |
| 6,440,707 B1 | 8/2002 | Kwok et al. | |
| 6,458,544 B1 | 10/2002 | Miller | |
| 6,458,556 B1 | 10/2002 | Hayashizaki | |
| 6,472,185 B2 | 10/2002 | McCasky Feazel et al. | |
| 6,475,736 B1 | 11/2002 | Stanton, Jr. | |
| 6,479,235 B1 | 11/2002 | Schumm et al. | |
| 6,479,242 B1 | 11/2002 | Guo et al. | |
| 6,479,244 B1 | 11/2002 | Belouchi et al. | |
| 6,498,023 B1 | 12/2002 | Abarzua | |
| 6,506,563 B1 | 1/2003 | Ward et al. | |
| 6,531,283 B1 | 3/2003 | Kingsmore et al. | |
| 6,573,051 B2 | 6/2003 | Alsmadi et al. | |
| 6,617,137 B2 * | 9/2003 | Dean | C12Q 1/6806 435/91.1 |
| 6,632,609 B2 | 10/2003 | Lizardi | |
| 6,635,425 B2 | 10/2003 | Bandaru et al. | |
| 6,642,034 B2 | 11/2003 | Lizardi | |
| 6,670,126 B2 | 12/2003 | Kingsmore et al. | |
| 6,686,157 B2 | 2/2004 | Ward et al. | |
| 6,703,228 B1 * | 3/2004 | Landers et al. | 435/91.2 |
| 6,703,885 B1 | 3/2004 | Fan et al. | |
| 6,706,519 B1 | 3/2004 | Kellogg et al. | |
| 6,713,257 B2 | 3/2004 | Shoemaker et al. | |
| 6,777,183 B2 | 8/2004 | Abarzua | |
| 6,797,474 B2 | 9/2004 | Lizardi | |
| 6,811,986 B2 | 11/2004 | Bandaru et al. | |
| 6,830,884 B1 | 12/2004 | Hafner et al. | |
| 6,846,626 B1 * | 1/2005 | Senapathy | C12N 15/1096 435/6.16 |
| 6,861,222 B2 | 3/2005 | Ward et al. | |
| 6,861,231 B2 | 3/2005 | Shao | |
| 6,884,586 B2 | 4/2005 | Van Ness | |
| 6,921,642 B2 | 7/2005 | Kingsmore et al. | |
| 6,942,972 B2 | 9/2005 | Farooqui et al. | |
| 6,977,148 B2 * | 12/2005 | Dean et al. | 435/6 |
| 6,977,153 B2 | 12/2005 | Kumar et al. | |
| RE39,007 E | 3/2006 | Dattagupta et al. | |
| 7,041,480 B2 | 5/2006 | Abarz a | |
| 7,074,600 B2 | 7/2006 | Dean et al. | |
| 7,297,485 B2 | 11/2007 | Bornarth et al. | |
| 7,358,047 B2 | 4/2008 | Hafner et al. | |
| 7,553,619 B2 | 6/2009 | Kumar et al. | |
| 7,618,776 B2 | 11/2009 | Lizardi | |
| 8,101,564 B2 * | 1/2012 | Choi et al. | 514/1.1 |
| 2001/0041340 A1 | 11/2001 | Kingsmore et al. | |
| 2002/0009716 A1 | 1/2002 | Abarzua | |
| 2002/0026046 A1 | 2/2002 | Pasloske et al. | |
| 2002/0042052 A1 | 4/2002 | Nilsen et al. | |
| 2002/0119465 A1 | 8/2002 | Zhao et al. | |
| 2002/0120409 A1 | 8/2002 | Cao et al. | |
| 2002/0172972 A1 | 11/2002 | Tabor et al. | |
| 2002/0192649 A1 | 12/2002 | Lizardi | |
| 2002/0192658 A1 | 12/2002 | Ward et al. | |
| 2002/0197694 A1 | 12/2002 | Shao | |
| 2003/0008313 A1 | 1/2003 | Wiltshire | |
| 2003/0022167 A1 | 1/2003 | Alsmadi et al. | |
| 2003/0032014 A1 | 2/2003 | Wei et al. | |
| 2003/0032024 A1 | 2/2003 | Lizardi | |
| 2003/0059786 A1 | 3/2003 | Ward et al. | |
| 2003/0092901 A1 | 5/2003 | Farooqui et al. | |
| 2003/0099954 A1 | 5/2003 | Miltenyi et al. | |
| 2003/0108902 A1 | 6/2003 | Abarzua | |
| 2003/0121338 A1 | 7/2003 | Yates | |
| 2003/0129658 A1 | 7/2003 | Yamaji et al. | |
| 2003/0143613 A1 | 7/2003 | Kingsmore et al. | |
| 2003/0152932 A1 | 8/2003 | Kumar et al. | |
| 2003/0165948 A1 | 9/2003 | Alsmadi et al. | |
| 2003/0175788 A1 | 9/2003 | Alsmadi et al. | |
| 2003/0186288 A1 | 10/2003 | Spivack et al. | |
| 2003/0207267 A1 | 11/2003 | Lasken et al. | |
| 2003/0207279 A1 * | 11/2003 | Crothers et al. | 435/6 |
| 2003/0207323 A1 | 11/2003 | Bandaru et al. | |
| 2003/0219751 A1 | 11/2003 | Lao et al. | |
| 2003/0235849 A1 | 12/2003 | Lizardi et al. | |
| 2004/0018489 A1 | 1/2004 | Ma et al. | |
| 2004/0023271 A1 * | 2/2004 | Kurn et al. | 435/6 |
| 2004/0063144 A1 | 4/2004 | Lizardi | |
| 2004/0072217 A1 * | 4/2004 | Kennedy | 435/6 |
| 2004/0091857 A1 | 5/2004 | Nallur et al. | |
| 2004/0121338 A1 | 6/2004 | Alsmadi et al. | |

(56) References Cited

U.S. PATENT DOCUMENTS

| | | |
|---|---|---|
| 2004/0126770 A1 | 7/2004 | Kumar et al. |
| 2004/0191784 A1 | 9/2004 | Abarzua et al. |
| 2004/0248103 A1 | 12/2004 | Feaver et al. |
| 2004/0248105 A1 | 12/2004 | Kumar |
| 2004/0265897 A1 | 12/2004 | Lizardi |
| 2005/0003369 A1 | 1/2005 | Christians et al. |
| 2005/0003410 A1 | 1/2005 | Frazer et al. |
| 2005/0069938 A1 | 3/2005 | Wang |
| 2005/0069939 A1 | 3/2005 | Wang |
| 2005/0074804 A1 | 4/2005 | Wang |
| 2005/0079523 A1 | 4/2005 | Hafner et al. |
| 2005/0112639 A1 | 5/2005 | Wang |
| 2006/0083683 A1 | 4/2006 | Hsei et al. |
| 2006/0126764 A1 | 6/2006 | Eklund et al. |
| 2006/0166227 A1 | 7/2006 | Kingsmore et al. |
| 2006/0188892 A1 | 8/2006 | Latham et al. |
| 2008/0057543 A1 | 3/2008 | Korfhage |
| 2008/0096258 A1 | 4/2008 | Korfhage et al. |
| 2011/0112173 A1 | 5/2011 | Brown et al. |

FOREIGN PATENT DOCUMENTS

| | | |
|---|---|---|
| AU | 10240/97 | 11/1996 |
| AU | 5850996 | 11/1996 |
| AU | 97915/98 | 10/1998 |
| AU | 27819/00 | 12/1999 |
| AU | 714486 | 1/2000 |
| AU | 200253328 | 6/2000 |
| AU | 18040/01 | 11/2000 |
| AU | 2001/251359 | 4/2001 |
| AU | 2001255331 | 4/2001 |
| AU | 2001268725 | 6/2001 |
| AU | 2001269944 | 6/2001 |
| AU | 2001271722 | 7/2001 |
| AU | 2002/239809 | 1/2002 |
| AU | 749560 | 6/2002 |
| AU | 2002362874 | 10/2002 |
| AU | 2003297891 | 12/2003 |
| AU | 2003299694 | 12/2003 |
| BE | 96940601.6 | 11/1996 |
| CA | 2236161 | 11/1996 |
| CA | 2308004 | 10/1998 |
| CA | 2394800 | 12/1999 |
| CA | 2360342 | 11/2000 |
| CA | 2405456 | 4/2001 |
| CA | 2405687 | 4/2001 |
| CA | 2410951 | 6/2001 |
| CA | 2411838 | 6/2001 |
| CA | 2411794 | 7/2001 |
| CA | PCT/US02/00005 | 1/2002 |
| CA | 2463933 | 10/2002 |
| CA | 2510587 | 12/2003 |
| CA | 2512196 | 12/2003 |
| CH | 96940601.6 | 11/1996 |
| CN | 01811542.X | 6/2001 |
| DE | 862656 | 11/1996 |
| DE | 69838950.6 | 10/1998 |
| DE | 1946712.5 | 6/2001 |
| DE | 1950759.9 | 7/2001 |
| DE | 60130763.1 | 7/2001 |
| DK | 96940601.6 | 11/1996 |
| EP | 0 070 685 | 7/1982 |
| EP | 0 070 685 B1 | 7/1982 |
| EP | 0 128 332 | 12/1984 |
| EP | 0 310 030 | 4/1989 |
| EP | 0 320 308 | 6/1989 |
| EP | 0 356 021 | 2/1990 |
| EP | 0 379 369 | 7/1990 |
| EP | 0 395 398 | 10/1990 |
| EP | 0 439 182 | 7/1991 |
| EP | 0 466 520 | 7/1991 |
| EP | 0 466 520 | 1/1992 |
| EP | 0 505 012 | 9/1992 |
| EP | 0 531 080 | 3/1993 |
| EP | 0 278 340 | 8/1993 |
| EP | 0 640 691 | 3/1995 |
| EP | 0 667 393 | 8/1995 |
| EP | 0 678 582 | 10/1995 |
| EP | 96940601.6 | 11/1996 |
| EP | 0 745 690 | 12/1996 |
| EP | 0 745 690 A2 | 12/1996 |
| EP | 0 756 009 | 1/1997 |
| EP | 0 866 071 | 3/1998 |
| EP | 98952147.1 | 10/1998 |
| EP | 99935725.4 | 7/1999 |
| EP | 99969209.8 | 12/1999 |
| EP | 938263.1 | 6/2000 |
| EP | 980827 | 11/2000 |
| EP | 1924731.1 | 4/2001 |
| EP | 1928481 | 4/2001 |
| EP | 1928481.9 | 4/2001 |
| EP | 1946712.5 | 6/2001 |
| EP | 1948505.1 | 6/2001 |
| EP | 1950759.9 | 7/2001 |
| EP | 1 056 884 | 12/2001 |
| EP | 2705674.6 | 1/2002 |
| EP | 2801776.2 | 10/2002 |
| EP | 3796961.5 | 12/2003 |
| EP | 3799976 | 12/2003 |
| EP | 1 132 470 | 9/2005 |
| EP | 7118804.9 | 10/2007 |
| FR | 96940601.6 | 11/1996 |
| FR | 1946712.5 | 6/2001 |
| GB | 96940601.6 | 11/1996 |
| GB | 98952147.1 | 10/1998 |
| GB | 2332516 | 6/1999 |
| GB | 1946712.5 | 6/2001 |
| GB | 1950759.9 | 7/2001 |
| HK | 1100606.5 | 1/2001 |
| IE | 96940601.6 | 11/1996 |
| IL | 153097 | 6/2001 |
| IT | 1946712.5 | 6/2001 |
| IT | 3796961.5 | 12/2003 |
| JP | 4262799 | 9/1992 |
| JP | 4304900 | 10/1992 |
| JP | 5130869 | 5/1993 |
| JP | 5146299 | 6/1993 |
| JP | 9-519942 | 11/1996 |
| JP | 2000-515033 | 10/1998 |
| JP | 2000-588388 | 12/1999 |
| JP | 469290-19 | 6/2000 |
| JP | 469290-68 | 11/2000 |
| JP | 2001-575244 | 4/2001 |
| JP | 2001-577404 | 4/2001 |
| JP | 2002-503102 | 6/2001 |
| JP | 2002/506247 | 6/2001 |
| JP | 2002-508032 | 7/2001 |
| JP | 2004-565385 | 12/2003 |
| JP | 2005-510007 | 12/2003 |
| JP | 2005304396 | 11/2005 |
| JP | 2007-276942 | 10/2007 |
| JP | 2010-042086 | 2/2010 |
| LU | 96940601.6 | 11/1996 |
| MC | 96940601.6 | 11/1996 |
| NL | 96940601.6 | 11/1996 |
| SE | 96940601.6 | 11/1996 |
| SG | 200207285-8 | 6/2001 |
| TW | 90114960 | 6/2001 |
| TW | 91102150 | 2/2002 |
| WO | WO 94/16106 | 7/1984 |
| WO | WO 94/16108 | 7/1984 |
| WO | WO 89/09824 | 10/1989 |
| WO | WO 90/11372 | 10/1990 |
| WO | WO 91/06643 | 5/1991 |
| WO | WO 91/08307 | 6/1991 |
| WO | WO 91/16446 | 10/1991 |
| WO | WO 92/01813 | 2/1992 |
| WO | WO 94/24312 | 10/1994 |
| WO | WO 95/03430 | 2/1995 |
| WO | WO 95/03432 | 2/1995 |
| WO | WO 95/25180 | 9/1995 |
| WO | WO 95/22623 | 11/1995 |
| WO | WO 95/35390 | 12/1995 |
| WO | WO 96/00795 | 1/1996 |

(56) References Cited

FOREIGN PATENT DOCUMENTS

| | | |
|---|---|---|
| WO | WO 96/14406 | 5/1996 |
| WO | WO 96/33207 | 10/1996 |
| WO | PCT/US96/18812 | 11/1996 |
| WO | WO 98/02449 | 1/1997 |
| WO | WO 97/07235 | 2/1997 |
| WO | WO 98/14610 | 4/1997 |
| WO | WO 97/16566 | 5/1997 |
| WO | WO 97/17076 | 5/1997 |
| WO | WO 97/17471 | 5/1997 |
| WO | WO 97/19193 | 5/1997 |
| WO | WO 97/20948 | 6/1997 |
| WO | WO 97/42346 | 11/1997 |
| WO | WO 98/04746 | 2/1998 |
| WO | WO 98/07833 | 2/1998 |
| WO | WO 98/14610 | 4/1998 |
| WO | WO 98/16248 | 4/1998 |
| WO | WO 98/39485 | 9/1998 |
| WO | PCT/US98/21177 | 10/1998 |
| WO | WO 99/18241 | 4/1999 |
| WO | WO 99/31276 | 6/1999 |
| WO | PCT/US99/16373 | 7/1999 |
| WO | WO 99/46392 | 9/1999 |
| WO | WO 99/54452 | 10/1999 |
| WO | PCT/AU99/01110 | 12/1999 |
| WO | WO 00/04193 | 1/2000 |
| WO | WO 00/15779 | 3/2000 |
| WO | WO 00/15849 | 3/2000 |
| WO | PCT/US00/16130 | 6/2000 |
| WO | WO 00/36141 | 6/2000 |
| WO | WO 99/18241 | 9/2000 |
| WO | PCT/US00/32370 | 11/2000 |
| WO | WO 00/70095 | 11/2000 |
| WO | WO 00/71562 | 11/2000 |
| WO | WO 00/71562 A1 | 11/2000 |
| WO | WO 01/20039 | 3/2001 |
| WO | PCT/US01/11151 | 4/2001 |
| WO | PCT/US01/11947 | 4/2001 |
| WO | WO 01/27326 | 4/2001 |
| WO | WO 01/38580 | 5/2001 |
| WO | PCT/US01/19657 | 6/2001 |
| WO | PCT/US01/20217 | 6/2001 |
| WO | WO 01/40516 | 6/2001 |
| WO | PCT/US01/20933 | 7/2001 |
| WO | WO 01/61037 | 8/2001 |
| WO | WO 01/64952 | 9/2001 |
| WO | WO 01/77390 | 10/2001 |
| WO | WO 01/79240 | 10/2001 |
| WO | WO 01/88190 | 11/2001 |
| WO | WO 01/97616 | 12/2001 |
| WO | PCT/US02/00005 | 1/2002 |
| WO | PCT/US02/02601 | 1/2002 |
| WO | WO 02/00934 | 1/2002 |
| WO | WO 02/02792 | 1/2002 |
| WO | PCT/US02/15045 | 5/2002 |
| WO | PCT/US02/19443 | 6/2002 |
| WO | WO 02/053780 | 7/2002 |
| WO | PCT/US02/27097 | 8/2002 |
| WO | PCT/US02/33244 | 10/2002 |
| WO | WO 02/077256 | 10/2002 |
| WO | WO 02/103058 | 12/2002 |
| WO | PCT/US03/00678 | 1/2003 |
| WO | WO 03/008538 | 1/2003 |
| WO | WO 03/08538 | 1/2003 |
| WO | WO 03/033724 | 4/2003 |
| WO | WO 03/66908 | 8/2003 |
| WO | WO 03/066908 | 8/2003 |
| WO | WO 03/072809 | 9/2003 |
| WO | PCT/US03/39430 | 12/2003 |
| WO | PCT/US03/40364 | 12/2003 |
| WO | WO 2004/009814 | 1/2004 |
| WO | WO 2004/09814 | 1/2004 |
| WO | WO 2004/58987 | 7/2004 |
| WO | WO 2004/058987 | 7/2004 |
| WO | WO 2004/61119 | 7/2004 |
| WO | WO 2004/061119 | 7/2004 |

OTHER PUBLICATIONS

Aliotta et al. Thelmostable *Bst* DNA polymerase I lacks a 3'-> 5' proofreading exonuclease activity. *Genet. Anal. (Netherlands)* 12:185-195 (1996).

Arnold et al. Assay formats involving acridinium-ester-labeled DNA probes. *Clinical Chemistry* 35(8):1588-1594 (1989).

Asseline et al. Solid-phase preparation on 5', 3'-Heterobifunctional oligonucleotides using modified solid supports. *Tetrahedron.* 48(7):1233-1254 (1992).

Baner et al. Signal amplification of padlock probes by rolling circle replication. *Nucleic Acids Res.* 26(22):5073-5078 (1998).

Beaucage et al. Deoxynucleoside phosphoramidites—a new class of key intermediates for deoxypolynucleotide synthesis. *Tetrahedron Lett.* 22(20):1859-1862 (1981).

Beigelman et al. Synthesis of 1-Deoxy-D-Ribofuranose phosphoramidite and the incorporation of abasic nucleotides in stem-loop II of a hammerhead ribozyme. *Bioorganic & Medicinal Chemistry Letters* 4(14)1715-1720 (1994).

Biragyn et al. Mediators of innate immunity that target immature, but not mature, dendritic cells induce antitumor immunity when genetically fused with nonimmunogenic tumor antigens. *J of Immunol* 167:6644-6653 (2001).

Birkenmeyer et al. DNA probe amplification methods. *J. Virol. Meth.* 35:117-126 (1991).

Blanco et al. Highly efficient DNA synthesis by the phage φ29 DNA polymerase.*J. Biol. Chem.* 264(15):8935-8940 (1989).

Bloch et al. Alpha-anomeric DNA: beta-RNA hybrids as new synthetic inhibitors of *Escherichia coli* RNase H, *Drosophila* embryo RNase H and M-MLV reverse transcriptase: *Gene.* 72:349-360 (1988).

Boehmer et al. Herpes simplex virus type 1 ICP8: helix-destabilizing properties. *J. Virol.* 67(2):711.715 (1993).

Brownie et al. The elimination of primer-dimer accumulation in PCR. *Nucleic Acids Res.* 25(16):3235-3241 (1997).

Brownstein et al. Modulation of non-templated nucleotide addition by Taq DNA polymerase: primer modifications that facilitate genotyping. Biotechniques 20(6)1004-1010 (1996).

Buchanan et al. Long DOP-PCR of rare archival anthropological samples, *Hum. Biol.* 72(6):911-925 (2000).

Chatterjee et al. Cloning and overexpression of the gene encoding bacteriopha DNA polymerase. *Gene* 97:13-19 (1991).

Cheung et al. Whole genome amplification using a degenerate oligonucleotide primer allows hundreds of genotypes to be performed on less than one nanogram of genomic DNA, *Proc Natl Acad Sci USA* 93:14676-14679 (1996).

Cocuzza. A phosphoramidite reagent for automated solid phase synthesis of 5'-biotinylated oligonucleotides. *Tetrahedron Lett.* 30(46):6287-6290 (1989).

Compton. Nucleic acid sequence-based amplification. *Nature.* 350(6313):91-92 (1991).

Connolly. The synthesis of oligonucleotides containing a primary amino group at the 5'-terminus. *Nucleic Acids Res.* 15(7):3131-3139 (1987).

Connolly et al. Chemical synthesis of oligonucleotides containing a free sulphydryl group and subsequent attachment of thiol specific probes. *Nucleic Acids Res.* 13(12):4485-4502 (1985).

Craxton et al. Linear amplification sequencing, a powerful method for sequencing DNA. *Methods: A Companion in Methods in Enzymology.* 3(1):20-26 (1991).

Dolinnaya et al. Oligonucleotide circularization by template-directed chemical ligation. *Nucleic Acids Res.* 21(23):5403-5407 (1993).

Dreyer et al. Sequence-specific cleavage of single-stranded DNA: oligodeoxynucleotide-EDTA Fe(II). *Proc. Natl. Acad. Sci. USA* 82:968-972 (1985).

Durand et al. Circular dichroism studies of an oligodeoxyribonucleotide containing a hairpin loop made of a hexaethylene glycol chain: conformation and stability. *Nucleic Acids Res.* 18(21):6353-6359 (1990).

Eckert et al. DNA polymerase fidelity and the polymerase chain reaction, *PCR Methods and Applications* 1:17-24 (1991).

(56) References Cited

OTHER PUBLICATIONS

Egholm et al. Peptide nucleic acids (PNA). Oligonucleotide analogues with an achiral peptide backbone. *J. Am. Chem. Soc.* 114:1895-1897 (1992).

Englisch et al. Chemically modified oligonucleotides as probes and inhibitors. *Angewandte Chemie*, International Edition in English 30(6):613-629 (1991).

Ernst et al. Cyanine dye labeling reagents for sulfhydryl groups. *Cytometry* 10:3-10 (1989).

Esteban et al. Fidelity of φ29 DNA polymerase. comparison between protein-primed initiation and DNA polymerization, *J. Biol. Chem.* 268(4):2719-2726 (1993).

Faruqi et al. High-throughput genotyping of single nucleotide polymorphisms with rolling circle amplification, *BMC Genomics* 2:4 (2001).

Ferrie et al. Development, multiplexing, and application of ARMS tests for common mutations in the CFTR gene. *Am. J. Hum. Genet.* 51:251-262 (1992).

Gait. Oligoribonucleotides. *Antisense Research and Applications*, Crooke et al., eds., CRC Press. Chapter 16, 289-301.

Gillespie et al. HLA class II typing of whole genome amplified mouth swab DNA, *Tissue Antigens* 56:530-538 (2000).

Grzybowski et al. Synthesis and antibody-mediated detection of oligonucleotides containing multiple 2,4-dinitrophenyl reporter groups. *Nucleic Acids Res.* 21(8):1705-1712 (1993).

Guillier-Gencik et al. Generation of whole-chromosome painting probes specific to each chicken macrochromosome, *Cytogenet Cell Genet.* 87:282-285 (1999).

Guo et al. Direct fluorescence snalysis of genetic polymorphisms by hybridization with oligonucleotide arrays on glass supports, *Nucl. Acids Res.* 22(24):5456-5465 (1994).

Gupta et al. A universal solid support for the synthesis of 3'-thiol group containing oligonucleotides. *Tetrahedron Lett.* 31(17):2471-2474 (1990).

Gusev et al. Rolling circle amplification: a new approach to increase sensitivity for immunohistochemistry and flow cytometry. *American Journal of Pathology* 159(1):63-69 (2001).

Hall et al. Mixed anhydrides as Intermediates in the synthesis of dinucleoside phosphates. *J. Chem. Soc.* 3291-3296 (1957).

Hall et al. Sensitive detection of DNA polymorphisms by the serial invasive signal amplification reaction. *Proc. Natl. Acad. Sci. USA* 97:8272-8277 (2000).

Harper et al. Recent advances and future developments in PGD, *Prenat. Diagn.* 19:1193-1199 (1999).

Henegarlu et al. Custom fluorescent-nucleotide synthesis as an alternative method for nucleic acid labeling. *Nature Biotechnology* 18:345-348 (2000).

Holland et al. Detection of specific polymerase chain reaction product by utilizing the 5' -> 3" exonuclease activity of *Thermus aquaticus* DNA polymerase. *Proc. Natl. Sci. USA* 88:7276-7280 (1991).

Holton et al. A simple and efficient method for direct cloning of PCR products using ddT-tailed vectors. *Nucl. Acids Res.* 19(5):1156 (1991).

Hoy et al. Bromodeoxyuridine/DNA analysis of replication in CHO cells after exposure to UV light, *Mutat Res.* 290:217-230 (1993).

Huryn et al. AIDS-driven nucleoside chemistry. *Chem. Rev.* 92:1745-1768 (1992).

Itakura et al. Synthesis and use of synthetic oligonucleotides. *Ann. Rev. Biochem.* 53:323-356 (1984).

Iyer et al. 3H-1, 2-benzodithiole-3-one 1, 1-dioxide as an Improved sulfurizing reagent in the solid-phase synthesis of oligodeoxyribonucleoside phosphorothioates. *J. Am. Chem. Soc.* 112:1253-1254 (1990).

Jablonski et al. Preparation of oligodeoxynucleotide-alkaline phosphatase conjugates and their use as hybridization probes. *Nucleic Acids Res.* 14(15):6115-6128 (1986).

Jacobsen et al. The N-Terminal amino-acid sequences of DNA polymerase I from *Escherichia coli* and of the large and the small fragments obtained by a limited proteolysis. *Eur. J. Biochem.* 45:623-627 (1974).

Jones et al. Studies on the alkylation of 2', 3'-o-isopropylideneuridine. *J. Carbohydrates, Nucleosides, Nucleotides* 4(5):301-308 (1977).

Jun-Dong et al. Application of Wittig reaction to adenosine derivatives. *Synthesis* 909-911 (1990).

Jung et al. Bacteriophage PRD1 DNA polymerases: evolution of DNA polymerases. *Proc. Natl. Acad. Sci. USA* 84:8287-8291 (1987).

Kaboord et al. Accessory proteins function as matchmakers in the assembly of the T4 DNA polymerase holoenzyme. *Curr. Biol.* 5(2):149-157 (1995).

Kalnik et al. NMR studies of abasic sites in DNA duplexes: deoxyadenosine stacks into the helix opposite the cyclic analogue of 2-deoxyribose. *Biochemistry* 27:924-931 (1998).

Kerkhof. A comparison of substrates for quantifying the signal from a nonradiolabeled DNA probe, *Anal. Biochem.* 205:359-364 (1992).

Khrapko et al. Hybridization of DNA with oligonucleotides iimobilized in gel: a convenient method for detecting single base substitutions. *Mol Biol (Mosk) (USSR)* 581-591 (1991).

Khrapko et al. Hybridization of DNA with oligonucleotides immobilized in gel: a convenient method for detecting single base substitutions. *Mol. Biol. (Mosk) USSR* 25:718-730.

Kim et al. Whole genome amplification and molecular genetic analysis of DNA from paraffin-embedded prostate adenocarcinoma tumor tissue, *J. Urol.* 162:1512-1518 (1999).

Klein et al. Comparative genomic hybridization, loss of heterozygosity, and DNA sequence analysis of single cells, *Proc Natl Acad Sci USA* 96:4494-4499 (1999).

Kong et al. Characterization of a DNA polymerase from the hyperthermophile archaea *Thermococcus litoralis*. *J. Biol. Chem.* 268(3)1985-1975 (1993).

Kuukasjarvl et al. Optimizing DOP-PCR for universal amplification of small DNA samples in comparative genomic hybridization. *Genes, Chromosomes and Cancer* 18:94-101 (1997).

Kumar et al. A simple method for Introducing a thiol group at the 5'-end of synthetic oligonucleotides. *Nucleic Acids Res.* 19(16):4561 (1991).

Landegren. Molecular mechanics of nucleic acid sequence amplification, *Trends Genetics* 9(6):199-202 (1993).

Landegren et al. A ligase-mediated gene detection technique. *Science* 241:1077-1080 (1988).

Langer et al. Enzymatic synthesis of biotin-labeled polynucleotides: Novel inucleic affinity probes, *Proc. Natl. Acad. Sci. USA* 78(11):6633-8637 (1981).

Lantz et al. Biotechnical use of polymerase chain reaction for microbiological analysis of biological samples. *Biotechnol. Annu. Rev.* 5:87-130 (2000).

Lesnick et al. Relative thermodynamic stability of DNA, RNA, and DNA: RNA hybrid duplexes: relationship with base composition and structure. *Biochemistry* 34:10807-10815 (1995).

Letsinger et al. Synthesis of thymidine oligonucleotides by phosphite triester Intermediates. *J. Am. Chem. Soc.* 9:3655-3661 (1976).

Li et al. Enzyme-linked synthetic oligonucleotide probes: non-radioactive detection of enterotoxigenic *Escherichia coli* in faecal specimens, *Nucleid Acids Res.* 15(13):5275-5287 (1987).

Little et al. Molecular diagnostics and genetics. *Clin. Chem.* 45(6):777-784 (1999).

Lizardi et al. Mutation detection and single-molecule counting using isothermal rolling-circle amplification. *Nature Genetics* 19:225-232 (1998).

Lockhart et al. Expression monitoring by hybridization to high-density oligonucleotide arrays. *Nature Biotechnology* 14:1675-1680 (1996).

Mackellar et al. Synthesis and physical properties of anti-HIV antisense oligonucleotides bearing terminal lipophilic groups. *Nucleic Acids Res.* 20(13):3411-3417 (1992).

Matray et al. A specific partner for abasic damage in DNA. *Nature*. 399:704-708 (1999).

(56) References Cited

OTHER PUBLICATIONS

Matsumoto et al. Primary structure of bacteriophage M2 DNA polymerase: conserved segments within protein-priming DNA polymerases and DNA polymerase I of *Escherichia coli. Gene* 84:247-255(1989).
Matteucci et al. Synthesis of deoxyoligonucleotides on a polymer support. *J. Am. Chem. Soc.* 103:3185-3191 (1981).
McGraw et al. Sequence-dependent oligonucleotide-target duplex stabilities: rules from empirical studies with a set of twenty-mers. *Biotechniques* B(6):674-678 (1990).
Moran et al. Non-hydrogen bonding 'terminator' nucleosides increase the 3'-end homogeneity of enzymatic RNA and DNA synthesis. *Nucleic Acids Res.* 24(11):2044-2052 (1996).
Mujumdar et al. Cyanine dye labeling reagents comtaining isothiocyanate groups. *Cytometry* 10:11-19 (1989).
Mullenix et al. Allergen-specific IgE detection on microarrays using rolling circle amplification: correlation with in vitro assays for serum IGE. *Clinical Chemistry* 47(10):1926-1929 (2001).
Narang et al. Chemical synthesis of deoxyoligonucleotides by the modified triester method. *Meth. Enzymol.* 65:610-620 (1980).
Nazerenko et al. A closed tube format for amplification and detection of DNA based on energy transfer. *Nucleic Acids Res.* 25(12):2516-2521 (1997).
Nelson. Rapid detection of genetic mutations using the chemiluminescent bydridization protection assay (HPA): overview and comparison with other methods. *Crit. Rev. Clin. Lab. Sci.* 35(5):369-414 (1998).
Nelson et al. Oligonucleotide labeling methods 3. Direct labeling of oligonucleotides employing a novel, on-nucleosidic,2-aminobutyl-1,3-propanediol backbone. *Nucleic Acids Res.* 20(23):6253-6259 (1992).
Nielsen et al. Peptide nucleic acid (PNA). A DNA mimic with a peptide backbone. *Bioconjug. Chem.* 5:3-7 (1994).
Nielsen et al. Sequence-selective recognition of DNA by strand displacement with a thymine-substiuted poiyamide. *Science* 254:1497-1500 (1991).
Parker et al. Targeted gene walking polymerase chain reaction. *Nucleic Acids Research* 19(11):3055-3060(1991).
Paulson et al. Loss of heterozygosity analysis using whole genome amplification, cell sorting, and fluorescence-based PCR, *Genome Res.* 9:482-491 (1999).
Paunio et al. Preimplantation diagnosis by whole-genome amplification, PCR amplification, and solid-phase minisequencing of blastomere DNA. *Clin. Chem.* 42(9):1382-1390 (1996).
Pieles et al. Psoralen covalently linked to oligodeoxyribonucleotides: synthesis, sequence specific recognition of DNA and photo-cross-linking to pyrimidine residues of DNA. *Nucleic Acids Res.* 17(1):285-299 (1989).
Pieles et al. Preparation of a novel psoralen containing deoxyadenosine building block for the facile solid phase synthesis of psoralen-modified oligonucleotides for a sequence specific crosslink to a given targe sequence. Nucleic Acids Res. 17(22):8967-8978 (1989).
Pease et al. Light-generated oligonucleotide arrays for rapid DNA sequence analysis. *Proc. Natl. Acad. Sci. USA*, 91:5022-5026 (1994).
Pless et al. Solid support synthesis of oligothymidylates using phosphorochloridates and 1-alkylimidazoles. *Nucl. Acids Res.* 2(6):773-786 (1975).
Pruckler et al. Comparison of *Legionella pneumophila* isolates by arbitrarily primed PCR and pulsed-field gel electrophoresis: analysis from seven epidemic investigations. *J. Clin. Microbiol.* 33(11):2872-2875 (1995).
Ray et al. Novel thymidine analogues via reaction of unprotected 5'-Deoxy-5'-iodothymidine with dianions. *Heterocycles* 31(10):1777-1780 (1990).
Rigler et al. Differences in the mechanism of stimulation of T7 DNA polymerase by two binding modes of *Escherichia coli* single-stranded DNA-binding protein. *J. Biol. Chem* 270(15):8910-8919 (1995).

Robins et al. Fluorination at C5' of nucleosides, synthesis of the new class of 5'-Fluoro-5'-S-Aryl (Alkyl) thionucleosides from adenosine. *Tetrahedron Lett.* 29(45):5729-5732 (1988).
Rychlik et al. Optimization of the annealing temperature for DNA amplification in vitro. *Nucl. Acids Res.* 18(21):6409-6412 (1990).
Saiki et al. Primer-directed enzymatic amplification of DNA with a thermostable DNA Polymerase, *Science* 239:487-491 (1988).
Salunkhe et al. Control of folding and binding of oligonucleotides by use of a nonnucleotide linker. *J. Amer. Chem. Soc.* 114:8788-8772 (1992).
Sambrook et al. *Molecular Cloning: A Laboratory Manual*, 2' Edition (Cold Spring Harbor Laboratory Press, Cold Spring Harbor, NY) Chapters 5, 6 (1989).
Sanghvi. Chapter 15, Heterocyclic base modifications in nucleic acids and their applications in antisense oligonucleotides. *Antisense Res. and Appl.* p. 273-301 (1993).
Sano et al. Detection of heavy methylation in human repetitive DNA subsets by a monoclonal antibody against 5-methylcytosine. *Biochim. Biophys. Acta* 951:157-165 (1988).
Schena et al. Quantitative monitoring of gene expression patterns with a complementary DNA microarray. *Science* 270:486-470 (1995).
Schweitzer et al. Combining nucleic acid amplification and detection. *Curr. Opin. Biotech.* 12:21-27 (2001).
Schweitzer et al. Immunoassays with rolling circle DNA amplification: A versatile platform for ultrasensitive antigen detection. *PNAS* 97(18):10113-10119 (2000).
Schweitzer et al. Multiplexed protein profiling on microarrays by rolling-circle amplification. *Nature Biotechnology* 20:359-365 (2002).
Sequin. Nucleosides and nucleotides. Part 7. Four dithymidine monophosphates with different anomeric configurations, their synthesis and behaviour towards phosphodiesterases. *Helv. Chim. Acta.* 57(1):68-81 (1974).
Siegal et al. A novel DNA helicase from calf thymus. J. Biol. Chem. 267(19):13629-13635 (1992).
Sinha et al. The preparation and application of functionalized synthetic oligonucleotides: III. Use of H-phosphonate derivatives of protected amino-hexanol and mercapto-propanol or -hexanol. *Nucleic Acids Res.* 16(6):2659-2669 (1988).
Skaliter et al. Rolling circle DNA replication in vitro by a complex of herpes simplex virus Type 1-encoded enzymes. *Proc. Natl. Acad. Sci. USA* 91(22):10665-10669 (1994).
Southern. Detection of specific sequences among DNA fragments separated by electrophoresis, *J. Mol. Biol.* 98:503-517 (1975).
Speicher et al. Karyotyping human chromosomes by combinatorial multi-fluor FISH *Nature Genetics* 12:368-375 (1996).
Sproat et al. The synthesis of protected 5'-mercapto-2',5'-dideoxyribonucleoside-3'-O-phosphoramidites; uses of 5'-mercapto-oligodeoxyribonucleotides. *Nucleic Acids Res.* 15(12):4837-4848 (1987).
Stein et al. Mode of action of 5'-linked cholesteryl phosphorothioate oiigodeoxynucieotides in inhibiting syncytia formation and infection by HIV-1 and HIV-2 in vitro. *Biochemistry* 30:2439-2444 (1991).
Stimpson et al. Real-time detection of DNA hybridization and melting on oligonucleotide arrays by using optical wave guides. *Proc Natl. Acad. Sci. USA*, 92:6379-6383 (1995).
Stump et al. The use of modified primers to eliminate cycle sequencing artifacts. *Nucleic Acids Res.* 27(23):4642-4648 (1999).
Takasugi et al. Sequence-specific photo-induced cross-linking of the two strands of double-helical DNA by a psoralen covalentiy linked to a triple helix-forming oligonucleotide. *Proc. Natl. Acad. Sci. USA* 88:5602-5606 (1991).
Takeshita et al. Oligodeoxynucleotides containing synthetic abasic sites. Model substrates for DNA polymerases and apurinic/apyrimidinic endonucleases. *J. Biol. Chem.* 262(21):10171-10179 (1987).
Tanaka et al. Cleavage of a nucleosidic oxetane with carbanions: synthesis of a highly promising candidate for anti-HIV agents: a phosphokate isosters O AZI' 5'-phosphate. *Tetrahedron Lett.* 30(19):2567-2570 (1989).

(56) References Cited

OTHER PUBLICATIONS

Tani et al. Defensins act as potent adjuvants that promote cellular and humoral immune responses in mice to a lymphoma idiotype and carrier antigens. International Immunology 12(5):691-700 (2000).
Telenius et al. Degenerate oligonucleotide-primed PCR: general amplification of target DNA by a single degenerate primer. *Genomics* 13:718-725 (1992).
Tenover et al. Comparison of traditional and molecular methods of typing isolates of *Staphylococcus aureus*. *J. Clin. Microbiol.* 32(2):407-415 (1994).
Thelwell et al. Mode of action and application of Scorpion primers to mutation detection. *Nucleic Acids Res.* 28(19):3752-3761 (2000).
Thomas et al. Amplification of padlock probes for DNA diagnostics by cascade rolling circle amplification or the polymerase chain reaction. *Arch. Pathol. Lab. Med.* 123(12):1170-1176 (1999).
Thoung et al. Solid phase synthesis of oligo- and oligo-β-deoxynucleotides. *Tetrahedron Lett.* 29(46):5905-5908 (1988).
Tsurumi et al. Functional interaction between Epstein-Barr Virus DNA polymerase catalytic subunit and its accessory subunit In Vitro. *J. Virol.* 67(12):7648-7653 (1993).
Tyagi et al. Molecular beacons: probes that fluoresce upon hybridization. *Nat. Biotech.*, 14:303-308 (1996).
Villemain et al. The N-Terminal B-Domain of T4 Gene 32 protein modulates the lifetime of cooperatively bound Gp32-ss nucleic acid complexes. *Biochemistry* 35:14395-14404 (1996).
Waggoner. Covalent labeling of proteins and nucleic acids with fluorophores. *Meth. Enzymology* 246:362-373 (1995).
Walker et al. Strand displacement amplification—an isothermal, in vitro DNA amplification technique. *Nucleic Acids Res.* 20(7):1691-1696 (1992).
Walker et al. Isothermal in vitro amplification of DNA by a restriction enzyme/DNA polymerase system. *Proc. Natl. Acad, Sci. USA.* 89:392-396 (1992).
Walker et al. Detection of *Mycobacterium tuberculosis* DNA with thermophilic strand displacement amplification and fluorescence polarization. *Clinical Chemistry* 42(10):1604-1608(1996).
Wansink et al. Flourescent labeling of nascent RNA reveals transcription by RNA polymerase II in domains scattered throughout the nucleus. *J. of Cell Biol.* 122(2):283-293 (1993).
Wells et al. Comprehensive chromosomal analysis of human preimplantation embryos using whole genome amplification and single cell comparative genomic hybridization. *Mel. Hum. Reprod.* 6(11):1055-1062 (2000).
Wells et al. Detailed chromosomal and molecular genetic analysis of single cells by whole genome amplification and comparative genomic hybridization, *Nucl. Acids Res.* 27(4):1214-1218 (1999).
Will et al. The synthesis of oligonucleotides that contain 2,4-dinitrophenyl reporter groups. *Carbohydr. Res.* 216:315-322 (1991).
Yu et al., Cyanine dye dUTP analogs for enzymatic labeling of DNA probes, *Nucl. Acids Res.*, 22(15):3226-3232 (1994).
Zhang et al. Amplification of target-specific, ligation-dependent circular probe. *Gene* 211:277-285 (1998).
Zhang et al. Whole genome amplification from a single cell: implications for genetic analysis. *Proc Natl Acad Sci USA* 89:5847-5851 (1992).
Zhu et al. Purification and characterization of PRD1 DNA polymerase. *Biochim. Biophys. Acta* 1219:267-276 (1994).
Zijderveld et al. Helix-destabilizing properties of the adenovirus DNA-binding protein. *J. Virol.* 68(2)1158-1164 (1994).
Zuckerman et al. Efficient methods for attachment of thiol specific probes to the 3'-ends of synthetic oligodeoxyribonucleotides. *Nucleic Acids Res.* 15(13):5305-5321 (1987).
Nuovo, et al. In Situ Amplification Using Universal Energy Transfer-labeled Primers, *The Journal of Histochemistry & Cytochemistry, The Histochemical Society, Inc.*, New York, New York 43(3):273-279 (1999), XP008002684.
U.S. Appl. No. 11/870,715, filed Oct. 11, 2007, Korfhage et al.
U.S. Appl. No. 11/887,678, filed Mar. 27, 2006, Korfhage, C.
U.S. Appl. No. 11/991,435, filed May 4, 2007, Korfhage, C.
U.S. Appl. No. 09/803,713, filed Mar. 9, 2001, Alsmadi, O.A.
U.S. Appl. No. 10/325,490, filed Dec. 19, 2002, Alsmadi, O.A.
U.S. Appl. No. 10/404,944, filed Mar. 31, 2003, Alsmadi, O.A.
U.S. Appl. No. 09/547,757, filed Apr. 12, 2000, Faruqi, A.F.
U.S. Appl. No. 09/597,836, filed Jun. 20, 2000, Kingsmore, S.
U.S. Appl. No. 10/341,287, filed Jan. 13, 2003, Kingsmore, S.
U.S. Appl. No. 11/187,537, filed Jul. 22, 2005, Kingsmore, S.
U.S. Appl. No. 09/897,259, filed Jul. 2, 2001, Ward, D.C.
U.S. Appl. No. 09/910,383, filed Jul. 20, 2001, Nallur, G.
U.S. Appl. No. 09/977,868, filed Oct. 15, 2001, Bornarth, C.
U.S. Appl. No. 09/982,212, filed Oct. 18, 2001, Bomarth, C.
U.S. Appl. No. 10/272,465, filed Oct. 15, 2002, Bornarth, C.
U.S. Appl. No. 10/429,229, filed May 2, 2003, Bornarth, C.
U.S. Appl. No. 11/871,707, filed Oct. 12, 2007, Bornarth, C.
U.S. Appl. No. 08/754,681, filed Nov. 21, 1996, Lizardi, P.
U.S. Appl. No. 09/602,428, filed Jun. 23, 2000, Lizardi, P.
U.S. Appl. No. 09/841,513, filed Apr. 24, 2001, Lizardi, P.
U.S. Appl. No. 10/413,041, filed Apr. 10, 2003, Lizardi, P.
U.S. Appl. No. 10/072,666, filed Feb. 8, 2002, Kumar, G.
U.S. Appl. No. 09/460,078, filed Dec. 14, 1999, Hafner, G.
U.S. Appl. No. 10/917,580, filed Aug. 13, 2004, Hafner, G.
U.S. Appl. No. 10/325,665, filed Dec. 19, 2002, Alsmadi, O.
U.S. Appl. No. 10/335,573, filed Dec. 31, 2002, Kumar, G.
U.S. Appl. No. 11/201,339, filed Aug. 10, 2005, Kumar, G.
U.S. Appl. No. 10/405,822, filed Mar. 31, 2003, Abarzua, P.
U.S. Appl. No. 10/454,946, filed Jun. 4, 2003, Feaver, W.J.
U.S. Appl. No. 09/605,192, filed Jun. 28, 2000, Lasken, R.
U.S. Appl. No. 09/920,571, filed Jul. 31, 2001, Lasken, R.
U.S. Appl. No. 09/577,444, filed May 24, 2000, Kingsmore, S.
U.S. Appl. No. 09/897,665, filed Jul. 2, 2001, Kingsmore, S.
U.S. Appl. No. 09/910,372, filed Jul. 20, 2001, Bandaru, R.
U.S. Appl. No. 10/465,759, filed Jun. 19, 2003, Bandaru, R.
U.S. Appl. No. 09/723,685, filed Nov. 28, 2000, Abarzua, P.
U.S. Appl. No. 10/196,539, filed Jul. 16, 2002 Abarzua, P.
U.S. Appl. No. 11/429,549, filed May 5, 2006, Abarzua, P.
U.S. Appl. No. 09/827,289, filed Apr. 5, 2001, Abarzua, P.
U.S. Appl. No. 10/177,629, filed Jun. 19, 2002, Wiltshire, S.
U.S. Appl. No. 09/931,736, filed Aug. 17, 2001, Shao, W.
U.S. Appl. No. 10/931,015, filed Aug. 31, 2004, Shao, W.
U.S. Appl. No. 11/870,715, filed Oct. 11, 2007, Korfhage, C.
U.S. Appl. No. 11/744,553, filed May 4, 2007, Korfhage, C.
U.S. Appl. No. 11/887,678, Korfhage, C.
U.S. Appl. No. 11/991,435, Korfhage, C.
U.S. Appl. No. 08/563,912, filed Nov. 21, 1995, Lizardi, P.
U.S. Appl. No. 09/132,553, filed Aug. 11, 1998, Lizardi, P.
U.S. Appl. No. 09/644,723, filed Aug. 23, 2000, Lizardi, P.
U.S. Appl. No. 09/132,552, filed Aug. 11, 1998, Lizardi, P.
U.S. Appl. No. 10/038,718, filed Jan. 2, 2002, Lizardi, P.
U.S. Appl. No. 10/896,513, filed Jul. 22, 2004, Lizardi, P.
U.S. Appl. No. 08/946,732, filed Oct. 8, 1997, Lizardi, P.
U.S. Appl. No. 09/397,915, filed Sep. 17, 1999, Lizardi, P.
U.S. Appl. No. 09/911,226, filed Jul. 23, 2001, Lizardi, P.
U.S. Appl. No. 10/700,018, filed Nov. 3, 2003, Lizardi, P.
U.S. Appl. No. 09/357,487, filed Jul. 20, 1999, Lizardi, P.
U.S. Appl. No. 09/803,713, Alsmadi et al., filed Mar. 9, 2001, Issue Notification, May 14, 2003.
U.S. Appl. No. 09/803,713, Alsmadi et al., filed Mar. 9, 2001, Notice of Allowance, Feb. 4, 2003.
U.S. Appl. No. 09/803,713, Alsmadi et al., filed Mar. 9, 2001, Supplemental Amendment, Jan. 23, 2003.
U.S. Appl. No. 09/803,713, Alsmadi et al., filed Mar. 9, 2001, Response after Non-Final Action, Nov. 5, 2002.
U.S. Appl. No. 09/803,713, Alsmadi et al., filed Mar. 9, 2001, Non-Final Rejection, Jun. 5, 2002.
U.S. Appl. No. 09/803,713, Alsmadi et al., filed Mar. 9, 2001, Response to Election / Restriction, Mar. 21, 2002.
U.S. Appl. No. 09/803,713, Alsmadi et al., filed Mar. 9, 2001, Restriction Requirement, Feb. 21, 2002.
U.S. Appl. No. 10/325,490, Alsmadi et al., filed Dec. 19, 2002, Abandonment for Failure to Respond to Office Action, Mar. 8, 2007.
U.S. Appl. No. 10/325,490, Alsmadi et al., filed Dec. 19, 2002, Non-Final Rejection, Aug. 9, 2006.
U.S. Appl. No. 10/325,490, Alsmadi et al., filed Dec. 19, 2002, Response after Non-Final Action, May 25, 2006.

(56) References Cited

OTHER PUBLICATIONS

U.S. Appl. No. 10/325,490, Alsmadi et al., filed Dec. 19, 2002, Non-Final Rejection, Jan. 24, 2006.
U.S. Appl. No. 10/325,490, Alsmadi et al., filed Dec. 19, 2002, Summary of Examiner Interview, Jan. 10, 2006.
U.S. Appl. No. 10/325,490, Alsmadi et al., filed Dec. 19, 2002, Response to Election / Restriction, Oct. 21, 2005.
U.S. Appl. No. 10/325,490, Alsmadi et al., filed Dec. 19, 2002, Restriction Requirement, Sep. 16, 2005.
U.S. Appl. No. 10/404,944, Alsmadi et al., filed Mar. 31, 2003, Abandonment for Failure to Respond to Office Action, Nov. 27, 2006.
U.S. Appl. No. 10/404,944, Alsmadi et al., filed Mar. 31, 2003, Non-Final Rejection, May 9, 2006.
U.S. Appl. No. 10/404,944, Alsmadi et al., filed Mar. 31, 2003, Response after Non-Final Action, Mar. 6, 2006.
U.S. Appl. No. 10/404,944, Alsmadi et al., filed Mar. 31, 2003, Non-Final Rejection, Dec. 5, 2005.
U.S. Appl. No. 09/547,757, Faruqi, filed Apr. 12, 2000, Issue Notification, Mar. 21, 2002.
U.S. Appl. No. 09/547,757, Faruqi, filed Apr. 12, 2000, Notice of Allowance, Aug. 31, 2001.
U.S. Appl. No. 09/597,836, Kingsmore et al., filed Jun. 20, 2000, Issue Notification, Feb. 20, 2003.
U.S. Appl. No. 09/597,836, Kingsmore et al., filed Jun. 20, 2000, Notice of Allowance, Nov. 17, 2002.
U.S. Appl. No. 09/597,836, Kingsmore et al., filed Jun. 20, 2000, Response to Office Action, Sep. 18, 2002.
U.S. Appl. No. 09/597,836, Kingsmore et al., filed Jun. 20, 2000, Final Rejection, Mar. 19, 2002.
U.S. Appl. No. 09/597,836 Kingsmore et al., filed Jun. 20, 2000, Response after Non-Final Action, Feb. 5, 2002.
U.S. Appl. No. 09/597,836, Kingsmore et al., filed Jun. 20, 2000, Non-Final Rejection, Nov. 5, 2001.
U.S. Appl. No. 09/597,836, Kingsmore et al., filed Jun. 20, 2000, Response after Non-Final Action, Sep. 20, 2001.
U.S. Appl. No. 09/597,836, Kingsmore et al., filed Jun. 20, 2000, Non-Final Rejection, Mar. 20, 2001.
U.S. Appl. No. 09/597,836, Kingsmore et al., filed Jun. 20, 2000, Amendment, Oct. 23, 2000.
U.S. Appl. No. 10/341,287, Kingsmore et al., filed Jan. 13, 2003, Post Issue Communication—Certificate of Correction, Sep. 7, 2005.
U.S. Appl. No. 10/341,287, Kingsmore et al., filed Jan. 13, 2003, Request for Certificate of Correction, Aug. 25, 2005.
U.S. Appl. No. 10/341,287, Kingsmore et al., filed Jan. 13, 2003, Issue Notification, Jul. 6, 2005.
U.S. Appl. No. 10/341,287, Kingsmore et al., filed Jan. 13, 2003, Notice of Allowance, Mar. 15, 2005.
U.S. Appl. No. 10/341,287, Kingsmore et al., filed Jan. 13, 2003, Response after Non-Final Action, Jan. 4, 2005.
U.S. Appl. No. 10/341,287, Kingsmore et al., filed Jan. 13, 2003, Terminal Disclaimer, Jan. 4, 2005.
U.S. Appl. No. 10/341,287, Kingsmore et al., filed Jan. 13, 2003, Non-Final Rejection, Oct. 22, 2004.
U.S. Appl. No. 11/187,537, Kingsmore et al., filed Jul. 22, 2005, Requirement for Restriction / Election, Oct. 22, 2004.
U.S. Appl. No. 11/187,537, Kingsmore et al., filed Jul. 22, 2005, Miscellaneous Communication to Applicant Notice of Defective Declaration, Oct. 4, 2007.
U.S. Appl. No. 11/187,537, Kingsmore et al., filed Jul. 22, 2005, Petition Decision—Granted, Mar. 2, 2006.
U.S. Appl. No. 11/187,537, Kingsmore et al., filed Jul. 22, 2005, Petition Entered, Dec. 23, 2005.
U.S. Appl. No. 09/897,259, Ward et al., filed Jul. 2, 2001, Issue Notification, Jan. 15, 2004.
U.S. Appl. No. 09/897,259, Ward et al., filed Jul. 2, 2001, Communication from Examiner, Dec. 8, 2003.
U.S. Appl. No. 09/897,259, Ward et al., filed Jul. 2, 2001, Notice of Allowance, Jul. 1, 2003.
U.S. Appl. No. 09/897,259, Ward et al., filed Jul. 2, 2001, Amendment, Apr. 11, 2003.
U.S. Appl. No. 09/897,259, Ward et al., filed Jul. 2, 2001, Non-Final Rejection, Jan. 17, 2003.
U.S. Appl. No. 09/897,259, Ward et al., filed Jul. 2, 2001, Response to Election / Restriction, Nov. 4, 2002.
U.S. Appl. No. 09/897,259, Ward et al., filed Jul. 2, 2001, Restriction Requirement, Sep. 30, 2002.
U.S. Appl. No. 09/910,383, Nallur et al., filed Jul. 20, 2001, Abandonment for Failure to Respond to Office Action, Nov. 14, 2007.
U.S. Appl. No. 09/910,383, Nallur et al., filed Jul. 20, 2001, Advisory Action, May 1, 2007.
U.S. Appl. No. 09/910,383, Nallur et al., filed Jul. 20, 2001, Amendment/Argument after Notice of Appeal, Apr. 18, 2007.
U.S. Appl. No. 09/910,383, Nallur et al., filed Jul. 20, 2001, Notice of Appeal, Apr. 18, 2007.
U.S. Appl. No. 09/910,383, Nallur et al., filed Jul. 20, 2001, Examiner Interview Summary, Apr. 9, 2007.
U.S. Appl. No. 09/910,383, Nallur et al., filed Jul. 20, 2001, Final Rejection, Dec. 13, 2006.
U.S. Appl. No. 09/910,383, Nallur et al., filed Jul. 20, 2001, Response after Non-Final Action, Oct. 2, 2006.
U.S. Appl. No. 09/910,383, Nallur et al., filed Jul. 20, 2001, Non-Final Rejection, Jun. 15, 2006.
U.S. Appl. No. 09/910,383, Nallur et al., filed Jul. 20, 2001, Response after Non-Final Action, Mar. 22, 2006.
U.S. Appl. No. 09/910,383, Nallur et al., filed Jul. 20, 2001, Advisory Action, Dec. 13, 2005.
U.S. Appl. No. 09/910,383, Nallur et al., filed Jul. 20, 2001, Amendment after Final Rejection, Nov. 23, 2005.
U.S. Appl. No. 09/910,383, Nallur et al., filed Jul. 20, 2001, Examiner Interview Summary Record, Oct. 12, 2005.
U.S. Appl. No. 09/910,383, Nallur et al., filed Jul. 20, 2001, Advisory Action, Sep. 14, 2005.
U.S. Appl. No. 09/910,383, Nallur et al., filed Jul. 20, 2001, Amendment after Final Rejection, Aug. 26, 2005.
U.S. Appl. No. 09/910,383, Nallur et al., filed Jul. 20, 2001, Final Rejection, May 23, 2005.
U.S. Appl. No. 09/910,383, Nallur et al., filed Jul. 20, 2001, Response after Non-Final Action, Mar. 14, 2005.
U.S. Appl. No. 09/910,383, Nallur et al., filed Jul. 20, 2001, Non-Final Rejection, Jan. 27, 2005.
U.S. Appl. No. 09/910,383, Nallur et al., filed Jul. 20, 2001, Response after Non-Final Action, Nov. 22, 2004.
U.S. Appl. No. 09/910,383, Nallur et al., filed Jul. 20, 2001, Non-Final Rejection, Jun. 23, 2004.
U.S. Appl. No. 09/977,868, Dean et al., filed Oct. 15, 2001, Issue Notification, Nov. 30, 2005.
U.S. Appl. No. 09/977,868, Dean et al., filed Oct. 15, 2001, Notice of Allowance, Feb. 22, 2005.
U.S. Appl. No. 09/977,868, Dean et al., filed Oct. 15, 2001, Examiner's Amendment, Feb. 22, 2005.
U.S. Appl. No. 09/977,868, Dean et al., filed Oct. 15, 2001, Response after Non-Final Action, Jan. 4, 2005.
U.S. Appl. No. 09/977,868, Dean et al., filed Oct. 15, 2001, Non-Final Rejection, Sep. 9, 2004.
U.S. Appl. No. 09/977,868, Dean et al., filed Oct. 15, 2001, Preliminary Amendment, Apr. 11, 2002.
U.S. Appl. No. 09/982,212, Dean et al., filed Oct. 18, 2001, Issue Notification, Aug. 21, 2003.
U.S. Appl. No. 09/982,212, Dean et al., filed Oct. 18, 2001, Notice of Allowance, May 20, 2003.
U.S. Appl. No. 09/982,212, Dean et al., filed Oct. 18, 2001, Response after Non-Final Action, May 7, 2003.
U.S. Appl. No. 09/982,212, Dean et al., filed Oct. 18, 2001, Non-Final Rejection, Apr. 18, 2003.
U.S. Appl. No. 09/982,212, Dean et al., filed Oct. 18, 2001, $2^{nd}$ Preliminary Amendment, Oct. 25, 2002.
U.S. Appl. No. 09/982,212, Dean et al., filed Oct. 18, 2001, Preliminary Amendment, Oct. 18, 2001.
U.S. Appl. No. 10/272,465, Dean et al., filed Oct. 15, 2002, Decision on Petition to Revive, May 22, 2006.

(56) References Cited

OTHER PUBLICATIONS

U.S. Appl. No. 10/272,465, Dean et al., filed Oct. 15, 2002, Petition to Revive Application, Mar. 16, 2006.
U.S. Appl. No. 10/272,465, Dean et al., filed Oct. 15, 2002, Issue Notification, Jun. 21, 2006.
U.S. Appl. No. 10/272,465, Dean et al., filed Oct. 15, 2002, Notice of Allowance, Dec. 13, 2005.
U.S. Appl. No. 10/272,465, Dean et al., filed Oct. 15, 2002, Examiner's Amendment, Dec. 13, 2005.
U.S. Appl. No. 10/272,465, Dean et al., filed Oct. 15, 2002, Terminal Disclaimer, Sep. 6, 2005.
U.S. Appl. No. 10/272,465, Dean et al., filed Oct. 15, 2002, Response after Non-Final Action, Sep. 6, 2005.
U.S. Appl. No. 10/272,465, Dean et al., filed Oct. 15, 2002, Non-Final Rejection, Aug. 5, 2005.
U.S. Appl. No. 10/429,229, Bomarth et al., filed May 2, 2003, Issue Fee Payment Received, Sep. 17, 2007.
U.S. Appl. No. 10/429,229, Bomarth et al., filed May 2, 2003, Supplemental Notice of Allowance, Jul. 31, 2007.
U.S. Appl. No. 10/429,229, Bornarth et al., filed May 2, 2003, Notice of Allowance, Jun. 18, 2007.
U.S. Appl. No. 10/429,229, Bornarth et al., filed May 2, 2003, Examiner Interview Summary, Jun. 18, 2007.
U.S. Appl. No. 10/429,229, Bornarth et al., filed May 2, 2003, Examiner's Amendment, Jun. 18, 2007.
U.S. Appl. No. 10/429,229, Bornarth et al., filed May 2, 2003, Amendment after Final Rejection, Jun. 5, 2007.
U.S. Appl. No. 10/429,229, Bornarth et al., filed May 2, 2003, Final Rejection, Feb. 28, 2007.
U.S. Appl. No. 10/429,229, Bornarth et al., filed May 2, 2003, Response after Non-Final Action & Terminal Disclaimer, Dec. 18, 2006.
U.S. Appl. No. 10/429,229, Bornarth et al., filed May 2, 2003, Non-Final Rejection, Jun. 20, 2006.
U.S. Appl. No. 10/429,229, Bornarth et al., filed May 2, 2003, Response to Election / Restriction, Apr. 21, 2006.
U.S. Appl. No. 10/429,229, Bornarth et al., filed May 2, 2003, Restriction Requirement, Feb. 16, 2006.
U.S. Appl. No. 11/871,707, Bornarth et al., filed Oct. 12, 2007, Non-Final Rejection, Jan. 28, 2009.
U.S. Appl. No. 11/871,707, Bornarth et al., filed Oct. 12, 2007, Notice of Publication, Jun. 5, 2008.
U.S. Appl. No. 11/871,707, Bornarth et al., filed Oct. 12, 200, Preliminary Amendment, Jan. 31, 2008.
U.S. Appl. No. 08/754,681, Lizardi et al., filed Nov. 21, 1996, Issue Notification, Oct. 20, 2000.
U.S. Appl. No. 08/754,681, Lizardi et al., filed Nov. 21, 1996, Issue Fee Payment Verified, Jun. 23, 2000.
U.S. Appl. No. 08/754,681, Lizardi et al., filed Nov. 21, 1996, Notice of Allowance, Mar. 28, 2000.
U.S. Appl. No. 08/754,681, Lizardi et al., filed Nov. 21, 1996, Notice of Appeal, Feb. 7, 2000.
U.S. Appl. No. 08/754,681, Lizardi et al., filed Nov. 21, 1996, Amendment after Final Rejection & Terminal Disclaimer, Dec. 30, 1999.
U.S. Appl. No. 08/754,681, Lizardi et al., filed Nov. 21, 1996, Final Rejection, Aug. 4, 1999.
U.S. Appl. No. 08/754,681, Lizardi et al., filed Nov. 21, 1996, Supplemental Response, Apr. 12, 1999.
U.S. Appl. No. 08/754,681, Lizardi et al., filed Nov. 21, 1996, Response after Non-Final Action, Apr. 1, 1999.
U.S. Appl. No. 08/754,681, Lizardi et al., filed Nov. 21, 1996, Non-Final Rejection, Oct. 1, 1998.
U.S. Appl. No. 08/754,681, Lizardi et al., filed Nov. 21, 1996, Response after Non-Final Action, Jul. 6, 1998.
U.S. Appl. No. 08/754,681, Lizardi et al., filed Nov. 21, 1996, Non-Final Rejection, Jan. 6, 1998.
U.S. Appl. No. 08/754,681, Lizardi et al., filed Nov. 21, 1996, Response after Non-Final Action, Oct. 21, 1997.
U.S. Appl. No. 08/754,681, Lizardi et al., filed Nov. 21, 1996, Restriction Requirement, Jun. 17, 1997.
U.S. Appl. No. 09/602,428, Lizardi et al., filed Jun. 23, 2000, Notice of Allowance, Jun. 28, 2001.
U.S. Appl. No. 09/602,428, Lizardi et al., filed Jun. 23, 2000, Terminal Disclaimer, Apr. 12, 2001.
U.S. Appl. No. 09/602,428, Lizardi et al., filed Jun. 23, 2000, Response after Non-Final Action, Apr. 12, 2001.
U.S. Appl. No. 09/602,428, Lizardi et al., filed Jun. 23, 2000, Non-Final Rejection, Nov. 22, 2000.
U.S. Appl. No. 09/602,428, Lizardi et al., filed Jun. 23, 2000, Preliminary Amendment, Jun. 23, 2000.
U.S. Appl. No. 09/841,513, Lizardi, filed Apr. 24, 2001, Terminal Disclaimer, May 7, 2003.
U.S. Appl. No. 09/841,513, Lizardi, filed Apr. 24, 2001, Notice of Allowance, Jan. 16, 2003.
U.S. Appl. No. 09/841,513, Lizardi, filed Apr. 24, 2001, Terminal Disclaimer, Oct. 18, 2002.
U.S. Appl. No. 09/841,513, Lizardi, filed Apr. 24, 2001, Response after Non-Final Action, Oct. 18, 2002.
U.S. Appl. No. 09/841,513, Lizardi, filed Apr. 24, 2001, Non-Final Rejection, Apr. 30, 2002.
U.S. Appl. No. 09/841,513, Lizardi, filed Apr. 24, 2001, Preliminary Amendment, Apr. 24, 2001.
U.S. Appl. No. 10/413,041, Lizardi et al., filed Apr. 10, 2003, Abandonment for Failure to Respond to Office Action, Apr. 5, 2006.
U.S. Appl. No. 10/413,041, Lizardi et al., filed Apr. 10, 2003, Restriction Requirement, Sep. 22, 2005.
U.S. Appl. No. 10/072,666, Kumar et al., filed Feb. 8, 2002, Notice of Allowance, Jan. 27, 2009.
U.S. Appl. No. 10/072,666, Kumar et al., filed Feb. 8, 2002, Notice of Allowance, Sep. 26, 2008.
U.S. Appl. No. 10/072,666, Kumar et al., filed Feb. 8, 2002, Examiner Amendment Communication, Sep. 22, 2008.
U.S. Appl. No. 10/072,666, Kumar et al., filed Feb. 8, 2002, Terminal Disclaimer, Sep. 10, 2008.
U.S. Appl. No. 10/072,666, Kumar et al., filed Feb. 8, 2002, Amendment after Final Rejection, Sep. 10, 2008.
U.S. Appl. No. 10/072,666, Kumar et al., filed Feb. 8, 2002, Final Rejection, Jul. 15, 2008.
U.S. Appl. No. 10/072,666, Kumar et al., filed Feb. 8, 2002, Response to Non-Final Action, Apr. 30, 2008.
U.S. Appl. No. 10/072,666, Kumar et al., filed Feb. 8, 2002, Non-Final Rejection, Feb. 1, 2008.
U.S. Appl. No. 10/072,666, Kumar et al., filed Feb. 8, 2002, Response after Non-Final Action, Nov. 15, 2007.
U.S. Appl. No. 10/072,666, Kumar et al., filed Feb. 8, 2002, Non-Final Rejection, Jul. 9, 2007.
U.S. Appl. No. 10/072,666, Kumar et al., filed Feb. 8, 2002, Response after Non-Final Action, Apr. 24, 2007.
U.S. Appl. No. 10/072,666, Kumar et al., filed Feb. 8, 2002, Non-Final Rejection, Jan. 24, 2007.
U.S. Appl. No. 10/072,666, Kumar et al., filed Feb. 8, 2002, Response t/o Office Action, Nov. 30, 2006.
U.S. Appl. No. 10/072,666, Kumar et al., filed Feb. 8, 2002, Advisory Action, Nov. 8, 2006.
U.S. Appl. No. 10/072,666, Kumar et al., filed Feb. 8, 2002, Amendment after Final Rejection, Oct. 20, 2006.
U.S. Appl. No. 10/072,666, Kumar et al., filed Feb. 8, 2002, Final Rejection, Jul. 31, 2006.
U.S. Appl. No. 10/072,666, Kumar et al., filed Feb. 8, 2002, Response after Non-Final Action, May 15, 2006.
U.S. Appl. No. 10/072,666, Kumar et al., filed Feb. 8, 2002, Non-Final Rejection, Jan. 27, 2006.
U.S. Appl. No. 10/072,666, Kumar et al., filed Feb. 8, 2002, Examiner Interview Summary, Aug. 11, 2005.
U.S. Appl. No. 10/072,666, Kumar et al., filed Feb. 8, 2002, Response to Office Action, Nov. 11, 2005.
U.S. Appl. No. 10/072,666, Kumar et al., filed Feb. 8, 2002, Final Rejection, Jul. 11, 2005.
U.S. Appl. No. 10/072,666, Kumar et al., filed Feb. 8, 2002, Response after Non-Final Action, Apr. 27, 2005.

(56) References Cited

OTHER PUBLICATIONS

U.S. Appl. No. 10/072,666, Kumar et al., filed Feb. 8, 2002, Notice of Restarted Response Period, Feb. 10, 2005.
U.S. Appl. No. 10/072,666, Kumar et al., filed Feb. 8, 2002, Non-Final Rejection, Dec. 2, 2004.
U.S. Appl. No. 10/072,666, Kumar et al., filed Feb. 8, 2002, Response after Non-Final Action, Aug. 4, 2004.
U.S. Appl. No. 10/072,666, Kumar et al., filed Feb. 8, 2002, Non-Final Rejection, Apr. 19, 2004.
U.S. Appl. No. 10/072,666, Kumar et al., filed Feb. 8, 2002, Response after Non-Final Action, Nov. 10, 2003.
U.S. Appl. No. 10/072,666, Kumar et al., Feb. 8, 2002, Non-Final Rejection, May 8, 2003.
U.S. Appl. No. 09/460,078, Hafner et al., filed Dec. 14, 1999, Issue Notification, Nov. 25, 2004.
U.S. Appl. No. 09/460,078, Hafner et al., filed Dec. 14, 1999, Notice of Allowance, Jul. 14, 2004.
U.S. Appl. No. 09/460,078, Hafner et al., filed Dec. 14, 1999, Amendment after Final Rejection, Jun. 17, 2004.
U.S. Appl. No. 09/460,078, Hafner et al., filed Dec. 14, 1999, Examiner Interview Summary, May 25, 2004.
U.S. Appl. No. 09/460,078, Hafner et al., filed Dec. 14, 1999, Final Rejection, Feb. 13, 2004.
U.S. Appl. No. 09/460,078, Hafner et al., filed Dec. 14, 1999, Response after Non-Final Action, Nov. 24, 2003.
U.S. Appl. No. 09/460,078, Hafner et al., filed Dec. 14, 1999, Non-Final Rejection, May 19, 2003.
U.S. Appl. No. 09/460,078, Hafner et al., filed Dec. 14, 1999, Response after Non-Final Action, Jan. 14, 2003.
U.S. Appl. No. 09/460,078, Hafner et al., filed Dec. 14, 1999, Non-Final Rejection, Sep. 4, 2002.
U.S. Appl. No. 09/460,078, Hafner et al., filed Dec. 14, 1999, Amendment and Response, Jun. 17, 2002.
U.S. Appl. No. 09/460,078, Hafner et al., filed Dec. 14, 1999, Notice of Appeal, Jan. 25, 2002.
U.S. Appl. No. 09/460,078, Hafner et al., filed Dec. 14, 1999, Final Rejection, Jul. 17, 2001.
U.S. Appl. No. 09/460,078, Hafner et al., filed Dec. 14, 1999, Response after Non-Final Action, May 23, 2001.
U.S. Appl. No. 09/460,078, Hafner et al., filed Dec. 14, 1999, Non-Final Rejection, Nov. 20, 2000.
U.S. Appl. No. 09/460,078, Hafner et al., filed Dec. 14, 1999, Response to Election / Restriction, Oct. 3, 2000.
U.S. Appl. No. 09/460,078, Hafner et al., filed Dec. 14, 1999, Notice of Restarted Response Period, Jun. 30, 2000.
U.S. Appl. No. 09/460,078, Hafner et al., filed Dec. 14, 1999, Restriction Requirement, May 23, 2000.
U.S. Appl. No. 10/917,580, Hafner et al., filed Aug. 13, 2004, Issue Notification, Mar. 26, 2008.
U.S. Appl. No. 10/917,580, Hafner et al., filed Aug. 13, 2004, Notice of Allowance, Nov. 30, 2007.
U.S. Appl. No. 10/917,580, Hafner et al., filed Aug. 13, 2004, Examiner's Amendment Communication, Nov. 30, 2007.
U.S. Appl. No. 10/917,580, Hafner et al., filed Aug. 13, 2004, Terminal Disclaimer, Oct. 1, 2007.
U.S. Appl. No. 10/917,580, Hafner et al., filed Aug. 13, 2004, Response after Non-Final Action, Oct. 1, 2007.
U.S. Appl. No. 10/917,580, Hafner et al., filed Aug. 13, 2004, Non-Final Rejection, Jun. 25, 2007.
U.S. Appl. No. 10/917,580, Hafner et al., filed Aug. 13, 2004, Response to Election / Restriction, May 10, 2007.
U.S. Appl. No. 10/917,580, Hafner et al., filed Aug. 13, 2004, Restriction Requirement, Jan. 11, 2007.
U.S. Appl. No. 10/917,580, Hafner et al., filed Aug. 13, 2004, $2^{nd}$ Preliminary Amendment, Nov. 19, 2004.
U.S. Appl. No. 10/917,580, Hafner et al., filed Aug. 13, 2004, Preliminary Amendment, Aug. 13, 2004.
U.S. Appl. No. 10/325,665, Alsmadi et al., filed Dec. 19, 2002, Abandonment for failure to respond to office action, Nov. 10, 2008.
U.S. Appl. No. 10/325,665, Alsmadi et al., filed Dec. 19, 2002, Non-Final Rejection, Apr. 17, 2008.
U.S. Appl. No. 10/325,665, Alsmadi et al., filed Dec. 19, 2002, Examiner Interview Summary, Apr. 17, 2008.
U.S. Appl. No. 10/325,665, Alsmadi et al., filed Dec. 19, 2002, Non-Final Rejection, Oct. 25, 2007.
U.S. Appl. No. 10/325,665, Alsmadi et al., filed Dec. 19, 2002, Amendment/Argument after Notice of Appeal, Sep. 25, 2007.
U.S. Appl. No. 10/325,665, Alsmadi et al., filed Dec. 19, 2002, Notice of Appeal, Sep. 25, 2007.
U.S. Appl. No. 10/325,665, Alsmadi et al., filed Dec. 19, 2002, Final Rejection, Mar. 26, 2007.
U.S. Appl. No. 10/325,665, Alsmadi et al., filed Dec. 19, 2002, Response after Non-Final Action, Dec. 22, 2006.
U.S. Appl. No. 10/325,665, Alsmadi et al., filed Dec. 19, 2002, Non-Final Rejection, Aug. 3, 2006.
U.S. Appl. No. 10/325,665, Alsmadi et al., filed Dec. 19, 2002, Response after Non-Final Action & Terminal Disclaimer, Apr. 18, 2006.
U.S. Appl. No. 10/325,665, Alsmadi et al., filed Dec. 19, 2002, Non-Final Rejection, Dec. 30, 2005.
U.S. Appl. No. 10/325,665, Alsmadi et al., filed Dec. 19, 2002, Response to Election / Restriction, Sep. 21, 2005.
U.S. Appl. No. 10/325,665, Alsmadi et al., filed Dec. 19, 2002, Restriction Requirement, Apr. 21, 2005.
U.S. Appl. No. 10/335,573, Kumar et al., filed Dec. 31, 2002, Issue Notification, Nov. 30, 2005.
U.S. Appl. No. 10/335,573, Kumar et al., filed Dec. 31, 2002, Notice of Allowance, Mar. 29, 2005.
U.S. Appl. No. 10/335,573, Kumar et al., filed Dec. 31, 2002, Response after Non-Final Action, Dec. 1, 2004.
U.S. Appl. No. 10/335,573, Kumar et al., filed Dec. 31, 2002, Non-Final Rejection, Jul. 29, 2004.
U.S. Appl. No. 11/201,339, Kumar et al., filed Aug. 10, 2005, Abandonment for Failure to Respond to Office Action, May 12, 2008.
U.S. Appl. No. 11/201,339, Kumar et al., filed Aug. 10, 2005, Restriction Requirement, Sep. 25, 2007.
U.S. Appl. No. 11/201,339, Kumar et al., filed Aug. 10, 2005, Preliminary Amendment, Aug. 10, 2005.
U.S. Appl. No. 10/405,822, Abarzua et al., filed Mar. 31, 2003, Non-Final Rejection, Jun. 1, 2009.
U.S. Appl. No. 10/405,822, Abarzua et al., filed Mar. 31, 2003, Amendment and Response, Mar. 11, 2009.
U.S. Appl. No. 10/405,822, Abarzua et al., filed Mar. 31, 2003, Advisory Action, Feb. 27, 2009.
U.S. Appl. No. 10/405,822, Abarzua et al., filed Mar. 31, 2003, Amendment and Response after Final Rejection, Feb. 11, 2009.
U.S. Appl. No. 10/405,822, Abarzua et al., filed Mar. 31, 2003, Examiner Interview Summary, Dec. 11, 2008.
U.S. Appl. No. 10/405,822, Abarzua et al., filed Mar. 31, 2003, Final Rejection, Sep. 11, 2008.
U.S. Appl. No. 10/405,822, Abarzua et al., filed Mar. 31, 2003, Amendment and Response, May 30, 2008.
U.S. Appl. No. 10/405,822, Abarzua et al., filed Mar. 31, 2003, Non-Final Rejection, Mar. 28, 2008.
U.S. Appl. No. 10/405,822, Abarzua et al., filed Mar. 31, 2003, Applicant Arguments/Remarks Made in an Amendment, Dec. 28, 2007.
U.S. Appl. No. 10/405,822, Abarzua et al., filed Mar. 31, 2003, Mail Advisory Action, Nov. 9, 2007.
U.S. Appl. No. 10/405,822, Abarzua et al., filed Mar. 31, 2003, Amendment/Argument after Notice of Appeal, Oct. 30, 2007.
U.S. Appl. No. 10/405,822, Abarzua et al., filed Mar. 31, 2003, Notice of Appeal, Oct. 30, 2007.
U.S. Appl. No. 10/405,822, Abarzua et al., filed Mar. 31, 2003, Mail Final Rejection, Apr. 30, 2007.
U.S. Appl. No. 10/405,822, Abarzua et al., filed Mar. 31, 2003, Response after Non-Final Action, Jan. 25, 2007.
U.S. Appl. No. 10/405,822, Abarzua et al., filed Mar. 31, 2003, Mail Non-Final Rejection, Aug. 2, 2006.
U.S. Appl. No. 10/405,822, Abarzua et al., filed Mar. 31, 2003, Response to Election / Restriction, Jun. 6, 2006.

(56) References Cited

OTHER PUBLICATIONS

U.S. Appl. No. 10/405,822, Abarzua et al., filed Mar. 31, 2003, Mail Restriction Requirement, Dec. 13, 2005.
U.S. Appl. No. 10/454,946, Feaver et al., filed Jun. 4, 2003, Notice of Abandonment, Jun. 5, 2009.
U.S. Appl. No. 10/454,946, Feaver et al., filed Jun. 4, 2003, Non-Final Rejection, Nov. 24, 2008.
U.S. Appl. No. 10/454,946, Feaver et al., filed Jun. 4, 2003, Amendment and Response, Aug. 29, 2008.
U.S. Appl. No. 10/454,946, Feaver et al., filed Jun. 4, 2003, Advisory Action, Mar. 25, 2008.
U.S. Appl. No. 10/454,946, Feaver et al., filed Jun. 4, 2003, Amendment after Final, Mar. 25, 2008.
U.S. Appl. No. 10/454,946, Feaver et al., filed Jun. 4, 2003, Notice of Appeal, Mar. 17, 2008.
U.S. Appl. No. 10/454,946, Feaver et al., filed Jun. 4, 2003, Amendment after Final, Feb. 8, 2008.
U.S. Appl. No. 10/454,946, Feaver et al., filed Jun. 4, 2003, Examiner Interview Summary, Jan. 29, 2008.
U.S. Appl. No. 10/454,946, Feaver et al., filed Jun. 4, 2003, Final Rejection, Sep. 18, 2007.
U.S. Appl. No. 10/454,946, Feaver et al., filed Jun. 4, 2003, Response after Non-Final Action, Jul. 5, 2007.
U.S. Appl. No. 10/454,946, Feaver et al., filed Jun. 4, 2003, Non-Final Rejection, Feb. 9, 2007.
U.S. Appl. No. 10/454,946, Feaver et al., filed Jun. 4, 2003, Response after Non-Final Action, Nov. 20, 2006.
U.S. Appl. No. 10/454,946, Feaver et al., filed Jun. 4, 2003, Non-Final Rejection, Jul. 26, 2006.
U.S. Appl. No. 10/454,946, Feaver et al., filed Jun. 4, 2003, Response to Election / Restriction, May 4, 2006.
U.S. Appl. No. 10/454,946, Feaver et al., filed Jun. 4, 2003, Restriction Requirement, Feb. 6, 2006.
U.S. Appl. No. 10/456,056, Kumar et al., Jun. 6, 2003, Response to Office Action, May 27, 2009.
U.S. Appl. No. 10/456,056, Kumar et al., filed Jun. 6, 2003, Amendment and Response, Oct. 23, 2008.
U.S. Appl. No. 10/456,056, Kumar et al., filed Jun. 6, 2003, Non-Final Rejection, Aug. 8, 2008.
U.S. Appl. No. 10/456,056, Kumar et al., filed Jun. 6, 2003, Amendment and Response, Apr. 7, 2008.
U.S. Appl. No. 10/456,056, Kumar et al., filed Jun. 6, 2003, Amendment and Response, Mar. 7, 2008.
U.S. Appl. No. 10/456,056, Kumar et al., filed Jun. 6, 2003, Notice of Appeal, Sep. 6, 2007.
U.S. Appl. No. 10/456,056, Kumar et al., filed Jun. 6, 2003, Examiner Interview Summary, Apr. 17, 2007.
U.S. Appl. No. 10/456,056, Kumar et al., filed Jun. 6, 2003, Final Rejection, Mar. 6, 2007.
U.S. Appl. No. 10/456,056, Kumar et al., filed Jun. 6, 2003, Amendment and Response, Dec. 11, 2006.
U.S. Appl. No. 10/456,056, Kumar et al., filed Jun. 6, 2003, Non-Final Rejection, Aug. 2, 2006.
U.S. Appl. No. 10/456,056, Kumar et al., filed Jun. 6, 2003, Response to Election / Restriction, May 15, 2006.
U.S. Appl. No. 10/456,056, Kumar et al., filed Jun. 6, 2003, Requirement for Restriction / Election, Feb. 23, 2006.
U.S. Appl. No. 09/605,192, Lasken et al., filed Jun. 28, 2000, Response to 312 Amendment, Aug. 17, 2001.
U.S. Appl. No. 09/605,192, Lasken et al., filed Jun. 28, 2000, Amendment after Notice of Allowance (Rule 312), Jul. 31, 2001.
U.S. Appl. No. 09/605,192, Lasken et al., filed Jun. 28, 2000, Notice of Allowance, May 11, 2001.
U.S. Appl. No. 09/605,192, Lasken et al., filed Jun. 28, 2000, Interview Summary, Apr. 27, 2001.
U.S. Appl. No. 09/605,192, Lasken et al., filed Jun. 28, 2000, Interview Summary, Apr. 25, 2001.
U.S. Appl. No. 09/605,192, Lasken et al., filed Jun. 28, 2000, Response after Non-Final Action, Mar. 16, 2001.
U.S. Appl. No. 09/605,192, Lasken et al., filed Jun. 28, 2000, Non-Final Rejection, Nov. 16, 2000.
U.S. Appl. No. 09/920,571, Lasken et al., filed Jul. 31, 2001, Notice of Abandonment, May 27, 2009.
U.S. Appl. No. 09/920,571, Lasken et al., filed Jul. 31, 2001, Final Rejection, Sep. 15, 2008.
U.S. Appl. No. 09/920,571, Lasken et al., filed Jul. 31, 2001, Response after Non-Final Action, Jul. 2, 2008.
U.S. Appl. No. 09/920,571, Lasken et al., filed Jul. 31, 2001, Non-Final Rejection, Mar. 11, 2008.
U.S. Appl. No. 09/920,571, Lasken et al., filed Jul. 31, 2001, Response after Non-Final Action, Dec. 27, 2007.
U.S. Appl. No. 09/920,571, Lasken et al., filed Jul. 31, 2001, Non-Final Rejection, Jun. 28, 2007.
U.S. Appl. No. 09/920,571, Lasken et al., filed Jul. 31, 2001, Response to Election/Restriction, May 7, 2007.
U.S. Appl. No. 09/920,571, Lasken et al., filed Jul. 31, 2001, Mail Restriction Requirement, Mar. 6, 2007.
U.S. Appl. No. 09/920,571, Lasken et al., filed Jul. 31, 2001, Amendment and Response to Office Action, Dec. 11, 2006.
U.S. Appl. No. 09/920,571, Lasken et al., filed Jul. 31, 2001, Mail Final Rejection, Jun. 12, 2006.
U.S. Appl. No. 09/920,571, Lasken et al., filed Jul. 31, 2001, Response after Non-Final Rejection, Mar. 29, 2006.
U.S. Appl. No. 09/920,571, Lasken et al., filed Jul. 31, 2001, Mail Non-Final Rejection, Nov. 1, 2005.
U.S. Appl. No. 09/920,571, Lasken et al., filed Jul. 31, 2001, Response to Office Action, Aug. 19, 2005.
U.S. Appl. No. 09/920,571, Lasken et al., filed Jul. 31, 2001, Mail Advisory Action, Jun. 20, 2005.
U.S. Appl. No. 09/920,571, Lasken et al., filed Jul. 31, 2001, Amendment/Argument after Notice of Appeal, Jun. 2, 2005.
U.S. Appl. No. 09/920,571, Lasken et al., filed Jul. 31, 2001, Notice of Appeal, Jun. 2, 2005.
U.S. Appl. No. 09/920,571, Lasken et al., filed Jul. 31, 2001, Mail final Rejection, Feb. 14, 2005.
U.S. Appl. No. 09/920,571, Lasken et al., filed Jul. 31, 2001, Response after Non-Final Action, Nov. 24, 2004.
U.S. Appl. No. 09/920,571, Lasken et al., filed Jul. 31, 2001, Mail Non-Final Rejection, Aug. 25, 2004.
U.S. Appl. No. 09/920,571, Lasken et al., filed Jul. 31, 2001, Mail Advisory Action, Jun. 23, 2004.
U.S. Appl. No. 09/920,571, Lasken et al., filed Jul. 31, 2001, Amendment/Argument after Notice of Appeal, Jun. 1, 2004.
U.S. Appl. No. 09/920,571, Lasken et al., filed Jul. 31, 2001, Notice of Appeal, Jun. 1, 2004.
U.S. Appl. No. 09/920,571, Lasken et al., filed Jul. 31, 2001, Mail Final Rejection, Feb. 18, 2004.
U.S. Appl. No. 09/920,571, Lasken et al., filed Jul. 31, 2001, Response after Non-Final Action, Oct. 17, 2003.
U.S. Appl. No. 09/920,571, Lasken et al., filed Jul. 31, 2001, Mail Non-Final Rejection, Dec. 20, 2002.
U.S. Appl. No. 09/920,571, Lasken et al., filed Jul. 31, 2001, Supplemental Response, Oct. 3, 2002.
U.S. Appl. No. 09/920,571, Lasken et al., filed Jul. 31, 2001, Supplemental Response, Sep. 20, 2002.
U.S. Appl. No. 09/920,571, Lasken et al., filed Jul. 31, 2001, Mail Notice of Informal or Non-Responsive Amendment, Aug. 27, 2002.
U.S. Appl. No. 09/920,571, Lasken et al., filed Jul. 31, 2001, Mail Non-Final Rejection, Dec. 12, 2001.
U.S. Appl. No. 09/577,444, Kingsmore et al., filed May 24, 2000, Notice of Allowance, Mar. 29, 2001.
U.S. Appl. No. 09/577,444, Kingsmore et al., filed May 24, 2000, Examiner Interview Summary, Mar. 22, 2001.
U.S. Appl. No. 09/897,665, Kingsmore et al., filed Jul. 2, 2001, Notice of Allowance, Jul. 30, 2003.
U.S. Appl. No. 09/897,665, Kingsmore et al., filed Jul. 2, 2001, Notice of Appeal, May 27, 2003.
U.S. Appl. No. 09/897,665, Kingsmore et al., filed Jul. 2, 2001, Amendment and Terminal Disclaimer, May 27, 2003.
U.S. Appl. No. 09/897,665, Kingsmore et al., filed Jul. 2, 2001, Final Rejection, Feb. 25, 2003.

(56) References Cited

OTHER PUBLICATIONS

U.S. Appl. No. 09/897,665, Kingsmore et al., filed Jul. 2, 2001, Response after Non-Final Action, Dec. 4, 2002.
U.S. Appl. No. 09/897,665, Kingsmore et al., filed Jul. 2, 2001, Non-Final Rejection, Jul. 19, 2002.
U.S. Appl. No. 09/897,665, Kingsmore et al., filed Jul. 2, 2001, Preliminary Amendment, Jul. 1, 2001.
U.S. Appl. No. 09/910,372, Bandaru et al., filed Jul. 20, 2001, Notice of Allowance, Apr. 8, 2003.
U.S. Appl. No. 09/910,372, Bandaru et al., filed Jul. 20, 2001, Supplemental Response, Mar. 20, 2003.
U.S. Appl. No. 09/910,372, Bandaru et al., filed Jul. 20, 2001, Amendment and Response, Jan. 17, 2003.
U.S. Appl. No. 09/910,372, Bandaru et al., filed Jul. 20, 2001, Non-Final Rejection, Nov. 13, 2002.
U.S. Appl. No. 09/910,372, Bandaru et al., filed Jul. 20, 2001, Response to Election / Restriction, Sep. 27, 2002.
U.S. Appl. No. 09/910,372, Bandaru et al., filed Jul. 20, 2001, Restriction Requirement, Sep. 17, 2002.
U.S. Appl. No. 10/465,759, Bandaru et al., filed Jun. 19, 2003, Notice of Allowance, May 4, 2004.
U.S. Appl. No. 10/465,759, Bandaru et al., filed Jun. 19, 2003, Response after Non-Final Action, Apr. 12, 2004.
U.S. Appl. No. 10/465,759, Bandaru et al., filed Jun. 19, 2003, Non-Final Rejection, Jan. 8, 2004.
U.S. Appl. No. 09/723,685, Abarzua, filed Nov. 28, 2000, Notice of Allowance, Apr. 17, 2002.
U.S. Appl. No. 09/723,685, Abarzua, filed Nov. 28, 2000, Examiner Interview Summary, Apr. 4, 2002.
U.S. Appl. No. 09/723,685, Abarzua, filed Nov. 28, 2000, Response after Non-Final Action, Dec. 10, 2001.
U.S. Appl. No. 09/723,685, Abarzua, filed Nov. 28, 2000, Non-Final Rejection, Aug. 28, 2001.
U.S. Appl. No. 09/723,685, Abarzua, filed Nov. 28, 2000, Response after Non-Final Action, Jun. 13, 2001.
U.S. Appl. No. 09/723,685, Abarzua, filed Nov. 28, 2000, Non-Final Rejection, Mar. 13, 2001.
U.S. Appl. No. 10/196,539, Abarzua, filed Jul. 16, 2002, Issue Notification, Apr. 19, 2006.
U.S. Appl. No. 10/196,539, Abarzua, filed Jul. 16, 2002, Notice of Allowance, Nov. 15, 2005.
U.S. Appl. No. 10/196,539, Abarzua, filed Jul. 16, 2002, Terminal Disclaimer, Aug. 12, 2005.
U.S. Appl. No. 10/196,539, Abarzua, filed Jul. 16, 2002, Response after Non-Final Action, Aug. 12, 2005.
U.S. Appl. No. 10/196,539, Abarzua, filed Jul. 16, 2002, Non-Final Rejection, Mar. 10, 2005.
U.S. Appl. No. 11/429,549, Abarzua, filed May 5, 2006, Examiner Interview Summary, Oct. 15, 2008.
U.S. Appl. No. 11/429,549, Abarzua, filed May 5, 2006, Abandonment, Oct. 15, 2008.
U.S. Appl. No. 11/429,549, Abarzua, filed May 5, 2006, Non-Final Rejection, Mar. 26, 2008.
U.S. Appl. No. 11/429,549, Abarzua, filed May 5, 2006, Notice of Publication, Jan. 18, 2007.
U.S. Appl. No. 11/429,549, Abarzua, filed May 5, 2006, Preliminary Amendment, May 5, 2006.
U.S. Appl. No. 09/827,289, Abarzua, filed Apr. 5, 2001, Issue Notification, Jul. 29, 2004.
U.S. Appl. No. 09/827,289, Abarzua, filed Apr. 5, 2001, Notice of Allowance, Apr. 1, 2004.
U.S. Appl. No. 09/827,289, Abarzua, filed Apr. 5, 2001, Supplemental Response, Feb. 17, 2004.
U.S. Appl. No. 09/827,289, Abarzua, filed Apr. 5, 2001, Notice of Informal or Non-Responsive Amendment, Feb. 2, 2004.
U.S. Appl. No. 09/827,289, Abarzua, filed Apr. 5, 2001, Response after Non-Final Action, Jan. 22, 2004.
U.S. Appl. No. 09/827,289, Abarzua, filed Apr. 5, 2001, Non-Final Rejection, Sep. 29, 2003.
U.S. Appl. No. 09/827,289, Abarzua, filed Apr. 5, 2001, Amendment after Non-Final Rejection, Aug. 6, 2003.
U.S. Appl. No. 09/827,289, Abarzua, filed Apr. 5, 2001, Advisory Action, Jun. 2, 2003.
U.S. Appl. No. 09/827,289, Abarzua, filed Apr. 5, 2001, Amendment after Final Rejection, May 15, 2003.
U.S. Appl. No. 09/827,289, Abarzua, filed Apr. 5, 2001, Final Rejection, Feb. 10, 2003.
U.S. Appl. No. 09/827,289, Abarzua, filed Apr. 5, 2001, Response after Non-Final Action, Jan. 21, 2003.
U.S. Appl. No. 09/827,289, Abarzua, filed Apr. 5, 2001, Non-Final Rejection, Jul. 29, 2002.
U.S. Appl. No. 09/827,289, Abarzua, filed Apr. 5, 2001, Response to Election / Restriction, Jun. 24, 2002.
U.S. Appl. No. 09/827,289, Abarzua, filed Apr. 5, 2001, Restriction Requirement, Jun. 11, 2002.
U.S. Appl. No. 10/177,629, Wiltshire, filed Jun. 19, 2002, Examiner Interview Summary, Sep. 20, 2007.
U.S. Appl. No. 10/177,629, Wiltshire, filed Jun. 19, 2002, Abandonment for failure to respond to office action, Sep. 15, 2007.
U.S. Appl. No. 10/177,629, Wiltshire, filed Jun. 19, 2002, Final Rejection, Aug. 21, 2006.
U.S. Appl. No. 10/177,629, Wiltshire, filed Jun. 19, 2002, Response after Non-Final Action & Terminal Disclaimer, Jun. 12, 2006.
U.S. Appl. No. 10/177,629, Wiltshire, filed Jun. 19, 2002, Non-Final Rejection, Jan. 10, 2006.
U.S. Appl. No. 10/177,629, Wiltshire, filed Jun. 19, 2002, Response to Election / Restriction, Oct. 27, 2005.
U.S. Appl. No. 10/177,629, Wiltshire, filed Jun. 19, 2002, Notice of Informal or Non-Responsive Amendment, Sep. 30, 2005.
U.S. Appl. No. 10/177,629, Wiltshire, filed Jun. 19, 2002, Response to Election / Restriction, Sep. 19, 2005.
U.S. Appl. No. 10/177,629, Wiltshire, filed Jun. 19, 2002, Restriction Requirement, Mar. 17, 2005.
U.S. Appl. No. 09/931,736, Shao, filed Aug. 17, 2001, Issue Notification, Feb. 9, 2005.
U.S. Appl. No. 09/931,736, Shao, filed Aug. 17, 2001, Notice of Allowance, Nov. 18, 2004.
U.S. Appl. No. 09/931,736, Shao, filed Aug. 17, 2001, Appeal Brief, Aug. 27, 2004.
U.S. Appl. No. 09/931,736, Shao, filed Aug. 17, 2001, Advisory Action, May 4, 2004.
U.S. Appl. No. 09/931,736, Shao, filed Aug. 17, 2001, Amendment/Argument after Notice of Appeal, Mar. 1, 2004.
U.S. Appl. No. 09/931,736, Shao, filed Aug. 17, 2001, Notice of Appeal, Mar. 1, 2004.
U.S. Appl. No. 09/931,736, Shao, filed Aug. 17, 2001, Final Rejection, Dec. 3, 2003.
U.S. Appl. No. 09/931,736, Shao, filed Aug. 17, 2001, Response after Non-Final Action, Sep. 22, 2003.
U.S. Appl. No. 09/931,736, Shao, filed Aug. 17, 2001, Non-Final Rejection, Jun. 30, 2003.
U.S. Appl. No. 09/931,736, Shao, filed Aug. 17, 2001, Response to Election / Restriction, May 16, 2003.
U.S. Appl. No. 09/931,736, Shao, filed Aug. 17, 2001, Restriction Requirement, Apr. 15, 2003.
U.S. Appl. No. 10/931,015, Shao, filed Aug. 31, 2004, Abandonment for Failure to Respond to Office Action, Aug. 8, 2006.
U.S. Appl. No. 10/931,015, Shao, filed Aug. 31, 2004, Interview Summary Record, Jul. 25, 2006.
U.S. Appl. No. 10/931,015, Shao, filed Aug. 31, 2004, Final Rejection, Jan. 9, 2006.
U.S. Appl. No. 10/931,015, Shao, filed Aug. 31, 2004, Amendment and Response after Non-Final Action, Aug. 24, 2005.
U.S. Appl. No. 10/931,015, Shao, filed Aug. 31, 2004, Non-Final Rejection, May 24, 2005.
U.S. Appl. No. 10/931,015, Shao, filed Aug. 31, 2004, Response to Election / Restriction, Feb. 24, 2005.
U.S. Appl. No. 10/931,015, Shao, filed Aug. 31, 2004, Restriction Requirement, Jan. 24, 2005.
U.S. Appl. No. 10/931,015, Shao, filed Aug. 31, 2004, Preliminary Amendment, Aug. 31, 2004.

(56) References Cited

OTHER PUBLICATIONS

U.S. Appl. No. 11/870,715, Korfhage, et al., filed Oct. 11, 2007, Final Rejection, May 13, 2009.
U.S. Appl. No. 11/870,715, Korfhage, et al., filed Oct. 11, 2007, Response after Non-Final Action, Feb. 9, 2009.
U.S. Appl. No. 11/870,715, Korfhage, et al., filed Oct. 11, 2007, Non-Final Rejection, Nov. 12, 2008.
U.S. Appl. No. 11/744,553, Korfhage, et al., filed May 4, 2007, Final Rejection, Apr. 15, 2009.
U.S. Appl. No. 11/744,553, Korfhage, et al., filed May 4, 2007, Amendment and Response, Dec. 17, 2008.
U.S. Appl. No. 11/744,553, Korfhage, et al., filed May 4, 2007, Examiner Interview Summary, Dec. 15, 2008.
U.S. Appl. No. 11/744,553, Korfhage, et al., filed May 4, 2007, Non-Final Rejection, Aug. 19, 2008.
U.S. Appl. No. 11/744,553, Korfhage, et al., filed May 4, 2007, Response to Restriction Requirement, Jun. 5, 2008.
U.S. Appl. No. 11/744,553, Korfhage, et al., filed May 4, 2007, Requirement for Restriction, May 16, 2008.
U.S. Appl. No. 11/744,553, Korfhage, et al., filed May 4, 2007, Notice of Publication, Mar. 6, 2008.
U.S. Appl. No. 11/887,678, Korfhage, No Transaction History Generated.
U.S. Appl. No. 11/991,435, Korfhage, Preliminary Amendment, Mar. 3, 2008.
U.S. Appl. No. 08/563,912, Lizardi, filed Nov. 21, 1995, Issue Notification, Nov. 23, 1998.
U.S. Appl. No. 08/563,912, Lizardi, filed Nov. 21, 1995, Notice of Allowance, Aug. 14, 1998.
U.S. Appl. No. 08/563,912, Lizardi, filed Nov. 21, 1995, Examiner Interview Summary, Aug. 10, 1998.
U.S. Appl. No. 08/563,912, Lizardi, filed Nov. 21, 1995, Amendment/Argument after Notice of Appeal, Aug. 6, 1998.
U.S. Appl. No. 08/563,912, Lizardi, filed Nov. 21, 1995, Notice of Appeal, Jun. 9, 1998.
U.S. Appl. No. 08/563,912, Lizardi, filed Nov. 21, 1995, Final Rejection, Dec. 9, 1997.
U.S. Appl. No. 08/563,912, Lizardi, filed Nov. 21, 1995, Amendment and Response, Aug. 27, 1997.
U.S. Appl. No. 08/563,912, Lizardi, filed Nov. 21, 1995, Office Action, Feb. 28, 1997.
U.S. Appl. No. 08/563,912, Lizardi, filed Nov. 21, 1995, Response to Election / Restriction, Oct. 24, 1996.
U.S. Appl. No. 08/563,912, Lizardi, filed Nov. 21, 1995, Restriction Requirement, Sep. 24, 1996.
U.S. Appl. No. 09/132,553, Lizardi, filed Aug. 11, 1998, Notice of Allowance, Nov. 7, 2000.
U.S. Appl. No. 09/132,553, Lizardi, filed Aug. 11, 1998, Preliminary Amendment, Aug. 11, 2000.
U.S. Appl. No. 09/132,553, Lizardi, filed Aug. 11, 1998, Non-Final Rejection, Apr. 11, 2000.
U.S. Appl. No. 09/132,553, Lizardi, filed Aug. 11, 1998, Response after Non-Final Action & Terminal Disclaimer, 01-139-2000.
U.S. Appl. No. 09/132,553, Lizardi, filed Aug. 11, 1998, Non-Final Rejection, Sep. 13, 1999.
U.S. Appl. No. 09/132,553, Lizardi, filed Aug. 11, 1998, Preliminary Amendment, Aug. 11, 1998.
U.S. Appl. No. 09/644,723, Lizardi, filed Aug. 23, 2000, Notice of Allowance, Oct. 1, 2001.
U.S. Appl. No. 09/644,723, Lizardi, filed Aug. 23, 2000, Response after Non-Final Action & Terminal Disclaimer, Jul. 16, 2001.
U.S. Appl. No. 09/644,723, Lizardi, filed Aug. 23, 2000, Non-Final Rejection, Mar. 13, 2001.
U.S. Appl. No. 09/132,552, Lizardi, filed Aug. 11, 1998, Notice of Allowance, Jul. 12, 2000.
U.S. Appl. No. 09/132,552, Lizardi, filed Aug. 11, 1998, Amendment after Final Rejection, Jun. 14, 2000.
U.S. Appl. No. 09/132,552, Lizardi, filed Aug. 11, 1998, Final Rejection, Apr. 6, 2000.
U.S. Appl. No. 09/132,552, Lizardi, filed Aug. 11, 1998, Response after Non-Final Action & Terminal Disclaimer, Jan. 19, 2000.
U.S. Appl. No. 09/132,552, Lizardi, filed Aug. 11, 1998, Non-Final Rejection, Sep. 13, 1999.
U.S. Appl. No. 09/132,552, Lizardi, filed Aug. 11, 1998, Preliminary Amendment, Aug. 11, 1998.
U.S. Appl. No. 10/038,718, Lizardi, filed Jan. 2, 2002, Notice of Allowance, Apr. 21, 2004.
U.S. Appl. No. 10/038,718, Lizardi, filed Jan. 2, 2002, Interview Summary Record, Apr. 9, 2004.
U.S. Appl. No. 10/038,718, Lizardi, filed Jan. 2, 2002, Response after Non-Final Action & Terminal Disclaimer, Jan. 20, 2004.
U.S. Appl. No. 10/038,718, Lizardi, filed Jan. 2, 2002, Non-Final Rejection, Oct. 22, 2003.
U.S. Appl. No. 10/038,718, Lizardi, filed Jan. 2, 2002, Response to Election / Restriction, Jul. 16, 2003.
U.S. Appl. No. 10/038,718, Lizardi, filed Jan. 2, 2002, Restriction Requirement, Mar. 13, 2003.
U.S. Appl. No. 10/038,718, Lizardi, filed Jan. 2, 2002, Preliminary Amendment, Jan. 2, 2002.
U.S. Appl. No. 10/896,513, Lizardi, filed Jul. 22, 2004, Amendment and Response, Mar. 26, 2009.
U.S. Appl. No. 10/896,513, Lizardi, filed Jul. 22, 2004, Interview Summary, Mar. 12, 2009.
U.S. Appl. No. 10/896,513, Lizardi, filed Jul. 22, 2004, Non-Final Rejection, Nov. 17, 2008.
U.S. Appl. No. 10/896,513, Lizardi, filed Jul. 22, 2004, Amendment and Response, Aug. 29, 2008.
U.S. Appl. No. 10/896,513, Lizardi, filed Jul. 22, 2004, Advisory Action, Jul. 23, 2008.
U.S. Appl. No. 10/896,513, Lizardi, filed Jul. 22, 2004, Amendment After Final Rejection, Jun. 16, 2008.
U.S. Appl. No. 10/896,513, Lizardi, filed Jul. 22, 2004, Final Rejection, Mar. 18, 2008.
U.S. Appl. No. 10/896,513, Lizardi, filed Jul. 22, 2004, Amendment After Non-Final Rejection, Dec. 11, 2007.
U.S. Appl. No. 10/896,513, Lizardi, filed Jul. 22, 2004, Non-Final Rejection, Jun. 11, 2007.
U.S. Appl. No. 10/896,513, Lizardi, filed Jul. 22, 2004, Response to Election / Restriction, Mar. 29, 2007.
U.S. Appl. No. 10/896,513, Lizardi, filed Jul. 22, 2004, Restriction Requirement, Jan. 19, 2007.
U.S. Appl. No. 10/896,513, Lizardi, filed Jul. 22, 2004, Preliminary Amendment, Jan. 25, 2005.
U.S. Appl. No. 08/946,732, Lizardi, filed Oct. 8, 1997, Notice of Allowance, Jun. 22, 1999.
U.S. Appl. No. 08/946,732, Lizardi, filed Oct. 8, 1997, Examiner Interview Summary, Jun. 9, 1999.
U.S. Appl. No. 08/946,732, Lizardi, filed Oct. 8, 1997, Amendment and Response, Mar. 31, 1999.
U.S. Appl. No. 08/946,732, Lizardi, filed Oct. 8, 1997, Non-Final Rejection, Oct. 1, 1998.
U.S. Appl. No. 09/397,915, Lizardi, filed Sep. 17, 1999, Notice of Allowance, Apr. 9, 2001.
U.S. Appl. No. 09/397,915, Lizardi, filed Sep. 17, 1999, Examiner Interview Summary, Apr. 4, 2001.
U.S. Appl. No. 09/397,915, Lizardi, filed Sep. 17, 1999, Terminal Disclaimer, Jan. 24, 2001.
U.S. Appl. No. 09/397,915, Lizardi, filed Sep. 17, 1999, Response after Non-Final Action, Jan. 16, 2001.
U.S. Appl. No. 09/397,915, Lizardi, filed Sep. 17, 1999, Non-Final Rejection, Aug. 14, 2000.
U.S. Appl. No. 09/397,915, Lizardi, filed Sep. 17, 1999, Preliminary Amendment, Sep. 17, 1999.
U.S. Appl. No. 09/911,226, Lizardi, filed Jul. 23, 2001, Notice of Allowance, Jun. 3, 2003.
U.S. Appl. No. 09/911,226, Lizardi, filed Jul. 23, 2001, Amendment and Response & Terminal Disclaimer, Mar. 19, 2003.
U.S. Appl. No. 09/911,226, Lizardi, filed Jul. 23, 2001, Non-Final Rejection, Dec. 18, 2002.
U.S. Appl. No. 09/397,915, Lizardi, filed Sep. 17, 1999, Preliminary Amendment, Jul. 23, 2001.

(56) References Cited

OTHER PUBLICATIONS

U.S. Appl. No. 10/700,018, Lizardi, filed Nov. 3, 2003, Advisory Action, Apr. 2, 2009.
U.S. Appl. No. 10/700,018, Lizardi, filed Nov. 3, 2003, Notice of Appeal, Mar. 13, 2009.
U.S. Appl. No. 10/700,018, Lizardi, filed Nov. 3, 2003, Amendment after Final Rejection, Jan. 27, 2009.
U.S. Appl. No. 10/700,018, Lizardi, filed Nov. 3, 2003, Final Rejection, Sep. 15, 2008.
U.S. Appl. No. 10/700,018, Lizardi, filed Nov. 3, 2003, Amendment after Non-Final Rejection, Jun. 12, 2008.
U.S. Appl. No. 10/700,018, Lizardi, filed Nov. 3, 2003, Non-Final Rejection, Jan. 24, 2008.
U.S. Appl. No. 10/700,018, Lizardi, filed Nov. 3, 2003, Response after Non-Final Action, Oct. 31, 2007.
U.S. Appl. No. 10/700,018, Lizardi, filed Nov. 3, 2003, Non-Final Rejection, Aug. 8, 2007.
U.S. Appl. No. 10/700,018, Lizardi, filed Nov. 3, 2003, Response after Non-Final Action, May 14, 2007.
U.S. Appl. No. 10/700,018, Lizardi, filed Nov. 3, 2003, Non-Final Rejection, Nov. 14, 2006.
U.S. Appl. No. 10/700,018, Lizardi, filed Nov. 3, 2003, Response after Non-Final Action, Aug. 28, 2006.
U.S. Appl. No. 10/700,018, Lizardi, filed Nov. 3, 2003, Non-Final Rejection, May 18, 2006.
U.S. Appl. No. 10/700,018, Lizardi, filed Nov. 3, 2003, Preliminary Amendment, Nov. 3, 2003.
U.S. Appl. No. 09/357,487, Lizardi, filed Jul. 20, 1999, Notice of Allowance, Jun. 5, 2001.
U.S. Appl. No. 09/357,487, Lizardi, filed Jul. 20, 1999, Examiner Interview Summary, May 30, 2001.
U.S. Appl. No. 09/357,487, Lizardi, filed Jul. 20, 1999, Amendment and Response, May 18, 2001.
U.S. Appl. No. 09/357,487, Lizardi, filed Jul. 20, 1999, Final Rejection, Feb. 13, 2001.
U.S. Appl. No. 09/357,487, Lizardi, filed Jul. 20, 1999, Amendment and Response, Jan. 25, 2001.
U.S. Appl. No. 09/357,487, Lizardi, filed Jul. 20, 1999, Non-Final Rejection, Oct. 25, 2000.
U.S. Appl. No. 09/357,487, Lizardi, filed Jul. 20, 1999, Amendment and Response, Sep. 12, 2000.
U.S. Appl. No. 09/357,487, Lizardi, filed Jul. 20, 1999, Non-Final Rejection, May 12, 2000.
PCT, PCT/US02/02601, Jan. 30, 2002, Molecular Staging, Inc., International Preliminary Examination Report, Mar. 29, 2004.
PCT, PCT/US02/02601, Jan. 30, 2002, Molecular Staging, Inc., International Search Report, Oct. 3, 2002.
TW, 91102150, Feb. 7, 2002, Molecular Staging, Inc.
EP, 01928481.9, Apr. 12, 2001, Molecular Staging, Inc., Communication under Rule 51(4) EPC, Sep. 11, 2007.
EP, 01928481.9, Apr. 12, 2001, Molecular Staging, Inc., Response to Examination Report, Nov. 27, 2006.
EP, 01928481.9, Apr. 12, 2001, Molecular Staging, Inc., Consultation by Telephone, Nov. 10, 2006.
EP, 01928481.9, Apr. 12, 2001, Molecular Staging, Inc., Response to Examination Report, Mar. 6, 2006.
EP, 01928481.9, Apr. 12, 2001, Molecular Staging, Inc., Examination Report, May 25, 2005.
PCT, PCT/US01/11947, Apr. 12, 2001, Molecular Staging, Inc., International Preliminary Examination Report, Apr. 30, 2003.
AU, 2001255331, Apr. 12, 2001, Molecular Staging, Inc.
CA, 2405456, Apr. 12, 2001, Molecular Staging, Inc., Notice of Abandonment, Jun. 7, 2007.
CA, 2405456, Apr. 12, 2001, Molecular Staging, Inc., Notice of Reinstatement, 0/10/2005.
CA, 2405456, Apr. 12, 2001, Molecular Staging, Inc., Notice of Abandonment, Jun. 8, 2004.
JP, 2001-577404, Apr. 12, 2001, Molecular Staging, Inc.
AU, 2001269944, Jun. 20, 2001, Molecular Staging, Inc., Abandoned Application, Feb. 26, 2007.
AU, 2001269944, Jun. 20, 2001, Molecular Staging, Inc., Examination Report, May 26, 2006.
AU, 2001269944, Jun. 20, 2001, Molecular Staging, Inc., Response to Examination Report, May 16, 2006.
AU, 2001269944, Jun. 20, 2001, Molecular Staging, Inc., Examination Report, May 19, 2005.
CA, 2411838, Jun. 20, 2001, Molecular Staging, Inc., Notice of Abandonment, Aug. 15, 2007.
CA, 2411838, Jun. 20, 20021, Molecular Staging, Inc., Notice of National Entry, Feb. 25, 2003.
CN, 01811542.X, Jun. 20, 2001, Molecular Staging, Inc., Reponse to Examination Report, Nov. 23, 2005.
CN, 01811542.X, Jun. 20, 2001, Molecular Staging, Inc., Instructions for Responding to Aug. 7, 2005 Examination Report with List of Claims, Nov. 21, 2005.
CN, 01811542.X, Jun. 20, 2001, Molecular Staging, Inc., Examination Report, Jul. 8, 2005.
EP, 1948505.1, Jun. 20, 2001, Molecular Staging, Inc., Notification of European Publication, Feb. 19, 2003.
JP, 2002-503102, Jun. 20, 2001, Molecular Staging, Inc., Request for Examination, Jan. 11, 2007.
PCT, PCT/US01/19657, Jun. 20, 2001, Molecular Staging, Inc., International Preliminary Examination Report, Sep. 27, 2002.
PCT, PCT/US01/19657, Jun. 20, 2001, Molecular Staging, Inc., International Search Report, Aug. 29, 2001.
SG, 200207285-8, Jun. 20, 2001, Molecular Staging, Inc., Issue Notification, Dec. 13, 2002.
TW, 90114960, Jun. 28, 2001, Molecular Staging, Inc., Office Action, Oct. 3, 2005.
TW, 90114960, Jun. 28, 2001, Molecular Staging, Inc., Response to Office Action (no translation), Sep. 13, 2005.
TW, 90114960, Jun. 28, 2001, Molecular Staging, Inc., Instructions for Responding to Office Action, Jun. 30, 2005.
TW, 90114960, Jun. 28, 2001, Molecular Staging, Inc., Office Action, May 16, 2005.
AU, 2001271722, Jul. 2, 2001, Molecular Staging, Inc, Notice of Acceptance, Mar. 26, 2006.
AU, 2001271722, Jul. 2, 2001, Molecular Staging, Inc., Response to Examination Report, Mar. 17, 2006.
AU, 2001271722, Jul. 2, 2001, Molecular Staging, Inc., Examination Report, Jun. 17, 2005.
CA, 2411794, Jul. 2, 2001, Molecular Staging, Inc., Notice of Abandonment, Aug. 28, 2007.
CA, 2411794, Jul. 2, 2001, Molecular Staging, Inc., Notice of National Entry, Jan. 16, 2003.
DE, 1950759.9, Jul. 2, 2001, Molecular Staging, Inc.
EP, 01950759.9, Jul. 2, 2001, Molecular Staging, Inc., Decision to Grant, Sep. 6, 2007.
EP, 01950759.9, Jul. 2, 2001, Molecular Staging, Inc., Response to Communication under Rule 51(4), Aug. 17, 2007.
EP, 01950759.9, Jul. 2, 2001, Molecular Staging, Inc., Communication under Rule 51(4), Apr. 26, 2007.
EP, 01950759.9, Jul. 2, 2001, Molecular Staging, Inc., Response to Examination Report, Jul. 7, 2006.
AP, 01950759.9, Jul. 2, 2001, Molecular Staging, Inc., Examination Report, Apr. 24, 2006.
AP, 01950759.9, Jul. 2, 2001, Molecular Staging, Inc., Response to Examination Report, Oct. 24, 2005.
EP, 01950759.9, Jul. 2, 2001, Molecular Staging, Inc., Examination Report, Jun. 16, 2005.
EP, 01950759.9, Jul. 2, 2001, Molecular Staging, Inc., European Search Report, Jul. 1, 2004.
JP, 2002-508032, Jul. 2, 2001, Molecular Staging, Inc., Application Open for Public Inspection, Jan. 29, 2004.
PCT/PCT/US01/20933, Jul. 2, 2001, Molecular Staging, Inc., Yale University, International Preliminary Examination Report, Dec. 30, 2002.
PCT, PCT/US01/20933, Jul. 2, 2001, Molecular Staging, Inc., Yale University, International Search Report, Jan. 10, 2002.
PCT, PCT/US02/15045, May 20, 2002, Molecular Staging, Inc., International Preliminary Examination Report, Oct. 26, 2004.
PCT, PCT/US02/15045, May 10, 2002, Molecular Staging, Inc., International Search Report, Apr. 10, 2003.

(56) References Cited

OTHER PUBLICATIONS

AU, 2002362874, Oct. 15, 2002, Molecular Staging, Inc., Examination Report, Jan. 8, 2007.
CA, 246933, Oct. 15, 2002, Molecular Staging, Inc., Notice of Abandonment, Dec. 10, 2007.
CA, 246933, Oct. 15, 2002, Molecular Staging, Inc., Notice of National Entry, Jun. 1, 2004.
EP, 02801776.2, Oct. 15, 2002, Molecular Staging, Inc., Response to Examination Report, Dec. 5, 2007.
EP, 02801776.2, Oct. 15, 2002, Molecular Staging, Inc., Examination Report, Aug. 7, 2007.
EP, 02801776.2, Oct. 15, 2002, Molecular Staging, Inc., European Search Report, Nov. 4, 2007.
EP, 02801776.2, Oct. 15, 2002, Molecular Staging, Inc., Letter Regarding European Search Report, Dec. 7, 2006.
EP, 02801776.2, Oct. 15, 2002, Molecular Staging, Inc., European Search Report, Nov. 7, 2006.
PCT, PCT/US02/33244, Oct. 15, 2002, Molecular Staging, Inc., International Preliminary Examination Report, Jul. 13, 2004.
PCT, PCT/US02/33244, Oct. 15, 2002, Molecular Staging, Inc., International Search Report, Apr. 29, 2004.
AU, 10240/97, Nov. 21, 1996, Yale University, Notice of Acceptance, Nov. 22, 1999.
AU, 10240/97, Nov. 21, 1996, Yale University, Response to Examination Report, Nov. 16, 1999.
AU, 10240/97, Nov. 21, 1996, Yale University, Examination Report, Apr. 30, 1999.
BE, 96940601.6, Nov. 21, 1996, Yale University, Notice of National Processing Completion, Apr. 20, 2001
CH, 96940601.6, Nov. 21, 1996, Yale University.
DE, 826656, Nov. 21, 1996, Yale University, Patent Granted, Sep. 11, 2001.
DK, 96940601.6, Nov. 21, 1996, Yale University.
FR, 96940601.6, Nov. 21, 1996, Yale University.
GB, 96940601.6, Nov. 21, 1996, Yale University.
CA, 2236161, Nov. 21, 1996, Yale University, Notice of Allowance, Jun. 13, 2007.
CA, 2236161, Nov. 21, 1996, Yale University, Response to Examination Report, Oct. 4, 2006.
CA, 2236161, Nov. 21, 1996, Yale University, Examination Report, Apr. 4, 2006.
EP, 96940601.6, Nov. 21, 1996, Yale University, Decision to Grant, Jan. 25, 2001.
EP, 96940601.6, Nov. 21, 1996, Yale University, Response to Communication under Rule 51(4), Dec. 21, 1999.
EP, 96940601.6, Nov. 21, 1996, Yale University, Communication under Rule 51(4), Jul. 1, 1999.
JP, 9-519942, Nov. 21, 1996, Yale University, Notice of Allowance, May 9, 2007.
JP, 9-519942, Nov. 21, 1996, Yale University, Instructions for Responding to Jun. 27, 2006 Examination Report, Dec. 13, 2006.
JP, 9-519942, Nov. 21, 1996, Yale University, Examination Report, Jun. 27, 2006.
LU, 96940601.6, Nov. 21, 1996, Yale University.
MC, 96940601.6, Nov. 21, 1996, Yale University.
NL, 96940601.6, Nov. 21, 1996, Yale University.
PCT, PCT/US96/18812, Nov. 21, 1996, Yale University, International Preliminary Examination Report, Jan. 28, 1998.
PCT, PCT/US96/18812, Nov. 21, 1996, Yale University, International Search Report, Jun. 30, 1997.
PCT, PCT/US96/18812, Nov. 21, 1996, Yale University, Response to Written Opinion, Nov. 18, 1997.
PCT, PCT/US96/18812, Nov. 21, 1996, Yale University, Written Opinion, Aug. 21, 1997.
PCT, PCT/US96/18812, Nov. 21, 1996, Yale University, International Search Report, Nov. 21, 1995.
SE, 96940601.6, Nov. 21, 1996, Yale University.
PCT, PCT/US03/00678, Jan. 9, 2003, Molecular Staging, Inc., International Search Report, Aug. 14, 2003.

AU, 27819/00, Dec. 14, 1999, Molecular Staging, Inc., Notice of Acceptance, May 12, 2005.
AU, 27819/00, Dec. 14, 1999, Molecular Staging, Inc., Response to Examination Report, Apr. 15, 2005.
AU, 27819/00, Dec. 14, 1999, Molecular Staging, Inc., Examination Report, Dec. 8, 2004.
AU, 27819/00, Dec. 14, 1999, Moleular Staging, Inc., Response to Examination Report, Nov. 30, 2004.
AU, 27819/00, Dec. 14, 1999, Molecular Staging, Inc., Examination Report, Oct. 13, 2004.
AU, 27819/00, Dec. 14, 1999, Moleculear Staging, Inc., Response to Examination Report, Sep. 22, 2004.
AU, 27819/00, Dec. 14, 1999, Molecular Staging, Inc., Examination Report, Aug. 8, 2003.
CA, 2394800, Dec. 14, 1999, Molecular Staging, Inc., Notice of Abandonment, Feb. 11, 2008.
CA, 2394800, Dec. 14, 1999, Molecular Staging, Inc., Notice of Reinstatement, Jan. 5, 2005.
CA, 2394800, Dec. 14, 1999, Molecular Staging, Inc., Notice of Abandonment, Feb. 9, 2004.
CA, 2394800, Dec. 14, 1999, Molecular Staging, Inc., Notice of National Entry, Sep. 27, 2002.
EP, 99969209.8, Dec. 14, 1999, Molecular Staging, Inc., European Search Report, Feb. 21, 2003.
JP, 2000-588388, Dec. 14, 1999, Molecular Staging, Inc., Notice of Allowance, Jul. 22, 2008.
JP, 2000-588388, Dec. 14, 1999, Molecular Staging, Inc., Examination Report, Jul. 24, 2007.
PCT, PCT/AU99/01110, Dec. 14, 1999, Diatech Pty. Ltd., International Search, Mar. 7, 2000.
AU, 2003297891, Dec. 11, 2003, Qiagen GMBH.
CA, 2512196, Dec. 11, 2003, Qiagen GMBH, Notice of Abandonment, Feb. 5, 2008.
CA, 2512196, Dec. 11, 2003, Qiagen GMBH, Notice of National Entry, Oct. 3, 2005.
EP, 03796961.5, Dec. 11, 2003, Qiagen GMBH, Response to Examination Report, Jun. 29, 2007.
EP, 03796961.5, Dec. 11, 2003, Qiagen GMBH, European Search Report, Jan. 16, 2007.
JP, 2004-565385, Dec. 11, 2003, Qiagen GMBH, Request for Examination, Nov. 22, 2006.
PCT, PCT/US03/39430, Dec. 11, 2003, Qiagen GMBH, International Search Report, Aug. 23, 2004.
AU, 2001268725, Jun. 27, 2001, Qiagen GMBH, Notice of Abandonment, Feb. 4, 2008.
AU, 2001268725, Jun. 27, 2001, Qiagen GMBH, Notice of Acceptance, Jul. 20, 2006.
AU, 2001268725, Jun. 27, 2001, Qiagen GMBH, Response to Examination Report, Jun. 23, 2006.
AU, 2001268725, Jun. 27, 2001, Qiagen GMBH, Examination Report, Jul. 18, 2005.
CA, 2410951, Jun. 27, 2001, Qiagen GMBH, Notice of Abandonment, Aug. 22, 2007.
CA, 2410951, Jun. 27, 2001, Qiagen GMBH, Notice of National Entry, Jan. 14, 2003.
DE, 01946712.5, Jun. 27, 2001, Qiagen GMBH.
EP, 01946712.5, Jun. 27, 2001, Molecular Staging, Inc., Decision to Grant, Sep. 21, 2006.
AP, 01946712.5, Jun. 27, 2001, Molecular Staging, Inc., Response to Communication under Rule 51(4), Aug. 18, 2006.
EP, 01946712.5, Jun. 27, 2001, Molecular Staging, Inc., Communication under Rule 51(4), Apr. 19, 2006.
EP, 01946712.5, Jun. 27, 2001, Molecular Staging, Inc., Response to Examination Report, Feb. 7, 2006.
EP, 01946712.5, Jun. 27, 2001, Molecular Staging, Inc., Observations by Third Parties, Jan. 23, 2006.
EP, 01946712.5, Jun. 27, 2001, Molecular Staging, Inc., Transmittal of Third Party Observations, Jan. 9, 2006.
EP, 01946712.5, Jun. 27, 2001, Molecular Staging, Inc., Observations by Third Parties, Dec. 28, 2005.
EP, 01946712.5, Jun. 27, 2001, Molecular Staging, Inc., Consultation by Phone, Dec. 15, 2005.

(56) References Cited

OTHER PUBLICATIONS

EP, 01946712.5, Jun. 27, 2001, Molecular Staging, Inc., Notification Concerning Date of Oral Proceedings, Dec. 6, 2005.
EP, 01946712.5, Jun. 27, 2001, Molecular Staging, Inc., Letter Dealing with Oral Proceedings, Nov. 29, 2005.
EP, 01946712.5, Jun. 27, 2001, Molecular Staging, Inc., Consultation by Phone, Nov. 16, 2005.
EP, 01946712.5, Jun. 27, 2001, Molecular Staging, Inc., Letter Dealing with Oral Proceedings, Oct. 31, 2005.
EP, 01946712.5, Jun. 27, 2001, Molecular Staging, Inc., Summons to attend Oral Proceedings, Jul. 1, 2005.
EP, 01946712.5, Jun. 27, 2001, Molecular Staging, Inc., Preparation for Oral Proceedings, Jun. 28, 2005.
EP, 01946712.5, Jun. 27, 2001, Molecular Staging, Inc., Response to Examination Report, Dec. 21, 2004.
EP, 01946712.5, Jun. 27, 2001, Molecular Staging, Inc., Examination Report, Nov. 11, 2004.
EP, 01946712.5, Jun. 27, 2001, Molecular Staging, Inc., Acknowledgment of Receipt of Third Party Observations, Oct. 29, 2004.
EP, 01946712.5, Jun. 27, 2001, Molecular Staging, Inc., Observations by Thid Parties, Oct. 19, 2004.
EP, 01946712.5, Jun. 27, 2001, Molecular Staging, Inc., Response to Examination Report, Jul. 29, 2004.
EP, 01946712.5, Jun. 27, 2001, Molecular Staging, Inc., Examination Report, Mar. 19, 2004.
EP, 01946712.5, Jun. 27, 2001, Molecular Staging, Inc., Response to Examination Report, Jan. 30, 2004.
EP, 01946712.5, Jun. 27, 2001, Molecular Staging, Inc., Examination Report, Jul. 24, 2003.
FR, 01946712.5, Jun. 27, 2001, Molecular Staging, Inc.
IL, 153097, Jun. 27, 2001, Molecular Staging, Inc.
IT, 01946712.5, Jun. 27, 2001, Molecular Staging, Inc.
JP, 2002/506247, Jun. 27, 2001, Molecular Staging, Inc., No prosecution history generated.
PCT, PCT/US01/20217, Jun. 27, 2001, Molecular Staging, Inc., International Preliminary Examination Report, Dec. 6, 2004.
PCT, PCT/US01/20217, Jun. 27, 2001, Molecular Staging, Inc., International Search Report, Dec. 20, 2002.
AU, 200253328, Jun. 12, 2000, Molecular Staging, Inc.
EPC, 938263.1, Jun. 12, 2000, Molecular Staging, Inc.
JP, 469290-19, Jun. 12, 2000, Molecular Staging, Inc.
PCT, PCT/US00/16130, Jun. 12, 2000, Molecular Staging, Inc., International Preliminary Examination Report, Dec. 28, 2004.
PCT, PCT/US00/16130, Jun. 12, 2000, Molecular Staging, Inc., International Search Report, Mar. 13, 2003.
AU, 2002/239809, Jan. 4, 2002, Molecular Staging, Inc.
CA, PCT/US02/00005, Jan. 4, 2002, Molecular Staging, Inc.
EPC, 2705674.6, Jan. 4, 2002, Molecular Staging, Inc.
PCT, PCT/US02/00005, Jan. 4, 2002, Molecular Staging, Inc., International Preliminary Examination Report, May 12, 2003.
PCT, PCT/US02/00005, Jan. 4, 2002, Molecular Staging, Inc., International Search Report, Feb. 19, 2003.
AU, 18040/01, Nov. 28, 2000, Molecular Staging, Inc.
CA, 2360342, Nov. 28, 2000, Molecular Staging, Inc.
EP, 00980827.0, Nov. 28, 2000, Molecular Staging, Inc., Response to Communication Pursuant to Rules 109 and 110 EPC, Oct. 17, 2001.
EP, 00980827.0, Nov. 28, 2000, Molecular Staging, Inc., Communication Pursuant to Rules 109 and 110 EPC, Sep. 13, 2001.
JP, 269290-68, Nov. 28, 2000, Molecular Staging, Inc.
PCT, PCT/US00/32370, Nov. 28, 2000, Molecular Staging, Inc., International Search Report, Jul. 11, 2002.
AU, 2001/251359, Apr. 2001, Molecular Staging, Inc.
CA, 2405687, Apr. 5, 2001, Molecular Staging, Inc.
EPC, 1924731.1, Apr. 5, 2001, Molecular Staging, Inc.
JP, 2001-575244, Apr. 5, 2001, Molecular Staging, Inc.
PCT, PCT/US01/11151, Apr. 5, 2001, Molecular Staging, Inc., International Preliminary Examination Report, Oct. 15, 2004.
PCT, PCT/US01/11151, Apr. 5, 2001, Molecular Staging, Inc., International Search Report, Oct. 18, 2002.
PCT, PCT/US02/19443, Jun. 19, 2002, Molecular Staging, Inc., International Preliminary Examination Report, Feb. 13, 2006.
PCT, PCT/US02/19443, Jun. 19, 2002, Molecular Staging, Inc., International Search Report, Oct. 10, 2003.
PCT, PCT/US02/27097, Aug. 14, 2002, Molecular Staging, Inc., International Preliminary Examination Report, Oct. 6, 2004.
PCT, PCT/US02/27097, Aug. 14, 2002, Molecular Staging, Inc., International Search Report, Jan. 29, 2003.
EPC, 7118804.9, Oct. 18, 2007, Qiagen GMBH, European Search Report, Feb. 15, 2008.
AU, 97915/98, Oct. 8, 1998, Yale University, Issue Notification, Oct. 10, 2002.
AU, 97915/98, Oct. 8, 1998, Yale University, Notice of Acceptance, May 20, 2002.
AU, 97915/98, Oct. 8, 1998, Yale University, Response to Examination, Mar. 27, 2002.
AU, 97915/98, Oct. 8, 1998, Yale University, Examination Report, May 25, 2001.
CA, 2308004, Oct. 8, 1998, Yale University, Notice of Abandonment, Dec. 4, 2007.
CA, 2308004, Oct. 8, 1998, Yale University, Notice of Acceptance, Oct. 23, 2006.
CA, 2308004, Oct. 8, 1998, Yale University, Response to Examination, Dec. 23, 2004.
CA, 2308004, Oct. 8, 1998, Yale University, Examination Report, Jun. 30, 2004.
EP, 98952147.1, Oct. 8, 1998, Yale University, Decision to Grant, Dec. 6, 2007.
EP, 98952147.1, Oct. 8, 1998, Yale University, Rseponse to Communication under Rule 51(4), Oct. 5, 2007.
EP, 98952147.1, Oct. 8, 1998, Yale University, Communication under Rule 51(4), Jun. 6, 2007.
EP, 98952147.1, Oct. 8, 1998, Yale University, Response to Examination Report, May 15, 2007.
EP, 98952147.1, Oct. 8, 1998, Yale University, Consultation by Phone, Apr. 16, 2007.
EP, 98952147.1, Oct. 8, 1998, Yale University, Response to Examination Report, Mar. 13, 2007.
EP, 98952147.1, Oct. 8, 1998, Yale University, Consultation by Phone, Dec. 29, 2006.
EP, 98952147.1, Oct. 8, 1998, Yale University, Response to Examination Report, Mar. 6, 2006.
EP, 98952147.1, Oct. 8, 1998, Yale University, Examination Report, Sep. 21, 2005.
JP, 2000-515033, Oct. 8, 1998, Yale University, Report Concerning Reconsideration before Appeal
JP, 2000-515033, Oct. 8, 1998, Yale University, Letter from Foreign Associate re Filing Amendment and Response to Official Action, Mar. 24, 2006.
JP, 2000-515033, Oct. 8, 1998, Yale University, Final Rejection, Sep. 2, 2005.
JP, 2000-515033, Oct. 8, 1998, Yale University, Response to Examiantion (no translation), Nov. 11, 2004.
JP, 2000-515033, Oct. 8, 1998, Yale University, Examination Report, May 7, 2004.
PCT, PCT/US98/21177, Oct. 8, 1998, Yale University, International Preliminary Examination Report, Oct. 12, 1999.
PCT, PCT/US98/21177, Oct. 8, 1998, Yale University, International Search Report, Mar. 10, 1999.
EP, 99935725.4, Jul. 20, 1999, Yale University, Examination Report, Aug. 13, 2003.
PCT, PCT/US99/16373, Jul. 20, 1999, Yale University, International Search Report, Dec. 2, 1999.
Walker, G., Terrance, Nadeau, James, G., Spears, Patricia, A., Schram, James, L., Nycz, Colleen, M., and Shank, Daryl, D. Multiplex strand displacement amplification (SDA) and detection of DNA sequences from *Mycobacterium tuberculosis* and other mycobacteria Nucleic Acids Research, 1994(22)13 2620-2677.
Andras, Calin, S. Power, J. Brian, Cocking, Edward, C. and Davey, Michael, R., Strategies for Signal Amplification in Nucleic Acid Detection *Molecular Biotechnology* 2001 (19) 29-44.
Detter, John C., Jett, James M., Lucas, Susan M., Dalin, Eileen, Arellano Andre R., Wang, Mei, Nelson, John R., Chapman, Jarrod,

(56) References Cited

OTHER PUBLICATIONS

Lou, Yunian, Rokhsar, Dan, Hawkins, Trevor L., and Richardson, Paul M. Isothermal Strand-Displacement Amplification Applications for High-Throughput Genomics *Genomics* (80)6 12(2002) 691-698.
Blanco et al. (1984) Characterization and purification of a phage Æ 29-encoded DNA polymerase required for the initiation of replication. Proc. Natl. Acad. Sci. USA 81: 5325-5329.
Blanco et al. (1989) Highly Efficient DNA Synthesis by the Phage Æ 29 DNA Polymerase. J. Biol. Chem. 264(15): 8935-8940.
Breslow et al. (1991) Effects of metal ions, including $Mg^{2+}$ and lanthanides, on the cleavage of ribonucleotides and RNA model compounds. PNAS 88 : 4080-4083.
Christian et al. (2001) Detection of DNA point mutations and mRNA expression levels by rolling circle amplification in individual cells. Proc Natl Acad Sci U S A. 98(25): 14238-142.
Dean et al. (2001) Rapid Amplification of Plasmid and Phage DNA Using Phi29 DNA Polymerase and Multiply-Primed Rolling Circle Amplification. Genome Res. 11: 10951099.
Fermentas Life Sciences. (2010) Thermophilic DNA Polymerases Product Page (p. 13). Retrieved from Fermentas Website Product page on Sep. 13, 2010 at http://www.fermentas.com/en/products/all/modifying-enzymes/thermophilic-polymerases.
GE Healthcare. (2010) GE Healthcare Life Sciences: "TempliPhi FAQ" Retrieved from the Internet: http://www.gelifesciences.com/aptrix/2 upp01077.nsf/Content sample_preparation-product_selection_category-roll ing_circle_amplification-sample_templiphi faq [retrieved on Jul. 29, 2010].
Gupta et al. (1990) A universal solid support for the synthesis of 3 '-thiol group containing oligonucleotides. Tetrahedron Letters. 31(17): 2471-2474.
Gusev et al. (2001) Rolling circle amplification: a new approach to increase sensitivity for immunohistochemistry and flow cytometry. American Journal of Pathology. 159(1): 6369.
Hata et al. (1988) Structure of the human ornithine transcarbamylase gene. J Biochem. 103: 302-308.
Holland et al. (1991) Detection of specific polymerase chain reaction product by utilizing the 5'-->3' exonuclease activity of Thermus aquaticus DNA polymerase. Proc. Natl. Acad. Sci. USA 88: 7276-7280.
Kälin et al. (1992) Evaluation of the ligase chain reaction (LCR) for the detection of point mutations. Mutation Research. 283(2): 119-128.
Kimpton et al. (1993) Automated DNA Profiling Employing Multiplex Amplification ofShort Tandem Repeat Loci. PCR Methods and Applications. 3: 13-22.
Kinoshita et al. (1997) Fluorescence-, isotope- or biotin-labeling of the 5 '-end of single-stranded DNA/RNA using T4 RNA ligase. Nucleic Acids Res. 25(18): 3747-8.
Lee HH. (1996) Ligase chain reaction. Biologicals. 24(3) :197-9.
Lu et al. (1993) High concentration of peripheral blood mononuclear cells harboring infectious virus correlates with rapid progression of human immunodeficiency virus Type1-related diseases. JID 168(5): 1165-8116.
Lyons et al. (1994) Immunosuppressant FK506 promotes neurite outgrowth in cultures ofPC12 cells and sensory ganglia. Proc Natl Acad Sci USA. 91(8): 3191-3195.
Morvan et al. (1986) alpha-DNA. I. Synthesis, characterization by high field 1H-NMR, and base-pairing properties of the unnatural hexadeoxyribonucleotide alpha[d(CpCpTpTpCpC)] with its complement beta-[d(GpGpApApGpG)]. Nucleic Acids Res. 14(12): 5019-35.
New England BioLabs. Polymerase from Neb" printed information from New England BioLabs webpage (3 total pages), retrieved on Jul. 26, 2007 at http://www.neb.com/nebecomm/tech_reference/polymerases/polymerase_from_neb.asp
Orum et al. (1993) Single base pair mutation analysis by PNA directed PCR clamping. Nucleic Acids Research. 21(23): 5332-5336.

Saksela et al. (1994) Human immunodeficiency virus type 1 mRNA expression in peripheral blood cells predicts disease progression independently of the numbers of CD4+ lymphocytes. Proc Natl Acad Sci USA. 91(3): 1104-1108.
Santoro et al. A general purpose RNA-cleaving DNA enzyme. PNAS 94 : 4262 (1997).
Schnierle et al., Cap-specific mRNA (nucleoside-02'-)-methyltransferase and poly(A) polymerase stimulatory activities of vaccinia virus are mediated by a single protein. PNAS 89 (7) : 2897 (1992).
Sørensen et al. (2000) Branched oligonucleotides containing bicyclic nucleotides as branching points and DNA or LNA as triplex forming branch. Bioorg Med Chem Lett. 10(16): 1853-1856.
Stein et al. (1991) Mode of action of 5'-linked cholesteryl phosphorothioate oligodeoxynucleotides in inhibiting syncytia formation and infection by HIV-1 and HIV-2 in vitro. Biochemistry. 30(9): 2439-44.
Vogelstein et al. (1980) Supercoiled loops and eucaryotic DNA replication. Cell. 22: 7985.
Wang et al. (1998) Large-scale identification, mapping, and genotyping of singlemucleotide polymorphisms in the human genome. Science. 280: 1077-1082.
Wemmer et al. (1985). Preparation and melting of single strand circular DNA loops. Nucleic Acids Res. 13(23): 8611-21.
Zehavi et al. (1972) Light-sensitive glycosides. II. 2-Nitrobenzyl 6-deoxy-.alpha.-Lmannopyranoside and 2-nitrobenzyl 6-deoxy-.beta.-L-galactopyranoside Uri. J. Org. Chem., 37 (14), pp. 2285-2288.
Zirvi et al. (1999) Ligase-based detection of mononucleotide repeat sequences. Nucleic Acids Res. 27(24) :e40.
Issue Notification issued May 14, 2003 for U.S. Appl. No. 09/803,713, filed Mar. 9, 2001 (Inventors—Alsmadi et al.).
Notice of Allowance issued Feb. 4, 2003 for U.S. Appl. No. 09/803,713, filed Mar. 9, 2001 (Inventors—Alsmadi et al.).
Supplemental Amendment filed Jan. 23, 2003 for U.S. Appl. No. 09/803,713, filed Mar. 9, 2001 (Inventors—Alsmadi et al.).
Response after Non-Final Action filed Nov. 5, 2002 for U.S. Appl. No. 09/803,713, filed Mar. 9, 2001 (Inventors—Alsmadi et al.).
Non-Final Rejection issued Jun. 5, 2002 for U.S. Appl. No. 09/803,713, filed Mar. 9, 2001 (Inventors—Alsmadi et al.).
Response to Election / Restriction filed Mar. 21, 2002 for U.S. Appl. No. 09/803,713, filed Mar. 9, 2001 (Inventors—Alsmadi et al.).
Restriction Requirement issued Feb. 21, 2002 for U.S. Appl. No. 09/803,713, filed Mar. 9, 2001 (Inventors—Alsmadi et al.).
Notice of Abandonment issued Mar. 8, 2007 for U.S. Appl. No. 10/325,490, filed Dec. 19, 2002 (Alsmadi et al.).
Non-Final Rejection issued Aug. 9, 2006 for U.S. Appl. No. 10/325,490, filed Dec. 19, 2002 (Alsmadi et al.).
Response after Non-Final Action filed May 22, 2006 for U.S. Appl. No. 10/325,490, filed Dec. 19, 2002 (Alsmadi et al.).
Non-Final Rejection issued Jan. 24, 2006 for U.S. Appl. No. 10/325,490, filed Dec. 19, 2002 (Alsmadi et al.).
Response to Election / Restriction filed Oct. 19, 2005 for U.S. Appl. No. 10/325,490, filed Dec. 19, 2002 (Alsmadi et al.).
Restriction Requirement issued Sep. 16, 2005 for U.S. Appl. No. 10/325,490, filed Dec. 19, 2002 (Alsmadi et al.).
Notice of Abandonment issued Nov. 27, 2006 for U.S. Appl. No. 10/404,944, filed Mar. 31, 2003 (Alsmadi et al.).
Non-Final Rejection issued May 9, 2006 for U.S. Appl. No. 10/404,944, filed Mar. 31, 2003 (Alsmadi et al.).
Response after Non-Final Action filed Mar. 2, 2006 for U.S. Appl. No. 10/404,944, filed Mar. 31, 2003 (Alsmadi et al.).
Non-Final Rejection issued Dec. 5, 2005 for U.S. Appl. No. 10/404,944, filed Mar. 31, 2003 (Alsmadi et al.).
Preliminary Amendment filed Mar. 31, 2003 for U.S. Appl. No. 10/404,944, filed Mar. 31, 2003 (Alsmadi et al.).
Issue Notification issued Mar. 21, 2002 for U.S. Appl. No. 09/547,757, filed Apr. 12, 2000 (Faruqi).
Notice of Allowance issued Aug. 31, 2001 for U.S. Appl. No. 09/547,757, filed Apr. 12, 2000 (Faruqi).
Issue Notification issued Feb. 20, 2003 for U.S. Appl. No. 09/597,836, filed Jun. 20, 2000 (Kingsmore et al.).

(56) References Cited

OTHER PUBLICATIONS

Notice of Allowance issued Nov. 17, 2002 for U.S. Appl. No. 09/597,836, filed Jun. 20, 2000 (Kingsmore et al.).
Response to Office Action filed Sep. 18, 2002 for U.S. Appl. No. 09/597,836, filed Jun. 20, 2000 (Kingsmore et al.).
Final Rejection issued Mar. 19, 2002 for U.S. Appl. No. 09/597,836, filed Jun. 20, 2000 (Kingsmore et al.).
Response after Non-Final Action issued Feb. 5, 2002 for U.S. Appl. No. 09/597,836, filed Jun. 20, 2000 (Kingsmore et al.).
Non-Final Rejection issued Nov. 5, 2001 for U.S. Appl. No. 09/597,836, filed Jun. 20, 2000 (Kingsmore et al.).
Response after Non-Final Action filed Sep. 20, 2001 for U.S. Appl. No. 09/597,836, filed Jun. 20, 2000 (Kingsmore et al.).
Non-Final Rejection issued Mar. 20, 2001 for U.S. Appl. No. 09/597,836, filed Jun. 20, 2000 (Kingsmore et al.).
Response filed Oct. 23, 2000 for U.S. Appl. No. 09/597,836, filed Jun. 20, 2000 (Kingsmore et al.).
Certificate of Correction issued Sep. 27, 2005 for U.S. Appl. No. 10/341,287, filed Jan. 13, 2003 (Kingsmore et al.).
Request for Certificate of Correction filed Aug. 23, 2005 for U.S. Appl. No. 10/341,287, filed Jan. 13, 2003 (Kingsmore et al.).
Issue Notification issued Jul. 6, 2005 for U.S. Appl. No. 10/341,287, filed Jan. 13, 2003 (Kingsmore et al.).
Notice of Allowance issued Mar. 15, 2005 for U.S. Appl. No. 10/341,287, filed Jan. 13, 2003 (Kingsmore et al.).
Response after Non-Final Action filed Jan. 4, 2005 for U.S. Appl. No. 10/341,287, filed Jan. 13, 2003 (Kingsmore et al.).
Non-Final Rejection issued Oct. 22, 2004 for U.S. Appl. No. 10/341,287, filed Jan. 13, 2003 (Kingsmore et al.).
Preliminary Amendment filed Jan. 13, 2003 for U.S. Appl. No. 10/341,287, filed Jan. 13, 2003 (Kingsmore et al.).
Notice of Abandonment issued Jun. 10, 2009 for U.S. Appl. No. 11/187,537, filed Jul. 22, 2005 (Kingsmore et al.).
Requirement for Restriction / Election issued Oct. 6, 2008 for U.S. Appl. No. 11/187,537, filed Jul. 22, 2005 (Kingsmore et al.).
Issue Notification issued Jan. 15, 2004 for U.S. Appl. No. 09/897,259, filed Jul. 2, 2001 (Ward et al.).
Notice of Allowance issued Jul. 1, 2003 for U.S. Appl. No. 09/897,259, filed Jul. 2, 2001 (Ward et al.).
Response after Non-Final Rejection filed Apr. 11, 2003 for U.S. Appl. No. 09/897,259, filed Jul. 2, 2001 (Ward et al.).
Non-Final Rejection issued Jan. 17, 2003 for U.S. Appl. No. 09/897,259, filed Jul. 2, 2001 (Ward et al.).
Response to Election / Restriction filed Oct. 30, 2002 for U.S. Appl. No. 09/897,259, filed Jul. 2, 2001 (Ward et al.).
Restriction Requirement issued Sep. 30, 2002 for U.S. Appl. No. 09/897,259, filed Jul. 2, 2001 (Ward et al.).
Notice of Abandonment issued Nov. 14, 2007 for U.S. Appl. No. 09/910,383, filed Jul. 20, 2001 (Nallur et al.).
Advisory Action issued May 1, 2007 for U.S. Appl. No. 09/910,383, filed Jul. 20, 2001 (Nallur et al.).
Amendment/Argument after Notice of Appeal filed Apr. 18, 2007 for U.S. Appl. No. 09/910,383, filed Jul. 20, 2001 (Nallur et al.).
Notice of Appeal issued Apr. 18, 2007 for U.S. Appl. No. 09/910,383, filed Jul. 20, 2001 (Nallur et al.).
Examiner Interview Summary issued Apr. 9, 2007 for U.S. Appl. No. 09/910,383, filed Jul. 20, 2001 (Nallur et al.).
Final Rejection issued Dec. 13, 2006 for U.S. Appl. No. 09/910,383, filed Jul. 20, 2001 (Nallur et al.).
Response after Non-Final Action filed Sep. 29, 2006 for U.S. Appl. No. 09/910,383, filed Jul. 20, 2001 (Nallur et al.).
Non-Final Rejection issued Jun. 15, 2006 for U.S. Appl. No. 09/910,383, filed Jul. 20, 2001 (Nallur et al.).
Communication withdrawing Notice of Non-Compliant Amendment issued Apr. 7, 2006 for U.S. Appl. No. 09/910,383, filed Jul. 20, 2001 (Nallur et al.).
Response after Non-Final Action filed Mar. 22, 2006 for U.S. Appl. No. 09/910,383, filed Jul. 20, 2001 (Nallur et al.).
Advisory Action issued Dec. 13, 2005 for U.S. Appl. No. 09/910,383, filed Jul. 20, 2001 (Nallur et al.).
Amendment after Final Rejection filed Nov. 23, 2005 for U.S. Appl. No. 09/910,383, filed Jul. 20, 2001 (Nallur et al.).
Examiner Interview Summary Record issued Oct. 12, 2005 for U.S. Appl. No. 09/910,383, filed Jul. 20, 2001 (Nallur et al.).
Advisory Action issued Sep. 14, 2005 for U.S. Appl. No. 09/910,383, filed Jul. 20, 2001 (Nallur et al.).
Amendment after Final Rejection filed Aug. 26, 2005 for U.S. Appl. No. 09/910,383, filed Jul. 20, 2001 (Nallur et al.).
Final Rejection issued May 23, 2005 for U.S. Appl. No. 09/910,383, filed Jul. 20, 2001 (Nallur et al.).
Response after Non-Final Action filed Mar. 10, 2005 for U.S. Appl. No. 09/910,383, filed Jul. 20, 2001 (Nallur et al.).
Non-Final Rejection issued Jan. 27, 2005 for U.S. Appl. No. 09/910,383, filed Jul. 20, 2001 (Nallur et al.).
Response after Non-Final Action filed Nov. 19, 2004 for U.S. Appl. No. 09/910,383, filed Jul. 20, 2001 (Nallur et al.).
Non-Final Rejection issued Jun. 23, 2004 for U.S. Appl. No. 09/910,383, filed Jul. 20, 2001 (Nallur et al.).
Issue Notification issued Nov. 30, 2005 for U.S. Appl. No. 09/977,868, filed Oct. 15, 2001 (Dean et al.).
Notice of Allowance issued Feb. 22, 2005 for U.S. Appl. No. 09/977,868, filed Oct. 15, 2001 (Dean et al.).
Response after Non-Final Action filed Jan. 4, 2005 for U.S. Appl. No. 09/977,868, filed Oct. 15, 2001 (Dean et al.).
Non-Final Rejection issued Sep. 9, 2004 for U.S. Appl. No. 09/977,868, filed Oct. 15, 2001 (Dean et al.).
Petition for Withdrawal of Holding of Abandonment filed Feb. 13, 2004 for U.S. Appl. No. 09/977,868, filed Oct. 15, 2001 (Dean et al.).
Preliminary Amendment filed Mar. 29, 2002 for U.S. Appl. No. 09/977,868, filed Oct. 15, 2001 (Dean et al.).
Issue Notification issued Aug. 21, 2003 for U.S. Appl. No. 09/982,212, filed Oct. 18, 2001 (Dean et al.).
Notice of Allowance issued May 20, 2003 for U.S. Appl. No. 09/982,212, filed Oct. 18, 2001 (Dean et al.).
Response after Non-Final Action filed May 7, 2003 for U.S. Appl. No. 09/982,212, filed Oct. 18, 2001 (Dean et al.).
Non-Final Rejection issued Apr. 18, 2003 for U.S. Appl. No. 09/982,212, filed Oct. 18, 2001 (Dean et al.).
Second Preliminary Amendment filed Oct. 25, 2001 for U.S. Appl. No. 09/982,212, filed Oct. 18, 2001 (Dean et al.).
Preliminary Amendment filed Oct. 18, 2001 for U.S. Appl. No. 09/982,212, filed Oct. 18, 2001 (Dean et al.).
Issue Notification issued Jun. 21, 2006 for U.S. Appl. No. 10/272,465, filed Oct. 15, 2002 (Dean et al.).
Decision on Petition to Revive issued May 22, 2006 for U.S. Appl. No. 10/272,465, filed Oct. 15, 2002 (Dean et al.).
Petition to Revive Application filed Mar. 14, 2006 for U.S. Appl. No. 10/272,465, filed Oct. 15, 2002 (Dean et al.).
Notice of Allowance issued Dec. 13, 2005 for U.S. Appl. No. 10/272,465, filed Oct. 15, 2002 (Dean et al.).
Response after Non-Final Action filed Sep. 2, 2005 for U.S. Appl. No. 10/272,465, filed Oct. 15, 2002 (Dean et al.).
Non-Final Rejection issued Aug. 5, 2005 for U.S. Appl. No. 10/272,465, filed Oct. 15, 2002 (Dean et al.).
Issue Notification issued Oct. 31, 2007 for U.S. Appl. No. 10/429,229, filed May 2, 2003 (Bornarth et al.).
Supplemental Notice of Allowance issued Jul. 31, 2007 for U.S. Appl. No. 10/429,229, filed May 2, 2003 (Bornarth et al.).
Notice of Allowance issued Jun. 18, 2007 for U.S. Appl. No. 10/429,229, filed May 2, 2003 (Bornarth et al.).
Examiner Interview Summary issued Jun. 18, 2007 for U.S. Appl. No. 10/429,229, filed May 2, 2003 (Bornarth et al.).
Amendment after Final Rejection filed Jun. 5, 2007 for U.S. Appl. No. 10/429,229, filed May 2, 2003 (Bornarth et al.).
Final Rejection issued Feb. 28, 2007 for U.S. Appl. No. 10/429,229, filed May 2, 2003 (Bornarth et al.).
Response after Non-Final Action filed Dec. 14, 2006 for U.S. Appl. No. 10/429,229, filed May 2, 2003 (Bornarth et al.).
Non-Final Rejection issued Jun. 20, 2006 for U.S. Appl. No. 10/429,229, filed May 2, 2003 (Bornarth et al.).
Response to Election / Restriction filed Apr. 17, 2006 for U.S. Appl. No. 10/429,229, filed May 2, 2003 (Bornarth et al.).

(56) References Cited

OTHER PUBLICATIONS

Restriction Requirement issued Feb. 16, 2006 for U.S. Appl. No. 10/429,229, filed May 2, 2003 (Bornarth et al.).
Notice of Abandonment issued May 25, 2010 for U.S. Appl. No. 11/871,707, filed Oct. 12, 2007 (Bornarth et al.).
Final Rejection issued Oct. 29, 2009 for U.S. Appl. No. 11/871,707, filed Oct. 12, 2007 (Bornarth et al.).
Response after Non-Final Rejection filed Jun. 22, 2009 for U.S. Appl. No. 11/871,707, filed Oct. 12, 2007 (Bornarth et al.).
Non-Final Rejection issued Jan. 28, 2009 for U.S. Appl. No. 11/871,707, filed Oct. 12, 2007 (Bornarth et al.).
Preliminary Amendment filed Jan. 31, 2008 for U.S. Appl. No. 11/871,707, filed Oct. 12, 2007 (Bornarth et al.).
Issue Notification issued Oct. 20, 2000 for U.S. Appl. No. 08/754,681, filed Nov. 21, 1996 (Lizardi et al.).
Notice of Allowance issued Mar. 28, 2000 for U.S. Appl. No. 08/754,681, filed Nov. 21, 1996 (Lizardi et al.).
Notice of Appeal filed Feb. 4, 2000 for U.S. Appl. No. 08/754,681, filed Nov. 21, 1996 (Lizardi et al.).
Amendment after Final Rejection filed Dec. 28, 1999 for U.S. Appl. No. 08/754,681, filed Nov. 21, 1996 (Lizardi et al.).
Final Rejection issued Aug. 4, 1999 for U.S. Appl. No. 08/754,681, filed Nov. 21, 1996 (Lizardi et al.).
Supplemental Response filed Apr. 12, 1999 for U.S. Appl. No. 08/754,681, filed Nov. 21, 1996 (Lizardi et al.).
Response after Non-Final Action filed Apr. 1, 1999 for U.S. Appl. No. 08/754,681, filed Nov. 21, 1996 (Lizardi et al.).
Non-Final Rejection issued Oct. 1, 1998 for U.S. Appl. No. 08/754,681, filed Nov. 21, 1996 (Lizardi et al.).
Response after Non-Final Action filed Jul. 6, 1998 for U.S. Appl. No. 08/754,681, filed Nov. 21, 1996 (Lizardi et al.).
Non-Final Rejection issued Jan. 6, 1998 for U.S. Appl. No. 08/754,681, filed Nov. 21, 1996 (Lizardi et al.).
Response after Non-Final Action filed Oct. 21, 1997 for U.S. Appl. No. 08/754,681, filed Nov. 21, 1996 (Lizardi et al.).
Restriction Requirement issued Jun. 17, 1997 for U.S. Appl. No. 08/754,681, filed Nov. 21, 1996 (Lizardi et al.).
Issue Notification issued Nov. 21, 2001 for U.S. Appl. No. 09/602,428, filed Jun. 23, 2000 (Lizardi et al.).
Notice of Allowance issued Jun. 28, 2001 for U.S. Appl. No. 09/602,428, filed Jun. 23, 2000 (Lizardi et al.).
Response after Non-Final Action filed Apr. 9, 2001 for U.S. Appl. No. 09/602,428, filed Jun. 23, 2000 (Lizardi et al.).
Non-Final Rejection issued Nov. 22, 2000 for U.S. Appl. No. 09/602,428, filed Jun. 23, 2000 (Lizardi et al.).
Preliminary Amendment filed Jun. 23, 2000 for U.S. Appl. No. 09/602,428, filed Jun. 23, 2000 (Lizardi et al.).
Issue Notification issued Sep. 25, 2003 for U.S. Appl. No. 09/841,513, filed Apr. 24, 2001 (Lizardi).
Notice of Allowance issued Jan. 16, 2003 for U.S. Appl. No. 09/841,513, filed Apr. 24, 2001 (Lizardi).
Response after Non-Final Action filed Oct. 18, 2002 for U.S. Appl. No. 09/841,513, filed Apr. 24, 2001 (Lizardi).
Non-Final Rejection issued Apr. 30, 2002 for U.S. Appl. No. 09/841,513, filed Apr. 24, 2001 (Lizardi).
Preliminary Amendment filed Apr. 24, 2001 for U.S. Appl. No. 09/841,513, filed Apr. 24, 2001 (Lizardi).
Notice of Abandonment issued Apr. 5, 2006 for U.S. Appl. No. 10/413,041, filed Apr. 10, 2003 (Lizardi et al.).
Restriction Requirement issued Sep. 22, 2005 for U.S. Appl. No. 10/413,041, filed Apr. 10, 2003 (Lizard et al.).
Decision on Petition issued Jul. 3, 2003 for U.S. Appl. No. 10/413,041, filed Apr. 10, 2003 (Lizard et al.).
Petition to Correct Filing Date filed May 8, 2003 for U.S. Appl. No. 10/413,041, filed Apr. 10, 2003 (Lizard et al.).
Preliminary Amendment filed Apr. 10, 2003 for U.S. Appl. No. 10/413,041, filed Apr. 10, 2003 (Lizardi et al.).
Issue Notification issued Jun. 10, 2009 for U.S. Appl. No. 10/072,666, filed Feb. 8, 2002 (Kumar et al.).
Notice of Allowance issued Jan. 27, 2009 for U.S. Appl. No. 10/072,666, filed Feb. 8, 2002 (Kumar et al.).
Notice of Allowance issued Sep. 26, 2008 for U.S. Appl. No. 10/072,666, filed Feb. 8, 2002 (Kumar et al.).
Amendment after Final Rejection filed Sep. 10, 2008 for U.S. Appl. No. 10/072,666, filed Feb. 8, 2002 (Kumar et al.).
Final Rejection issued Jul. 15, 2008 for U.S. Appl. No. 10/072,666, filed Feb. 8, 2002 (Kumar et al.).
Response to Non-Final Action filed Apr. 30, 2008 for U.S. Appl. No. 10/072,666, filed Feb. 8, 2002 (Kumar et al.).
Non-Final Rejection issued Feb. 1, 2008 for U.S. Appl. No. 10/072,666, filed Feb. 8, 2002 (Kumar et al.).
Response after Non-Final Action filed Nov. 15, 2007 for U.S. Appl. No. 10/072,666, filed Feb. 8, 2002 (Kumar et al.).
Non-Final Rejection issued Jul. 9, 2007 for U.S. Appl. No. 10/072,666, filed Feb. 8, 2002 (Kumar et al.).
Response after Non-Final Action filed Apr. 24, 2007 for U.S. Appl. No. 10/072,666, filed Feb. 8, 2002 (Kumar et al.).
Response to Office Action filed Nov. 30, 2006 for U.S. Appl. No. 10/072,666, filed Feb. 8, 2002 (Kumar et al.).
Advisory Action issued Nov. 8, 2006 for U.S. Appl. No. 10/072,666, filed Feb. 8, 2002 (Kumar et al.).
Amendment after Final Rejection filed Oct. 20, 2006 for U.S. Appl. No. 10/072,666, filed Feb. 8, 2002 (Kumar et al.).
Final Rejection issued Jul. 31, 2006 for U.S. Appl. No. 10/072,666, filed Feb. 8, 2002 (Kumar et al.).
Response after Non-Final Action issued May 12, 2006 for U.S. Appl. No. 10/072,666, filed Feb. 8, 2002 (Kumar et al.).
Non-Final Rejection issued Jan. 27, 2006 for U.S. Appl. No. 10/072,666, filed Feb. 8, 2002 (Kumar et al.).
Response to Office Action issued Nov. 11, 2005 for U.S. Appl. No. 10/072,666, filed Feb. 8, 2002 (Kumar et al.).
Final Rejection issued Jul. 11, 2005 for U.S. Appl. No. 10/072,666, filed Feb. 8, 2002 (Kumar et al.).
Response after Non-Final Action filed Apr. 25, 2005 for U.S. Appl. No. 10/072,666, filed Feb. 8, 2002 (Kumar et al.).
Non-Final Rejection issued Feb. 10, 2005 for U.S. Appl. No. 10/072,666, filed Feb. 8, 2002 (Kumar et al.).
Response after Non-Final Action filed Aug. 4, 2004 for U.S. Appl. No. 10/072,666, filed Feb. 8, 2002 (Kumar et al.).
Non-Final Rejection issued Apr. 19, 2004 for U.S. Appl. No. 10/072,666, filed Feb. 8, 2002 (Kumar et al.).
Response after Non-Final Action filed Nov. 10, 2003 for U.S. Appl. No. 10/072,666, filed Feb. 8, 2002 (Kumar et al.).
Non-Final Rejection issued May 8, 2003 for U.S. Appl. No. 10/072,666, filed Feb. 8, 2002 (Kumar et al.).
Issue Notification issued Nov. 25, 2004 for U.S. Appl. No. 09/460,078, filed Dec. 14, 1999 (Hafner et al.).
Notice of Allowance issued Jul. 14, 2004 for U.S. Appl. No. 09/460,078, filed Dec. 14, 1999 (Hafner et al.).
Amendment after Final Rejection filed Jun. 14, 2004 for U.S. Appl. No. 09/460,078, filed Dec. 14, 1999 (Hafner et al.).
Examiner Interview Summary issued May 25, 2004 for U.S. Appl. No. 09/460,078, filed Dec. 14, 1999 (Hafner et al.).
Final Rejection issued Feb. 13, 2004 for U.S. Appl. No. 09/460,078, filed Dec. 14, 1999 (Hafner et al.).
Response after Non-Final Action filed Nov. 19, 2003 for U.S. Appl. No. 09/460,078, filed Dec. 14, 1999 (Hafner et al.).
Non-Final Rejection issued May 19, 2003 for U.S. Appl. No. 09/460,078, filed Dec. 14, 1999 (Hafner et al.).
Response after Non-Final Action filed Jan. 14, 2003 for U.S. Appl. No. 09/460,078, filed Dec. 14, 1999 (Hafner et al.).
Non-Final Rejection issued Sep. 4, 2002 for U.S. Appl. No. 09/460,078, filed Dec. 14, 1999 (Hafner et al.).
Amendment and Response filed Jun. 17, 2002 for U.S. Appl. No. 09/460,078, filed Dec. 14, 1999 (Hafner et al.).
Notice of Appeal filed Jan. 17, 2002 for U.S. Appl. No. 09/460,078, filed Dec. 14, 1999 (Hafner et al.).
Final Rejection issued Jul. 17, 2001 for U.S. Appl. No. 09/460,078, filed Dec. 14, 1999 (Hafner et al.).
Response after Non-Final Action filed May 21, 2001 for U.S. Appl. No. 09/460,078, filed Dec. 14, 1999 (Hafner et al.).

(56) References Cited

OTHER PUBLICATIONS

Non-Final Rejection issued Nov. 20, 2000 for U.S. Appl. No. 09/460,078, filed Dec. 14, 1999 (Hafner et al.).
Response to Election / Restriction filed Mar. 29, 2000 for U.S. Appl. No. 09/460,078, filed Dec. 14, 1999 (Hafner et al.).
Restriction Requirement issued Jun. 30, 2000 for U.S. Appl. No. 09/460,078, filed Dec. 14, 1999 (Hafner et al.).
Issue Notification issued Mar. 26, 2008 for U.S. Appl. No. 10/917,580, filed Aug. 13, 2004 (Hafner et al.).
Notice of Allowance issued Nov. 30, 2007 for U.S. Appl. No. 10/917,580, filed Aug. 13, 2004 (Hafner et al.).
Response after Non-Final Action filed Oct. 1, 2007 for U.S. Appl. No. 10/917,580, filed Aug. 13, 2004 (Hafner et al.).
Non-Final Rejection issued Jun. 25, 2007 for U.S. Appl. No. 10/917,580, filed Aug. 13, 2004 (Hafner et al.).
Response to Election / Restriction filed May 10, 2007 for U.S. Appl. No. 10/917,580, filed Aug. 13, 2004 (Hafner et al.).
Restriction Requirement issued Jan. 11, 2007 for U.S. Appl. No. 10/917,580, filed Aug. 13, 2004 (Hafner et al.).
Second Preliminary Amendment filed Nov. 15, 2004 for U.S. Appl. No. 10/917,580, filed Aug. 13, 2004 (Hafner et al.).
Preliminary Amendment filed Aug. 13, 2004 for U.S. Appl. No. 10/917,580, filed Aug. 13, 2004 (Hafner et al.).
Notice of Abandonment issued Nov. 13, 2008 for U.S. Appl. No. 10/325,665, filed Dec. 19, 2002 (Alsmadi et al.).
Non-Final Rejection issued Apr. 17, 2008 for U.S. Appl. No. 10/325,665, filed Dec. 19, 2002 (Alsmadi et al.).
Non-Final Rejection issued Oct. 25, 2007 for U.S. Appl. No. 10/325,665, filed Dec. 19, 2002 (Alsmadi et al.).
Amendment/Argument with Notice of Appeal filed Sep. 25, 2007 for U.S. Appl. No. 10/325,665, filed Dec. 19, 2002 (Alsmadi et al.).
Final Rejection issued Mar. 26, 2007 for U.S. Appl. No. 10/325,665, filed Dec. 19, 2002 (Alsmadi et al.).
Response after Non-Final Action filed Dec. 22, 2006 for U.S. Appl. No. 10/325,665, filed Dec. 19, 2002 (Alsmadi et al.).
Non-Final Rejection issued Aug. 3, 2006 for U.S. Appl. No. 10/325,665, filed Dec. 19, 2002 (Alsmadi et al.).
Response after Non-Final Action filed Apr. 13, 2006 for U.S. Appl. No. 10/325,665, filed Dec. 19, 2002 (Alsmadi et al.).
Non-Final Rejection issued Dec. 30, 2005 for U.S. Appl. No. 10/325,665, filed Dec. 19, 2002 (Alsmadi et al.).
Response to Election / Restriction filed Sep. 21, 2005 for U.S. Appl. No. 10/325,665, filed Dec. 19, 2002 (Alsmadi et al.).
Restriction Requirement issued Apr. 21, 2005 for U.S. Appl. No. 10/325,665, filed Dec. 19, 2002 (Alsmadi et al.).
Issue Notification issued Nov. 30, 2005 for U.S. Appl. No. 10/335,573, filed Dec. 31, 2002 (Kumar et al.).
Notice of Allowance issued Mar. 29, 2005 for U.S. Appl. No. 10/335,573, filed Dec. 31, 2002 (Kumar et al.).
Response after Non-Final Action filed Dec. 1, 2004 for U.S. Appl. No. 10/335,573, filed Dec. 31, 2002 (Kumar et al.).
Non-Final Rejection issued Jul. 29, 2004 for U.S. Appl. No. 10/335,573, filed Dec. 31, 2002 (Kumar et al.).
Notice of Abandonment issued May 12, 2008 for U.S. Appl. No. 11/201,339, filed Aug. 10, 2005 (Kumar et al.).
Restriction Requirement issued Sep. 25, 2007 for U.S. Appl. No. 11/201,339, filed Aug. 10, 2005 (Kumar et al.).
Preliminary Amendment filed Aug. 10, 2005 for U.S. Appl. No. 11/201,339, filed Aug. 10, 2005 (Kumar et al.).
Response to Final Rejection filed May 26, 2010 for U.S. Appl. No. 10/327,602, filed Dec. 20, 2002 (Lasken).
Notice of Appeal issued Apr. 27, 2010 for U.S. Appl. No. 10/327,602, filed Dec. 20, 2002 (Lasken).
Interview Summary issued Dec. 24, 2009 for U.S. Appl. No. 10/327,602, filed Dec. 20, 2002 (Lasken).
Supplemental Non-Final Rejection issued Oct. 27, 2009 for U.S. Appl. No. 10/327,602, filed Dec. 20, 2002 (Lasken).
Non-Final Rejection issued Oct. 15, 2009 for U.S. Appl. No. 10/327,602, filed Dec. 20, 2002 (Lasken).
Amendment and Response to Final Office Action filed Sep. 10, 2009 for U.S. Appl. No. 10/327,602, filed Dec. 20, 2002 (Lasken).
Final Rejection issued Jun. 10, 2009 for U.S. Appl. No. 10/327,602, filed Dec. 20, 2002 (Lasken).
Amendment and Response filed Mar. 31, 2009 for U.S. Appl. No. 10/327,602, filed Dec. 20, 2002 (Lasken).
Non-Final Rejection issued Jan. 6, 2009 for U.S. Appl. No. 10/327,602, filed Dec. 20, 2002 (Lasken).
Response after Final Rejection filed Dec. 11, 2008 for U.S. Appl. No. 10/327,602, filed Dec. 20, 2002 (Lasken).
Advisory Action issued Nov. 26, 2008 for U.S. Appl. No. 10/327,602, filed Dec. 20, 2002 (Lasken).
Amendment after Final Rejection filed Nov. 10, 2008 for U.S. Appl. No. 10/327,602, filed Dec. 20, 2002 (Lasken).
Final Rejection issued Aug. 12, 2008 for U.S. Appl. No. 10/327,602, filed Dec. 20, 2002 (Lasken).
Response after Final Rejection filed May 15, 2008 for U.S. Appl. No. 10/327,602, filed Dec. 20, 2002 (Lasken).
Non-Final Rejection issued Jan. 17, 2008 for U.S. Appl. No. 10/327,602, filed Dec. 20, 2002 (Lasken).
Amendment after Final Rejection filed Oct. 25, 2007 for U.S. Appl. No. 10/327,602, filed Dec. 20, 2002 (Lasken).
Advisory Action issued Oct. 16, 2007 for U.S. Appl. No. 10/327,602, filed Dec. 20, 2002 (Lasken).
Amendment after Final filed Oct. 1, 2007 for U.S. Appl. No. 10/327,602, filed Dec. 20, 2002 (Lasken).
Final Rejection issued May 23, 2007 for U.S. Appl. No. 10/327,602, filed Dec. 20, 2002 (Lasken).
Response after Non-Final Rejection filed Mar. 15, 2007 for U.S. Appl. No. 10/327,602, filed Dec. 20, 2002 (Lasken).
Non-Final Rejection issued Nov. 14, 2006 for U.S. Appl. No. 10/327,602, filed Dec. 20, 2002 (Lasken).
Response after Non-Final Rejection filed Aug. 24, 2006 for U.S. Appl. No. 10/327,602, filed Dec. 20, 2002 (Lasken).
Restriction Requirement issued Jun. 26, 2006 for U.S. Appl. No. 10/327,602, filed Dec. 20, 2002 (Lasken).
Notice of Allowance issued Jun. 13, 2011 for U.S. Appl. No. 10/405,822, filed Mar. 31, 2003 (Abarzua et al.).
Notice of Allowance issued Feb. 4, 2011 for U.S. Appl. No. 10/405,822, filed Mar. 31, 2003 (Abarzua et al.).
Examiner Interview Summary issued Jan. 25, 2011 for U.S. Appl. No. 10/405,822, filed Mar. 31, 2003 (Abarzua et al.).
Response to Final Rejection filed Jan. 13, 2011 for U.S. Appl. No. 10/405,822, filed Mar. 31, 2003 (Abarzua et al.).
Final Rejection issued Dec. 8, 2010 for U.S. Appl. No. 10/405,822, filed Mar. 31, 2003 (Abarzua et al.).
Response to Final Rejection filed Sep. 3, 2010 for U.S. Appl. No. 10/405,822, filed Mar. 31, 2003 (Abarzua et al.).
Examiner Interview Summary issued Aug. 18, 2010 for U.S. Appl. No. 10/405,822, filed Mar. 31, 2003 (Abarzua et al.).
Final Rejection issued Mar. 4, 2010 for U.S. Appl. No. 10/405,822, filed Mar. 31, 2003 (Abarzua et al.).
Response after Non-Final Rejection filed Nov. 25, 2009 for U.S. Appl. No. 10/405,822, filed Mar. 31, 2003 (Abarzua et al.).
Non-Final Rejection issued Jun. 1, 2009 for U.S. Appl. No. 10/405,822, filed Mar. 31, 2003 (Abarzua et al.).
Response after Final Rejection filed Mar. 11, 2009 for U.S. Appl. No. 10/405,822, filed Mar. 31, 2003 (Abarzua et al.).
Advisory Action issued Feb. 27, 2009 for U.S. Appl. No. 10/405,822, filed Mar. 31, 2003 (Abarzua et al.).
Response after Final Rejection filed Feb. 11, 2009 for U.S. Appl. No. 10/405,822, filed Mar. 31, 2003 (Abarzua et al.).
Examiner Interview Summary issued Dec. 15, 2008 for U.S. Appl. No. 10/405,822, filed Mar. 31, 2003 (Abarzua et al.).
Final Rejection issued Sep. 11, 2008 for U.S. Appl. No. 10/405,822, filed Mar. 31, 2003 (Abarzua et al.).
Response to Non-Final Rejection filed May 30, 2008 for U.S. Appl. No. 10/405,822, filed Mar. 31, 2003 (Abarzua et al.).
Non-Final Rejection issued Mar. 28, 2008 for U.S. Appl. No. 10/405,822, filed Mar. 31, 2003 (Abarzua et al.).
Response after Final Rejection filed Dec. 28, 2007 for U.S. Appl. No. 10/405,822, filed Mar. 31, 2003 (Abarzua et al.).

(56) References Cited

OTHER PUBLICATIONS

Advisory Action issued Nov. 9, 2007 for U.S. Appl. No. 10/405,822, filed Mar. 31, 2003 (Abarzua et al.).
Response after Final Rejection with Notice of Appeal filed Oct. 30, 2007 for U.S. Appl. No. 10/405,822, filed Mar. 31, 2003 (Abarzua et al.).
Final Rejection issued Apr. 30, 2007 for U.S. Appl. No. 10/405,822, filed Mar. 31, 2003 (Abarzua et al.).
Response after Non-Final Action filed Jan. 23, 2007 for U.S. Appl. No. 10/405,822, filed Mar. 31, 2003 (Abarzua et al.).
Non-Final Rejection issued Aug. 2, 2006 for U.S. Appl. No. 10/405,822, filed Mar. 31, 2003 (Abarzua et al.).
Response to Election / Restriction filed May 31, 2006 for U.S. Appl. No. 10/405,822, filed Mar. 31, 2003 (Abarzua et al.).
Restriction Requirement issued Dec. 13, 2005 for U.S. Appl. No. 10/405,822, filed Mar. 31, 2003 (Abarzua et al.).
Notice of Abandonment issued Jun. 5, 2009 for U.S. Appl. No. 10/454,946, filed Jun. 4, 2003 (Feaver et al.).
Non-Final Rejection issued Nov. 26, 2008 for U.S. Appl. No. 10/454,946, filed Jun. 4, 2003 (Feaver et al.).
Amendment and Response filed Aug. 29, 2008 for U.S. Appl. No. 10/454,946, filed Jun. 4, 2003 (Feaver et al.).
Examiner Interview Summary issued Aug. 8, 2008 for U.S. Appl. No. 10/454,946, filed Jun. 4, 2003 (Feaver et al.).
Advisory Action issued Mar. 25, 2008 for U.S. Appl. No. 10/454,946, filed Jun. 4, 2003 (Feaver et al.).
Notice of Appeal filed Mar. 17, 2008 for U.S. Appl. No. 10/454,946, filed Jun. 4, 2003 (Feaver et al.).
Amendment after Final filed Feb. 8, 2008 for U.S. Appl. No. 10/454,946, filed Jun. 4, 2003 (Feaver et al.).
Examiner Interview Summary issued Jan. 29, 2008 for U.S. Appl. No. 10/454,946, filed Jun. 4, 2003 (Feaver et al.).
Final Rejection issued Sep. 18, 2007 for U.S. Appl. No. 10/454,946, filed Jun. 4, 2003 (Feaver et al.).
Response after Non-Final Action filed Jul. 5, 2007 for U.S. Appl. No. 10/454,946, filed Jun. 4, 2003 (Feaver et al.).
Non-Final Rejection issued Feb. 9, 2007 for U.S. Appl. No. 10/454,946, filed Jun. 4, 2003 (Feaver et al.).
Response after Non-Final Action filed Nov. 16, 2006 for U.S. Appl. No. 10/454,946, filed Jun. 4, 2003 (Feaver et al.).
Non-Final Rejection issued Jul. 26, 2006 for U.S. Appl. No. 10/454,946, filed Jun. 4, 2003 (Feaver et al.).
Response to Election / Restriction filed May 3, 2006 for U.S. Appl. No. 10/454,946, filed Jun. 4, 2003 (Feaver et al.).
Restriction Requirement issued Feb. 6, 2006 for U.S. Appl. No. 10/454,946, filed Jun. 4, 2003 (Feaver et al.).
Issue Notification issued May 18, 2011 for U.S. Appl. No. 10/456,056, filed Jun. 6, 2003 (Kumar et al.).
Notice of Allowance issued Apr. 1, 2011 for U.S. Appl. No. 10/456,056, filed Jun. 6, 2003 (Kumar et al.).
Notice of Allowance issued Jan. 25, 2011 for U.S. Appl. No. 10/456,056, filed Jun. 6, 2003 (Kumar et al.).
Response after Non-Final Action filed Dec. 13, 2010 for U.S. Appl. No. 10/456,056, filed Jun. 6, 2003 (Kumar et al.).
Notice of Non-Compliant Amendment issued Dec. 7, 2010 for U.S. Appl. No. 10/456,056, filed Jun. 6, 2003 (Kumar et al.).
Response to Final Rejection filed Nov. 23, 2010 for U.S. Appl. No. 10/456,056, filed Jun. 6, 2003 (Kumar et al.).
Non-Final Rejection issued Jun. 24, 2010 for U.S. Appl. No. 10/456,056, filed Jun. 6, 2003 (Kumar et al.).
Response after Final Rejection filed Feb. 4, 2010 for U.S. Appl. No. 10/456,056, filed Jun. 6, 2003 (Kumar et al.).
Examiner Interview Summary issued Nov. 17, 2009 for U.S. Appl. No. 10/456,056, filed Jun. 6, 2003 (Kumar et al.).
Final Rejection issued Aug. 4, 2009 for U.S. Appl. No. 10/456,056, filed Jun. 6, 2003 (Kumar et al.).
Response to Final Rejection filed May 27, 2009 for U.S. Appl. No. 10/456,056, filed Jun. 6, 2003 (Kumar et al.).
Final Rejection issued Feb. 12, 2009 for U.S. Appl. No. 10/456,056, filed Jun. 6, 2003 (Kumar et al.).
Response after Non-Final Action filed Oct. 23, 2008 for U.S. Appl. No. 10/456,056, filed Jun. 6, 2003 (Kumar et al.).
Non-Final Rejection issued Aug. 8, 2008 for U.S. Appl. No. 10/456,056, filed Jun. 6, 2003 (Kumar et al.).
Response to Final Rejection filed Apr. 7, 2008 for U.S. Appl. No. 10/456,056, filed Jun. 6, 2003 (Kumar et al.).
Response to Final Rejection filed Mar. 7, 2008 for U.S. Appl. No. 10/456,056, filed Jun. 6, 2003 (Kumar et al.).
Notice of Appeal filed Sep. 6, 2007 for U.S. Appl. No. 10/456,056, filed Jun. 6, 2003 (Kumar et al.).
Examiner Interview Summary issued Apr. 17, 2007 for U.S. Appl. No. 10/456,056, filed Jun. 6, 2003 (Kumar et al.).
Final Rejection issued Mar. 6, 2007 for U.S. Appl. No. 10/456,056, filed Jun. 6, 2003 (Kumar et al.).
Response after Non-Final Action filed Dec. 7, 2006 for U.S. Appl. No. 10/456,056, filed Jun. 6, 2003 (Kumar et al.).
Non-Final Rejection issued Aug. 2, 2006 for U.S. Appl. No. 10/456,056, filed Jun. 6, 2003 (Kumar et al.).
Response to Election / Restriction filed May 12, 2006 for U.S. Appl. No. 10/456,056, filed Jun. 6, 2003 (Kumar et al.).
Requirement for Restriction / Election issued Feb. 23, 2006 for U.S. Appl. No. 10/456,056, filed Jun. 6, 2003 (Kumar et al.).
Issue Notification issued Nov. 9, 2001 for U.S. Appl. No. 09/605,192, filed Jun. 28, 2000 (Lasken et al.).
Response to 312 Amendment issued Aug. 17, 2001 for U.S. Appl. No. 09/605,192, filed Jun. 28, 2000 (Lasken et al.).
Amendment after Notice of Allowance filed Jul. 31, 2001 for U.S. Appl. No. 09/605,192, filed Jun. 28, 2000 (Lasken et al.).
Notice of Allowance issued May 11, 2001 for U.S. Appl. No. 09/605,192, filed Jun. 28, 2000 (Lasken et al.).
Response after Non-Final Action filed Mar. 16, 2001 for U.S. Appl. No. 09/605,192, filed Jun. 28, 2000 (Lasken et al.).
Non-Final Rejection issued Nov. 16, 2000 for U.S. Appl. No. 09/605,192, filed Jun. 28, 2000 (Lasken et al.).
Notice of Abandonment issued May 27, 2009 for U.S. Appl. No. 09/920,571, filed Jul. 31, 2001 (Lasken et al.).
Final Rejection issued Sep. 15, 2008 for U.S. Appl. No. 09/920,571, filed Jul. 31, 2001 (Lasken et al.).
Response after Non-Final Action filed Jul. 2, 2008 for U.S. Appl. No. 09/920,571, filed Jul. 31, 2001 (Lasken et al.).
Non-Final Rejection issued Mar. 17, 2008 for U.S. Appl. No. 09/920,571, filed Jul. 31, 2001 (Lasken et al.).
Response after Non-Final Action filed Dec. 27, 2007 for U.S. Appl. No. 09/920,571, filed Jul. 31, 2001 (Lasken et al.).
Non-Final Rejection issued Jun. 28, 2007 for U.S. Appl. No. 09/920,571, filed Jul. 31, 2001 (Lasken et al.).
Response to Election/Restriction filed May 7, 2007 for U.S. Appl. No. 09/920,571, filed Jul. 31, 2001 (Lasken et al.).
Restriction Requirement issued Mar. 6, 2007 for U.S. Appl. No. 09/920,571, filed Jul. 31, 2001 (Lasken et al.).
Response to Final Rejection filed Dec. 7, 2006 for U.S. Appl. No. 09/920,571, filed Jul. 31, 2001 (Lasken et al.).
Final Rejection issued Jun. 12, 2006 for U.S. Appl. No. 09/920,571, filed Jul. 31, 2001 (Lasken et al.).
Response after Non-Final Action filed Mar. 27, 2006 for U.S. Appl. No. 09/920,571, filed Jul. 31, 2001 (Lasken et al.).
Non-Final Rejection issued Nov. 1, 2005 for U.S. Appl. No. 09/920,571, filed Jul. 31, 2001 (Lasken et al.).
Response to Final Rejection filed Aug. 15, 2005 for U.S. Appl. No. 09/920,571, filed Jul. 31, 2001 (Lasken et al.).
Advisory Action issued Jun. 20, 2005 for U.S. Appl. No. 09/920,571, filed Jul. 31, 2001 (Lasken et al.).
Response to Final Rejection with Notice of Appeal filed May 31, 2005 for U.S. Appl. No. 09/920,571, filed Jul. 31, 2001 (Lasken et al.).
Final Rejection issued Feb. 14, 2005 for U.S. Appl. No. 09/920,571, filed Jul. 31, 2001 (Lasken et al.).
Response after Non-Final Action filed Nov. 22, 2004 for U.S. Appl. No. 09/920,571, filed Jul. 31, 2001 (Lasken et al.).
Non-Final Rejection issued Aug. 25, 2004 for U.S. Appl. No. 09/920,571, filed Jul. 31, 2001 (Lasken et al.).
Advisory Action issued Jun. 23, 2004 for U.S. Appl. No. 09/920,571, filed Jul. 31, 2001 (Lasken et al.).

(56) References Cited

OTHER PUBLICATIONS

Response to Final Rejection with Notice of Appeal filed May 25, 2004 for U.S. Appl. No. 09/920,571, filed Jul. 31, 2001 (Lasken et al.).
Final Rejection issued Feb. 18, 2004 for U.S. Appl. No. 09/920,571, filed Jul. 31, 2001 (Lasken et al.).
Response after Non-Final Action filed Oct. 15, 2003 for U.S. Appl. No. 09/920,571, filed Jul. 31, 2001 (Lasken et al.).
Miscellaneous Communication issued Oct. 7, 2003 for U.S. Appl. No. 09/920,571, filed Jul. 31, 2001 (Lasken et al.).
Response after Non-Final Action filed Jun. 12, 2003 for U.S. Appl. No. 09/920,571, filed Jul. 31, 2001 (Lasken et al.).
Non-Final Rejection issued Dec. 20, 2002 for U.S. Appl. No. 09/920,571, filed Jul. 31, 2001 (Lasken et al.).
Supplemental Response filed Sep. 27, 2002 for U.S. Appl. No. 09/920,571, filed Jul. 31, 2001 (Lasken et al.).
Supplemental Response filed Sep. 16, 2002 for U.S. Appl. No. 09/920,571, filed Jul. 31, 2001 (Lasken et al.).
Notice of Informal or Non-Responsive Amendment issued Aug. 27, 2002 for U.S. Appl. No. 09/920,571, filed Jul. 31, 2001 (Lasken et al.).
Response after Non-Final Action filed Jun. 12, 2002 for U.S. Appl. No. 09/920,571, filed Jul. 31, 2001 (Lasken et al.).
Non-Final Rejection issued Dec. 12, 2001 for U.S. Appl. No. 09/920,571, filed Jul. 31, 2001 (Lasken et al.).
Preliminary Amendment filed Aug. 1, 2001 for U.S. Appl. No. 09/920,571, filed Jul. 31, 2001 (Lasken et al.).
Request for Certificate of Correction filed Aug. 27, 2002 for U.S. Appl. No. 09/577,444, filed May 24, 2000 (Kingsmore et al.).
Issue Notification issued Aug. 30, 2001 for U.S. Appl. No. 09/577,444, filed May 24, 2000 (Kingsmore et al.).
Notice of Allowance issued Mar. 29, 2001 for U.S. Appl. No. 09/577,444, filed May 24, 2000 (Kingsmore et al.)
Decision regarding Certificate of Correction issued Mar. 22, 2004 for U.S. Appl. No. 09/897,665, filed Jul. 2, 2001 (Kingsmore et al.).
Request for Certificate of Correction filed Feb. 25, 2004 for U.S. Appl. No. 09/897,665, filed Jul. 2, 2001 (Kingsmore et al.).
Issue Notification issued Dec. 11, 2003 for U.S. Appl. No. 09/897,665, filed Jul. 2, 2001 (Kingsmore et al.).
Notice of Allowance issued Jul. 30, 2003 for U.S. Appl. No. 09/897,665, filed Jul. 2, 2001 (Kingsmore et al.).
Notice of Appeal filed May 27, 2003 for U.S. Appl. No. 09/897,665, filed Jul. 2, 2001 (Kingsmore et al.).
Response to Final Rejection and Terminal Disclaimer filed May 27, 2003 for U.S. Appl. No. 09/897,665, filed Jul. 2, 2001 (Kingsmore et al.).
Final Rejection issued Feb. 25, 2003 for U.S. Appl. No. 09/897,665, filed Jul. 2, 2001 (Kingsmore et al.).
Response after Non-Final Action filed Dec. 4, 2002 for U.S. Appl. No. 09/897,665, filed Jul. 2, 2001 (Kingsmore et al.).
Non-Final Rejection issued Jul. 19, 2002 for U.S. Appl. No. 09/897,665, filed Jul. 2, 2001 (Kingsmore et al.).
Preliminary Amendment filed Jul. 2, 2001 for U.S. Appl. No. 09/897,665, filed Jul. 2, 2001 (Kingsmore et al.).
Issue Notification issued Oct. 2, 2003 for U.S. Appl. No. 09/910,372, filed Jul. 20, 2001 (Bandaru et al.).
Notice of Allowance issued Apr. 8, 2003 for U.S. Appl. No. 09/910,372, filed Jul. 20, 2001 (Bandaru et al.).
Supplemental Response filed Mar. 20, 2003 for U.S. Appl. No. 09/910,372, filed Jul. 20, 2001 (Bandaru et al.).
Amendment and Response filed Jan. 17, 2003 for U.S. Appl. No. 09/910,372, filed Jul. 20, 2001 (Bandaru et al.).
Non-Final Rejection issued Nov. 13, 2002 for U.S. Appl. No. 09/910,372, filed Jul. 20, 2001 (Bandaru et al.).
Response to Election / Restriction filed Sep. 27, 2002 for U.S. Appl. No. 09/910,372, filed Jul. 20, 2001 (Bandaru et al.).
Restriction Requirement issued Sep. 17, 2002 for U.S. Appl. No. 09/910,372, filed Jul. 20, 2001 (Bandaru et al.).
Issue Notification issued Oct. 14, 2004 for U.S. Appl. No. 10/465,759, filed Jun. 19, 2003 (Bandaru et al.).
Notice of Allowance issued May 4, 2004 for U.S. Appl. No. 10/465,759, filed Jun. 19, 2003 (Bandaru et al.).
Response after Non-Final Action filed Apr. 12, 2004 for U.S. Appl. No. 10/465,759, filed Jun. 19, 2003 (Bandaru et al.).
Non-Final Rejection issued Jan. 8, 2004 for U.S. Appl. No. 10/465,759, filed Jun. 19, 2003 (Bandaru et al.).
Issue Notification issued Dec. 5, 2002 for U.S. Appl. No. 09/723,685, filed Nov. 28, 2000 (Abarzua).
Notice of Allowance issued Apr. 17, 2002 for U.S. Appl. No. 09/723,685, filed Nov. 28, 2000 (Abarzua).
Response after Non-Final Action filed Dec. 10, 2001 for U.S. Appl. No. 09/723,685, filed Nov. 28, 2000 (Abarzua).
Non-Final Rejection issued Aug. 28, 2001 for U.S. Appl. No. 09/723,685, filed Nov. 28, 2000 (Abarzua).
Response after Non-Final Action filed Jun. 13, 2001 for U.S. Appl. No. 09/723,685, filed Nov. 28, 2000 (Abarzua).
Non-Final Rejection issued Mar. 13, 2001 for U.S. Appl. No. 09/723,685, filed Nov. 28, 2000 (Abarzua).
Issue Notification issued Apr. 19, 2006 for U.S. Appl. No. 10/196,539, filed Jul. 16, 2002 (Abarzua).
Notice of Allowance issued Nov. 15, 2005 for U.S. Appl. No. 10/196,539, filed Jul. 16, 2002 (Abarzua).
Response after Non-Final Action with Terminal Disclaimer filed Aug. 10, 2005 for U.S. Appl. No. 10/196,539, filed Jul. 16, 2002 (Abarzua).
Non-Final Rejection issued Mar. 10, 2005 for U.S. Appl. No. 10/196,539, filed Jul. 16, 2002 (Abarzua).
Notice of Abandonment issued Oct. 15, 2008 for U.S. Appl. No. 11/429,549, filed May 5, 2006 (Abarzua).
Non-Final Rejection issued Mar. 26, 2008 for U.S. Appl. No. 11/429,549, filed May 5, 2006 (Abarzua).
Preliminary Amendment filed May 5, 2006 for U.S. Appl. No. 11/429,549, filed May 5, 2006 (Abarzua).
Issue Notification issued Jul. 29, 2004 for U.S. Appl. No. 09/827,289, filed Apr. 5, 2001 (Abarzua).
Notice of Allowance issued Apr. 1, 2004 for U.S. Appl. No. 09/827,289, filed Apr. 5, 2001 (Abarzua).
Supplemental Response filed Feb. 12, 2004 for U.S. Appl. No. 09/827,289, filed Apr. 5, 2001 (Abarzua).
Notice of Informal or Non-Responsive Amendment issued Feb. 2, 2004 for U.S. Appl. No. 09/827,289, filed Apr. 5, 2001 (Abarzua).
Response after Non-Final Action filed Jan. 19, 2004 for U.S. Appl. No. 09/827,289, filed Apr. 5, 2001 (Abarzua).
Non-Final Rejection issued Sep. 29, 2003 for U.S. Appl. No. 09/827,289, filed Apr. 5, 2001 (Abarzua).
Response after Final Rejection filed Aug. 6, 2003 for U.S. Appl. No. 09/827,289, filed Apr. 5, 2001 (Abarzua).
Advisory Action issued Jun. 2, 2003 for U.S. Appl. No. 09/827,289, filed Apr. 5, 2001 (Abarzua).
Amendment after Final Rejection filed May 6, 2003 for U.S. Appl. No. 09/827,289, filed Apr. 5, 2001 (Abarzua).
Final Rejection issued Feb. 10, 2003 for U.S. Appl. No. 09/827,289, filed Apr. 5, 2001 (Abarzua).
Response after Non-Final Action filed Jan. 13, 2003 for U.S. Appl. No. 09/827,289, filed Apr. 5, 2001 (Abarzua).
Non-Final Rejection issued Jul. 29, 2002 for U.S. Appl. No. 09/827,289, filed Apr. 5, 2001 (Abarzua).
Response to Election / Restriction filed Jun. 19, 2002 for U.S. Appl. No. 09/827,289, filed Apr. 5, 2001 (Abarzua).
Restriction Requirement issued Jun. 11, 2002 for U.S. Appl. No. 09/827,289, filed Apr. 5, 2001 (Abarzua).
Notice of Abandonment issued Sep. 20, 2007 for U.S. Appl. No. 10/177,629, filed Jun. 19, 2002 (Wiltshire).
Final Rejection issued Aug. 21, 2006 for U.S. Appl. No. 10/177,629, filed Jun. 19, 2002 (Wiltshire).
Response after Non-Final Action & Terminal Disclaimer filed Jun. 9, 2006 for U.S. Appl. No. 10/177,629, filed Jun. 19, 2002 (Wiltshire).
Non-Final Rejection issued Jan. 10, 2006 for U.S. Appl. No. 10/177,629, filed Jun. 19, 2002 (Wiltshire).
Response to Notice of Non-Compliant Amendment filed Oct. 25, 2005 for U.S. Appl. No. 10/177,629, filed Jun. 19, 2002 (Wiltshire).

(56) References Cited

OTHER PUBLICATIONS

Notice of Informal or Non-Responsive Amendment issued Sep. 30, 2005 for U.S. Appl. No. 10/177,629, filed Jun. 19, 2002 (Wiltshire).
Response to Election / Restriction filed Sep. 16, 2005 for U.S. Appl. No. 10/177,629, filed Jun. 19, 2002 (Wiltshire).
Restriction Requirement issued Mar. 17, 2005 for U.S. Appl. No. 10/177,629, filed Jun. 19, 2002 (Wiltshire).
Issue Notification issued Feb. 9, 2005 for U.S. Appl. No. 09/931,736, filed Aug. 17, 2001 (Shao).
Notice of Allowance issued Nov. 18, 2004 for U.S. Appl. No. 09/931,736, filed Aug. 17, 2001 (Shao).
Appeal Brief filed Aug. 27, 2004 for U.S. Appl. No. 09/931,736, filed Aug. 17, 2001 (Shao).
Advisory Action issued May 4, 2004 for U.S. Appl. No. 09/931,736, filed Aug. 17, 2001 (Shao).
Response after Notice of Appeal filed Feb. 27, 2004 for U.S. Appl. No. 09/931,736, filed Aug. 17, 2001 (Shao).
Notice of Appeal filed Feb. 27, 2004 for U.S. Appl. No. 09/931,736, filed Aug. 17, 2001 (Shao).
Final Rejection issued Dec. 3, 2003 for U.S. Appl. No. 09/931,736, filed Aug. 17, 2001 (Shao).
Response after Non-Final Action filed Sep. 18, 2003 for U.S. Appl. No. 09/931,736, filed Aug. 17, 2001 (Shao).
Non-Final Rejection issued Jun. 30, 2003 for U.S. Appl. No. 09/931,736, filed Aug. 17, 2001 (Shao).
Response to Election / Restriction filed May 14, 2003 for U.S. Appl. No. 09/931,736, filed Aug. 17, 2001 (Shao).
Restriction Requirement issued Apr. 15, 2003 for U.S. Appl. No. 09/931,736, filed Aug. 17, 2001 (Shao).
Notice of Abandonment issued Aug. 8, 2006 for U.S. Appl. No. 10/931,015, filed Aug. 31, 2004 (Shao).
Final Rejection issued Jan. 9, 2006 for U.S. Appl. No. 10/931,015, filed Aug. 31, 2004 (Shao).
Response after Non-Final Action filed Aug. 24, 2005 for U.S. Appl. No. 10/931,015, filed Aug. 31, 2004 (Shao).
Non-Final Rejection issued May 24, 2005 for U.S. Appl. No. 10/931,015, filed Aug. 31, 2004 (Shao).
Response to Election / Restriction filed Feb. 24, 2005 for U.S. Appl. No. 10/931,015, filed Aug. 31, 2004 (Shao).
Restriction Requirement issued Jan. 24, 2005 for U.S. Appl. No. 10/931,015, filed Aug. 31, 2004 (Shao).
Preliminary Amendment filed Aug. 31, 2004 for U.S. Appl. No. 10/931,015, filed Aug. 31, 2004 (Shao).
Response after Final Action filed Aug. 8, 2011 for U.S. Appl. No. 11/744,553, filed May 4, 2007 (Korfhage et al.).
Final Rejection issued May 31, 2011 for U.S. Appl. No. 11/744,553, filed May 4, 2007 (Korfhage et al.).
Response after Non-Final Action filed Feb. 22, 2011 for U.S. Appl. No. 11/744,553, filed May 4, 2007 (Korfhage et al.).
Non-Final Rejection issued Sep. 14, 2010 for U.S. Appl. No. 11/744,553, filed May 4, 2007 (Korfhage et al.).
Response to Final Rejection filed Mar. 1, 2010 for U.S. Appl. No. 11/744,553, filed May 4, 2007 (Korfhage et al.).
Advisory Action issued Feb. 17, 2010 for U.S. Appl. No. 11/744,553, filed May 4, 2007 (Korfhage et al.).
Response after Non-Final Action filed Jan. 28, 2010 for U.S. Appl. No. 11/744,553, filed May 4, 2007 (Korfhage et al.).
Final Rejection issued Apr. 15, 2009 for U.S. Appl. No. 11/744,553, filed May 4, 2007 (Korfhage et al.).
Response after Non-Final Action filed Dec. 17, 2008 for U.S. Appl. No. 11/744,553, filed May 4, 2007 (Korfhage et al.).
Examiner Interview Summary issued Dec. 15, 2008 for U.S. Appl. No. 11/744,553, filed May 4, 2007 (Korfhage et al.).
Non-Final Rejection issued Aug. 19, 2008 for U.S. Appl. No. 11/744,553, filed May 4, 2007 (Korfhage et al.).
Response to Restriction Requirement filed Jun. 5, 2008 for U.S. Appl. No. 11/744,553, filed May 4, 2007 (Korfhage et al.).
Restriction Requirement issued May 16, 2008 for U.S. Appl. No. 11/744,553, filed May 4, 2007 (Korfhage et al.).
Non-Final Rejection issued on May 31, 2011 for U.S. Appl. No. 11/887,678, filed N/A (Korfhage).
Preliminary Amendment filed Apr. 3, 2009 for U.S. Appl. No. 11/887,678, filed N/A (Korfhage).
Preliminary Amendment filed Mar. 3, 2008 for U.S. Appl. No. 11/991,435, filed N/A (Korfhage).
Issue Notification issued Nov. 23, 1998 for U.S. Appl. No. 08/563,912, filed Nov. 21, 1995 (Lizardi)
Notice of Allowance issued Aug. 14, 1998 for U.S. Appl. No. 08/563,912, filed Nov. 21, 1995 (Lizardi).
Amendment/Argument filed Aug. 6, 1998 for U.S. Appl. No. 08/563,912, filed Nov. 21, 1995 (Lizardi).
Notice of Appeal filed Jun. 9, 1998 for U.S. Appl. No. 08/563,912, filed Nov. 21, 1995 (Lizardi).
Final Rejection issued Dec. 9, 1997 for U.S. Appl. No. 08/563,912, filed Nov. 21, 1995 (Lizardi).
Amendment and Response filed Aug. 28, 1997 for U.S. Appl. No. 08/563,912, filed Nov. 21, 1995 (Lizardi).
Non-Final Office Action issued Feb. 28, 1997 for U.S. Appl. No. 08/563,912, filed Nov. 21, 1995 (Lizardi).
Response to Election / Restriction filed Oct. 24, 1996 for U.S. Appl. No. 08/563,912, filed Nov. 21, 1995 (Lizardi).
Restriction Requirement issued Sep. 24, 1996 for U.S. Appl. No. 08/563,912, filed Nov. 21, 1995 (Lizardi).
Issue Notification issued Mar. 15, 2001 for U.S. Appl. No. 09/132,553, filed Aug. 11, 1998 (Lizardi).
Notice of Allowance issued Nov. 7, 2000 for U.S. Appl. No. 09/132,553, filed Aug. 11, 1998 (Lizardi).
Response to Office Action filed Aug. 11, 2000 for U.S. Appl. No. 09/132,553, filed Aug. 11, 1998 (Lizardi).
Non-Final Rejection issued Apr. 11, 2000 for U.S. Appl. No. 09/132,553, filed Aug. 11, 1998 (Lizardi).
Response after Non-Final Action with Terminal Disclaimer filed Jan. 13, 2000 for U.S. Appl. No. 09/132,553, filed Aug. 11, 1998 (Lizardi).
Non-Final Rejection issued Sep. 13, 1999 for U.S. Appl. No. 09/132,553, filed Aug. 11, 1998 (Lizardi).
Preliminary Amendment filed Aug. 11, 1998 for U.S. Appl. No. 09/132,553, filed Aug. 11, 1998 (Lizardi).
Issue Notification issued Jan. 18, 2002 for U.S. Appl. No. 09/644,723, filed Aug. 23, 2000 (Lizardi).
Notice of Allowance issued Oct. 1, 2001 for U.S. Appl. No. 09/644,723, filed Aug. 23, 2000 (Lizardi).
Response after Non-Final Action with Terminal Disclaimer filed Jul. 13, 2001 for U.S. Appl. No. 09/644,723 filed Aug. 23, 2000 (Lizardi).
Non-Final Rejection issued Mar. 13, 2001 for U.S. Appl. No. 09/644,723, filed Aug. 23, 2000 (Lizardi).
Preliminary Amendment filed Aug. 23, 2000 for U.S. Appl. No. 09/644,723, filed Aug. 23, 2000 (Lizardi).
Issue Notification issued Jan. 19, 2001 for U.S. Appl. No. 09/132,552, filed Aug. 11, 1998 (Lizardi).
Notice of Allowance issued Jul. 12, 2000 for U.S. Appl. No. 09/132,552, filed Aug. 11, 1998 (Lizardi).
Amendment and Response filed Jun. 14, 2000 for U.S. Appl. No. 09/132,552, filed Aug. 11, 1998 (Lizardi).
Final Rejection issued Apr. 6, 2000 for U.S. Appl. No. 09/132,552, filed Aug. 11, 1998 (Lizardi).
Response after Non-Final Action & Terminal Disclaimer filed Jan. 13, 2000 for U.S. Appl. No. 09/132,552, filed Aug. 11, 1998 (Lizardi).
Non-Final Rejection issued Sep. 13, 1999 for U.S. Appl. No. 09/132,552, filed Aug. 11, 1998 (Lizardi).
Preliminary Amendment filed Aug. 11, 1998 for U.S. Appl. No. 09/132,552, filed Aug. 11, 1998 (Lizardi).
Issue Notification issued Sep. 9, 2004 for U.S. Appl. No. 10/038,718, filed Jan. 2, 2002 (Lizardi).
Notice of Allowance issued Apr. 21, 2004 for U.S. Appl. No. 10/038,718, filed Jan. 2, 2002 (Lizardi).
Response after Non-Final Action & Terminal Disclaimer filed Jan. 16, 2004 for U.S. Appl. No. 10/038,718, filed Jan. 2, 2002 (Lizardi).
Non-Final Rejection issued Oct. 22, 2003 for U.S. Appl. No. 10/038,718, filed Jan. 2, 2002 (Lizardi).

(56) References Cited

OTHER PUBLICATIONS

Response to Election / Restriction filed Jul. 14, 2003 for U.S. Appl. No. 10/038,718, filed Jan. 2, 2002 (Lizardi).
Restriction Requirement issued Mar. 13, 2003 for U.S. Appl. No. 10/038,718, filed Jan. 2, 2002 (Lizardi).
Preliminary Amendment filed Jan. 2, 2002 for U.S. Appl. No. 10/038,718, filed Jan. 2, 2002 (Lizardi).
Certificate of Correction issued Oct. 26, 2010 for U.S. Appl. No. 10/896,513, filed Jul. 22, 2004 (Lizardi).
Issue Notification issued Oct. 28, 2009 for U.S. Appl. No. 10/896,513, filed Jul. 22, 2004 (Lizardi).
Notice of Allowance issued Jul. 9, 2009 for U.S. Appl. No. 10/896,513, filed Jul. 22, 2004 (Lizardi).
Amendment and Response filed Mar. 26, 2009 for U.S. Appl. No. 10/896,513, filed Jul. 22, 2004 (Lizardi).
Interview Summary issued Mar. 12, 2009 for U.S. Appl. No. 10/896,513, filed Jul. 22, 2004 (Lizardi).
Non-Final Rejection issued Nov. 17, 2008 for U.S. Appl. No. 10/896,513, filed Jul. 22, 2004 (Lizardi).
Amendment and Response filed Aug. 29, 2008 for U.S. Appl. No. 10/896,513, filed Jul. 22, 2004 (Lizardi).
Advisory Action issued Jul. 23, 2008 for U.S. Appl. No. 10/896,513, filed Jul. 22, 2004 (Lizardi).
Amendment After Final Rejection filed Jun. 18, 2008 for U.S. Appl. No. 10/896,513, filed Jul. 22, 2004 (Lizardi).
Interview Summary issued Jun. 13, 2008 for U.S. Appl. No. 10/896,513, filed Jul. 22, 2004 (Lizardi).
Final Rejection issued Mar. 18, 2008 for U.S. Appl. No. 10/896,513, filed Jul. 22, 2004 (Lizardi).
Amendment After Non-Final Rejection with Terminal Disclaimer filed Dec. 11, 2007 for U.S. Appl. No. 10/896,513, filed Jul. 22, 2004 (Lizardi).
Non-Final Rejection issued Jun. 11, 2007 for U.S. Appl. No. 10/896,513, filed Jul. 22, 2004 (Lizardi).
Response to Election / Restriction filed Mar. 29, 2007 for U.S. Appl. No. 10/896,513, filed Jul. 22, 2004 (Lizardi).
Restriction Requirement issued Jan. 19, 2007 for U.S. Appl. No. 10/896,513, filed Jul. 22, 2004 (Lizardi).
Preliminary Amendment filed Jan. 25, 2005 for U.S. Appl. No. 10/896,513, filed Jul. 22, 2004 (Lizardi).
Issue Notification issued Sep. 8, 2000 for U.S. Appl. No. 08/946,732, filed Oct. 8, 1997 (Lizardi).
Office Communication issued May 3, 2000 for U.S. Appl. No. 08/946,732, filed Oct. 8, 1997 (Lizardi).
Notice of Allowance issued Jun. 22, 1999 for U.S. Appl. No. 08/946,732, filed Oct. 8, 1997 (Lizardi).
Amendment and Response filed Mar. 31, 1999 for U.S. Appl. No. 08/946,732, filed Oct. 8, 1997 (Lizardi).
Non-Final Rejection issued Oct. 1, 1998 for U.S. Appl. No. 08/946,732, filed Oct. 8, 1997 (Lizardi).
Issue Notification issued Aug. 9, 2001 for U.S. Appl. No. 09/397,915, filed Sep. 17, 1999 (Lizardi).
Notice of Allowance issued Apr. 9, 2001 for U.S. Appl. No. 09/397,915, filed Sep. 17, 1999 (Lizardi).
Response after Non-Final Action with Terminal Disclaimer filed Jan. 16, 2001 for U.S. Appl. No. 09/397,915, filed Sep. 17, 1999 (Lizardi).
Non-Final Rejection issued Aug. 14, 2000 for U.S. Appl. No. 09/397,915, filed Sep. 17, 1999 (Lizardi).
Preliminary Amendment filed Sep. 17, 1999 for U.S. Appl. No. 09/397,915, filed Sep. 17, 1999 (Lizardi).
Issue Notification issued Oct. 16, 2003 for U.S. Appl. No. 09/911,226, filed Jul. 23, 2001 (Lizardi).
Notice of Allowance issued Jun. 3, 2003 for U.S. Appl. No. 09/911,226, filed Jul. 23, 2001 (Lizardi).
Amendment and Response & Terminal Disclaimer filed Mar. 19, 2003 for U.S. Appl. No. 09/911,226, filed Jul. 23, 2001 (Lizardi).
Non-Final Rejection issued Dec. 18, 2002 for U.S. Appl. No. 09/911,226, filed Jul. 23, 2001 (Lizardi).
Preliminary Amendment filed Jul. 23, 2001 for U.S. Appl. No. 09/911,226, filed Jul. 23, 2001 (Lizardi).
Notice of Abandonment issued Oct. 28, 2009 for U.S. Appl. No. 10/700,018, filed Nov. 3, 2003 (Lizardi).
Advisory Action issued Apr. 2, 2009 for U.S. Appl. No. 10/700,018, filed Nov. 3, 2003 (Lizardi).
Notice of Appeal filed Mar. 13, 2009 for U.S. Appl. No. 10/700,018, filed Nov. 3, 2003 (Lizardi).
Amendment after Final Rejection filed Jan. 27, 2009 for U.S. Appl. No. 10/700,018, filed Nov. 3, 2003 (Lizardi).
Final Rejection issued Sep. 15, 2008 for U.S. Appl. No. 10/700,018, filed Nov. 3, 2003 (Lizardi).
Amendment after Non-Final Rejection filed Jun. 12, 2008 for U.S. Appl. No. 10/700,018, filed Nov. 3, 2003 (Lizardi).
Non-Final Rejection issued Jan. 24, 2008 for U.S. Appl. No. 10/700,018, filed Nov. 3, 2003 (Lizardi).
Response after Non-Final Action filed Oct. 31, 2007 for U.S. Appl. No. 10/700,018, filed Nov. 3, 2003 (Lizardi).
Non-Final Rejection issued Aug. 8, 2007 for U.S. Appl. No. 10/700,018, filed Nov. 3, 2003 (Lizardi).
Response after Non-Final Action filed May 14, 2007 for U.S. Appl. No. 10/700,018, filed Nov. 3, 2003 (Lizardi).
Non-Final Rejection issued Nov. 14, 2006 for U.S. Appl. No. 10/700,018, filed Nov. 3, 2003 (Lizardi).
Response after Non-Final Action filed Aug. 24, 2006 for U.S. Appl. No. 10/700,018, filed Nov. 3, 2003 (Lizardi).
Non-Final Rejection issued May 18, 2006 for U.S. Appl. No. 10/700,018, filed Nov. 3, 2003 (Lizardi).
Preliminary Amendment filed Nov. 3, 2003 for U.S. Appl. No. 10/700,018, filed Nov. 3, 2003 (Lizardi).
Issue Notification issued Oct. 25, 2001 for U.S. Appl. No. 09/357,487, filed Jul. 20, 1999 (Lizardi).
Notice of Allowance issued Jun. 5, 2001 for U.S. Appl. No. 09/357,487, filed Jul. 20, 1999 (Lizardi).
Amendment and Response filed May 18, 2001 for U.S. Appl. No. 09/357,487, filed Jul. 20, 1999 (Lizardi).
Final Rejection issued Feb. 13, 2001 for U.S. Appl. No. 09/357,487, filed Jul. 20, 1999 (Lizardi).
Amendment and Response filed Jan. 25, 2001 for U.S. Appl. No. 09/357,487, filed Jul. 20, 1999 (Lizardi).
Non-Final Rejection issued Oct. 25, 2000 for U.S. Appl. No. 09/357,487, filed Jul. 20, 1999 (Lizardi).
Amendment and Response filed Sep. 12, 2000 for U.S. Appl. No. 09/357,487, filed Jul. 20, 1999 (Lizardi).
Non-Final Rejection issued May 12, 2000 for U.S. Appl. No. 09/357,487, filed Jul. 20, 1999 (Lizardi).
Response after Non-Final Rejection filed May 19, 2011 for U.S. Appl. No. 11/870,715, filed Oct. 11, 2007 (Korfhage et al.).
Non-Final Rejection issued Feb. 16, 2011 for U.S. Appl. No. 11/870,715, filed Oct. 11, 2007 (Korfhage et al.).
Response after Final Rejection filed Nov. 30, 2009 for U.S. Appl. No. 11/870,715, filed Oct. 11, 2007 (Korfhage et al.).
Final Rejection issued Oct. 16, 2009 for U.S. Appl. No. 11/870,715, filed Oct. 11, 2007 (Korfhage et al.).
Response after Final Rejection filed Jul. 24, 2009 for U.S. Appl. No. 11/870,715, filed Oct. 11, 2007 (Korfhage et al.).
Examiner Interview Summary issued Jul. 15, 2009 for U.S. Appl. No. 11/870,715, filed Oct. 11, 2007 (Korfhage et al.).
Final Rejection issued May 13, 2009 for U.S. Appl. No. 11/870,715, filed Oct. 11, 2007 (Korfhage et al.).
Response after Non-Final Action filed Feb. 9, 2009 for U.S. Appl. No. 11/870,715, filed Oct. 11, 2007 (Korfhage et al.).
Non-Final Rejection issued Nov. 12, 2008 for U.S. Appl. No. 11/870,715, filed Oct. 11, 2007 (Korfhage et al.).
Communication pursuant to Article 96(2) EPC issued Apr. 24, 2006 for EP 1950759.9, which claims priority to PCT/US01/20933 filed on Jul. 2, 2001 (Applicant—Molecular.
Notice of National Processing Completion issued Apr. 20, 2001 for BE 96940601.6, which claims priority to PCT/US96/18.812 filed on Nov. 21, 1996 (Applicant—Yale University).
Examination Report issued Apr. 4, 2006 for CA 2236161, which claims priority to PCT/US96/18812 filed on Nov. 21, 1996 (Applicant—Yale University).

(56) References Cited

OTHER PUBLICATIONS

Response to Art. 96(2) EPC Communication filed Dec. 17, 2007 for EP 3799976, which claims priority to PCT/US03/40364 filed on Dec. 19, 2003 (Applicant—.
Communication from European Examining Division filed Aug. 20, 2009 for EP Application No. EP2006723749 filed on Oct. 24, 2007 (Applicant—Qiagen GMBH).
Communication from European Examining Division filed Nov. 24, 2009 for EP Application No. EP2006723749 filed on Oct. 24, 2007 (Applicant—Qiagen GMBH).
Communication from European Examining Division filed Apr. 9, 2010 for EP Application No. EP2006723749 filed on Oct. 24, 2007 (Applicant—Qiagen GMBH).
Communication filed on Jan. 4, 2011 for EP Application No. EP07118804 filed on Oct. 18, 2007 (Applicant—Qiagen GMBH).
Communication from European Examining Division filed on Sep. 29, 2008 for EP Application No. EP07118804 filed on Oct. 18, 2007 (Applicant—Qiagen GMBH).
U.S. Appl. No. 09/803,713, filed Mar. 9, 2001, Alsmadi et al.
U.S. Appl. No. 10/325,490, filed Dec. 19, 2002, Alsmadi et al.
U.S. Appl. No. 10/404,944, filed Mar. 31, 2003, Alsmadi et al.
U.S. Appl. No. 09/547,757, filed Apr. 12, 2000, A. Fawad Faruqi.
U.S. Appl. No. 09/597,836, filed Jun. 20, 2000, Kingsmore et al.
U.S. Appl. No. 10/341,287, filed Jan. 13, 2003, Kingsmore et al.
U.S. Appl. No. 11/187,537, filed Jul. 22, 2005, Kingsmore et al.
U.S. Appl. No. 60/215,639, filed Jun. 30, 2000, Ward et al.
U.S. Appl. No. 09/897,259, filed Jul. 2, 2001, Ward et al.
U.S. Appl. No. 09/910,383, filed Jul. 20, 2001, Nallur et al.
U.S. Appl. No. 09/977,868, filed Oct. 15, 2001, Laskin et al.
U.S. Appl. No. 09/982,212, filed Oct. 18, 2001, Laskin et al.
U.S. Appl. No. 10/272,465, filed Oct. 15, 2002, Laskin et al.
U.S. Appl. No. 10/429,229, filed May 2, 2003, Bornarth et al.
U.S. Appl. No. 11/871,707, filed Oct. 12, 2007, Bornarth et al.
U.S. Appl. No. 60/016,677, filed May 1, 1996, Paul M. Lizardi.
U.S. Appl. No. 08/754,681, filed Nov. 21, 1996, Lizard et al.
U.S. Appl. No. 09/602,428, filed Jun. 23, 2000, Lizard et al.
U.S. Appl. No. 09/841,513, filed Apr. 24, 2001, Paul M. Lizardi.
U.S. Appl. No. 10/413,041, filed Apr. 10, 2003, Paul M. Lizardi.
U.S. Appl. No. 10/072,666, filed Feb. 8, 2002, Kumar et al.
U.S. Appl. No. 60/112,370, filed Dec. 15, 1998, Hafner et al.
U.S. Appl. No. 09/460,078, filed Dec. 14, 1999, Hafner et al.
U.S. Appl. No. 10/917,880, filed Aug. 13, 2004, Hafner et al.
U.S. Appl. No. 10/325,665, filed Dec. 19, 2002, Alsamdi et al.
U.S. Appl. No. 10/335,573, filed Dec. 31, 2002, Kumar et al.
U.S. Appl. No. 11/201,339, filed Aug. 10, 2005, Kumar et al.
U.S. Appl. No. 10/405,822, filed Mar. 31, 2003, Abarzua et al.
U.S. Appl. No. 10/454,946, filed Jun. 4, 2003, Feaver et al.
U.S. Appl. No. 10/456,056, filed Jun. 6, 2003, Gyanendra Kumar.
U.S. Appl. No. 09/605,192, filed Jun. 28, 2000, Lasken et al.
U.S. Appl. No. 09/920,571, filed Jul. 31, 2001, Lasken et al.
U.S. Appl. No. 60/204057, filed May 12, 2000, Kingsmore et al.
U.S. Appl. No. 09/577,444, filed May 24, 2000, Kingsmore et al.
U.S. Appl. No. 09/897,665, filed Jul. 2, 2001, Kingsmore et al.
U.S. Appl. No. 60/259,918, filed Jan. 5, 2001, Bandaru et al.
U.S. Appl. No. 09/910,372, filed Jul. 20, 2001, Bandaru et al.
U.S. Appl. No. 10/465,759, filed Jun. 19, 2003, Bandaru et al.
U.S. Appl. No. 60/168,511, filed Dec. 2, 1999, Patricio Abarzua.
U.S. Appl. No. 09/723,685, filed Nov. 28, 2000, Patricio Abarzua.
U.S. Appl. No. 10/196,539, filed Jul. 16, 2002, Patricio Abarzua.
U.S. Appl. No. 11/429,549, filed May 5, 2006, Patricio Abarzua.
U.S. Appl. No. 60/194,843, filed Apr. 5, 2000, Patricio Abarzua.
U.S. Appl. No. 09/827,289, filed Apr. 5, 2001, Patricio Abarzua.
U.S. Appl. No. 60/299,345, filed Jun. 19, 2001, Richard Whitshire.
U.S. Appl. No. 10/177,629, filed Jun. 19, 2002, Richard Whitshire.
U.S. Appl. No. 09/931,736, filed Aug. 17, 2001, Weiping Shao.
U.S. Appl. No. 10/931,015, filed Aug. 31, 2004, Gilfillan et al.
U.S. Appl. No. 60/862,678, filed Oct. 24, 2006, Korfhage et al.
U.S. Appl. No. 11/991,435, filed Sep. 11, 2006, Korfhage et al.
U.S. Appl. No. 08/563,912, filed Nov. 21, 1995, Paul M. Lizardi.
U.S. Appl. No. 09/132,553, filed Aug. 11, 1998, Paul M. Lizardi.
U.S. Appl. No. 09/644,723, filed Aug. 23, 2000, Paul M. Lizardi.
U.S. Appl. No. 09/132,552, filed Aug. 11, 1998, Paul M. Lizardi.
U.S. Appl. No. 10/038,718, filed Jan. 2, 2002, Paul M. Lizardi.
U.S. Appl. No. 10/896,513, filed Jul. 22, 2004, Paul M. Lizardi.
U.S. Appl. No. 08/946,732, filed Oct. 8, 1997, Paul M. Lizardi.
U.S. Appl. No. 09/397,915, filed Sep. 17, 1999, Paul M. Lizardi.
U.S. Appl. No. 09/911,226, filed Jul. 23, 2001, Paul M. Lizardi.
U.S. Appl. No. 10/700,018, filed Nov. 3, 2003, Paul M. Lizardi.
U.S. Appl. No. 60/093,479, filed Jul. 20, 1998, Lizardi et al.
U.S. Appl. No. 09/357,487, filed Jul. 20, 1999, Lizardi et al.
U.S. Appl. No. 11/887,678, filed Mar. 27, 2006, Korfhage et al.
U.S. Appl. No. 11/744,553, filed May 24, 2007, Korfhage et al.
U.S. Appl. No. 011/870,715, filed Oct. 11, 2007, Korfhage et al.
AAAI Board of Directors. (1995) Measurement of specific and nonspecific IgG4 levels as diagnostic and prognostic tests for clinical allergy. J Allergy Clin Immunol. 95: 652-654.
Abravaya et al. (1995) Detection of point mutations with a modified ligase chain reaction (Gap-LCR). Nucleic Acids Res. 23(4): 675-682.
Alsmadi et al. (2009) Specific and complete human genome amplification with improved yield achieved by phi29 DNA polymerase and a novel primer at elevated temperature. BMC Res Notes. 2: 48.
Altschul et al. (1997) Gapped BLAST and PSI-BLAST: a new generation of protein database search programs. Nucleic Acids Res. 25(17): 3389-402.
Alves et al. (1988) Dot blot detection of point mutations with adjacently hybridising synthetic oligonucleotide probes. Nucleic Acids Res. 16(17): 8723.
Anderson et al. (1997) A comparison of selected mRNA and protein abundances in human liver. Electrophoresis. 18: 533-537.
Andras et al. (2001) Strategies for signal amplification in nucleic acid detection. Mol Biotechnol. 19(1): 29-44.
Ansari-Lari et al. (1996) Improved ligation-anchored PCR strategy for identification of 5' ends of transcripts. Biotechniques. 21(1): 34-6, 38.
Applied Biosystems. "Avoiding DNA contamination in RT-PCR" internet webpage retrieved from http://www.ambion.com/techlib/tb/tb_176.html on Jan. 14, 2011.
Applied Biosystems. "Methods to remove DNA contamination from RNA samples" internet webpage retrieved from http://www.ambion.com/techlib/tb/tb_181.html on Jan. 14, 2011.
Apweiler et al. (2001) The InterPro database, an integrated documentation resource for protein families, domains and functional sites. Nucleic Acids Res. 29(1): 37-40.
Armitage et al. (1998) Hairpin-forming peptide nucleic acid oligomers. Biochemistry. 37(26): 9417-25.
Arn et al. (1996) The 2'-5' RNA ligase of *Escherichia coli*. Purification, cloning, and genomic disruption. J. Biol. Chem. 271(49): 31145-53.
Arnold et al. (1989) Assay formats involving acridinium-ester-labeled DNA probes. Clin Chem. 35(8): 1588-1594.
Asseline et al. (1992) Solid-phase preparation of 5',3'-heterobifunctional oligodeoxyribonucleotides using modified solid supports. Tetrahedron. 48(7): 1233-1254.
Atencia et al. (1999) T4 RNA ligase catalyzes the synthesis of dinucleoside polyphosphates. Eur J Biochem. 261(3): 802-11.
Auer et al. (1996) Selective amplification of RNA utilizing the nucleotide analog dITP and Thermus thermophilus DNA polymerase. Nucleic Acids Res. 24(24): 5021-5.
Ausubel et al. (Eds). (1987). Current Protocols in Molecular Biology. vol. 1, Unit 1.6—Minipreps of Plasmid DNA, Unit 1.7—CsCl/Ethidium Bromide Preparations of Pplasmid DNA, Unit 2.2—Preparation of Genomic DNA from Mammalian Tissue.
Baldauf et al. (2000) A kingdom-level phylogeny of eukaryotes based on combined protein data. Science. 290(5493): 972-7.
Baner et al. (1998) Signal amplification of padlock probes by rolling circle replication. Nucl. Acid Res. 26(22): 5073-5078.
Barany. (1991) Genetic disease detection and DNA amplification using cloned thermostable ligase. Proc. Natl. Acad. Sci. USA 88: 189-193.
Barbato et al. (1987) Solid Phasse Synthesis of Cyclic Oligodeoxyribonucleotides. Tetrahedron Letters. 28(46): 5727-5728.

(56) References Cited

OTHER PUBLICATIONS

Bauer et al. (1997) Use of manganese in RT-PCR eliminates PCR artifacts resulting from DNase I digestion, Biotechniques. 22(6):1128-32.
Beaucage et al. (1981) Deoxynucleoside phosphoramidites—a new class of key intermediates for deoxypolynucleotide synthesis. Tetrahedron Lett. 22(20): 1859-1862.
Becker et al. (1999) LMPCR for detection of oligonucleotide-directed triple helix formation: a cautionary note. Antisense Nucleic Acid Drug Dev. 9(3): 313-6.
Becker et al. (2000) PCR bias in ecological analysis: a case study for quantitative Taq nuclease assays in analyses of microbial communities. Appl Environ Microbiol. 66(11): 4945-53.
Beier et al. (1999) Versatile derivatisation of solid support media for covalent bonding on DNA-microchips. Nucleic Acids Res. 27(9): 1970-7.
Beigelman et al. (1994) Synthesis of 1-deoxy-d-ribofuranose phosphoramidite & the incorporation of abasic nucleotides in stem-loop II of a hammerhead ribozyme. Bioorganic & Medicinal Chemistry Letters. 4(14): 1715-1720.b.
Bertina et al. (1994) Mutation in blood coagulation factor V associated with resistance to activated protein C. Nature. 369: 64-67.
Betz et al. (1981) Variants of a cloned synthetic lactose operator. I. A palindromic dimer lactose operator derived from one stand of the cloned 40-base pair operator. Gene. 13(1): 1-12.
Bi et al. (1997) CCR: a rapid and simple approach for mutation detection. Nucleic Acids Res. 25(14): 2949-51.
Birkenmeyer et al. (1991) DNA probe amplification methods. J.Virol. Meth. 35: 117-126.
Birnboim HC. (1983) A rapid alkaline extraction method for the isolation of plasmid DNA. Methods Enzymol. 100: 243-255.
Blanc et al. (1999) The mitochondrial RNA ligase from Leishmania tarentolae can join RNA molecules bridged by a complementary RNA. J. Biol. Chem. 274(34): 24289-96.
Blanco et al. (1984) Characterization and purification of a phage Æ 29-encoded DNA polymerase required for the initiation of replication. Proc. Natl. Acad. Sci. USA 81: 53255329.
Blanco et al. (1989) Highly Efficient DNA Synthesis by the Phage Æ 29 DNA Polymerase. J. Biol. Chem. 264(15): 8935-8940.
Blanco et al. (1994) Terminal protein-primed DNA amplification. Proc Natl Acad Sci USA. 91:12198-12202.
Bloch et al. (1988) Alpha-anomeric DNA: beta-RNA hybrids as new synthetic inhibitors of Escherichia coli RNase H, Drosophila embryo RNase H and M-MLV reverse transcriptase. Gene. 72(1-2): 349-60.
Boehmer et al. (1993) Herpes Simplex Virus Type 1 ICP8: Helix-Destabilizing Properties. J. Virol. 67(2): 711-715.
Bonaldo et al. (1996) Normalization and subtraction: two approaches to facilitate gene discovery. Genome Res. 6(9): 791-806.
Bonnet et al. (1999) Thermodynamic basis of the enhanced specificity of structured DNA probes. Proc. Natl. Acad. Sci. USA. 96(11): 6171-6176.
Boore et al. (2005) Sequencing and comparing whole mitochondrial genomes of animals. Methods Enzymol. 395: 311-48.
Brandenburg et al. (1995) Branched oligodeoxynucleotides: a new synthetic strategy and formation of strong intra- and intermolecular triple helical complexes Bioorganic & Medicinal Chemistry Letters. 5(8): 791-794.
Braun et al. (1999) Cholera toxin suppresses interleukin (IL)-12 production and IL-12 receptor beta1 and beta2 chain expression. J Exp Med. 189(3): 541-52.
Brennan et al. (1983) Using T4 RNA ligase with DNA substrates. Methods Enzymol. 100: 38-52.
Breslow et al. (1991) Effects of metal ions, including Mg2+ and lanthanides, on the cleavage of ribonucleotides and RNA model compounds. PNAS 88: 4080-4083.
Broude et al. (1994) Enhanced DNA sequencing by hybridization. Proc Natl Acad Sci U S A. 91(8): 3072-6.

Brownstein et al. (1996) Modulation of non-templated nucleotide addition by Taq DNA polymerase: primer modifications that facilitate genotyping. Biotechniques. 20(6): 1004-6, 1008-10.
Brush. (1998) Dye hard: protein gel staining products. The Scientist. 12: 16-22.
Bryant et al. (1982) Phosphorothioate substrates for T4 RNA ligase. Biochemistry. 21(23): 5877-85.
Buchanan et al. (2000) Long DOP-PCR of rare archival anthropological samples. Hum Biol. 72(6): 911-25.
Burgess et al. (1996) A new photolabile protecting group for nucleotides. Abstracts of Papers, Part 2; 211th ACS National Meeting, American Chemical Society. New Orleans, LA.
Butler et al. (1982) Bacteriophage SP6-specific RNA polymerase. J. Biol. Chem. 257(10): 5772-5778.
Cameron et al. (2000) A sea urchin genome project: sequence scan, virtual map, and additional resources. Proc Natl Acad Sci U S A. 97(17): 9514-8.
Capobianco et al. (1990) One pot solution synthesis of cyclic oligodeoxyribonucleotides. Nucleic Acids Res. 18(9): 2661-9.
Carninci et al. (1998) Thermostabilization and thermoactivation of thermolabile enzymes by trehalose and its application for the synthesis of full length cDNA. Proc Natl Acad Sci U S A. 95(2): 520-4.
CDP-Star CSPD & AMPPD Substrates for Al Phosphatase. Printout on Mar. 24, 2000 from webpage (www.tropix.com/alkasubs.htm).
Chandler DP. (1998) Redifining relativity: quantitative PCR at low template concentrations for industrial and environmental microbiology. J. Indust. Microbiol. Biotech. 21: 128-140.
Chang. (2000) The pharmacological basis of anti-IgE therapy. Nat Biotech. 18: 157-162.
Chatterjee et al. (1991) Cloning and overexpression of the gene encoding bacteriophage T5 DNA polymerase. Gene. 97: 13-19.
Chen et al. (1998) Amplification of closed circular DNA in vitro. Nucleic Acids Res. 26(23): 1126-7.
Chetverina et al. (1993) Cloning of RNA molecules in vitro. Nucl. Acids Res. 21(10): 2349-2353.
Cheung et al. (1996) Whole genome amplification using a degenerate oligonucleotide primer allows hundreds of genotypes to be performed on less than one nanogram of genomic DNA. Proc Natl Acad Sci USA. 93(25): 14676-79.
Choo et al. (1994) Differentiation-independent constitutive expression of the human papillomavirus type 16 E6 and E7 oncogenes in the CaSki cervical tumour cell line. J Gen Virol. 75 (Pt 5): 1139-47.
Christian et al. (2001) Detection of DNA point mutations and mRNA expression levels by rolling circle amplification in individual cells. Proc Natl Acad Sci U S A. 98(25): 14238142.
Colantuoni et al. (2001) Gene Expression Profiling in Postmortem Rett Syndrome Brain: Differential Gene Expression and Patient Classification. Neutoboil. Dis. 8: 847-865.
Colantuoni et al. High Throughput Analysis of Gene Expression in the Human Brain. J. Neurosci. Res. 59: 1-10.
Connolly BA. (1985) Chemical synthesis of oligonucleotides containing a free sulphydryl group and subsequent attachment of thiol specific probes. Nucleic Acids Res. 13(12): 4485-502.
Connolly BA. (1987) The synthesis of oligonucleotides containing a primary amino group at the 5'-terminus. Nucleic Acids Res. 15(7): 3131-9.
Craxton et al. (1991) Linear Amplification Sequencing, a Powerful Method for Sequencing DNA. Meth. Compan. Meth. Enzymol. 3(1): 20-26.
Cremer et al. (1988) Detection of chromosome aberrations in metaphase and interphase tumor cells by in situ hybridization using chromosome-specific library probes. Hum Genet. 80(3): 235-46.
Crollius et al. (2000) Characterization and repeat analysis of the compact genome of the freshwater pufferfish Tetraodon nigroviridis. Genome Res. 10(7): 939-49.
Crooke et al. (1996) Pharmacokinetic properties of several novel oligonucleotide analogs in mice. J Pharmacol Exp Ther. 277(2): 923-937.
Cummins et al. (1996) Biochemical and physicochemical properties of phosphorodithioate DNA. Biochemistry. 35(26): 8734-41.

(56) References Cited

OTHER PUBLICATIONS

Damha et al. (1998) Synthesis of a branched DNA/RNA chimera similar to the msDNA molecule of Myxococcus Xanthus. 39(23): 3907-3910.
Das et al. Full-length cDNAs: more than just reaching the ends. Physiological Genomics 6: 57 (2001).
Daubendiek et al. (1995) Rolling-circle RNA synthesis: circular oligonucleotides as efficient substrates for T7 RNA polymerase. J Am Chem Soc. 117: 7818-7819.
Daubendiek et al. (1997) Generation of catalytic RNAs by rolling transcription of synthetic DNA nanocircles. Nature Biotechnology. 15(3): 273-277.
Davanloo et al. (1984) Cloning and expression of the gene for bacteriophage T7 RNA polymerase. Proc Natl Acad Sci USA. 81: 2035-2039.
Davies et al. (1999) Profiling of amyloid beta peptide variants using SELDI Protein Chip arrays. Biotechniques. 27(6): 1258-61.
Davis et al. (1980) A Manual for Genetic Engineering. Advanced Bacterial Genetics. Cold Spring Harbor Laboratory. Cold Spring Harbor, NY.
de Baar, et al. (2001) Single rapid real-time monitored isothermal RNA amplification assay for quantification of human immunodeficiency virus type 1 isolates from groups M, N, and O. J Clin Microbiol. 39(4): 1378-84.
de Vega et al. (1997) An invariant lysine residue is involved in catalysis at the 3'-5' exonuclease active site of eukaryotic-type DNA polymerases. J Mol Biol. 270(1): 65-78.
de Vroom et al. (1988) Synthesis of cyclic oligonucleotides by a modified phosphotriester approach. Nucleic Acids Res. 16(10): 4607-20.
Dean et al. (2001) Rapid Amplification of Plasmid and Phage DNA Using Phi29 DNA Polymerase and Multiply-Primed Rolling Circle Amplification. Genome Res. 11: 1095-1099.
Dean et al. (2002) Comprehensive human genome amplification using multiple displacement amplification. Proc Natl Acad Sci USA. 99(8): 5261-66.
Detter et al. (2002) Isothermal strand-displacement amplification applications for high-throughput genomics. Genomics. 80(6): 691-98.
Diegelman et al. (1998) Generation of circular RNAs and trans-cleaving catalytic RNAs by rolling transcription of circular DNA oligonucleotides encoding hairpin ribozymes. Nucleic Acids Res. 26(13): 3235-41.
Doherty et al. (2000) Structural and mechanistic conservation in DNA ligases. Nucleic Acids Res. 28(21): 4051-8.
Dolinnaya et al. (1993) Oligonucleotide circularization by template-directed chemical ligation. Nucleic Acids Res. 21(23): 5403-7.
Dostie et al. Numerous microRNPs in neuronal cells containing novel microRNAs. RNA 9: 180 (2003).
Dreyer et al. (1985) Sequence-specific cleavage of single-stranded DNA: oligodeoxynucleotide-EDTA X Fe(II). Proc Natl Acad Sci U S A. 182(4): 968-72.
Durand et al. (1990) Circular dichroism studies of an oligodeoxyribonucleotide containing a hairpin loop made of a hexaethylene glycol chain: conformation and stability. Nucleic Acids Res. 18(21): 6353-9.
Dynal. (1995) DYNAL Technical Handbook. Biomagnetic techniques in molecular biology.
Eads et al. (1999) CpG island hypermethylation in human colorectal tumors is not associated with DNA methyltransferase overexpression. Cancer Res. 59(10): 2302-2306.
Eberwine et al. (1992) Analysis of gene expression in single live neurons. Proc Natl Acad Sci USA. 89(7): 3010-3014.
Eckert et al. (1991) DNA polymerase fidelity and the polymerase chain reaction. PCR Methods Appl. 1(1): 17-24.
Eckstein et al. (1989) Phosphorothioates in molecular biology. Trends Biochem Sci. 14(3): 97-100.
Egholm et al. (1992) Peptide nucleic acids (PNA). Oligonucleotide analogs with an achiral peptide backbone. J. Am. Chem. Soc., 114 (5), pp. 1895-1897.

Ekins et al. (1991) Multianalyte microspot immunoassay—microanalytical "compact disk" of the future. Review. Clin Chem. 37(11): 1955-67.
Ekins. (1998) Ligand assays: from electrophoresis to miniaturized microarrays. Clin Chem. 44(9): 2015-2030.
Englisch et al. (199) Chemically modified oligonucleotides as probes and inhibitors. Angewandte Chemie, Intl Ed. 30(6): 613-722.
Erie et al. (1989) Melting behavior of a covalently closed, single-stranded, circular DNA.Biochemistry. 28(1): 268-73.
Ernst et al. (1989) Cyanine dye labeling reagents for sulfhydryl groups. Cytometry. 10: 3-10.
Esteban et al. (1993) Fidelity of 29 DNA Polymerase. Journal of Biological Chemistry. 268(4): 2719-2726.
Faruqi et al. (2001) High-throughput genotyping of single nucleotide polymorphisms with rolling circle amplification. BMC Genomics. 2(1): 4.
Fermentas Life Sciences. (2010) Thermophilic DNA Polymerases Product Page (p. 1-3). Retrieved from Fermentas Website Product page on Sep. 13, 2010 at http://www.fermentas.com/en/products/all/modifying-enzymes/thermophilic-polymerases.
Fields et al. (1994) How many genes in the human genome? Nat Genet. 7:345-346.
Fire et al. (1995) Rolling replication of short DNA circles. Proc Natl Acad Sci USA. 92: 4641-4645.
Fleischmann et al. (1995) Whole-Genome Random Sequencing and Assembly of Haemophilus influenza Rd. Science 269:496-512.
Fu et al. (1994) Hammerhead Ribozymes Contianing Non-Nucleoside Linkers are Active RNA Catalysts. J. Am. Chem. Soc. 116: 4591-4598.
Gait MJ. (1993) Oligoribonucleotides. Antisense Research and Applications. (Crooke et al, eds., CRC Press) Chapter 16, pp. 289-301.
Galli et al. (1995) Transcriptional analysis of rolling circle replicating plasmid pVT736-1: evidence for replication control by antisense RNA. J Bacteriol. 177(15): 4474-4480.
Gasparini et al. (1999) Analysis of 31 CFTR mutations by polymerase chain reaction/oligonucleotide ligation assay in a pilot screening of 4476 newborns for cystic fibrosis. J Med Screen. 6(2): 67-9.
Gasparro et al. (1994) Site-specific targeting of psoralen photoadducts with a triple helix-forming oligonucleotide: characterization of psoralen monoadduct and crosslink formation. Nucleic Acids Research. 22(14): 2845-2852.
Ge H. (2000) UPA, a universal protein array system for quantitative detection of protein-protein, protein-DNA, protein-RNA and protein-ligand interactions. Nucleic Acids Res. 28(2): e3.
GE Healthcare. (2010) GE Healthcare Life Sciences: "TempliPhi FAQ" Retrieved from the Internet: http://www.gelifesciences.com/aptrix/2 uppO1077.nsf/Contentsample_preparation-product_selection _category-roll ing_circle_amplification-sample_templiphi faq [retrieved on Jul. 29, 2010].
Gerdes et al. (1994) Dynamic Changes in the Higher-Level Chromatin of Specific Sequences Revealed by In Situ Hybridization to Nuclear Halos. J. Cell Biol. 126(2): 289-304.
Gillespie et al. (2000) HLA class II typing of whole genome amplified mouth swab DNA. Tissue Antigens. 56(6): 530-8.
Gryaznov et al. (1993) Template controlled coupling and recombination of oligonucleotide blocks containing thiophosphoryl groups. Nucleic Acids Res. 21(6): 1403-8.
Grzybowski et al. (1993) Synthesis and antibody-mediated detection of oligonucleotides containing multiple 2,4-dinitrophenyl reporter groups. Nucleic Acids Res. 21(8): 1705-12.
Guatelli et al. (1990) Isothermal, in vitro amplification of nucleic acids by a multienzyme reaction molded after retroviral replication. Proc. Natl. Acad. Sci. USA 87: 1874-1878.
Guillier-Gencik et al. (1999) Generation of whole-chromosome painting probes specific to each chicken macrochromosome. Cytogenet Cell Genet. 87(3-4): 282-5.
Gumport et al. (1981) T4 RNA ligase as a nucleic acid synthesis and modification reagent. Gene Amplif Anal. 2: 313-45.
Gunji et al. (1992) Correlation between the serum level of hepatitis C virus RNA and disease activities in acute and chronic hepatitis C. Int J Cancer. 52(5): 726-730.

(56) References Cited

OTHER PUBLICATIONS

Guo et al. (1994) Direct fluorescence analysis of genetic polymorphisms by hybridization with oligonucleotide arrays on glass supports. Nucl. Acids Res. 22(24): 5456-5464.
Guo et al. (1997) Enhanced discrimination of single nucleotide polymorphisms by artificial mismatch hybridization. Nature Biotechnology. 15: 331-335.
Gupta et al. (1990) A universal solid support for the synthesis of 3'-thiol group containing oligonucleotides. Tetrahedron Letters. 31(17): 2471-2474.
Gupta et al. (1993) Expression of HIV-1 RNA in plasma correlates with the development of Aids: a multicenter AIDS cohort study (MACS) Ninth International Conference on AIDS/Fourth STD World Congress. Berlin, Germany (abstract).
Gusev et al. (2001) Rolling circle amplification: a new approach to increase sensitivity for immunohistochemistry and flow cytometry. American Journal of Pathology. 159(1): 63-69.
Gygi et al. (1999) Correlation between protein and mRNA abundance in yeast. Mol Cell Biol. 19(3): 1720-1730.
Haaf et al. (1994) High resolution ordering of YAC contigs using extended chromatin and chromosomes. Hum Mol Genet. 3(4): 629-33.
Hacia et al. (1996) Detection of heterozygous mutations in BRCA1 using high density oligonucleotide arrays and two-colour fluorescence analysis. Nat. Genet. 14: 441-447.
Haff et al. (1997) Single-nucleotide polymorphism identification assays using a thermostable DNA polymerase and delayed extraction MALDI-TOF mass spectrometry. Genome Res. 7(4): 378-88.
Hagiwara et al. (1993) Quantitation of hepatitis C virus RNA in serum of asymptomatic blood donors and patients with type C chronic liver disease. Hepatology. 17(4): 545-550.
Hall et al. (1957) Nucleotide. Part XLI. Mixed anhydrides an intermediate in the synthesis of dinucleoside phosphates. J Chem Soc. 3291-3296.
Hall et al. (2000) Sensitive detection of DNA polymorphisms by the serial invasive signal amplification reaction. Proc. Natl. Acad. Sci. USA 97(15): 8272-8277.
Hanvey et al. (1992) Antisense and antigene properties of peptide nucleic acids. Science. 258: 1481-1485.
Harada et al. (1993) In vitro selection of optimal DNA substrates for T4 RNA ligase. Proc Natl Acad Sci U S A. 90(4): 1576-9.
Harada et al. (1994) In vitro selection of optimal DNA substrates for ligation by a water-soluble carbodiimide. J Mol Evol. 38(6): 558-60.
Haralambidis et al. (1987) Preparation of base-modified nucleosides suitable for non-radioactive label attachment and their incorporation into synthetic oligodeoxyribonucleotides. Nucleic Acids Res. 15(12): 4857-76.
Harper et al. (1999) Recent advances and future developments in PGD. Prenat Diagn. 19(13): 1193-9.
Hata et al. (1988) Structure of the human ornithine transcarbamylase gene. J Biochem. 103: 302-308.
Hayward-Lester et al., Accurate and Absolute Quantitative Measurement of gene expression by single-tube RT-PCR and HPLC. Genome Research 5:494 (1995).
Heinonen et al. (1997) Simple triple-label detection of seven cystic fibrosis mutations by time-resolved fluorometry. Clin Chem. 43(7): 1142-1150.
Hendrickson et al. (1995) High sensitivity multianalyte immunoassay using covalent DNA-labeled antibodies and polymerase chain reaction. Nucleic Acids Res. 23(3): 522529.
Henegariu et al. (2000) Custom flourescent-nucleotide synthesis as an alternative method for nucleic acid labeling. Nat Biotech. 18: 345-346.
Hermanson et al. (1992) Immobilized Affinity Ligands. Academic Press, NY.
Higgins et al. (1979) Addition of oligonucleotides to the 5'-terminus of DNA by T4 RNA ligase. Nucleic Acids Res. 6(3): 1013-24.
Higgins et al. (1979) DNA-joining enzymes: a review. Methods Enzymol. 68: 50-71.
Hinton et al. (1978) T4 RNA Ligase joins 2'-deoxyribonucleoside 3',5'-bisphosphates to oligodeoxyribonucleotides. Biochemistry. 17(24): 5091-7.
Hinton et al. (1979) The synthesis of oligodeoxyribonucleotides using RNA ligase. Nucleic Acids Res. 7(2): 453-64.
Hinton et al. (1982) The preparative synthesis of oligodeoxyribonucleotides using RNA ligase. Nucleic Acids Res. 10(6): 1877-94.
Hoeltke et al. (1992) Multiple nucleic acid labeling and rainbow detection. Anal Biochem. 207: 24-31.
Holland et al. (1991) Detection of specific polymerase chain reaction product by utilizing the 5'—>3' exonuclease activity of Thermus aquaticus DNA polymerase. Proc. Natl. Acad. Sci. USA 88: 7276-7280.
Holloway et al. (1993) An exonuclease-amplification coupled capture technique improves detection of PCR product. Nucleic Acids Research. 21(16): 3905-3906.
Holmes et al. (Eds.) (1981) Large Scale Isolation of Plasmid DNA. Harvesting and Lysis of Bacteria. pp. 89-91.
Holton et al. (1991) A simple and efficient method for direct cloning of PCR products using ddT-tailed vectors. Nucleic Acids Res. 19(5): 1156.
Horn et al. (1997) Chemical synthesis and characterization of branched oligodeoxyribonucleotides (bDNA) for use as signal amplifiers in nucleic acid quantification assays. Nucleic Acids Res. 25(23): 4842-9.
Hoy et al. (1993) Bromodeoxyuridine/DNA analysis of replication in CHO cells after exposure to UV light. Mutat. Res. 290: 217-230.
Hsu et al. (2000) Hydration of [d(CGC)r(aaa)d(TTTGCG)]2. J. Mol. Biol. 295, 1129-1137.
Hsuih et al. (1995) Quantitative detection of HCV RNA using novel ligation-dependent polymerase chain reaction. American Association for the Study of Liver Diseases. (Chicago, IL) [poster abstract].
Hsuih et al. (1996) Novel, ligation-dependent PCR assay for detection of hepatitis C in serum. J Clin Microbiol. 34(3): 501-7.
Humphery-Smith et al. (1997) Proteome Analysis: Genomics via the Output Rather than the Input Code. J. Protein Chem. 16(5): 537-544.
Huryn et al. (1992) AIDS-driven nucleoside chemistry. Chem Rev. 92: 1745-1768.
Iakobashvili et al. (1999) Low temperature cycled PCR protocol for Klenow fragment of DNA polymerase I in the presence of proline. Nucleic Acids Res. 27(6): 1566-8.
Innis et al. (1988) DNA sequencing with Thermus aquaticus DNA polymerase and direct sequencing of polymerase chain reaction-amplified DNA. Proc Natl Acad Sci USA. 85(24): 9436-9440.
Intergen Company. Amplifluor™ Apoptosis Gene System. Retrieved on Jan. 3, 2002 from product webpage at http://www.intergenco.com/body_apoptosis_amplifluor.html (4 pages).
Intergen Company. Principles of the Amplifluor™ Universal Amplification and Detection System Procedure. Retrieved on Jan. 3, 2002 from product webpage at http://www.intergenco.com/body_apoptosis_uniprimer.html (2 pages).
Ishikawa et al. (1995) Sequence-based typing of HLA-A2 alleles using a primer with an extra base mismatch. Hum Immunol. 42(4): 315-318.
Itaka et al. (2002) Evaluation by fluorescence resonance energy transfer of the stability of nonviral gene delivery vectors under physiological conditions. Biomacromolecules. 3(4): 841-5.
Itakura et al. (1984) Synthesis and Use of Synthetic Oligonucleotides. Annu. Rev. Biochem. 53: 323-356.
Iuodka et al. (1991) [Substrate specificity of T4 RNA-ligase. The role of phosphate nucleotide residues in the formation of a covalent AMP-RNA-ligase complex]. [Article in Russian]. Biokhimiia. 56(5): 798-805.
Iyer et al. (1990) 3-H-1,2-benzodithiole-3-one 1, 1-dioxide as an improved sulfurizing reagent in the solid-phase synthesis of oligodeoxyribonucleosdie phosphorothioates. J Am Chem Soc. 112: 1253-1254.
Jablonski et al. (1986) Preparation of oligodeoxynucleotide-alkaline phosphatase conjugates and their use as hybridization probes. Nucleic Acids Res. 14(15): 6115-28.

(56) References Cited

OTHER PUBLICATIONS

Jacobsen et al. (1974) The N-terminal amino acid sequences of DNA polymerase I from *escherichia coli* and of the large and the small fragments obtained by a limited proteolysis. Eur J Biochem. 45: 623-627.

Jalanko et al. (1992) Screening for defined cystic fibrosis mutations by solid-phase minisequencing. Clin Chem. 38(1): 39-43.

James et al. (1997) Surprising fidelity of template-directed chemical ligation of oligonucleotides. Chem Biol. 4(8): 595-605.

Jiang et al. (1996) An efficient method for generation and subcloning of tandemly repeated DNA sequences with defined length, orientation and spacing. Nucl. Acids Res. 24(16): 3278-3279.

Johnstone et al. (1987) Immunochemistry in Practice, Blackwell Scientific Publications, Oxford, England, Chapters 2 and 3, pp. 30-85.

Johnstone et al. (1987) Immunochemistry in Practice, Blackwell Scientific Publications, Oxford, England, pp. 209-216 and 241-242.

Jonsson et al. (1995) Sequence of the DNA ligase-encoding gene from thermus scotoductus and conserved motifs in DNA ligases. Gene. 151: 177-180.

Jun-Dong et al. (1990) Application of Wittig Reaction to Adenosine Derivatives. Synthesis. Oct. 1990, 909-911.

Jung et al. (1987) Bacteriophage PRDI DNA polymerase: Evolution of DNA polymerases. Proc. Natl. Acad. Sci. USA 84: 8287-8291.

Kabanov et al. (1990) A new class of antivirals: antisense oligonucleotides combined with a hydrophobic substituent effectively inhibit influenze virus reproduction and synthesis of virus-specific proteins in MDCK cells. FEBS Lett. 259(2): 327-330.

Kabat. (1968) Structural Concepts in Immunology and Immunohistochemistry. Holt, Rinehart and Winston, Inc. pp. 162-168.

Kaboord et al. (1995) Accessory proteins function as matchmakers in the assembly of the T4 DNA polymerase holoenzyme. Current Biology. 5(2): 149-157.

Kahn et al. (1992) Evaluation of the ligase chain reaction (LCR) for the detection of point mutations. Mutation Research. 283(2): 119-128.

Kalnik et al. (1988) NMR studies of abasic sites in DNA duplexes: deoxyadenosine stacks into the helix opposite the cyclic analogue of 2-deoxyribose. Biochemistry. 27(3): 924-31.

Kaluz et al. (1995) Enzymatically produced composite primers: an application of T4 RNA ligase-coupled primers to PCR. Biotechniques. 19(2): 182-4, 186.

Kanaya et al. (1986) Template-directed polymerization of oligoadenylates using cyanogen bromide. Biochemistry. 25(23):7423-30.

Kang et al. (2000) Transcript quantitation in total yeast cellular RNA using kinetic PCR. Nucleic Acids Res. 28(2): e2.

Kaplan et al. (1978) Rapid Photolytic of Adenosine 5'-Triphosphate from a Protected Analogue: Utilization by the Na:K Pump of Human Red Blood Cell Ghosts. Biochemistry 17: 1929-1935.

Kapuschoc et al. (2002) Differential localization of nuclear-encoded tRNAs between the cytosol and Mitochondrion in Leishmania tarentolae. RNA. 8(1): 57-66.

Kazakov et al. (1998) RNA Padlocks: Locking out ribosomes. Presentation at IBC 5th Annual International Conference on Antisense. Coronado, CA.

Kellogg et al. (1994) TaqStart Antibody: "Hot Start" PCR facilitated by a neutralizing monoclonal antibody directed against Taq DNA polymerase. BioTechniques. 16(6): 1134-1137.

Kerkhof. (1994) A comparison of substrates for quantifying the signal from a nonradiolabeled DNA probe. Analytical Biochemistry. 205: 359-364.

Kessler. (1991) The digoxigenin:anti-dioxgenin (DIG) technology—a survey on the concept and realization of a novel bioanalytical indicator system. Mol Cell Probes. 5: 161-205.

Khrapko et al. (1991) Hybridization of DNA with oligonucleotides immobilized in gel: a convenient method for detecting single base substitutions. Molecular Biology (Mosk) (USSR). 25: 718-730.

Kim et al. (1999) Whole genome amplification and molecular genetic analysis of DNA from paraffin-embedded prostate adenocarcinoma tumor tissue. J Urol. 162(4): 1512-18.

Kim et al. (2000) Regulation of cell growth and HPV genes by exogenous estrogen in cervical cancer cells. Int J Gynecol Cancer. 10(2): 157-164.

Kimpton et al. (1993) Automated DNA Profiling Employing Multiplex Amplification of Short Tandem Repeat Loci. PCR Methods and Applications. 3: 13-22.

King et al. (1994) Bridging the Gap. Joining of nonhomologous ends by DNA polymerases. J. Biol. Chem. 269(18): 13061-13064.

Kinoshita et al. (1996) Strand Ligation in a Double-stranded DNA by T4 RNA Ligase. Chem. Lett. 25(9): 797-798.

Kinoshita et al. (1997) Fluorescence-, isotope- or biotin-labeling of the 5'-end of single-stranded DNA/RNA using T4 RNA ligase. Nucleic Acids Res. 25(18): 3747-8.

Klein et al. (1999) Comparative genomic hybridization, loss of heterozygosity, and DNA sequence analysis of single cells. Proc Natl Acad Sci USA. 96(8): 4494-9.

Kling J. (1994) Genetic Engineering Without Restriction. Double Twist.

Kobayashi et al. (1995) Fluorescence-based DNA minisequence analysis for detection of known single-base changes in genomic DNA. Mol Cell Probes. 9(3): 175-82.

Komura et al. (1998) Terminal transferase-dependent PCR: a versatile and sensitive method for in vivo footprinting and detection of DNA adducts. Nucleic Acids Res. 26(7): 1807-11.

Kong et al. (1993) Characterization of a DNA polymerase from the hyperthermophile archaea thermococcus litoralis. Journal of Biological Chemistry. 268(3): 1965-1975.

Kononen et al. (1998) Tissue microarrays for high-throughput molecular profiling of tumor specimens. Nat Med. 4(7): 844-7.

Kool. (1996) Circular oligonucleotides: new concepts in oligonucleotide design. Annual Rev Biomol Struct. 25: 1-28.

Kornberg et al. (1992) DNA Replication (2nd Edition). W.H. Freeman and Company, New York. Chapter 1, pp. 20-21.

Krichevsky et al. (2003) A microRNA array reveals extensive regulation of microRNAs during brain development. RNA 9: 1274-1281.

Kricka LJ. (1993) Ultrasensitive immunoassay techniques. Clin Biochem. 26(5): 325-31.

Kuchel et al. (Eds.). (1997) Schaum's Outline. Biochemistry. (2nd Edition).

Kumar et al. (1991) A simple method for introducing a thiol group at the 5'-end of synthetic oligonucleotides. Nucleic Acids Res. 19(16): 4561. No abstract available.

Kunkel et al. (1987) Rapid and efficient site-specific mutagenesis without phenotypic selection. Methods in Enzymology. 154: 367-382.

Kuukasjärvi et al. (1997) Optimizing DOP-PCR for universal amplification of small DNA samples in comparative genomic hybridization. Genes Chromosomes Cancer. 18(2): 94-101.

Kwoh et al. (1989) Transcription-based amplification system and detection of amplified human immunodeficiency virus type 1 with a bead-based sandwich hybridization format. Proc. Natl. Acad. Sci. USA 86: 1173-1177.

Kyle et al., A microfluorometric method for quantifying RNA and DNA in terrestrial insects, Journal of Insect Science, 3:1, pp. 1-7, 2003.

Laffler et al. (1993) The ligase chain reaction in DNA-based diagnosis. Ann Biol Clin (Paris). 51(9): 821-6.

Lage et al. (2003) Whole genome analysis of genetic alterations in small DNA samples using hyperbranched strand displacement amplification and array-CGH. Genome Res., 13(2): 294-307.

Lamture et al. (1994) Direct detection of nucleic acid hybridization on the surface of a charge coupled device. Nucleic Acids Research. 22(11): 2121-2125.

Landegren et al. (1988) A ligase-mediated gene detection technique. Science. 241: 1077-1080.

Landegren. (1993) Molecular mechanics of nucleic acid sequence amplification. Trends Genetics. 9(6): 199-202.

(56) References Cited

OTHER PUBLICATIONS

Langer et al. (1981) Enzymatic synthesis of biotin-labeled polynucleotides: novel nucleic acid affinity probes. Proc Natl Acad Sci USA. 78(11): 6633-6637.
Lantz et al. (2000) Biotechnical use of polymerase chain reaction for microbiological analysis of biological samples. Biotechnol Annu Rev. 5: 87-130.
Laval et al. (1989) Structural organization and expression of amplified chromosomal sequences, which include the rudimentary gene, in cultured Drosophila cells resistant to N-(phosphonacetyl)-L-aspartate. Mol Gen Genet. 220(1): 102-112.
Lawyer et al. (1993) High-level expression, purification, and enzymatic characterization of full-length thermus aquaticus DNA polymerase and a truncated form deficient in 5' to 3' exonuclease activity. PCR Methods Applications. 2(4): 275-287.
Lee et al. (1998) Coordinated leading and lagging strand DNA synthesis on a minicircular template. Mol Cell. (7): 1001-10.
Lee HH. (1996) Ligase chain reaction. Biologicals. 24(3):197-9.
LeFrere et al. (1992) Towards a new predictor of AIDS progression through the quantitation of HIV-1 DNA copies by PCR in HIV-infected individuals. British Journal of Haematology. 82(2): 467-471.
Lesnik et al. (1995) Relative Thermodynamic Stability of DNA, RNA, and DNA:RNA Hybrid Duplexes: Relationship with Base Composition and Structure. Biochemistry 34: 10807-10815.
Letsinger et al. (1976) Synthesis of thymidine oligonucleotides by phosphite triester intermediates. J Am Chem Soc. 98(12): 3655-3661.
Letsinger et al. (1989) Cholesteryl-conjugated oligonucleotides: synthesis, properties, and activity as inhibitors of replication of human immunodeficiency virus in cell culture. Proc Natl Acad Sci USA. 86: 6553-6556.
Letsinger et al. (1995) Use of a Stilbenedicarboxamide Bridge in Stabilizing, Monitoring, and Photochemically Altering Folded Conformations of Oligonucleotides. J. Am. Chem. Soc. 117: 7323-7328.
Li et al. (1987) Enzyme-linked synthetic oligonucleotide probes: non-radioactive detection of enterotoxigenic Escherichia coli in faecal specimens. Nucleic Acid Research. 15(13): 5275-5287.
Li et al. (1999) Synthesis by a Solvothermal Route and Characterization of CuInSe2 Nanowhiskers and Nanoparticles. Adv. Mater. 11(17): 1456-1459.
Lichter et al. (1990) High-resolution mapping of human chromosome 11 by in situ hybridization with cosmid clones. Science. 247: 64-69.
Lim et al. (1997) Synthesis of DNA Dumbbells: Chemical vs. Enzymatic Ligation of Self-Complementary Oligonucleotides. Nucleosides & Nucleotides. 16(1-2): 41-51.
Lin et al. (1995) Single-site polymerase chain reaction through single oligonucleotide ligation. Anal Biochem. 231(2): 449-52.
Ling et al. (1997) Approaches to DNA mutagenesis: an overview. Anal Biochem. 254(2): 157-78.
Little et al. (1999) Strand Displacement Amplification and Homogeneous Real-Time Detection Incorporated in a Second-Generation DNA Probe System, BDProbeTectET. Clin. Chem. 45(6): 777-784.
Liu et al. (1993) Mapping the 5' and 3' ends of Tetrahymena thermophila mRNAs using RNA ligase mediated amplification of cDNA ends (RLM-RACE). Nucleic Acids Res. 21(21): 4954-60.
Liu et al. (1996) Rolling Circle DNA Synthesis: Small Circular Oligonucleotides as Efficient Templates for DNA Polymerases. J Am Chem Soc. 118(7): 1587-1594.
Lizardi et al. (1997) FISH with a twist. Nat Genet. 16(3): 217-8.
Lizardi et al. (1998) Mutation detection and single-molecule counting using isothermal rolling-circle amplification. Nat Genet. 19: 225-232.
Loakes et al. (1994) 5-Nitroindole as an universal base analogue. Nucl. Acids Res. 22(20): 4039-4043.
Lockhart et al. (1996) Expression monitoring by hybridization to high-density oligonucleotide arrays. Nature Biotechnology. 14: 1675-1680.

Löffert et al. (1998) PCRoptimziation: degenerate primers. Qiagen News. (Issue 2).
Lu et al. (1993) High concentration of peripheral blood mononuclear cells harboring infectious virus correlates with rapid progression of human immunodeficiency virus Type1-related diseases. JID 168(5): 1165-8116.
Lukyanov et al. (1996) Molecule by molecule PCR amplification of complex DNA mixtures for direct sequencing: an approach to in vitro cloning. Nucleic Acids Research. 24(11): 2194-2195.
Luo et al. (1996) Improving the fidelity of thermus thermophilus DNA ligase. Nucl Acids Res. 24(14): 3071-3078.
Lyons et al. (1994) Immunosuppressant FK506 promotes neurite outgrowth in cultures of PC12 cells and sensory ganglia. Proc Natl Acad Sci USA. 91(8): 3191-3195.
MacKellar et al. (1992) Synthesis and physical properties of anti-HIV antisense oligonucleotides bearing terminal lipophilic groups. Nucleic Acids Res. 20(13):3411-7.
Mahadeva et al. (1998) A simple and efficient method for the isolation of differentially expressed genes. J Mol Biol. 284(5): 1391-8.
Malboeuf et al. (2001) Thermal effects on reverse transcription: improvement of accuracy and processivity in cDNA synthesis. Biotechniques. 30(5): 1074-8, 1080, 1082, passim.
Maniatis et al. (1982) Molecular Cloning: A Laboratory Manual. (Cold Spring Harbor Laboratory) Eds, pp. 280-281.
Manoharan et al. (1992) Chemical modifications to improve uptake and bioavailability of antisense oligonucleotides. Ann NY Acad Sci. 660: 306-309.
Manoharan et al. (1993) Introduction of a lipophilic thioether tether in the minor groove of nucleic acids for antisense applications. Bioorg Med Chem Let. 3(12): 2765-2770.
Manoharan et al. (1994) Cholic acid-oligonucleotide conjugates for antisense applications. Bioorg Med Chem Let. 4(8): 1053-1060.
Manoharan et al. (1995) Lipidic nucleic acids. Tetra Lett. 36(21): 3651-3654.
Manoharan et al. (1995) Oligonucletoide conjugates: alteration of the pharmacokinetic properties of antisense agents. Nucleosides & Nucleotides. 14: 969-973.
Marshall et al. (1994) Detection of HCV RNA by the asymmetric gap ligase chain reaction. PCR Methods and Applications. 4: 80-84.
Marshall et al. (1997) A biopolymer by any other name would bind as well: a comparison of the ligand-binding pockets of nucleic acids and proteins. Structure. 5(6): 729-734.
Maskos et al. (1992) Oligonucleotide hybridizations on glass supports: a novel linker for oligonucleotide synthesized in situ. Nucl. Acids Res. 20(7): 1679-1684.
Mathur et al. (2000) Cervical epidermal growth factor-receptor (EGF-R) and serum insulin-like growth factor II (IGF-II) levels are potential markers for cervical cancer. Am J Reprod Immunol. 44(4): 222-30.
Matray et al. (1998) Selective and Stable DNA Base Pairing without Hydrogen Bonds. J. Am. Chem. Soc. 120(24): 6191-6192.
Matray et al. (1999) A specific partner for abasic damage in DNA. Nature. 399(6737): 704-8.
Matsumoto et al. (1989) Primary structure of bacteriophage M2 DNA polymerase: conserved segments within protein-priming DNA polymerases and DNA polymerase I of escherichia coli. Gene. 84(2): 247-255.
Matteucci et al. (1981) Synthesis of deoxyoligonucleotides on a polymer support. J Am Chem Soc. 103:3185-3191.
Matz et al. (1999) Amplification of cDNA ends based on template-switching effect and step-out PCR. Nucleic Acid Research. 27(6): 1558-1560.
McCoy et al. (1980) T4 ribonucleic acid ligase joins single-strand oligo (deoxyribonucleotides). Biochemistry. 19(4): 635-42.
McCray et al. (1980) A new approach to time-resolved studies of ATP-requiring biological systems: laser flash photolysis of caged ATP. Proc Natl Acad Sci USA. 77(12): 7237-7241.
McGraw et al. (1990) Sequence-dependent oligonucleotide-target duplex stabilities: rules from empirical studies with a set of twenty-mers. Biotechniques. 8(1): 674-678 (1990).

(56) References Cited

OTHER PUBLICATIONS

Melton et al. (1984) Efficient in vitro synthesis of biologically active RNA and RNA hybridization probes from plasmids containing a bacteriophage SP6 promoter. Nucleic Acids Research. 12(18): 7035-7056.

Mendoza et al. (1999) High-throughput microarray-based enzyme-linked immunosorbent assay (ELISA). Biotechniques. 27(4): 778-80, 782-6, 788.

Metzker et al. (1994) Termination of DNA synthesis by novel 3'-modified-deoxyribonucleoside 5'-triphosphates. Nucleic Acids Research. 22(20): 4259-4267.

Milla et al. (1998) Use of the restriction enzyme AvaI and exo-Bst polymerase in strand displacement amplification. Biotechniques, 24(3): 392-96.

Mishra et al. (1995) Improved leishmanicidal effect of phosphorotioate antisense oligonucleotides by LDL-mediated delivery. Biochim Biophys Acta. 1264(2): 229-37.

Monji et al. (1987) A novel immunoassay system and bioseparation process based on thermal phase separating polymers. Appl Biochem Biotechnol. 14(2): 107-20.

Moore et al. (1992) Site-specific modification of pre-mRNA: the 2'-hydroxyl groups at the splice sites. Science. 256(5059): 992-7.

Moran et al. (1996) Non-hydrogen bonding 'terminator' nucleosides increase the 3'-end homogeneity of enzymatic RNA and DNA synthesis. Nucleic Acids Research. 24(11): 2044-2052.

Moretti et al. (1998) Enhancement of PCR amplification yield and specificity using AmpliTaq Gold DNA polymerase. Biotechniques. 25(4): 716-22.

Morvan et al. (1986) alpha-DNA. I. Synthesis, characterization by high field 1H-NMR, and base-pairing properties of the unnatural hexadeoxyribonucleotide alpha-[d(CpCpTpTpCpC)] with its complement beta-[d(GpGpApApGpG)]. Nucleic Acids Res. 14(12): 5019-35.

Mujumdar et al. (1989) Cyanine dye labeling reagents containng isothiocyanate groups. Cytometry. 10: 11-19.

Mullenix et al. (2001) Allergen-specific IgE detection on microarrays using rolling circle amplification: correlation with in vitro assays for serum IgE. Clinical Chemistry. 47(10): 1926-1929.

Myakishev et al. (2001) High-throughput SNP genotyping by allele-specific PCR with universal energy-transfer-labeled primers. Genome Res. 11(1):163-169.

Myers et al. (1991) Reverse transcription and DNA amplification by a Thermus thermophilus DNA polymerase. Biochemistry. 30(31): 7661-6.

Nagamine et al. (2001) Loop-mediated isothermal amplification reaction using a nondenatured template. Clin Chem., 47(9): 1742-3.

Nallur et al. (2001) Signal amplification by rolling circle amplification on DNA microarrays. Nucl. Acids. Res. 29(23): e118.

Narang et al. (1980) Chemical synthesis of deoxynucleotides by the modified tester method. Methods Enzymology. 65: 610-620.

Naritsin et al. (1991) Melting of oligodeoxynucleotides with various structures. J. Biomol. Struct. Dyn. 8(4): 813-25.

Navarro et al. (1996). A general strategy for cloning viroids and other small circular RNAs that uses minimal amounts of template and does not require prior knowledge of its sequence. J Virol Methods. 56(1): 59-66.

Nazarenko et al. (1997) A closed tube format for amplification and detection of DNA based on energy transfer. Nucleic Acids Res. 25(12): 2516-21.

Nelson et al. (2002) TempliPhi, phi29 DNA polymerase based rolling circle amplification of templates for DNA sequencing. Biotechniques. 32: S44-S47.

New England BioLabs. Polymerase from NEB printed information from New England BioLabs webpage (3 total pages), retrieved on Jul. 26, 2007 at http://www.neb.com/nebecomm/tech_reference/polymerases/polymerase_from_neb.asp.

New England BioLabs. Product Information for M-MuLV Reverste Trasncriptase from New England BioLabs website, retrieved on Apr. 4, 2007.

Newton et al. (1989) Analysis of any point mutation in DNA. The amplification refractory mutation system (ARMS). Nucl. Acids Res. 17(7): 2503-2516.

Nichols et al. (1994) A universal nucleoside for use at ambiguous sites in DNA primers. Nature. 369(6480): 492-493.

Nielsen et al. (1991) Sequence-Selective Recognition of DNA by Strand Displacement with a Thymine-Substituted Polyamide. Science 254: 1497-1500.

Nielsen et al. (1993) Peptide nucleic acids (PNAs): potential antisense and anti-gene agents. Anti-Cancer Drug Design. 8: 53-63.

Nielsen et al. (1994) Peptide nucleic acid (PNA). A DNA mimic with a peptide backbone. Bioconjugate Chemistry. 5: 3-7.

Nikiforov et al. (1994) Genetic bit analysis: a solid phase method for typing single nucleotide polymorphisms. Nucleic Acids Research. 22(20): 4167-4175.

Nikiforov et al. (1994) The use of phosphorothioate primers and exonuclease hydrolysis for the preparation of single-stranded PCR products and their detection by solid-phase hybridization. PCR Methods and Applications. 3: 285-291.

Nilsson et al. (1994) Padlock Probes: Circularizing Oligonucleotides for Localized DNA Detection. Science 265(5181): 2085-2088.

Nilsson et al. (1997) Padlock probes reveal single-nucleotide differences, parent of origin and in situ distribution of centromeric sequences in human chromosomes 13 and 21. Nature Genet. 16: 252-255.

Nilsson et al. (2002) Real-time monitoring of rolling-circle amplification using a modified molecular beacon design. Nucleic Acids Res. 30(14): e66.

Notomi et al. (2000) Loop-mediated isothermal amplification of DNA. Nucleic Acids Res., 28(12): E63.

Nuovo et al. (1999) In Situ Amplification Using Universal Energy Transfer-labeled Primers. J. Histochem. Cytochem. 47(3): 273-279.

Nycz et al. (1998) Quantitative reverse transcription strand displacement amplification: quantitation of nucleic acids using an isothermal amplification technique. Anal Biochem. 259(2): 226-34.

Oberhauser et al. (1992) Effective incorporation of 2'-O-methyl-oligoribonucleotides into liposomes and enhanced cell association through modification with thiocholesterol. Nucleic Acids Res. 20(3): 533-8.

Oda et al. (1999) Accurate quantitation of protein expression and site-specific phosphorylation. Proc Natl Acad Sci USA. 96: 6591-6596.

Okayama et al. (1982) High-efficiency cloning of full-length cDNA. Mol Cell Biol. 2(2): 161-170.

Ørum et al. (1993) Single base pair mutation analysis by PNA directed PCR clamping. Nucleic Acids Research. 21(23): 5332-5336.

Ott et al. (1987) Protection of oligonucleotide primers against degradation by DNA polymerase I. Biochemistry. 26(25): 8237-41.

Oyama et al. (1988) Avian myeloblastosis virus reverse transcriptase is easier to use than the Klenow fragment of DNA polymerase I for labeling the 3'-end of a DNA fragment. Anal Biochem. 172(2): 444-50.

Panasenko et al. (1978) A simple, three-step procedure for the large scale purification of DNA ligase from a hybird 1 lysogen construction in vitro. Journal Biological Chemistry. 253(13): 4590-4592.

Park et al. (1996) Detection of hepatitis C virus RNA using ligation-dependent polymerase chain reaction in formalin-fixed, paraffin-embedded liver tissues. Am J Pathol. 149(5): 1485-91.

Parker et al. (1991) Targeted gene walking polymerase chain reaction. Nucl Acids Res. 19: 3055-3060.

Parra et al. (1993) High resolution visual mapping of stretched DNA by fluorescent hybridization. Nat Genet. 5(1): 17-21.

Partha et al. (1990) Novel Thymidine Analogues via Reaction of Unprotected 5'-Deoxy-5'-iodothymidine with Dianions. vol. 31, Issue 10, pp. 1777-1780.

Patel et al. (1996) Formation of chimeric DNA primer extension products by template switching onto an annealed downstream oligonucleotide. Proc. Natl. Acad. Sci. USA. 93(7): 2969-2974.

(56) References Cited

OTHER PUBLICATIONS

Patton et al. (1995) Components of the Protein Synthesis and Folding Machinery Are Induced in Vascular Smooth Muscle Cells by Hypertrophic and Hyperplastic Agents. J. Biol. Chem. 270(36): 21404-21410.
Patton. (1999) Proteome analysis II. Protein subcellular redistribution: linking physiology to genomics via the proteome and separation techniques involved. J Chromatogr. B 722: 203-223.
Patton. (2000) Making Blind Robots See: The Snyergy Between Fluorscent Dyes and Imaging Devices in Automated Proteomics. Biotechniques 28(5): 944-957.
Paulson et al. (1999) Loss of heterozygosity analysis using whole genome amplification, cell sorting, and fluorescence-based PCR. Genome Res. 9(5): 482-91.
Paunio et al. (1996) Preimplantation diagnosis by whole-genome amplification, PCR amplification, and solid-phase minisequencing of blastomere DNA. Clin Chem. 42(9): 1382-90.
Pease et al. (1994) Light-generated oligonucleotide arrays for rapid DNA sequence analysis. Proc Natl Acad Sci USA. 91(11): 5022-5026.
Petrie et al. (1991) Ligation with T4 RNA ligase of an oligodeoxyribonucleotide to covalently-linked cross-sectional base-pair analogues of short, normal, and long dimensions. Nucleic Acids Res. 19(3): 585-90.
Piatak et al. (1993) High levels of HIV-1 in plasma during all stages of infection determined by competitive PCR. Science. 259: 1749-1754.
Pieles et al. (1989) Psoralen covalently linked to oligodeoxyribonucleotides: synthesis, sequence specific recognition of DNA and photo-cross-linking to pyrimidine residues of DNA. Nucleic Acids Res. 17(1): 285-99.
Pillai, V.N. Rajasekharan. (1980) Photoremovable protecting groups in organic synthesis. Synthesis. Jan. 1980 (1):1-26.
Pless et al. (1975) Solid support synthesis of oligothymidylates using phosphorochloridates and 1-alkylmidazoles. Nucl Acids Res. 2(6): 773-786.
Pokrovskaya et al. (1994) In vitro transcription: preparative RNA yields in analytical scale reactions. Analytical Biochemistry. 220: 420-423.
Porstmann et al. (1985) Quantitation of 5-bromo-2-deoxyuridine incorporation into DNA: an enzyme immunoassay for the assessment of the lymphoid cell proliferative response. J. Immunol Meth. 82: 169-179.
Prakash et al. (1991) Molecular recognition by circular oligonucleotides. Strong binding of single-stranded DNA and RNA. J. Chem. Soc., Chem. Commun., 1161-1163.
Prakash et al. (1992) Structural Effects in the Recognition of DNA by Circular Oligonucleotides. J. Amer. Chem. Soc. 114: 3523-3527.
Prober et al. (1987) A system for rapid DNA sequencing with fluorescent chain-terminating dideoxynucleotides. Science. 238: 336-341.
Pruckler et al. (1995) Comparison of Legionella pneumophila isolates by arbitrarily primed PCR and pulsed-field gel electrophoresis: analysis from seven epidemic investigations. J Clin Microbiol. 33(11): 2872-5.
Ramsing et al. (1989) Helix-Coil Transsition of Parallel-Stranded DNA. Thermodynamics of Hairpin and Linear Duplex Oligonucleotides. Biochemistry 28: 9528-9535.
Ray et al. (1990) Novel Thymidine Analogues via Reaction of Unprotected 5'-Deoxy-5'-Iodothymidine with Dianions. Heterocycles. 31(10): 1777-1780.
Rector et al. (2004) A sequence-independent strategy for detection and cloning of circular DNA virus genomes by using multiply primed rolling-circle amplification. J Virol. 78(10): 4993-4998.
Reese et al. (1999) The H-phosphonate approach to the solution phase synthesis of linear and cyclic oligoribonucleotides. Nucleic Acids Res. 27(4): 963-71.
Richards et al. (1997) Conditional mutator phenotypes in hMSH2-deficient tumor cell lines. Science. 277: 1523-1526.

Ried et al. (1982) Simultaneous visualization of seven different DNA probes by in situ hybridization using combinational fluorescence and digital imaging microscopy. Proc Natl Acad Sci USA. 89(4): 1388-1392.
Rigler et al. (1995) Difference in the mechanism of stimulation of T7 DNA polymerase by two binding modes of *escherichia coli* single-stranded DNA-binding protein. Journal of Biological Chemistry. 270(15): 8819-8919.
Robins et al. (1988) Fluorination at C5' of nucleosides. Synthesis of the new class of 5'fluoro-5'-S-aryl (alkyl) thionucleosides from adenosine. Tetrahedron Letters: 29(45): 5729-5732.
Rodriguez et al. (1998) Large scale isolation of genes as DNA fragment lengths by continuous elution electrophoresis through an agarose matrix. Electrophoresis. 19(5): 646-52.
Rossi et al. (1997) Functional characterization of the T4 DNA ligase: a new insight into the mechanism of action. Nucleic Acids Res. 25(11): 2106-13.
Rubin et al. (1995) Convergent DNA synthesis: a non-enzymatic dimerization approach to circular oligodeoxynucleotides. Nucleic Acids Res. 23(17): 3547-53.
Rudbeck et al. (1998) Rapid, simple alkaline extraction of human genomic DNA from whole blood, buccal epithelial cells, semen and forensic stains for PCR. Biotechniques. 25(4): 588-90, 592.
Ruiz et al. (1998) Homology-dependent gene silencing in Paramecium. Mol Biol Cell. 9(4): 931-43.
Rychlik et al. (1990) Optimizaton of the annealing temperature for DNA amplification in vitro. Nucleic Acids Research. 18(21): 6409-6412.
Ryo et al. (2000) A Modified Serial Analysis of Gene Expression That Generates Longer Sequence Tags by Nonpalindromic Cohesive Linker Ligation. Analytical Biochemistry. 277, 160-162.
Rys et al. (1993) Preventing False Positives: Quantitative Evaluatio of Three Protocols for Inactivation of Polymerase Chain Reaction Amplication Products. J. Clin. Microbiol. 31(9): 2356-2360.
Saiki et al. (1985) Enzymatic Amplifications of beta-Globin Genomic Sequences and Restiction Site Analysis for Diagnosis of Sickle Cell Anemia. Science 230: 1350-1354.
Saiki et al. (1988) Primer-Directed Enzymatic Amplification of DNA with a Thermostable DNA Polymerase. Science. 239: 487-491.
Saison-Behmoaras et al. (1991) Short modified antisense oligonucleotides directed against Ha-ras point mutation induce selective cleavage of the mRNA and inhibit T24 cells proliferation. EMBO J. 10(5): 1111-1118.
Saksela et al. (1994) Human immunodeficiency virus type 1 mRNA expression in peripheral blood cells predicts disease progression independently of the Nos. of CD4+ lymphocytes. Proc Natl Acad Sci USA. 91(3): 1104-1108.
Salunkhe et al. (1992) Control of folding and binding of oligonucleotides by use of a nonnucleotide linker. J. Am. Chem. Soc. 114: 8768-8772.
Sambrook et al. *Molecular Cloning: A Laboratory Manual.* 2nd Edition (Cold Spring Harbor Laboratory Press, Cold Spring Harbor, N.Y., 1989) Chapters 5, 6).
Sanghvi. (1993) Heterocyclic base modifications in nucleic acids and their applications in antisense oligonucleotides. Antisense Research and Applications. (Crooke et al, eds., CRC Press) Chapters 15-16, pp. 273-301.
Sano et al. (1988) Detection of heavy methylation in human repetitive DNA subsets by a monoclonal antibody against 5-methylcytosine. Biochim Biophys Acta. 951: 157-165.
Santoro et al. A general purpose RNA-cleaving DNA enzyme. PNAS 94: 4262 (1997).
Sanyal, et al., An effective method of completely removing contaminating genomic DNA from an RNA sample to be used for PCR, Molecular Biotechnology, vol. 8, No. 2, pp. 135-137, 1997.
Saris et al. (1982) Blotting of RNA onto RNA exchange paper allowing subsequent characterization by in situ translation in addition to blot hybridization. Nucleic Acids Res. 10(16): 4831-4843.
Sasvari-Szekely et al. (2000) Rapid genotyping of factor V Leiden mutation using single-tube bidirectional allele-specific amplification and automated ultrathin-layer agarose gel electrophoresis. Electrophoresis. 21(4): 816-21.

(56) References Cited

OTHER PUBLICATIONS

Schaefer BC. (1995) Revolutions in rapid amplification of cDNA ends: new strategies for polymerase chain reaction cloning of full-length cDNA ends. Anal Biochem. 227(2): 255-73.
Schena et al. (1994) Parallel human genome analysis: microarray-based expression monitoring of 1000 genes. Proc Natl Acad Sci USA. 93: 10614-10619.
Schena et al. (1995) Quantitative monitoring of gene expression patterns with a complementary DNA microarray. Science. 270: 467-470.
Schena et al. (2000) Genes, genomes, and chips. Chapter 1, pp. 1-16.
Schenborn et al. (1985) A novel transcription property of SP6 and T7 RNA polymerases: dependence on template structure. Nucleic Acids Research. 13(17): 6223-6236.
Schenk et al. (1995) The accessibility of thiophosphorylated groups in DNA fragments to the enzymatic activity of ligases and restriction endonuclease Bbs I. Biochem Mol Biol Int. 36(5): 1037-43.
Schnierle et al., Cap-specific mRNA (nucleoside-02'-)-methyltransferase and poly(A) polymerase stimulatory activities of vaccinia virus are mediated by a single protein. PNAS 89 (7): 2897 (1992).
Schwarz. (1990) Improved yields of long PCR products using gene 32 protein. Nucl Acids Res. 18(4): 1079.
Schweitzer et al. (2000) Immunoassays with rolling circle DNA amplification: a versatile platform for ultrasensitive antigen detection. PNAS. 97(18): 10113-10118.
Schweitzer et al. (2001) Combining nucleic acid amplification and detection. Curr Opin Biotechnol. 12(1): 21-27.
Schweitzer et al. (2002) Multiplexed protein profiling on microarrays by rolling-circle amplification. Nat. Biotech. 20: 359-365.
Séquin, Urs. (1974) Nucleosides and Nucleotides. Part 7. Four dithymidine monophosphates with different anomeric configurations, their synthesis and behaviour towards phosphodiesterases Helvetica Chimica Acta. 57: 68-81.
Shea et al. (1990) Synthesis, hybridization properties and antiviral activity of lipid-oligodeoxynucleotide conjugates. Nucl Acids Res. 18(13): 3777-3783.
Shumaker et al. (1996) Mutation detection by solid phase primer extension. Human Mutation. 7(4): 346-354.
Siegal et al. (1992) A Novel DNA Helicase from Calf Thymus. J. Biol. Chem. 267(19): 13629-13635.
Silber et al. (1972) Purification and properties of bacteriophage T4-induced RNA ligase. Proc Natl Acad Sci U S A. 69(10): 3009-13.
Silzel et al. (1998) Mass-sensing, multianalyte microarray immunoassay with imaging detection. Clin Chem. 44(9): 2036-43.
Simpson. (1997) The natural somatic mutation frequency and human carcinogenesis. Adv Cancer Res. 71: 209-240.
Sinha et al. (1988) The preparation and application of functionalised synthetic oligonucleotides: III. Use of H-phosphonate derivatives of protected amino-hexanol and mercapto-propanol or -hexanol. Nucleic Acids Res. 16(6): 2659-69.
Skaliter et al. (1994) Rolling circle DNA replication in vitro by a complex of herpes simplex virus type 1-encoded enzymes. Proc Natl Acad Sci USA. 91(22): 10665-10669.
Skerra A. (1992) Phosphorothioate primers improve the amplification of DNA sequences by DNA polymerases with proofreading activity. Nucleic Acids Res. 20(14): 3551-54.
Smart Notes from Cepheid. Sensitivity and Specificity Utilizing Amplifluor™ Primers. (2 pages).
Sorensen et al. (2000) Branched oligonucleotides containing bicyclic nucleotides as branching points and DNA or LNA as triplex forming branch. Bioorg Med Chem Lett. 10(16): 1853-1856.
Southern EM. (1975) Detection of specific sequences among DNA fragments separated by gel electrophoresis. J Mol Biol. 98(3): 503-17.
Speicher et al. (1996) Karyotyping human chromosomes by combinatorial multi-fluor FISH. Nature Genetics. 12(4): 368-375.
Sperling et al. (2002) Random sequencing of Paramecium somatic DNA. Eukaryot Cell. 1(3): 341-52.
Stefano et al. (1997) Rapid and sensitive detection of Chlamydia trachomatis using a ligatable binary RNA probe and Q beta replicase. Mol Cell Probes. 11(6): 407-26.
Stein et al. (1991) Mode of action of 5'-linked cholesteryl phosphorothioate oligodeoxynucleotides in inhibiting syncytia formation and infection by HIV-1 and HIV-2 in vitro. Biochemistry. 30(9): 2439-44.
Steller et al. (1995) Insulin-like growth factor II mediates epidermal growth factor-induced mitogenesis in cervical cancer cells. Proc Natl Acad Sci U S A. 92(26): 11970-4.
Stewart et al. (1998) A quantitative assay for assessing allelic proportions by iterative gap ligation.b Nucleic Acids Res. 26(4):961-6.
Stimpson et al. (1995) Real-time detection of DNA hybridization and metling on oligonucleotide arrays by using optical wave guides. Proc. Natl. Acad. Sci. USA 92(14): 6379-6383.
Stratagene Catalog. (1988) Gene characterization Kits, Table of Contents. p. 39.
Stratagene Catalog. (1992) Sequencing Thermalbase® Sequencing Kit, p. 76.
Stratagene Catalog. (1999) RT-PCR Systems and Kits, Stratagene Catalog, 1999 pp. 154-155.
Strauss et al. (1993) Quantitative measure of calretinin and b-actin mRNA in rat brain micropunches without prior isolation of RNA. Mol Brain Res. 20: 229-239.
Strong et al. (1997) Marked improvement of PAC and BAC cloning is achieved using electroelution of pulsed-field gel-separated partial digests of genomic DNA. Nucleic Acids Res. 25(19):3959-3961.
Studier et al. (1990) Use of T7 RNA Polymerase to Direct Expression of Cloned Genes. Meth. Enzymol. 185: 60-89.
Stump et al. (1999) The use of modified primers of eliminate cycle sequencing artifacts. Nucl. Acids Res. 27(23): 4642-4648.
Suzuki et al. (1994) Mechanistic studies on depurination and apurinic site chain breakage in oligodeoxyribonucleotides. Nucleic Acids Res. 22(23): 4997-5003.
Svinarchuk et al. (1993) Inhibition of HIV proliferation in MT-4 cells by antisense oligonucleotide conjugated to lipophilic groups. Biochimie. 75: 49-54.
Syvanen et al. (1986) Fast quantification of nucleic acid hybrids by affinity-based hybrid collection. Nucleic Acids Research. 14(12): 5037-5049.
Tabor et al. (1987) Selective oxidation of the exonuclease domain of bacteriophage T7 DNA polymerase. J. Biol. Chem. 262: 15330-15333.
Tabor et al. (1989) Effect of manganese ions on the incorporation of dideoxynucleotides by bacteriophage T7 DNA polymerase and *Escherichia coli* DNA polymerase I. Proc. Natl. Acad. Sci. USA. 86, 4076-4080.
Tabor et al. (1989) Selective inactivation of the exonuclease activity of bacteriohage T7 DNA polymerase by in vitro mutagenesis. J Biol Chem. 264(11): 6447-6458.
Takasugi et al. (1991) Sequence-specific photo-induced cross-linking of the two strands of double-helical DNA by a psoralen covalently linked to a triple helix-forming oligonucleotide. Proc Natl Acad Sci U S A. 88(13):5602-6.
Takeshita et al. (1987) Oligodeoxynucleotides containing synthetic abasic sites. Model substrates for DNA polymerases and apurinic/apyrimidinic endonucleases. J Biol Chem. 262(21): 10171-9.
Tanaka et al. (1989) Cleavage of a Nucleosidic Oxetane with Carbanions: Synthesis of a Highly Promising Candidate for Anti-HIV Agents—a Phosphonate Isotere of AZT 5'-Phosphate. Tetrahedron Lett. 30(19): 2567-2570.
Taylor, Richard (Ed.) (1991) .*Protein immobilization: fundamentals and applications*, M. Dekker, New York, 1991.
Telenius et al. (1992) Degenerate oligonucleotide-primed PCR: general amplification of target DNA by a single degenerate primer. Genomics. 13(3): 718-25.
Tenover et al. (1994) Comparison of traditional and molecular methods of typing isolates of *Staphylococcus aureus*. J. Clin. Microbiol. 32(2): 407-15.

(56) References Cited

OTHER PUBLICATIONS

Tessier et al. (1996) Ligation of single-stranded oligodeoxyribonucleotides by T4 RNA ligase. Anal Biochem. 158(1): 171-8.
Theillet C. (1998) Full speed ahead for tumor screening. Nat Med. 4(7): 767-8.
Thelwell et al. (2000) Mode of action and application of Scorpion primers to mutation detection. Nucl. Acids Res. 28(19):3752-3761.
Thomas et al. (1997) Cascade rolling circle amplification, a homogeneous fluorescence detection system for DNA diagnostics. Clin Chem. 43: 2219-2220.
Thomas et al. (1999) Amplification of padlock probes for DNA diagnostics by cascade rolling circle amplification or the polymerase chain reaction. Arch Pathol Lab Med. 123(12): 1170-1176.
Thorbjarnardottir et al. (1995) Cloning and sequence analysis of the DNA ligase-encoding gene of Rhodothermus marinus, overproduction, purification and characterization of two thermophilic DNA ligases. Gene 161: 1-6.
Thuong et al. Solid phase synthesis of oligo-α- and oligo-β-deoxynucleotidescovalently linked to an acridine. pp. 5905-5908. Tetrahedron Lett. 29(46): 5905-5908.
Tobe et al. (1996) Single-well genotyping of diallelic sequence variations by a two-color ELISA-based oligonucleotide ligation assay. Nucleic Acids Res. 24(19): 3728-32.
Troutt et al. (1992) Ligation-anchored PCR: a simple amplification technique with single-sided specificity. Proc Natl Acad Sci U S A. 89(20):9823-5.
Tsurumi et al. (1993) Functional interaction between Epstein-Barr virus DNA polymerase catalytic subunit and its accessory subunit in vitro. Journal of Virology. 67(12): 7648-7653.
Tuma et al. (1999) Characterization of SYBR Gold nucleic acid gel stain: a dye optimized for use with 300-nm ultraviolet transilluminators. Anal Biochem. 268(2): 278-88.
Tyagi et al. (1996) Extremely sensitive, background-free gene detection using binary probes and Q replicase. Proc. Natl. Acda. Sci. USA 93: 5395-5400.
Tyagi et al. (1996) Molecular beacons: probes that fluoresce upon hybridization. Nature Biotechnology. 14: 303-308.
Uemori et al. (1993) Cloning of the DNA Polymerase Gene of Bacillus caldotenax and Characterizaion of the Gene Product. J. Biochem. 113: 401-410.
Unrau et al. (1994) Non-cloning amplification of specific DNA fragments from whole genomic DNA digests using DNA 'indexers'. Gene. 145(2): 163-9.
Välimaa et al. (1998) Detection of HLA-B27 alleles by group-specific amplification and time-resolved fluorometry. J Immunol Methods. 219(1-2): 131-137.
Van Gelder et al. (1990) Amplified RNA synthesized from limited quantities of heterogeneous cDNA. Proc. Natl. Acad. Sci. USA. 87, 1663-1667.
Velculescu et al. (1995) Serial Analysis of Gene Expression. Science 270: 484-487.
Villemain et al. (1996) The N-terminal B-domain of T4 gene 32 protein modulates the lifetime of cooperatively bound Gp32-ss nucleic acid complexes. Biochemistry. 35: 14395-14404.
Vincent et al. (2004) Helicase-dependent isothermal DNA amplification. EMBO Rep., 5(8): 795-800.
Vogelstein et al. (1980) Supercoiled loops and eucaryotic DNA replication. Cell. 22: 79-85.
Voisey et al. (2001) Interrogation of multimeric DNA amplification products by competitive primer extension using bst DNA polymerase (large fragment). Biotechniques. 31(5): 1122-4, 1126, 1128-29.
Waggoner. (1995) Covalent labeling of proteins and nucleic acids with fluorophores. Meth Enzymology. 246: 362-373.
Walder et al. (1993) Use of PCR primers containing a 3'-terminal ribose residue to prevent cross-contamination of amplified sequences. Nucleic Acids Res. 21(18): 4339-43.

Walker et al. (1992) Isothermal in vitro amplification of DNA by a restriction enzyme/DNA polymerase system. Proc Natl Acad Sci USA. 89: 392-396.
Walker et al. (1992) Strand displacement amplification—an isothermal, in vitro DNA amplification technique. Nucleic Acids Research. 20(7): 1691-1696.
Walker et al. (1994) Multiplex strand displacement amplification (SDA) and detection of DNA sequences from *Mycobacterium tuberculosis* and other mycobacteria. Nucleic Acids Res. 22(13): 2670-2677.
Walker et al. (1996) Detection of *Mycobacterium tuberculosis* DNA with thermophilic strand displacement amplification and fluorescence polarization. Clin. Chem. 42(10): 1604-1608.
Walter et al. (1994) Strand displacement amplification as an in vitro model for rolling-circle replication: deletion formation and evolution during serial transfer. Proc Natl Acad Sci USA. 91: 7937-7941.
Wang et al. (1989) Quantitation of mRNA by the polymerase chain reaction. Proc Natl Acad Sci U S A. 86(24): 9717-21.
Wang et al. (1994) Circular RNA oligonucleotide. Synthesis, nucleic acid binding properties, and a comparison with circular DNAs. Nucl. Acids. Res. 22(12): 2326-2333.
Wang et al. (1998) Large-scale identification, mapping, and genotyping of single-nucleotide polymorphisms in the human genome. Science. 280: 1077-1082.
Wang et al. (1998) Oligoribonucleotide circularization by 'template-mediated' ligation with T4 RNA ligase: synthesis of circular hammerhead ribozymes. Nucleic Acids Res. 26(10): 2502-4.
Wang et al. (2004) DNA amplification method tolerant to sample degradation. Genome Res., 14(11): 2357-66.
Wansink et al. (1993) Fluorescent labeling of nascent RNA reveals transcription by RNA polymerase II in domains scattered throughout the nucleus. Journal of Cell Biology. 122(2): 283-293.
Warnecke et al. (1997) Detection and measurement of PCR bias in quantitative methylation analysis of bisulphite-treated DNA. Nucleic Acids Res. 25(21): 4422-26.
Welford et al. (1998) Detection of differentially expressed genes in primary tumor tissues using representational differences analysis coupled to microarray hybridization. Nucleic Acids Res. 26(12): 3059-65.
Wells et al. (1999) Detailed chromosomal and molecular genetic analysis of single cells by whole genome amplification and comparative genomic hybridisation. Nucleic Acids Res. 27(4): 1214-8.
Wells et al. (2000) Comprehensive chromosomal analysis of human preimplantation embryos using whole genome amplification and single cell comparative genomic hybridization. Mol Hum Reprod. 6(11): 1055-62.
Wemmer et al. (1985) Preparation and melting of single strand circular DNA loops. Nucleic Acids Res. 13(23): 8611-21.
Wharam et al. (2001) Specific detection of DNA and RNA targets using a novel isothermic nucleic acid amplification assay based on the formation of a three-way junction structure. Nucleic Acid Research. 29(11): e54.
White et al. (1991) Concatemer chain reaction: a Taq DNA polymerase-mediated mechanism for generating long tandemly repetitive DNA sequences. Anal Biochem. 199(2): 184-90.
Whiting et al. (1994) Strand displacement synthesis capability of Moloney murine leukemia virus reverse transcriptase. J. Virol. 68(8): 4747-58.
Wiedmann et al. (1994) Ligase chain reaction (LCR)—overview and applications. PCR Methods and Applications. (Cold Spring Harbor Laboratory Press, Cold Spring Harbor, NY) [pp. S51-S64].
Wiegant et al. (1992) High-resolution in situ hybridization using DNA halo preparations. Hum Mol Genet. 1(8): 587-91.
Will et al. (1991) The synthesis of oligonucleotides that contain 2,4-dinitrophenyl reporter groups. Carbohydr Res. 216: 315-22.
Wilson et al. (1993) Enzyme complex amplification—a signal amplification method for use in enzyme immunoassays. Anal Biochem. 209(1): 183-187.
Wiltshire et al. (2000) Detection of multiple allergen-specific IgEs on microarrays by immunoassay with rolling circle amplification. Clin Chem. 46(12): 1990-1993.

(56) References Cited

OTHER PUBLICATIONS

Winn-Deen et al. (1993) Non-radioactive detection of mycobacterium tuberculosis LCR products in a microtitre plate format. Molecular and Cellular Probes. (England) 7(3): 179-186.
Wirth et al. (1995) Staining methods in gel electrophoresis, including the use of multiple detection methods. J. Chromatogr. 698: 123-143.
Wolf et al. (1997) The Cloning Debates and Progress in Biotechnology. Clinical Chemistry. 43:2019-2020.
Xu et al. (2001) Nonenzymatic autoligation in direct three-color detection of RNA and DNA point mutations. Nat Biotechnol. 19(2): 148-52.
Yang et al. (1999) Combining SSH and cDNA microarrays for rapid identification of differentially expressed genes. Nucleic Acids Res. 27(6): 1517-23.
Yates et al. (2001) Quantitative detection of hepatitis B virus DNA by real-time nucleic acid sequence-based amplification with molecular beacon detection. J Clin Microbiol. 39(10): 3656-65.
Young et al. (1985) Quantitative analysis of solution hybridization. Nucleic Acid Hybridisation: A Practical Approach. (IRL Press) pp. 47-71.
Yu et al. (1994) Cyanine dye dUTP analogs for enzymatic labeling of DNA probes. Nucleic Acids Research. 22(15): 3226-3232.
Yunis et al. (1978) The characterization of high-resolution G-banded chromosomes of man. Chromosoma. 67(4): 293-307.
Zehavi et al. (1972) Light sensitive glycosides. I. 6-nitroveratryl b-D-glucopyranoside and 2-nitrobenzyl b-D-glucopyranoside. J. Organic Chem. 37(14): 2281-2285.
Zehavi et al. (1972) Light-sensitive glycosides. II. 2-Nitrobenzyl 6-deoxy-α-L-mannopyranoside and 2-nitrobenzyl 6-deoxy-.β-L-galactopyranoside Uri. J. Org. Chem., 37 (14), pp. 2285-2288.
Zhang et al. (1990) Amplification of target-specific, ligation-dependent circular probe. Gene 211: 277-285.
Zhang et al. (1992) Whole genome amplification from a single cell: Implications for genetic analysis. Proc. Natl. Acad. Sci. USA 89: 5847-5851.
Zhang et al. (1996) Single-stranded DNA ligation by T4 RNA ligase for PCR cloning of 5'-noncoding fragments and coding sequence of a specific gene. Nucleic Acids Res. 24(5): 990-1.
Zhao et al. (1995) Assessment of stress gene mRNAs (HSP-27, 60 and 70) in obstructed rabbit urinary bladder using a semi-quantitative RT-PCR method. Mol Cell Biochem. (1): 1-7.
Zhenodarova et al. (1989) [Substrate specificity of T4 RNA-ligase. The effect of the nucleotide composition of substrates and the size of phosphate donor on the effectiveness of intermolecular ligation]. Bioorg Khim. 15(4): 478-83.
Zhu et al. (1994) Purification and characterization of PRD1 DNA polymerase. Biochimica Biophysica Acta. 1219(2): 267-276.
Zhu et al. (2001) Global Analysis of Protein Activities Using Proteome Chips. Science 293: 2101-2105.
Zijderveld et al. (1994) Helix-Destabilizing Properties of the Adenovirus DNA-Binding Protein. J. Virol. 68(2): 1158-1164.
Zirvi et al. (1999) Improved fidelity of thermostable ligases for detection of microsatellite repeat sequences using nucleoside analogs. Nucleic Acids Res. 27(24): e41.
Zirvi et al. (1999) Ligase-based detection of mononucleotide repeat sequences. Nucleic Acids Res. 27(24):e40.
Zuckermann et al. (1987) Efficient methods for attachment of thiol specific probes to the 3'-ends of synthetic oligodeoxyribonucleotides. Nucleic Acids Res. 15(13): 5305-21.
Issue Notification issued May 14, 2003 for U.S. Appl. No. 09/803,713, filed on Mar. 9, 2001 (Inventors—Alsmadi et al.).
Notice of Allowance issued Feb. 4, 2003 for U.S. Appl. No. 09/803,713, filed on Mar. 9, 2001 (Inventors—Alsmadi et al.).
Supplemental Amendment filed Jan. 23, 2003 for U.S. Appl. No. 09/803,713, filed on Mar. 9, 2001 (Inventors—Alsmadi et al.).
Response after Non-Final Action filed Nov. 5, 2002 for U.S. Appl. No. 09/803,713, filed on Mar. 9, 2001 (Inventors—Alsmadi et al.).
Non-Final Rejection issued Jun. 5, 2002 for U.S. Appl. No. 09/803,713, filed on Mar. 9, 2001 (Inventors—Alsmadi et al.).

Response to Election/Restriction filed Mar. 21, 2002 for U.S. Appl. No. 09/803,713, filed on Mar. 9, 2001 (Inventors—Alsmadi et al.).
Restriction Requirement issued Feb. 21, 2002 for U.S. Appl. No. 09/803,713, filed on Mar. 9, 2001 (Inventors—Alsmadi et al.).
Notice of Abandonment issued Mar. 8, 2007 for U.S. Appl. No. 10/325,490, filed on Dec. 19, 2002 (Alsmadi et al.).
Non-Final Rejection issued Aug. 9, 2006 for U.S. Appl. No. 10/325,490, filed on Dec. 19, 2002 (Alsmadi et al.).
Response after Non-Final Action filed May 22, 2006 for U.S. Appl. No. 10/325,490, filed on Dec. 19, 2002 (Alsmadi et al.).
Non-Final Rejection issued Jan. 24, 2006 for U.S. Appl. No. 10/325,490, filed on Dec. 19, 2002 (Alsmadi et al.).
Response to Election/Restriction filed Oct. 19, 2005 for U.S. Appl. No. 10/325,490, filed on Dec. 19, 2002 (Alsmadi et al.).
Restriction Requirement issued Sep. 16, 2005 for U.S. Appl. No. 10/325,490, filed on Dec. 19, 2002 (Alsmadi et al.).
Notice of Abandonment issued Nov. 27, 2006 for U.S. Appl. No. 10/404,944, filed on Mar. 31, 2003 (Alsmadi et al.).
Non-Final Rejection issued May 9, 2006 for U.S. Appl. No. 10/404,944, filed on Mar. 31, 2003 (Alsmadi et al.).
Response after Non-Final Action filed Mar. 2, 2006 for U.S. Appl. No. 10/404,944, filed on Mar. 31, 2003 (Alsmadi et al.).
Non-Final Rejection issued Dec. 5, 2005 for U.S. Appl. No. 10/404,944, filed on Mar. 31, 2003 (Alsmadi et al.).
Preliminary Amendment filed Mar. 31, 2003 for U.S. Appl. No. 10/404,944, filed on Mar. 31, 2003 (Alsmadi et al.).
Issue Notification issued Mar. 21, 2002 for U.S. Appl. No. 09/547,757, filed on Apr. 12, 2000 (Faruqi).
Notice of Allowance issued Aug. 31, 2001 for U.S. Appl. No. 09/547,757, filed on Apr. 12, 2000 (Faruqi).
Issue Notification issued Feb. 20, 2003 for U.S. Appl. No. 09/597,836, filed on Jun. 20, 2000 (Kingsmore et al.).
Notice of Allowance issued Nov. 17, 2002 for U.S. Appl. No. 09/597,836, filed on Jun. 20, 2000 (Kingsmore et al.).
Response to Office Action filed Sep. 18, 2002 for U.S. Appl. No. 09/597,836, filed on Jun. 20, 2000 (Kingsmore et al.).
Final Rejection issued Mar. 19, 2002 for U.S. Appl. No. 09/597,836, filed on Jun. 20, 2000 (Kingsmore et al.).
Response after Non-Final Action issued Feb. 5, 2002 for U.S. Appl. No. 09/597,836, filed on Jun. 20, 2000 (Kingsmore et al.).
Non-Final Rejection issued Nov. 5, 2001 for U.S. Appl. No. 09/597,836, filed on Jun. 20, 2000 (Kingsmore et al.).
Response after Non-Final Action filed Sep. 20, 2001 for U.S. Appl. No. 09/597,836, filed on Jun. 20, 2000 (Kingsmore et al.).
Non-Final Rejection issued Mar. 20, 2001 for U.S. Appl. No. 09/597,836, filed on Jun. 20, 2000 (Kingsmore et al.).
Response filed Oct. 23, 2000 for U.S. Appl. No. 09/597,836, filed on Jun. 20, 2000 (Kingsmore et al.).
Certificate of Correction issued Sep. 27, 2005 for U.S. Appl. No. 10/341,287, filed on Jan. 13, 2003 (Kingsmore et al.).
Request for Certificate of Correction filed Aug. 23, 2005 for U.S. Appl. No. 10/341,287, filed on Jan. 13, 2003 (Kingsmore et al.).
Issue Notification issued Jul. 6, 2005 for U.S. Appl. No. 10/341,287, filed on Jan. 13, 2003 (Kingsmore et al.).
Notice of Allowance issued Mar. 15, 2005 for U.S. Appl. No. 10/341,287, filed on Jan. 13, 2003 (Kingsmore et al.).
Response after Non-Final Action filed Jan. 4, 2005 for U.S. Appl. No. 10/341,287, filed on Jan. 13, 2003 (Kingsmore et al.).
Non-Final Rejection issued Oct. 22, 2004 for U.S. Appl. No. 10/341,287, filed on Jan. 13, 2003 (Kingsmore et al.).
Preliminary Amendment filed Jan. 13, 2003 for U.S. Appl. No. 10/341,287, filed on Jan. 13, 2003 (Kingsmore et al.).
Notice of Abandonment issued Jun. 10, 2009 for U.S. Appl. No. 11/187,537, filed on Jul. 22, 2005 (Kingsmore et al.).
Requirement for Restriction/Election issued Oct. 6, 2008 for U.S. Appl. No. 11/187,537, filed on Jul. 22, 2005 (Kingsmore et al.).
Issue Notification issued Jan. 15, 2004 for U.S. Appl. No. 09/897,259, filed on Jul. 2, 2001 (Ward et al.).
Notice of Allowance issued Jul. 1, 2003 for U.S. Appl. No. 09/897,259, filed on Jul. 2, 2001 (Ward et al.).
Response after Non-Final Rejection filed Apr. 11, 2003 for U.S. Appl. No. 09/897,259, filed on Jul. 2, 2001 (Ward et al.).

(56) References Cited

OTHER PUBLICATIONS

Non-Final Rejection issued Jan. 17, 2003 for U.S. Appl. No. 09/897,259, filed on Jul. 2, 2001 (Ward et al.).
Response to Election/Restriction filed Oct. 30, 2002 for U.S. Appl. No. 09/897,259, filed on Jul. 2, 2001 (Ward et al.).
Restriction Requirement issued Sep. 30, 2002 for U.S. Appl. No. 09/897,259, filed on Jul. 2, 2001 (Ward et al.).
Notice of Abandonment issued Nov. 14, 2007 for U.S. Appl. No. 09/910,383, filed on Jul. 20, 2001 (Nallur et al.).
Advisory Action issued May 1, 2007 for U.S. Appl. No. 09/910,383, filed on Jul. 20, 2001 (Nallur et al.).
Amendment/Argument after Notice of Appeal filed Apr. 18, 2007 for U.S. Appl. No. 09/910,383, filed on Jul. 20, 2001 (Nallur et al.).
Notice of Appeal issued Apr. 18, 2007 for U.S. Appl. No. 09/910,383, filed on Jul. 20, 2001 (Nallur et al.).
Examiner Interview Summary issued Apr. 9, 2007 for U.S. Appl. No. 09/910,383, filed on Jul. 20, 2001 (Nallur et al.).
Final Rejection issued Dec. 13, 2006 for U.S. Appl. No. 09/910,383, filed on Jul. 20, 2001 (Nallur et al.).
Response after Non-Final Action filed Sep. 29, 2006 for U.S. Appl. No. 09/910,383, filed on Jul. 20, 2001 (Nallur et al.).
Non-Final Rejection issued Jun. 15, 2006 for U.S. Appl. No. 09/910,383, filed on Jul. 20, 2001 (Nallur et al.).
Communication withdrawing Notice of Non-Compliant Amendment issued Apr. 7, 2006 for U.S. Appl. No. 09/910,383, filed on Jul. 20, 2001 (Nallur et al.).
Response after Non-Final Action filed Mar. 22, 2006 for U.S. Appl. No. 09/910,383, filed on Jul. 20, 2001 (Nallur et al.).
Advisory Action issued Dec. 13, 2005 for U.S. Appl. No. 09/910,383, filed on Jul. 20, 2001 (Nallur et al.).
Amendment after Final Rejection filed Nov. 23, 2005 for U.S. Appl. No. 09/910,383, filed on Jul. 20, 2001 (Nallur et al.).
Examiner Interview Summary Record issued Oct. 12, 2005 for U.S. Appl. No. 09/910,383, filed on Jul. 20, 2001 (Nallur et al.).
Advisory Action issued Sep. 14, 2005 for U.S. Appl. No. 09/910,383, filed on Jul. 20, 2001 (Nallur et al.).
Amendment after Final Rejection filed Aug. 26, 2005 for U.S. Appl. No. 09/910,383, filed on Jul. 20, 2001 (Nallur et al.).
Final Rejection issued May 23, 2005 for U.S. Appl. No. 09/910,383, filed on Jul. 20, 2001 (Nallur et al.).
Response after Non-Final Action filed Mar. 10, 2005 for U.S. Appl. No. 09/910,383, filed on Jul. 20, 2001 (Nallur et al.).
Non-Final Rejection issued Jan. 27, 2005 for U.S. Appl. No. 09/910,383, filed on Jul. 20, 2001 (Nallur et al.).
Response after Non-Final Action filed Nov. 19, 2004 for U.S. Appl. No. 09/910,383, filed on Jul. 20, 2001 (Nallur et al.).
Non-Final Rejection issued Jun. 23, 2004 for U.S. Appl. No. 09/910,383, filed on Jul. 20, 2001 (Nallur et al.).
Issue Notification issued Nov. 30, 2005 for U.S. Appl. No. 09/977,868, filed on Oct. 15, 2001 (Dean et al.).
Notice of Allowance issued Feb. 22, 2005 for U.S. Appl. No. 09/977,868, filed on Oct. 15, 2001 (Dean et al.).
Response after Non-Final Action filed Jan. 4, 2005 for U.S. Appl. No. 09/977,868, filed on Oct. 15, 2001 (Dean et al.).
Non-Final Rejection issued Sep. 9, 2004 for U.S. Appl. No. 09/977,868, filed on Oct. 15, 2001 (Dean et al.).
Petition for Withdrawal of Holding of Abandonment filed Feb. 13, 2004 for U.S. Appl. No. 09/977,868, filed on Oct. 15, 2001 (Dean et al.).
Preliminary Amendment filed Mar. 29, 2002 for U.S. Appl. No. 09/977,868, filed on Oct. 15, 2001 (Dean et al.).
Issue Notification issued Aug. 21, 2003 for U.S. Appl. No. 09/982,212, filed on Oct. 18, 2001 (Dean et al.).
Notice of Allowance issued May 20, 2003 for U.S. Appl. No. 09/982,212, filed on Oct. 18, 2001 (Dean et al.).
Response after Non-Final Action filed May 7, 2003 for U.S. Appl. No. 09/982,212, filed on Oct. 18, 2001 (Dean et al.).
Non-Final Rejection issued Apr. 18, 2003 for U.S. Appl. No. 09/982,212, filed on Oct. 18, 2001 (Dean et al.).
Second Preliminary Amendment filed Oct. 25, 2001 for U.S. Appl. No. 09/982,212, filed on Oct. 18, 2001 (Dean et al.).
Preliminary Amendment filed Oct. 18, 2001 for U.S. Appl. No. 09/982,212, filed on Oct. 18, 2001 (Dean et al.).
Issue Notification issued Jun. 21, 2006 for U.S. Appl. No. 10/272,465, filed on Oct. 15, 2002 (Dean et al.).
Decision on Petition to Revive issued May 22, 2006 for U.S. Appl. No. 10/272,465, filed on Oct. 15, 2002 (Dean et al.).
Petition to Revive Application filed Mar. 14, 2006 for U.S. Appl. No. 10/272,465, filed on Oct. 15, 2002 (Dean et al.).
Notice of Allowance issued Dec. 13, 2005 for U.S. Appl. No. 10/272,465, filed on Oct. 15, 2002 (Dean et al.).
Response after Non-Final Action filed Sep. 2, 2005 for U.S. Appl. No. 10/272,465, filed on Oct. 15, 2002 (Dean et al.).
Non-Final Rejection issued Aug. 5, 2005 for U.S. Appl. No. 10/272,465, filed on Oct. 15, 2002 (Dean et al.).
Issue Notification issued Oct. 31, 2007 for U.S. Appl. No. 10/429,229, filed on May 2, 2003 (Bornarth et al.).
Supplemental Notice of Allowance issued Jul. 31, 2007 for U.S. Appl. No. 10/429,229, filed on May 2, 2003 (Bornarth et al.).
Notice of Allowance issued Jun. 18, 2007 for U.S. Appl. No. 10/429,229, filed on May 2, 2003 (Bornarth et al.).
Examiner Interview Summary issued Jun. 18, 2007 for U.S. Appl. No. 10/429,229, filed on May 2, 2003 (Bornarth et al.).
Amendment after Final Rejection filed Jun. 5, 2007 for U.S. Appl. No. 10/429,229, filed on May 2, 2003 (Bornarth et al.).
Final Rejection issued Feb. 28, 2007 for U.S. Appl. No. 10/429,229, filed on May 2, 2003 (Bornarth et al.).
Response after Non-Final Action filed Dec. 14, 2006 for U.S. Appl. No. 10/429,229, filed on May 2, 2003 (Bornarth et al.).
Non-Final Rejection issued Jun. 20, 2006 for U.S. Appl. No. 10/429,229, filed on May 2, 2003 (Bornarth et al.).
Response to Election/Restriction filed Apr. 17, 2006 for U.S. Appl. No. 10/429,229, filed on May 2, 2003 (Bornarth et al.).
Restriction Requirement issued Feb. 16, 2006 for U.S. Appl. No. 10/429,229, filed on May 2, 2003 (Bornarth et al.).
Notice of Abandonment issued May 25, 2010 for U.S. Appl. No. 11/871,707, filed on Oct. 12, 2007 (Bornarth et al.).
Final Rejection issued Oct. 29, 2009 for U.S. Appl. No. 11/871,707, filed on Oct. 12, 2007 (Bornarth et al.).
Response after Non-Final Rejection filed Jun. 22, 2009 for U.S. Appl. No. 11/871,707, filed on Oct. 12, 2007 (Bornarth et al.).
Non-Final Rejection issued Jan. 28, 2009 for U.S. Appl. No. 11/871,707, filed on Oct. 12, 2007 (Bornarth et al.).
Preliminary Amendment filed Jan. 31, 2008 for U.S. Appl. No. 11/871,707, filed on Oct. 12, 2007 (Bornarth et al.).
Issue Notification issued Oct. 20, 2000 for U.S. Appl. No. 08/754,681, filed on Nov. 21, 1996 (Lizardi et al.).
Notice of Allowance issued Mar. 28, 2000 for U.S. Appl. No. 08/754,681, filed on Nov. 21, 1996 (Lizardi et al.).
Notice of Appeal filed Feb. 4, 2000 for U.S. Appl. No. 08/754,681, filed on Nov. 21, 1996 (Lizardi et al.).
Amendment after Final Rejection filed Dec. 28, 1999 for U.S. Appl. No. 08/754,681, filed on Nov. 21, 1996 (Lizardi et al.).
Final Rejection issued Aug. 4, 1999 for U.S. Appl. No. 08/754,681, filed on Nov. 21, 1996 (Lizardi et al.).
Supplemental Response filed Apr. 12, 1999 for U.S. Appl. No. 08/754,681, filed on Nov. 21, 1996 (Lizardi et al.).
Response after Non-Final Action filed Apr. 1, 1999 for U.S. Appl. No. 08/754,681, filed on Nov. 21, 1996 (Lizardi et al.).
Non-Final Rejection issued Oct. 1, 1998 for U.S. Appl. No. 08/754,681, filed on Nov. 21, 1996 (Lizardi et al.).
Response after Non-Final Action filed Jul. 6, 1998 for U.S. Appl. No. 08/754,681, filed on Nov. 21, 1996 (Lizardi et al.).
Non-Final Rejection issued Jan. 6, 1998 for U.S. Appl. No. 08/754,681, filed on Nov. 21, 1996 (Lizardi et al.).
Response after Non-Final Action filed Oct. 21, 1997 for U.S. Appl. No. 08/754,681, filed on Nov. 21, 1996 (Lizardi et al.).
Restriction Requirement issued Jun. 17, 1997 for U.S. Appl. No. 08/754,681, filed on Nov. 21, 1996 (Lizardi et al.).
Issue Notification issued Nov. 21, 2001 for U.S. Appl. No. 09/602,428, filed on Jun. 23, 2000 (Lizardi et al.).

(56) References Cited

OTHER PUBLICATIONS

Notice of Allowance issued Jun. 28, 2001 for U.S. Appl. No. 09/602,428, filed on Jun. 23, 2000 (Lizardi et al.).
Response after Non-Final Action filed Apr. 9, 2001 for U.S. Appl. No. 09/602,428, filed on Jun. 23, 2000 (Lizardi et al.).
Non-Final Rejection issued Nov. 22, 2000 for U.S. Appl. No. 09/602,428, filed on Jun. 23, 2000 (Lizardi et al.).
Preliminary Amendment filed Jun. 23, 2000 for U.S. Appl. No. 09/602,428, filed on Jun. 23, 2000 (Lizardi et al.).
Issue Notification issued Sep. 25, 2003 for U.S. Appl. No. 09/841,513, filed on Apr. 24, 2001 (Lizardi).
Notice of Allowance issued Jan. 16, 2003 for U.S. Appl. No. 09/841,513, filed on Apr. 24, 2001 (Lizardi).
Response after Non-Final Action filed Oct. 18, 2002 for U.S. Appl. No. 09/841,513, filed on Apr. 24, 2001 (Lizardi).
Non-Final Rejection issued Apr. 30, 2002 for U.S. Appl. No. 09/841,513, filed on Apr. 24, 2001 (Lizardi).
Preliminary Amendment filed Apr. 24, 2001 for U.S. Appl. No. 09/841,513, filed on Apr. 24, 2001 (Lizardi).
Notice of Abandonment issued Apr. 5, 2006 for U.S. Appl. No. 10/413,041, filed on Apr. 10, 2003 (Lizardi et al.).
Restriction Requirement issued Sep. 22, 2005 for U.S. Appl. No. 10/413,041, filed on Apr. 10, 2003 (Lizard et al.).
Decision on Petition issued Jul. 3, 2003 for U.S. Appl. No. 10/413,041, filed on Apr. 10, 2003 (Lizard et al.).
Petition to Correct Filing Date filed May 8, 2003 for U.S. Appl. No. 10/413,041, filed on Apr. 10, 2003 (Lizard et al.).
Preliminary Amendment filed Apr. 10, 2003 for U.S. Appl. No. 10/413,041, filed on Apr. 10, 2003 (Lizardi et al.).
Issue Notification issued Jun. 10, 2009 for U.S. Appl. No. 10/072,666, filed on Feb. 8, 2002 (Kumar et al.).
Notice of Allowance issued Jan. 27, 2009 for U.S. Appl. No. 10/072,666, filed on Feb. 8, 2002 (Kumar et al.).
Notice of Allowance issued Sep. 26, 2008 for U.S. Appl. No. 10/072,666, filed on Feb. 8, 2002 (Kumar et al.).
Amendment after Final Rejection filed Sep. 10, 2008 for U.S. Appl. No. 10/072,666, filed on Feb. 8, 2002 (Kumar et al.).
Final Rejection issued Jul. 15, 2008 for U.S. Appl. No. 10/072,666, filed on Feb. 8, 2002 (Kumar et al.).
Response to Non-Final Action filed Apr. 30, 2008 for U.S. Appl. No. 10/072,666, filed on Feb. 8, 2002 (Kumar et al.).
Non-Final Rejection issued Feb. 1, 2008 for U.S. Appl. No. 10/072,666, filed on Feb. 8, 2002 (Kumar et al.).
Response after Non-Final Action filed Nov. 15, 2007 for U.S. Appl. No. 10/072,666, filed on Feb. 8, 2002 (Kumar et al.).
Non-Final Rejection issued Jul. 9, 2007 for U.S. Appl. No. 10/072,666, filed on Feb. 8, 2002 (Kumar et al.).
Response after Non-Final Action filed Apr. 24, 2007 for U.S. Appl. No. 10/072,666, filed on Feb. 8, 2002 (Kumar et al.).
Non-Final Rejection issued Jan. 24, 2007 for U.S. Appl. No. 10/072,666, filed Feb. 8, 2002 (Kumar et al.).
Response to Office Action filed Nov. 30, 2006 for U.S. Appl. No. 10/072,666, filed on Feb. 8, 2002 (Kumar et al.).
Advisory Action issued Nov. 8, 2006 for U.S. Appl. No. 10/072,666, filed on Feb. 8, 2002 (Kumar et al.).
Amendment after Final Rejection filed Oct. 20, 2006 for U.S. Appl. No. 10/072,666, filed on Feb. 8, 2002 (Kumar et al.).
Final Rejection issued Jul. 31, 2006 for U.S. Appl. No. 10/072,666, filed on Feb. 8, 2002 (Kumar et al.).
Response after Non-Final Action issued May 12, 2006 for U.S. Appl. No. 10/072,666, filed on Feb. 8, 2002 (Kumar et al.).
Non-Final Rejection issued Jan. 27, 2006 for U.S. Appl. No. 10/072,666, filed on Feb. 8, 2002 (Kumar et al.).
Response to Office Action issued Nov. 11, 2005 for U.S. Appl. No. 10/072,666, filed on Feb. 8, 2002 (Kumar et al.).
Final Rejection issued Jul. 11, 2005 for U.S. Appl. No. 10/072,666, filed on Feb. 8, 2002 (Kumar et al.).
Response after Non-Final Action filed Apr. 25, 2005 for U.S. Appl. No. 10/072,666, filed on Feb. 8, 2002 (Kumar et al.).
Non-Final Rejection issued Feb. 10, 2005 for U.S. Appl. No. 10/072,666, filed on Feb. 8, 2002 (Kumar et al.).
Response after Non-Final Action filed Aug. 4, 2004 for U.S. Appl. No. 10/072,666, filed on Feb. 8, 2002 (Kumar et al.).
Non-Final Rejection issued Apr. 19, 2004 for U.S. Appl. No. 10/072,666, filed on Feb. 8, 2002 (Kumar et al.).
Response after Non-Final Action filed Nov. 10, 2003 for U.S. Appl. No. 10/072,666, filed on Feb. 8, 2002 (Kumar et al.).
Non-Final Rejection issued May 8, 2003 for U.S. Appl. No. 10/072,666, filed on Feb. 8, 2002 (Kumar et al.).
Issue Notification issued Nov. 25, 2004 for U.S. Appl. No. 09/460,078, filed on Dec. 14, 1999 (Hather et al.).
Notice of Allowance issued Jul. 14, 2004 for U.S. Appl. No. 09/460,078, filed on Dec. 14, 1999 (Hather et al.).
Amendment after Final Rejection filed Jun. 14, 2004 for U.S. Appl. No. 09/460,078, filed on Dec. 14, 1999 (Hafner et al.).
Examiner Interview Summary issued May 25, 2004 for U.S. Appl. No. 09/460,078, filed on Dec. 14, 1999 (Hafner et al.).
Final Rejection issued Feb. 13, 2004 for U.S. Appl. No. 09/460,078, filed on Dec. 14, 1999 (Hafner et al.).
Response after Non-Final Action filed Nov. 19, 2003 for U.S. Appl. No. 09/460,078, filed on Dec. 14, 1999 (Hafner et al.).
Non-Final Rejection issued May 19, 2003 for U.S. Appl. No. 09/460,078, filed on Dec. 14, 1999 (Hafner et al.).
Response after Non-Final Action filed Jan. 14, 2003 for U.S. Appl. No. 09/460,078, filed on Dec. 14, 1999 (Hafner et al.).
Non-Final Rejection issued Sep. 4, 2002 for U.S. Appl. No. 09/460,078, filed on Dec. 14, 1999 (Hafner et al.).
Amendment and Response filed Jun. 17, 2002 for U.S. Appl. No. 09/460,078, filed on Dec. 14, 1999 (Hafner et al.).
Notice of Appeal filed Jan. 17, 2002 for U.S. Appl. No. 09/460,078, filed on Dec. 14, 1999 (Hafner et al.).
Final Rejection issued Jul. 17, 2001 for U.S. Appl. No. 09/460,078, filed on Dec. 14, 1999 (Hafner et al.).
Response after Non-Final Action filed May 21, 2001 for U.S. Appl. No. 09/460,078, filed on Dec. 14, 1999 (Hafner et al.).
Non-Final Rejection issued Nov. 20, 2000 for U.S. Appl. No. 09/460,078, filed on Dec. 14, 1999 (Hafner et al.).
Response to Election/Restriction filed Mar. 29, 2000 for U.S. Appl. No. 09/460,078, filed on Dec. 14, 1999 (Hafner et al.).
Restriction Requirement issued Jun. 30, 2000 for U.S. Appl. No. 09/460,078, filed on Dec. 14, 1999 (Hafner et al.).
Issue Notification issued Mar. 26, 2008 for U.S. Appl. No. 10/917,580, filed on Aug. 13, 2004 (Hafner et al.).
Notice of Allowance issued Nov. 30, 2007 for U.S. Appl. No. 10/917,580, filed on Aug. 13, 2004 (Hafner et al.).
Response after Non-Final Action filed Oct. 1, 2007 for U.S. Appl. No. 10/917,580, filed on Aug. 13, 2004 (Hafner et al.).
Non-Final Rejection issued Jun. 25, 2007 for U.S. Appl. No. 10/917,580, filed on Aug. 13, 2004 (Hafner et al.).
Response to Election/Restriction filed May 10, 2007 for U.S. Appl. No. 10/917,580, filed on Aug. 13, 2004 (Hafner et al.).
Restriction Requirement issued Jan. 11, 2007 for U.S. Appl. No. 10/917,580, filed on Aug. 13, 2004 (Hafner et al.).
Second Preliminary Amendment filed Nov. 15, 2004 for U.S. Appl. No. 10/917,580, filed on Aug. 13, 2004 (Hafner et al.).
Preliminary Amendment filed Aug. 13, 2004 for U.S. Appl. No. 10/917,580, filed on Aug. 13, 2004 (Hafner et al.).
Notice of Abandonment issued Nov. 13, 2008 for U.S. Appl. No. 10/325,665, filed on Dec. 19, 2002 (Alsmadi et al.).
Non-Final Rejection issued Apr. 17, 2008 for U.S. Appl. No. 10/325,665, filed on Dec. 19, 2002 (Alsmadi et al.).
Non-Final Rejection issued Oct. 25, 2007 for U.S. Appl. No. 10/325,665, filed on Dec. 19, 2002 (Alsmadi et al.).
Amendment/Argument with Notice of Appeal filed Sep. 25, 2007 for U.S. Appl. No. 10/325,665, filed on Dec. 19, 2002 (Alsmadi et al.).
Final Rejection issued Mar. 26, 2007 for U.S. Appl. No. 10/325,665, filed on Dec. 19, 2002 (Alsmadi et al.).
Response after Non-Final Action filed Dec. 22, 2006 for U.S. Appl. No. 10/325,665, filed on Dec. 19, 2002 (Alsmadi et al.).
Non-Final Rejection issued Aug. 3, 2006 for U.S. Appl. No. 10/325,665, filed on Dec. 19, 2002 (Alsmadi et al.).

(56) References Cited

OTHER PUBLICATIONS

Response after Non-Final Action filed Apr. 13, 2006 for U.S. Appl. No. 10/325,665, filed on Dec. 19, 2002 (Alsmadi et al.).
Non-Final Rejection issued Dec. 30, 2005 for U.S. Appl. No. 10/325,665, filed on Dec. 19, 2002 (Alsmadi et al.).
Response to Election / Restriction filed Sep. 21, 2005 for U.S. Appl. No. 10/325,665, filed on Dec. 19, 2002 (Alsmadi et al.).
Restriction Requirement issued Apr. 21, 2005 for U.S. Appl. No. 10/325,665, filed on Dec. 19, 2002 (Alsmadi et al.).
Issue Notification issued Nov. 30, 2005 for U.S. Appl. No. 10/335,573, filed on Dec. 31, 2002 (Kumar et al.).
Notice of Allowance issued Mar. 29, 2005 for U.S. Appl. No. 10/335,573, filed on Dec. 31, 2002 (Kumar et al.).
Response after Non-Final Action filed Dec. 1, 2004 for U.S. Appl. No. 10/335,573, filed on Dec. 31, 2002 (Kumar et al.).
Non-Final Rejection issued Jul. 29, 2004 for U.S. Appl. No. 10/335,573, filed on Dec. 31, 2002 (Kumar et al.).
Notice of Abandonment issued May 12, 2008 for U.S. Appl. No. 11/201,339, filed on Aug. 10, 2005 (Kumar et al.).
Restriction Requirement issued Sep. 25, 2007 for U.S. Appl. No. 11/201,339, filed on Aug. 10, 2005 (Kumar et al.).
Preliminary Amendment filed Aug. 10, 2005 for U.S. Appl. No. 11/201,339, filed on Aug. 10, 2005 (Kumar et al.).
Response to Final Rejection filed May 26, 2010 for U.S. Appl. No. 10/327,602, filed on Dec. 20, 2002 (Lasken).
Notice of Appeal issued Apr. 27, 2010 for U.S. Appl. No. 10/327,602, filed on Dec. 20, 2002 (Lasken).
Interview Summary issued Dec. 24, 2009 for U.S. Appl. No. 10/327,602, filed on Dec. 20, 2002 (Lasken).
Supplemental Non-Final Rejection issued Oct. 27, 2009 for U.S. Appl. No. 10/327,602, filed on Dec. 20, 2002 (Lasken).
Non-Final Rejection issued Oct. 15, 2009 for U.S. Appl. No. 10/327,602, filed on Dec. 20, 2002 (Lasken).
Amendment and Response to Final Office Action filed Sep. 10, 2009 for U.S. Appl. No. 10/327,602, filed on Dec. 20, 2002 (Lasken).
Final Rejection issued Jun. 10, 2009 for U.S. Appl. No. 10/327,602, filed on Dec. 20, 2002 (Lasken).
Amendment and Response filed Mar. 31, 2009 for U.S. Appl. No. 10/327,602, filed on Dec. 20, 2002 (Lasken).
Non-Final Rejection issued Jan. 6, 2009 for U.S. Appl. No. 10/327,602, filed on Dec. 20, 2002 (Lasken).
Response after Final Rejection filed Dec. 11, 2008 for U.S. Appl. No. 10/327,602, filed on Dec. 20, 2002 (Lasken).
Advisory Action issued Nov. 26, 2008 for U.S. Appl. No. 10/327,602, filed on Dec. 20, 2002 (Lasken).
Amendment after Final Rejection filed Nov. 10, 2008 for U.S. Appl. No. 10/327,602, filed on Dec. 20, 2002 (Lasken).
Final Rejection issued Aug. 12, 2008 for U.S. Appl. No. 10/327,602, filed on Dec. 20, 2002 (Lasken).
Response after Final Rejection filed May 15, 2008 for U.S. Appl. No. 10/327,602, filed on Dec. 20, 2002 (Lasken).
Non-Final Rejection issued Jan. 17, 2008 for U.S. Appl. No. 10/327,602, filed on Dec. 20, 2002 (Lasken).
Amendment after Final Rejection filed Oct. 25, 2007 for U.S. Appl. No. 10/327,602, filed on Dec. 20, 2002 (Lasken).
Advisory Action issued Oct. 16, 2007 for U.S. Appl. No. 10/327,602, filed on Dec. 20, 2002 (Lasken).
Amendment after Final filed Oct. 1, 2007 for U.S. Appl. No. 10/327,602, filed on Dec. 20, 2002 (Lasken).
Final Rejection issued May 23, 2007 for U.S. Appl. No. 10/327,602, filed on Dec. 20, 2002 (Lasken).
Response after Non-Final Rejection filed Mar. 15, 2007 for U.S. Appl. No. 10/327,602, filed on Dec. 20, 2002 (Lasken).
Non-Final Rejection issued Nov. 14, 2006 for U.S. Appl. No. 10/327,602, filed on Dec. 20, 2002 (Lasken).
Response after Non-Final Rejection filed Aug. 24, 2006 for U.S. Appl. No. 10/327,602, filed on Dec. 20, 2002 (Lasken).
Restriction Requirement issued Jun. 26, 2006 for U.S. Appl. No. 10/327,602, filed on Dec. 20, 2002 (Lasken).
Notice of Allowance issued Jun. 13, 2011 for U.S. Appl. No. 10/405,822, filed on Mar. 31, 2003 (Abarzua et al.).
Notice of Allowance issued Feb. 4, 2011 for U.S. Appl. No. 10/405,822, filed on Mar. 31, 2003 (Abarzua et al.).
Examiner Interview Summary issued Jan. 25, 2011 for U.S. Appl. No. 10/405,822, filed on Mar. 31, 2003 (Abarzua et al.).
Response to Final Rejection filed Jan. 13, 2011 for U.S. Appl. No. 10/405,822, filed on Mar. 31, 2003 (Abarzua et al.).
Final Rejection issued Dec. 8, 2010 for U.S. Appl. No. 10/405,822, filed on Mar. 31, 2003 (Abarzua et al.).
Response to Final Rejection filed Sep. 3, 2010 for U.S. Appl. No. 10/405,822, filed on Mar. 31, 2003 (Abarzua et al.).
Examiner Interview Summary issued Aug. 18, 2010 for U.S. Appl. No. 10/405,822, filed on Mar. 31, 2003 (Abarzua et al.).
Final Rejection issued Mar. 4, 2010 for U.S. Appl. No. 10/405,822, filed on Mar. 31, 2003 (Abarzua et al.).
Response after Non-Final Rejection filed Nov. 25, 2009 for U.S. Appl. No. 10/405,822, filed on Mar. 31, 2003 (Abarzua et al.).
Non-Final Rejection issued Jun. 1, 2009 for U.S. Appl. No. 10/405,822, filed on Mar. 31, 2003 (Abarzua et al.).
Response after Final Rejection filed Mar. 11, 2009 for U.S. Appl. No. 10/405,822, filed on Mar. 31, 2003 (Abarzua et al.).
Advisory Action issued Feb. 27, 2009 for U.S. Appl. No. 10/405,822, filed on Mar. 31, 2003 (Abarzua et al.).
Response after Final Rejection filed Feb. 11, 2009 for U.S. Appl. No. 10/405,822, filed on Mar. 31, 2003 (Abarzua et al.).
Examiner Interview Summary issued Dec. 15, 2008 for U.S. Appl. No. 10/405,822, filed on Mar. 31, 2003 (Abarzua et al.).
Final Rejection issued Sep. 11, 2008 for U.S. Appl. No. 10/405,822, filed on Mar. 31, 2003 (Abarzua et al.).
Response to Non-Final Rejection filed May 30, 2008 for U.S. Appl. No. 10/405,822, filed on Mar. 31, 2003 (Abarzua et al.).
Non-Final Rejection issued Mar. 28, 2008 for U.S. Appl. No. 10/405,822, filed on Mar. 31, 2003 (Abarzua et al.).
Response after Final Rejection filed Dec. 28, 2007 for U.S. Appl. No. 10/405,822, filed on Mar. 31, 2003 (Abarzua et al.).
Advisory Action issued Nov. 9, 2007 for U.S. Appl. No. 10/405,822, filed on Mar. 31, 2003 (Abarzua et al.).
Response after Final Rejection with Notice of Appeal filed Oct. 30, 2007 for U.S. Appl. No. 10/405,822, filed on Mar. 31, 2003 (Abarzua et al.).
Final Rejection issued Apr. 30, 2007 for U.S. Appl. No. 10/405,822, filed on Mar. 31, 2003 (Abarzua et al.).
Response after Non-Final Action filed Jan. 23, 2007 for U.S. Appl. No. 10/405,822, filed on Mar. 31, 2003 (Abarzua et al.).
Non-Final Rejection issued Aug. 2, 2006 for U.S. Appl. No. 10/405,822, filed on Mar. 31, 2003 (Abarzua et al.).
Response to Election/Restriction filed May 31, 2006 for U.S. Appl. No. 10/405,822, filed on Mar. 31, 2003 (Abarzua et al.).
Restriction Requirement issued Dec. 13, 2005 for U.S. Appl. No. 10/405,822, filed on Mar. 31, 2003 (Abarzua et al.).
Notice of Abandonment issued Jun. 5, 2009 for U.S. Appl. No. 10/454,946, filed on Jun. 4, 2003 (Feaver et al.).
Non-Final Rejection issued Nov. 26, 2008 for U.S. Appl. No. 10/454,946, filed on Jun. 4, 2003 (Feaver et al.).
Amendment and Response filed Aug. 29, 2008 for U.S. Appl. No. 10/454,946, filed on Jun. 4, 2003 (Feaver et al.).
Examiner Interview Summary issued Aug. 8, 2008 for U.S. Appl. No. 10/454,946, filed on Jun. 4, 2003 (Feaver et al.).
Advisory Action issued Mar. 25, 2008 for U.S. Appl. No. 10/454,946, filed on Jun. 4, 2003 (Feaver et al.).
Notice of Appeal filed Mar. 17, 2008 for U.S. Appl. No. 10/454,946, filed on Jun. 4, 2003 (Feaver et al.).
Amendment after Final filed Feb. 8, 2008 for U.S. Appl. No. 10/454,946, filed on Jun. 4, 2003 (Feaver et al.).
Examiner Interview Summary issued Jan. 29, 2008 for U.S. Appl. No. 10/454,946, filed on Jun. 4, 2003 (Feaver et al.).
Final Rejection issued Sep. 18, 2007 for U.S. Appl. No. 10/454,946, filed on Jun. 4, 2003 (Feaver et al.).
Response after Non-Final Action filed Jul. 5, 2007 for U.S. Appl. No. 10/454,946, filed on Jun. 4, 2003 (Feaver et al.).
Non-Final Rejection issued Feb. 9, 2007 for U.S. Appl. No. 10/454,946, filed on Jun. 4, 2003 (Feaver et al.).

(56) References Cited

OTHER PUBLICATIONS

Response after Non-Final Action filed Nov. 16, 2006 for U.S. Appl. No. 10/454,946, filed on Jun. 4, 2003 (Feaver et al.).
Non-Final Rejection issued Jul. 26, 2006 for U.S. Appl. No. 10/454,946, filed on Jun. 4, 2003 (Feaver et al.).
Response to Election/Restriction filed May 3, 2006 for U.S. Appl. No. 10/454,946, filed on Jun. 4, 2003 (Feaver et al.).
Restriction Requirement issued Feb. 6, 2006 for U.S. Appl. No. 10/454,946, filed on Jun. 4, 2003 (Feaver et al.).
Issue Notification issued May 18, 2011 for U.S. Appl. No. 10/456,056, filed on Jun. 6, 2003 (Kumar et al.).
Notice of Allowance issued Apr. 1, 2011 for U.S. Appl. No. 10/456,056, filed on Jun. 6, 2003 (Kumar et al.).
Notice of Allowance issued Jan. 25, 2011 for U.S. Appl. No. 10/456,056, filed on Jun. 6, 2003 (Kumar et al.).
Response after Non-Final Action filed Dec. 13, 2010 for U.S. Appl. No. 10/456,056, filed on Jun. 6, 2003 (Kumar et al.).
Notice of Non-Compliant Amendment issued Dec. 7, 2010 for U.S. Appl. No. 10/456,056, filed on Jun. 6, 2003 (Kumar et al.).
Response to Final Rejection filed Nov. 23, 2010 for U.S. Appl. No. 10/456,056, filed on Jun. 6, 2003 (Kumar et al.).
Non-Final Rejection issued Jun. 24, 2010 for U.S. Appl. No. 10/456,056, filed on Jun. 6, 2003 (Kumar et al.).
Response after Final Rejection filed Feb. 4, 2010 for U.S. Appl. No. 10/456,056, filed on Jun. 6, 2003 (Kumar et al.).
Examiner Interview Summary issued Nov. 17, 2009 for U.S. Appl. No. 10/456,056, filed on Jun. 6, 2003 (Kumar et al.).
Final Rejection issued Aug. 4, 2009 for U.S. Appl. No. 10/456,056, filed on Jun. 6, 2003 (Kumar et al.).
Response to Final Rejection filed May 27, 2009 for U.S. Appl. No. 10/456,056, filed on Jun. 6, 2003 (Kumar et al.).
Final Rejection issued Feb. 12, 2009 for U.S. Appl. No. 10/456,056, filed on Jun. 6, 2003 (Kumar et al.).
Response after Non-Final Action filed Oct. 23, 2008 for U.S. Appl. No. 10/456,056, filed on Jun. 6, 2003 (Kumar et al.).
Non-Final Rejection issued Aug. 8, 2008 for U.S. Appl. No. 10/456,056, filed on Jun. 6, 2003 (Kumar et al.).
Response to Final Rejection filed Apr. 7, 2008 for U.S. Appl. No. 10/456,056, filed on Jun. 6, 2003 (Kumar et al.).
Response to Final Rejection filed Mar. 7, 2008 for U.S. Appl. No. 10/456,056, filed on Jun. 6, 2003 (Kumar et al.).
Notice of Appeal filed Sep. 6, 2007 for U.S. Appl. No. 10/456,056, filed on Jun. 6, 2003 (Kumar et al.).
Examiner Interview Summary issued Apr. 17, 2007 for U.S. Appl. No. 10/456,056, filed on Jun. 6, 2003 (Kumar et al.).
Final Rejection issued Mar. 6, 2007 for U.S. Appl. No. 10/456,056, filed on Jun. 6, 2003 (Kumar et al.).
Response after Non-Final Action filed Dec. 7, 2006 for U.S. Appl. No. 10/456,056, filed on Jun. 6, 2003 (Kumar et al.).
Non-Final Rejection issued Aug. 2, 2006 for U.S. Appl. No. 10/456,056, filed on Jun. 6, 2003 (Kumar et al.).
Response to Election/Restriction filed May 12, 2006 for U.S. Appl. No. 10/456,056, filed on Jun. 6, 2003 (Kumar et al.).
Requirement for Restriction/Election issued Feb. 23, 2006 for U.S. Appl. No. 10/456,056, filed on Jun. 6, 2003 (Kumar et al.).
Issue Notification issued Nov. 9, 2001 for U.S. Appl. No. 09/605,192, filed on Jun. 28, 2000 (Lasken et al.).
Response to 312 Amendment issued Aug. 17, 2001 for U.S. Appl. No. 09/605,192, filed on Jun. 28, 2000 (Lasken et al.).
Amendment after Notice of Allowance filed Jul. 31, 2001 for U.S. Appl. No. 09/605,192, filed on Jun. 28, 2000 (Lasken et al.).
Notice of Allowance issued May 11, 2001 for U.S. Appl. No. 09/605,192, filed on Jun. 28, 2000 (Lasken et al.).
Response after Non-Final Action filed Mar. 16, 2001 for U.S. Appl. No. 09/605,192, filed on Jun. 28, 2000 (Lasken et al.).
Non-Final Rejection issued Nov. 16, 2000 for U.S. Appl. No. 09/605,192, filed on Jun. 28, 2000 (Lasken et al.).
Notice of Abandonment issued May 27, 2009 for U.S. Appl. No. 09/920,571, filed on Jul. 31, 2001 (Lasken et al.).
Final Rejection issued Sep. 15, 2008 for U.S. Appl. No. 09/920,571, filed on Jul. 31, 2001 (Lasken et al.).
Response after Non-Final Action filed Jul. 2, 2008 for U.S. Appl. No. 09/920,571, filed on Jul. 31, 2001 (Lasken et al.).
Non-Final Rejection issued Mar. 17, 2008 for U.S. Appl. No. 09/920,571, filed on Jul. 31, 2001 (Lasken et al.).
Response after Non-Final Action filed Dec. 27, 2007 for U.S. Appl. No. 09/920,571, filed on Jul. 31, 2001 (Lasken et al.).
Non-Final Rejection issued Jun. 28, 2007 for U.S. Appl. No. 09/920,571, filed on Jul. 31, 2001 (Lasken et al.).
Response to Election/Restriction filed May 7, 2007 for U.S. Appl. No. 09/920,571, filed on Jul. 31, 2001 (Lasken et al.).
Restriction Requirement issued Mar. 6, 2007 for U.S. Appl. No. 09/920,571, filed on Jul. 31, 2001 (Lasken et al.).
Response to Final Rejection filed Dec. 7, 2006 for U.S. Appl. No. 09/920,571, filed on Jul. 31, 2001 (Lasken et al.).
Final Rejection issued Jun. 12, 2006 for U.S. Appl. No. 09/920,571, filed on Jul. 31, 2001 (Lasken et al.).
Response after Non-Final Action filed Mar. 27, 2006 for U.S. Appl. No. 09/920,571, filed on Jul. 31, 2001 (Lasken et al.).
Non-Final Rejection issued Nov. 1, 2005 for U.S. Appl. No. 09/920,571, filed on Jul. 31, 2001 (Lasken et al.).
Response to Final Rejection filed Aug. 15, 2005 for U.S. Appl. No. 09/920,571, filed on Jul. 31, 2001 (Lasken et al.).
Advisory Action issued Jun. 20, 2005 for U.S. Appl. No. 09/920,571, filed on Jul. 31, 2001 (Lasken et al.).
Response to Final Rejection with Notice of Appeal filed May 31, 2005 for U.S. Appl. No. 09/920,571, filed on Jul. 31, 2001 (Lasken et al.).
Final Rejection issued Feb. 14, 2005 for U.S. Appl. No. 09/920,571, filed on Jul. 31, 2001 (Lasken et al.).
Response after Non-Final Action filed Nov. 22, 2004 for U.S. Appl. No. 09/920,571, filed on Jul. 31, 2001 (Lasken et al.).
Non-Final Rejection issued Aug. 25, 2004 for U.S. Appl. No. 09/920,571, filed on Jul. 31, 2001 (Lasken et al.).
Advisory Action issued Jun. 23, 2004 for U.S. Appl. No. 09/920,571, filed on Jul. 31, 2001 (Lasken et al.).
Response to Final Rejection with Notice of Appeal filed May 25, 2004 for U.S. Appl. No. 09/920,571, filed on Jul. 31, 2001 (Lasken et al.).
Final Rejection issued Feb. 18, 2004 for U.S. Appl. No. 09/920,571, filed on Jul. 31, 2001 (Lasken et al.).
Response after Non-Final Action filed Oct. 15, 2003 for U.S. Appl. No. 09/920,571, filed on Jul. 31, 2001 (Lasken et al.).
Miscellaneous Communication issued Oct. 7, 2003 for U.S. Appl. No. 09/920,571, filed on Jul. 31, 2001 (Lasken et al.).
Response after Non-Final Action filed Jun. 12, 2003 for U.S. Appl. No. 09/920,571, filed on Jul. 31, 2001 (Lasken et al.).
Non-Final Rejection issued Dec. 20, 2002 for U.S. Appl. No. 09/920,571, filed on Jul. 31, 2001 (Lasken et al.).
Supplemental Response filed Sep. 27, 2002 for U.S. Appl. No. 09/920,571, filed on Jul. 31, 2001 (Lasken et al.).
Supplemental Response filed Sep. 16, 2002 for U.S. Appl. No. 09/920,571, filed on Jul. 31, 2001 (Lasken et al.).
Notice of Informal or Non-Responsive Amendment issued Aug. 27, 2002 for U.S. Appl. No. 09/920,571, filed on Jul. 31, 2001 (Lasken et al.).
Response after Non-Final Action filed Jun. 12, 2002 for U.S. Appl. No. 09/920,571, filed on Jul. 31, 2001 (Lasken et al.).
Non-Final Rejection issued Dec. 12, 2001 for U.S. Appl. No. 09/920,571, filed on Jul. 31, 2001 (Lasken et al.).
Preliminary Amendment filed Aug. 1, 2001 for U.S. Appl. No. 09/920,571, filed on Jul. 31, 2001 (Lasken et al.).
Request for Certificate of Correction filed Aug. 27, 2002 for U.S. Appl. No. 09/577,444, filed on May 24, 2000 (Kingsmore et al.).
Issue Notification issued Aug. 30, 2001 for U.S. Appl. No. 09/577,444, filed on May 24, 2000 (Kingsmore et al.).
Notice of Allowance issued Mar. 29, 2001 for U.S. Appl. No. 09/577,444, filed on May 24, 2000 (Kingsmore et al.).
Decision regarding Certificate of Correction issued Mar. 22, 2004 for U.S. Appl. No. 09/897,665, filed on Jul. 2, 2001 (Kingsmore et al.).

(56) References Cited

OTHER PUBLICATIONS

Request for Certificate of Correction filed Feb. 25, 2004 for U.S. Appl. No. 09/897,665, filed on Jul. 2, 2001 (Kingsmore et al.).
Issue Notification issued Dec. 11, 2003 for U.S. Appl. No. 09/897,665, filed on Jul. 2, 2001 (Kingsmore et al.).
Notice of Allowance issued Jul. 30, 2003 for U.S. Appl. No. 09/897,665, filed on Jul. 2, 2001 (Kingsmore et al.).
Notice of Appeal filed May 27, 2003 for U.S. Appl. No. 09/897,665, filed on Jul. 2, 2001 (Kingsmore et al.).
Response to Final Rejection and Terminal Disclaimer filed May 27, 2003 for U.S. Appl. No. 09/897,665, filed on Jul. 2, 2001 (Kingsmore et al.).
Final Rejection issued Feb. 25, 2003 for U.S. Appl. No. 09/897,665, filed on Jul. 2, 2001 (Kingsmore et al.).
Response after Non-Final Action filed Dec. 4, 2002 for U.S. Appl. No. 09/897,665, filed on Jul. 2, 2001 (Kingsmore et al.).
Non-Final Rejection issued Jul. 19, 2002 for U.S. Appl. No. 09/897,665, filed on Jul. 2, 2001 (Kingsmore et al.).
Preliminary Amendment filed Jul. 2, 2001 for U.S. Appl. No. 09/897,665, filed on Jul. 2, 2001 (Kingsmore et al.).
Issue Notification issued Oct. 2, 2003 for U.S. Appl. No. 09/910,372, filed on Jul. 20, 2001 (Bandaru et al.).
Notice of Allowance issued Apr. 8, 2003 for U.S. Appl. No. 09/910,372, filed on Jul. 20, 2001 (Bandaru et al.).
Supplemental Response filed Mar. 20, 2003 for U.S. Appl. No. 09/910,372, filed on Jul. 20, 2001 (Bandaru et al.).
Amendment and Response filed Jan. 17, 2003 for U.S. Appl. No. 09/910,372, filed on Jul. 20, 2001 (Bandaru et al.).
Non-Final Rejection issued Nov. 13, 2002 for U.S. Appl. No. 09/910,372, filed on Jul. 20, 2001 (Bandaru et al.).
Response to Election/Restriction filed Sep. 27, 2002 for U.S. Appl. No. 09/910,372, filed on Jul. 20, 2001 (Bandaru et al.).
Restriction Requirement issued Sep. 17, 2002 for U.S. Appl. No. 09/910,372, filed on Jul. 20, 2001 (Bandaru et al.).
Issue Notification issued Oct. 14, 2004 for U.S. Appl. No. 10/465,759, filed on Jun. 19, 2003 (Bandaru et al.).
Notice of Allowance issued May 4, 2004 for U.S. Appl. No. 10/465,759, filed on Jun. 19, 2003 (Bandaru et al.).
Response after Non-Final Action filed Apr. 12, 2004 for U.S. Appl. No. 10/465,759, filed on Jun. 19, 2003 (Bandaru et al.).
Non-Final Rejection issued Jan. 8, 2004 for U.S. Appl. No. 10/465,759, filed on Jun. 19, 2003 (Bandaru et al.).
Issue Notification issued Dec. 5, 2002 for U.S. Appl. No. 09/723,685, filed on Nov. 28, 2000 (Abarzua).
Notice of Allowance issued Apr. 17, 2002 for U.S. Appl. No. 09/723,685, filed on Nov. 28, 2000 (Abarzua).
Response after Non-Final Action filed Dec. 10, 2001 for U.S. Appl. No. 09/723,685, filed on Nov. 28, 2000 (Abarzua).
Non-Final Rejection issued Aug. 28, 2001 for U.S. Appl. No. 09/723,685, filed on Nov. 28, 2000 (Abarzua).
Response after Non-Final Action filed Jun. 13, 2001 for U.S. Appl. No. 09/723,685, filed on Nov. 28, 2000 (Abarzua).
Non-Final Rejection issued Mar. 13, 2001 for U.S. Appl. No. 09/723,685, filed on Nov. 28, 2000 (Abarzua).
Issue Notification issued Apr. 19, 2006 for U.S. Appl. No. 10/196,539, filed on Jul. 16, 2002 (Abarzua).
Notice of Allowance issued Nov. 15, 2005 for U.S. Appl. No. 10/196,539, filed on Jul. 16, 2002 (Abarzua).
Response after Non-Final Action with Terminal Disclaimer filed Aug. 10, 2005 for U.S. Appl. No. 10/196,539, filed on Jul. 16, 2002 (Abarzua).
Non-Final Rejection issued Mar. 10, 2005 for U.S. Appl. No. 10/196,539, filed on Jul. 16, 2002 (Abarzua).
Notice of Abandonment issued Oct. 15, 2008 for U.S. Appl. No. 11/429,549, filed on May 5, 2006 (Abarzua).
Non-Final Rejection issued Mar. 26, 2008 for U.S. Appl. No. 11/429,549, filed on May 5, 2006 (Abarzua).
Preliminary Amendment filed May 5, 2006 for U.S. Appl. No. 11/429,549, filed on May 5, 2006 (Abarzua).
Issue Notification issued Jul. 29, 2004 for U.S. Appl. No. 09/827,289, filed on Apr. 5, 2001 (Abarzua).
Notice of Allowance issued Apr. 1, 2004 for U.S. Appl. No. 09/827,289, filed on Apr. 5, 2001 (Abarzua).
Supplemental Response filed Feb. 12, 2004 for U.S. Appl. No. 09/827,289, filed on Apr. 5, 2001 (Abarzua).
Notice of Informal or Non-Responsive Amendment issued Feb. 2, 2004 for U.S. Appl. No. 09/827,289, filed on Apr. 5, 2001 (Abarzua).
Response after Non-Final Action filed Jan. 19, 2004 for U.S. Appl. No. 09/827,289, filed on Apr. 5, 2001 (Abarzua).
Non-Final Rejection issued Sep. 29, 2003 for U.S. Appl. No. 09/827,289, filed on Apr. 5, 2001 (Abarzua).
Response after Final Rejection filed Aug. 6, 2003 for U.S. Appl. No. 09/827,289, filed on Apr. 5, 2001 (Abarzua).
Advisory Action issued Jun. 2, 2003 for U.S. Appl. No. 09/827,289, filed on Apr. 5, 2001 (Abarzua).
Amendment after Final Rejection filed May 6, 2003 for U.S. Appl. No. 09/827,289, filed on Apr. 5, 2001 (Abarzua).
Final Rejection issued Feb. 10, 2003 for U.S. Appl. No. 09/827,289, filed on Apr. 5, 2001 (Abarzua).
Response after Non-Final Action filed Jan. 13, 2003 for U.S. Appl. No. 09/827,289, filed on Apr. 5, 2001 (Abarzua).
Non-Final Rejection issued Jul. 29, 2002 for U.S. Appl. No. 09/827,289, filed on Apr. 5, 2001 (Abarzua).
Response to Election/Restriction filed Jun. 19, 2002 for U.S. Appl. No. 09/827,289, filed on Apr. 5, 2001 (Abarzua).
Restriction Requirement issued Jun. 11, 2002 for U.S. Appl. No. 09/827,289, filed on Apr. 5, 2001 (Abarzua).
Notice of Abandonment issued Sep. 20, 2007 for U.S. Appl. No. 10/177,629, filed on Jun. 19, 2002 (Wiltshire).
Final Rejection issued Aug. 21, 2006 for U.S. Appl. No. 10/177,629, filed on Jun. 19, 2002 (Wiltshire).
Response after Non-Final Action & Terminal Disclaimer filed Jun. 9, 2006 for U.S. Appl. No. 10/177,629, filed on Jun. 19, 2002 (Wiltshire).
Non-Final Rejection issued Jan. 10, 2006 for U.S. Appl. No. 10/177,629, filed on Jun. 19, 2002 (Wiltshire).
Response to Notice of Non-Compliant Amendment filed Oct. 25, 2005 for U.S. Appl. No. 10/177,629, filed on Jun. 19, 2002 (Wiltshire).
Notice of Informal or Non-Responsive Amendment issued Sep. 30, 2005 for U.S. Appl. No. 10/177,629, filed on Jun. 19, 2002 (Wiltshire).
Response to Election/Restriction filed Sep. 16, 2005 for U.S. Appl. No. 10/177,629, filed on Jun. 19, 2002 (Wiltshire).
Restriction Requirement issued Mar. 17, 2005 for U.S. Appl. No. 10/177,629, filed on Jun. 19, 2002 (Wiltshire).
Issue Notification issued Feb. 9, 2005 for U.S. Appl. No. 09/931,736, filed on Aug. 17, 2001 (Shao).
Notice of Allowance issued Nov. 18, 2004 for U.S. Appl. No. 09/931,736, filed on Aug. 17, 2001 (Shao).
Appeal Brief filed Aug. 27, 2004 for U.S. Appl. No. 09/931,736, filed on Aug. 17, 2001 (Shao).
Advisory Action issued May 4, 2004 for U.S. Appl. No. 09/931,736, filed on Aug. 17, 2001 (Shao).
Response after Notice of Appeal filed Feb. 27, 2004 for U.S. Appl. No. 09/931,736, filed on Aug. 17, 2001 (Shao).
Notice of Appeal filed Feb. 27, 2004 for U.S. Appl. No. 09/931,736, filed on Aug. 17, 2001 (Shao).
Final Rejection issued Dec. 3, 2003 for U.S. Appl. No. 09/931,736, filed on Aug. 17, 2001 (Shao).
Response after Non-Final Action filed Sep. 18, 2003 for U.S. Appl. No. 09/931,736, filed on Aug. 17, 2001 (Shao).
Non-Final Rejection issued Jun. 30, 2003 for U.S. Appl. No. 09/931,736, filed on Aug. 17, 2001 (Shao).
Response to Election / Restriction filed May 14, 2003 for U.S. Appl. No. 09/931,736, filed on Aug. 17, 2001 (Shao).
Restriction Requirement issued Apr. 15, 2003 for U.S. Appl. No. 09/931,736, filed on Aug. 17, 2001 (Shao).
Notice of Abandonment issued Aug. 8, 2006 for U.S. Appl. No. 10/931,015, filed on Aug. 31, 2004 (Shao).

(56) References Cited

OTHER PUBLICATIONS

Final Rejection issued Jan. 9, 2006 for U.S. Appl. No. 10/931,015, filed on Aug. 31, 2004 (Shao).
Response after Non-Final Action filed Aug. 24, 2005 for U.S. Appl. No. 10/931,015, filed on Aug. 31, 2004 (Shao).
Non-Final Rejection issued May 24, 2005 for U.S. Appl. No. 10/931,015, filed on Aug. 31, 2004 (Shao).
Response to Election/Restriction filed Feb. 24, 2005 for U.S. Appl. No. 10/931,015, filed on Aug. 31, 2004 (Shao).
Restriction Requirement issued Jan. 24, 2005 for U.S. Appl. No. 10/931,015, filed on Aug. 31, 2004 (Shao).
Preliminary Amendment filed Aug. 31, 2004 for U.S. Appl. No. 10/931,015, filed on Aug. 31, 2004 (Shao).
Response after Final Action filed Aug. 8, 2011 for U.S. Appl. No. 11/744,553, filed on May 4, 2007 (Korfhage et al.).
Final Rejection issued May 31, 2011 for U.S. Appl. No. 11/744,553, filed on May 4, 2007 (Korfhage et al.).
Response after Non-Final Action filed Feb. 22, 2011 for U.S. Appl. No. 11/744,553, filed on May 4, 2007 (Korfhage et al.).
Non-Final Rejection issued Sep. 14, 2010 for U.S. Appl. No. 11/744,553, filed on May 4, 2007 (Korfhage et al.).
Response to Final Rejection filed Mar. 1, 2010 for U.S. Appl. No. 11/744,553, filed on May 4, 2007 (Korfhage et al.).
Advisory Action issued Feb. 17, 2010 for U.S. Appl. No. 11/744,553, filed on May 4, 2007 (Korfhage et al.).
Response after Non-Final Action filed Jan. 28, 2010 for U.S. Appl. No. 11/744,553, filed on May 4, 2007 (Korfhage et al.).
Final Rejection issued Apr. 15, 2009 for U.S. Appl. No. 11/744,553, filed on May 4, 2007 (Korfhage et al.).
Response after Non-Final Action filed Dec. 17, 2008 for U.S. Appl. No. 11/744,553, filed on May 4, 2007 (Korfhage et al.).
Examiner Interview Summary issued Dec. 15, 2008 for U.S. Appl. No. 11/744,553, filed on May 4, 2007 (Korfhage et al.).
Non-Final Rejection issued Aug. 19, 2008 for U.S. Appl. No. 11/744,553, filed on May 4, 2007 (Korfhage et al.).
Response to Restriction Requirement filed Jun. 5, 2008 for U.S. Appl. No. 11/744,553, filed on May 4, 2007 (Korfhage et al.).
Restriction Requirement issued May 16, 2008 for U.S. Appl. No. 11/744,553, filed on May 4, 2007 (Korfhage et al.).
Non-Final Rejection issued on May 31, 2011 for U.S. Appl. No. 11/887,678, filed on N/A (Korfhage).
Preliminary Amendment filed Apr. 3, 2009 for U.S. Appl. No. 11/887,678, filed on N/A (Korfhage).
Preliminary Amendment filed Mar. 3, 2008 for U.S. Appl. No. 11/991,435, filed on N/A (Korfhage).
Issue Notification issued Nov. 23, 1998 for U.S. Appl. No. 08/563,912, filed on Nov. 21, 1995 (Lizardi).
Notice of Allowance issued Aug. 14, 1998 for U.S. Appl. No. 08/563,912, filed on Nov. 21, 1995 (Lizardi).
Amendment/Argument filed Aug. 6, 1998 for U.S. Appl. No. 08/563,912, filed on Nov. 21, 1995 (Lizardi).
Notice of Appeal filed Jun. 9, 1998 for U.S. Appl. No. 08/563,912, filed on Nov. 21, 1995 (Lizardi).
Final Rejection issued Dec. 9, 1997 for U.S. Appl. No. 08/563,912, filed on Nov. 21, 1995 (Lizardi).
Amendment and Response filed Aug. 28, 1997 for U.S. Appl. No. 08/563,912, filed on Nov. 21, 1995 (Lizardi).
Non-Final Office Action issued Feb. 28, 1997 for U.S. Appl. No. 08/563,912, filed on Nov. 21, 1995 (Lizardi).
Response to Election / Restriction filed Oct. 24, 1996 for U.S. Appl. No. 08/563,912, filed on Nov. 21, 1995 (Lizardi).
Restriction Requirement issued Sep. 24, 1996 for U.S. Appl. No. 08/563,912, filed on Nov. 21, 1995 (Lizardi).
Issue Notification issued Mar. 15, 2001 for U.S. Appl. No. 09/132,553, filed on Aug. 11, 1998 (Lizardi).
Notice of Allowance issued Nov. 7, 2000 for U.S. Appl. No. 09/132,553, filed on Aug. 11, 1998 (Lizardi).
Response to Office Action filed Aug. 11, 2000 for U.S. Appl. No. 09/132,553, filed on Aug. 11, 1998 (Lizardi).
Non-Final Rejection issued Apr. 11, 2000 for U.S. Appl. No. 09/132,553, filed on Aug. 11, 1998 (Lizardi).
Response after Non-Final Action with Terminal Disclaimer filed Jan. 13, 2000 for U.S. Appl. No. 09/132,553, filed on Aug. 11, 1998 (Lizardi).
Non-Final Rejection issued Sep. 13, 1999 for U.S. Appl. No. 09/132,553, filed on Aug. 11, 1998 (Lizardi).
Preliminary Amendment filed Aug. 11, 1998 for U.S. Appl. No. 09/132,553, filed on Aug. 11, 1998 (Lizardi).
Issue Notification issued Jan. 18, 2002 for U.S. Appl. No. 09/644,723, filed on Aug. 23, 2000 (Lizardi).
Notice of Allowance issued Oct. 1, 2001 for U.S. Appl. No. 09/644,723, filed on Aug. 23, 2000 (Lizardi).
Response after Non-Final Action with Terminal Disclaimer filed Jul. 13, 2001 for U.S. Appl. No. 09/644,723, filed on Aug. 23, 2000 (Lizardi).
Non-Final Rejection issued Mar. 13, 2001 for U.S. Appl. No. 09/644,723, filed on Aug. 23, 2000 (Lizardi).
Preliminary Amendment filed Aug. 23, 2000 for U.S. Appl. No. 09/644,723, filed on Aug. 23, 2000 (Lizardi).
Issue Notification issued Jan. 19, 2001 for U.S. Appl. No. 09/132,552, filed on Aug. 11, 1998 (Lizardi).
Notice of Allowance issued Jul. 12, 2000 for U.S. Appl. No. 09/132,552, filed on Aug. 11, 1998 (Lizardi).
Amendment and Response filed Jun. 14, 2000 for U.S. Appl. No. 09/132,552, filed on Aug. 11, 1998 (Lizardi).
Final Rejection issued Apr. 6, 2000 for U.S. Appl. No. 09/132,552, filed on Aug. 11, 1998 (Lizardi).
Response after Non-Final Action & Terminal Disclaimer filed Jan. 13, 2000 for U.S. Appl. No. 09/132,552, filed on Aug. 11, 1998 (Lizardi).
Non-Final Rejection issued Sep. 13, 1999 for U.S. Appl. No. 09/132,552, filed on Aug. 11, 1998 (Lizardi).
Preliminary Amendment filed Aug. 11, 1998 for U.S. Appl. No. 09/132,552, filed on Aug. 11, 1998 (Lizardi).
Issue Notification issued Sep. 9, 2004 for U.S. Appl. No. 10/038,718, filed on Jan. 2, 2002 (Lizardi).
Notice of Allowance issued Apr. 21, 2004 for U.S. Appl. No. 10/038,718, filed on Jan. 2, 2002 (Lizardi).
Response after Non-Final Action & Terminal Disclaimer filed Jan. 16, 2004 for U.S. Appl. No. 10/038,718, filed on Jan. 2, 2002 (Lizardi).
Non-Final Rejection issued Oct. 22, 2003 for U.S. Appl. No. 10/038,718, filed on Jan. 2, 2002 (Lizardi).
Response to Election/Restriction filed Jul. 14, 2003 for U.S. Appl. No. 10/038,718, filed on Jan. 2, 2002 (Lizardi).
Restriction Requirement issued Mar. 13, 2003 for U.S. Appl. No. 10/038,718, filed on Jan. 2, 2002 (Lizardi).
Preliminary Amendment filed Jan. 2, 2002 for U.S. Appl. No. 10/038,718, filed on Jan. 2, 2002 (Lizardi).
Certificate of Correction issued Oct. 26, 2010 for U.S. Appl. No. 10/896,513, filed on Jul. 22, 2004 (Lizardi).
Issue Notification issued Oct. 28, 2009 for U.S. Appl. No. 10/896,513, filed on Jul. 22, 2004 (Lizardi).
Notice of Allowance issued Jul. 9, 2009 for U.S. Appl. No. 10/896,513, filed on Jul. 22, 2004 (Lizardi).
Amendment and Response filed Mar. 26, 2009 for U.S. Appl. No. 10/896,513, filed on Jul. 22, 2004 (Lizardi).
Interview Summary issued Mar. 12, 2009 for U.S. Appl. No. 10/896,513, filed on Jul. 22, 2004 (Lizardi).
Non-Final Rejection issued Nov. 17, 2008 for U.S. Appl. No. 10/896,513, filed on Jul. 22, 2004 (Lizardi).
Amendment and Response filed Aug. 29, 2008 for U.S. Appl. No. 10/896,513, filed on Jul. 22, 2004 (Lizardi).
Advisory Action issued Jul. 23, 2008 for U.S. Appl. No. 10/896,513, filed on Jul. 22, 2004 (Lizardi).
Amendment After Final Rejection filed Jun. 18, 2008 for U.S. Appl. No. 10/896,513, filed on Jul. 22, 2004 (Lizardi).
Interview Summary issued Jun. 13, 2008 for U.S. Appl. No. 10/896,513, filed on Jul. 22, 2004 (Lizardi).
Final Rejection issued Mar. 18, 2008 for U.S. Appl. No. 10/896,513, filed on Jul. 22, 2004 (Lizardi).

(56) References Cited

OTHER PUBLICATIONS

Amendment After Non-Final Rejection with Terminal Disclaimer filed Dec. 11, 2007 for U.S. Appl. No. 10/896,513, filed on Jul. 22, 2004 (Lizardi).
Non-Final Rejection issued Jun. 11, 2007 for U.S. Appl. No. 10/896,513, filed on Jul. 22, 2004 (Lizardi).
Response to Election/Restriction filed Mar. 29, 2007 for U.S. Appl. No. 10/896,513, filed on Jul. 22, 2004 (Lizardi).
Restriction Requirement issued Jan. 19, 2007 for U.S. Appl. No. 10/896,513, filed on Jul. 22, 2004 (Lizardi).
Preliminary Amendment filed Jan. 25, 2005 for U.S. Appl. No. 10/896,513, filed on Jul. 22, 2004 (Lizardi).
Issue Notification issued Sep. 8, 2000 for U.S. Appl. No. 08/946,732, filed on Oct. 8, 1997 (Lizardi).
Office Communication issued May 3, 2000 for U.S. Appl. No. 08/946,732, filed on Oct. 8, 1997 (Lizardi).
Notice of Allowance issued Jun. 22, 1999 for U.S. Appl. No. 08/946,732, filed on Oct. 8, 1997 (Lizardi).
Amendment and Response filed Mar. 31, 1999 for U.S. Appl. No. 08/946,732, filed on Oct. 8, 1997 (Lizardi).
Non-Final Rejection issued Oct. 1, 1998 for U.S. Appl. No. 08/946,732, filed on Oct. 8, 1997 (Lizardi).
Issue Notification issued Aug. 9, 2001 for U.S. Appl. No. 09/397,915, filed on Sep. 17, 1999 (Lizardi).
Notice of Allowance issued Apr. 9, 2001 for U.S. Appl. No. 09/397,915, filed on Sep. 17, 1999 (Lizardi).
Response after Non-Final Action with Terminal Disclaimer filed Jan. 16, 2001 for U.S. Appl. No. 09/397,915, filed on Sep. 17, 1999 (Lizardi).
Non-Final Rejection issued Aug. 14, 2000 for U.S. Appl. No. 09/397,915, filed on Sep. 17, 1999 (Lizardi).
Preliminary Amendment filed Sep. 17, 1999 for U.S. Appl. No. 09/397,915, filed on Sep. 17, 1999 (Lizardi).
Issue Notification issued Oct. 16, 2003 for U.S. Appl. No. 09/911,226, filed on Jul. 23, 2001 (Lizardi).
Notice of Allowance issued Jun. 3, 2003 for U.S. Appl. No. 09/911,226, filed on Jul. 23, 2001 (Lizardi).
Amendment and Response & Terminal Disclaimer filed Mar. 19, 2003 for U.S. Appl. No. 09/911,226, filed on Jul. 23, 2001 (Lizardi).
Non-Final Rejection issued Dec. 18, 2002 for U.S. Appl. No. 09/911,226, filed on Jul. 23, 2001 (Lizardi).
Preliminary Amendment filed Jul. 23, 2001 for U.S. Appl. No. 09/911,226, filed on Jul. 23, 2001 (Lizardi).
Notice of Abandonment issued Oct. 28, 2009 for U.S. Appl. No. 10/700,018, filed on Nov. 3, 2003 (Lizardi).
Advisory Action issued Apr. 2, 2009 for U.S. Appl. No. 10/700,018, filed on Nov. 3, 2003 (Lizardi).
Notice of Appeal filed Mar. 13, 2009 for U.S. Appl. No. 10/700,018, filed on Nov. 3, 2003 (Lizardi).
Amendment after Final Rejection filed Jan. 27, 2009 for U.S. Appl. No. 10/700,018, filed on Nov. 3, 2003 (Lizardi).
Final Rejection issued Sep. 15, 2008 for U.S. Appl. No. 10/700,018, filed on Nov. 3, 2003 (Lizardi).
Amendment after Non-Final Rejection filed Jun. 12, 2008 for U.S. Appl. No. 10/700,018, filed on Nov. 3, 2003 (Lizardi).
Non-Final Rejection issued Jan. 24, 2008 for U.S. Appl. No. 10/700,018, filed on Nov. 3, 2003 (Lizardi).
Response after Non-Final Action filed Oct. 31, 2007 for U.S. Appl. No. 10/700,018, filed on Nov. 3, 2003 (Lizardi).
Non-Final Rejection issued Aug. 8, 2007 for U.S. Appl. No. 10/700,018, filed on Nov. 3, 2003 (Lizardi).
Response after Non-Final Action filed May 14, 2007 for U.S. Appl. No. 10/700,018, filed on Nov. 3, 2003 (Lizardi).
Non-Final Rejection issued Nov. 14, 2006 for U.S. Appl. No. 10/700,018, filed on Nov. 3, 2003 (Lizardi).
Response after Non-Final Action filed Aug. 24, 2006 for U.S. Appl. No. 10/700,018, filed on Nov. 3, 2003 (Lizardi).
Non-Final Rejection issued May 18, 2006 for U.S. Appl. No. 10/700,018, filed on Nov. 3, 2003 (Lizardi).
Preliminary Amendment filed Nov. 3, 2003 for U.S. Appl. No. 10/700,018, filed on Nov. 3, 2003 (Lizardi).
Issue Notification issued Oct. 25, 2001 for U.S. Appl. No. 09/357,487, filed on Jul. 20, 1999 (Lizardi).
Notice of Allowance issued Jun. 5, 2001 for U.S. Appl. No. 09/357,487, filed on Jul. 20, 1999 (Lizardi).
Amendment and Response filed May 18, 2001 for U.S. Appl. No. 09/357,487, filed on Jul. 20, 1999 (Lizardi).
Final Rejection issued Feb. 13, 2001 for U.S. Appl. No. 09/357,487, filed on Jul. 20, 1999 (Lizardi).
Amendment and Response filed Jan. 25, 2001 for U.S. Appl. No. 09/357,487, filed on Jul. 20, 1999 (Lizardi).
Non-Final Rejection issued Oct. 25, 2000 for U.S. Appl. No. 09/357,487, filed on Jul. 20, 1999 (Lizardi).
Amendment and Response filed Sep. 12, 2000 for U.S. Appl. No. 09/357,487, filed on Jul. 20, 1999 (Lizardi).
Non-Final Rejection issued May 12, 2000 for U.S. Appl. No. 09/357,487, filed on Jul. 20, 1999 (Lizardi).
Response after Non-Final Rejection filed May 19, 2011 for U.S. Appl. No. 11/870,715, filed on Oct. 11, 2007 (Korfhage et al.).
Non-Final Rejection issued Feb. 16, 2011 for U.S. Appl. No. 11/870,715, filed on Oct. 11, 2007 (Korfhage et al.).
Response after Final Rejection filed Nov. 30, 2009 for U.S. Appl. No. 11/870,715, filed on Oct. 11, 2007 (Korfhage et al.).
Final Rejection issued Oct. 16, 2009 for U.S. Appl. No. 11/870,715, filed on Oct. 11, 2007 (Korfhage et al.).
Response after Final Rejection filed Jul. 24, 2009 for U.S. Appl. No. 11/870,715, filed on Oct. 11, 2007 (Korfhage et al.).
Examiner Interview Summary issued Jul. 15, 2009 for U.S. Appl. No. 11/870,715, filed on Oct. 11, 2007 (Korfhage et al.).
Final Rejection issued May 13, 2009 for U.S. Appl. No. 11/870,715, filed on Oct. 11, 2007 (Korfhage et al.).
Response after Non-Final Action filed Feb. 9, 2009 for U.S. Appl. No. 11/870,715, filed on Oct. 11, 2007 (Korfhage et al.).
Non-Final Rejection issued Nov. 12, 2008 for U.S. Appl. No. 11/870,715, filed on Oct. 11, 2007 (Korfhage et al.).
International Preliminary Examination Report issued Mar. 3, 2004 for PCT/US02/02601 filed on Jan. 30, 2002 (Applicant—Molecular Staging, Inc.).
Written Opinion issued Jun. 6, 2003 for PCT/US02/02601 filed on Jan. 30, 2002 (Applicant—Molecular Staging, Inc.).
International Search Report issued May 7, 2002 for PCT/US02/02601 filed on Jan. 30, 2002 (Applicant—Molecular Staging, Inc.).
Communication regarding Expiry of Time Limit for Notice of Opposition issued Mar. 26, 2009 for EP 1928481.9, which claims priority to PCT/US01/11947 filed on Apr. 12, 2001 (Applicant—Molecular Staging, Inc.).
Communication under Rule 51(4) EPC issued Sep. 11, 2007 for EP 1928481.9, which claims priority to PCT/US01/11947 filed on Apr. 12, 2001 (Applicant—Molecular Staging, Inc.).
Response filed Nov. 27, 2006 for EP 1928481.9, which claims priority to PCT/US01/11947 filed on Apr. 12, 2001 (Applicant—Molecular Staging, Inc.).
Invitation pursuant to Article 96(2) EPC and Rule 51(2) EPC issued Nov. 10, 2006 for EP 1928481.9, which claims priority to PCT/US01/11947 filed on Apr. 12, 2001 (Applicant—Molecular Staging, Inc.).
Response filed Mar. 6, 2006 for EP 1928481.9, which claims priority to PCT/US01/11947, which claims priority to PCT/US01/11947 filed on Apr. 12, 2001 (Applicant—Molecular Staging, Inc.).
Communication pursuant to Article 96(2) EPC issued May 25, 2005 for EP 1928481.9, which claims priority to PCT/US01/11947 filed on Apr. 12, 2001 (Applicant—Molecular Staging, Inc.).
International Preliminary Examination Report issued Jan. 10, 2003 for PCT/US01/11947 filed on Apr. 12, 2001 (Applicant—Molecular Staging, Inc.).
International Search Report issued Oct. 30, 2002 for PCT/US01/11947 filed on Apr. 12, 2001 (Applicant—Molecular Staging, Inc.).
Notice of Abandonment issued Jun. 7, 2007 for CA 2405456, which claims priority to PCT/US01/11947 filed on Apr. 12, 2001 (Applicant—Molecular Staging, Inc.).

(56) References Cited

OTHER PUBLICATIONS

Notice of Reinstatement issued Jan. 10, 2005 for CA 2405456, which claims priority to PCT/US01/11947 filed on Apr. 12, 2001 (Applicant—Molecular Staging, Inc.).
Notice of Abandonment issued Jun. 8, 2004 for CA 2405456, which claims priority to PCT/US01/11947 filed on Apr. 12, 2001 (Applicant—Molecular Staging, Inc.).
Voluntary Amendment filed Apr. 11, 2003 for CA 2405456, which claims priority to PCT/US01/11947 filed on Apr. 12, 2001 (Applicant—Molecular Staging, Inc.).
Notice of Abandonment issued Feb. 26, 2007 for AU 2001269944, which claims priority to PCT/US01/19657 filed on Jun. 20, 2001 (Applicant—Molecular Staging, Inc.).
Examiner's Report #2 issued May 26, 2006 for AU 2001269944, which claims priority to PCT/US01/19657 filed on Jun. 20, 2001 (Applicant—Molecular Staging, Inc.).
Response filed May 16, 2006 for AU 2001269944, which claims priority to PCT/US01/19657 filed on Jun. 20, 2001 (Applicant—Molecular Staging, Inc.).
Examiner's Report #1 issued May 19, 2005 for AU 2001269944, which claims priority to PCT/US01/19657 filed on Jun. 20, 2001 (Applicant—Molecular Staging, Inc.).
Direction to Request Examination filed Oct. 30, 2003 for AU 2001269944, which claims priority to PCT/US01/19657 filed on Jun. 20, 2001 (Applicant—Molecular Staging, Inc.).
Notice of Abandonment issued Aug. 15, 2007 for CA 2411838, which claims priority to PCT/US01/19657 filed on Jun. 20, 2001 (Applicant—Molecular Staging, Inc.).
Response to Examination Report filed Nov. 23, 2005 for CN 01811542.X, which claims priority to PCT/US01/19657 filed on Jun. 20, 2001 (Applicant—Molecular Staging, Inc.).
Examination Report issued Jul. 8, 2005 for CN 01811542.X, which claims priority to PCT/US01/19657 filed on Jun. 20, 2001 (Applicant—Molecular Staging, Inc.).
Noting of Loss of Rights pursuant to Rule 112(1) EPC issued Sep. 13, 2010 for EP 1948505.1, which claims priority to PCT/US01/19657 filed on Jun. 20, 2001 (Applicant—Molecular Staging, Inc.).
Communication pursuant to Article 94(3) EPC issued Jan. 29, 2010 for EP 1948505.1, which claims priority to PCT/US01/19657 filed on Jun. 20, 2001 (Applicant—Molecular Staging, Inc.).
Response to Rule 70(2) EPC Communication filed Oct. 6, 2009 for EP 1948505.1, which claims priority to PCT/US01/19657 filed on Jun. 20, 2001 (Applicant—Molecular Staging, Inc.).
Supplementary European Search Report issued Jul. 27, 2009 for EP 1948505.1, which claims priority to PCT/US01/19657 filed on Jun. 20, 2001 (Applicant—Molecular Staging, Inc.).
Notice of Allowance issued Mar. 1, 2011 for JP 2002-503102, which claims priority to PCT/US01/19657 filed on Jun. 20, 2001 (Applicant—Molecular Staging, Inc.).
Argument and Amendment filed Mar. 19, 2010 for JP 2002-503102, which claims priority to PCT/US01/19657 filed on Jun. 20, 2001 (Applicant—Molecular Staging, Inc.).
Notice of Rejection issued Dec. 22, 2009 for JP 2002-503102, which claims priority to PCT/US01/19657 filed on Jun. 20, 2001 (Applicant—Molecular Staging, Inc.).
Request for Examination filed Jan. 11, 2007 for JP 2002-503102, which claims priority to PCT/US01/19657 filed on Jun. 20, 2001 (Applicant—Molecular Staging, Inc.).
International Preliminary Examination Report issued Sep. 27, 2002 for PCT/US01/19657 filed on Jun. 20, 2001 (Applicant—Molecular Staging, Inc.).
Written Opinion issued Jun. 26, 2002 for PCT/US01/19657 filed on Jun. 20, 2001 (Applicant—Molecular Staging, Inc.).
International Search Report issued Aug. 29, 2001 for PCT/US01/19657 filed on Jun. 20, 2001 (Applicant—Molecular Staging, Inc.).
Issue Notification issued Dec. 13, 2002 for SG 200207285-8, which claims priority to PCT/US01/19657 filed on Jun. 20, 2001 (Applicant—Molecular Staging, Inc.).
Office Action issued Oct. 3, 2005 for TW 90114960 filed on Jun. 28, 2001 (Applicant—Molecular Staging, Inc.).

Response to Office Action (no translation) filed Sep. 13, 2005 for TW 90114960 filed on Jun. 28, 2001 (Applicant—Molecular Staging, Inc.).
Office Action issued May 16, 2005 for TW90114960 filed on Jun. 28, 2001 (Applicant—Molecular Staging, Inc.).
Notice of Acceptance issued Mar. 29, 2006 for AU 2001271722, which claims priority to PCT/US01/20933 filed on Jul. 2, 2001 (Applicant—Molecular Staging, Inc).
Response to Examination Report filed Mar. 17, 2006 for AU 2001271722, which claims priority to PCT/US01/20933 filed on Jul. 2, 2001 (Applicant—Molecular Staging, Inc.).
Examination Report issued Jun. 17, 2005 for AU 2001271722, which claims priority to PCT/US01/20933 filed on Jul. 2, 2001 (Applicant—Molecular Staging, Inc.).
Communication pursuant to 45(3) issued Jul. 20, 2004 for AU 2001271722, which claims priority to PCT/US01/20933 filed on Jul. 2, 2001 (Applicant—Molecular Staging, Inc.).
Direction to Request Examination filed Nov. 6, 2003 for AU 2001271722, which claims priority to PCT/US01/20933 filed on Jul. 2, 2001 (Applicant—Molecular Staging.
Notice of Abandonment issued Aug. 28, 2007 for CA 2411794, which claims priority to PCT/US01/20933 filed on Jul. 2, 2001 (Applicant—Molecular Staging, Inc.).
Notice of National Entry issued Jan. 16, 2003 for CA 2411794, which claims priority to PCT/US01/20933 filed on Jul. 2, 2001 (Applicant—Molecular Staging, Inc.).
Communication re: the Expiry of the Time Limit to File Opposition issued Aug. 6, 2008 for EP 1950759.9, which claims priority to PCT/US01/20933 filed on Jul. 2, 2001 (Applicant—Molecular Staging, Inc.).
Decision to Grant pursuant to Article 97(2) EPC issued Sep. 6, 2007 for EP 1950759.9, which claims priority to PCT/US/01/20933 filed on Jul. 2, 2001 (Applicant—Molecular Staging, Inc.).
Response to Communication filed Aug. 17, 2007 for EP 1950759.9, which claims priority to PCT/US01/20933 filed on Jul. 2, 2001 (Applicant—Molecular Staging, Inc.).
Communication under Rule 51(4) issued Apr. 26, 2007 for EP 1950759.9, which claims priority to PCT/US01/20933 filed on Jul. 2, 2001 (Applicant—Molecular Staging, Inc.).
Response to Communication filed Jul. 5, 2006 for EP 1950759.9, which claims priority to PCT/US01/20933 filed on Jul. 2, 2001 (Applicant—Molecular Staging, Inc.).
Communication pursuant to Article 96(2) EPC issued Apr. 24, 2006 for EP 1950759.9, which claims priorityto PCT/US01/20933 filed on Jul 2, 2001 (Applicant—Molecular.
Response to Communication filed Oct. 24, 2005 for EP 1950759.9, which claims priority to PCT/US01/20933 filed on Jul. 2, 2001 (Applicant—Molecular Staging, Inc.).
Communication pursuant to Article 96(2) EPC issued Jun. 16, 2005 for EP 1950759.9, which claims priority to PCT/US01/20933 filed on Jul. 2, 2001 (Applicant—Molecular Staging, Inc.).
Response to Communication filed Sep. 7, 2004 for EP 1950759.9, which claims priority to PCT/US01/20933 filed on Jul. 2, 2001 (Applicant—Molecular Staging, Inc.).
Communication pursuant to Article 96(1) and Rule 51(1) EPC issued Jul. 6, 2004 for 1950759.9, which claims priority to PCT/US/01/20933 filed on Jul. 2, 2001 (Applicant—Molecular Staging, Inc.).
European Search Report issued Jul. 1, 2004 for EP 1950759.9, which claims priority to PCT/US01/20933 filed on Jul. 2, 2001 (Applicant—Molecular Staging, Inc.).
International Preliminary Examination Report issued Sep. 29, 2002 for PCT/US01/20933 filed on Jul. 2, 2001 (Applicants—Molecular Staging, Inc., Yale University).
International Search Report issued Nov. 6, 2001 for PCT/US01/20933 filed on Jul. 2, 2001 (Applicants—Molecular Staging, Inc., Yale University).
International Preliminary Examination Report issued Sep. 6, 2004 for PCT/US02/15045 filed on May 10, 2002 (Applicant—Molecular Staging, Inc.).
Written Opinion issued Mar. 19, 2004 for PCT/US02/15045 filed on May 10, 2002 (Applicant—Molecular Staging, Inc.).

(56) References Cited

OTHER PUBLICATIONS

International Search Report issued Feb. 10, 2003 for PCT/US02/15045 filed on May 10, 2002 (Applicant—Molecular Staging, Inc.).
Examination Report issued Jan. 8, 2007 for AU 2002362874, which claims priority to PCT/US02/33244 filed on Oct. 15, 2002 (Applicant—Molecular Staging, Inc.).
Notice of Abandonment issued Dec. 10, 2007 for CA 246933, which claims priority to PCT/US02/33244 filed on Oct. 15, 2002 (Applicant—Molecular Staging, Inc.).
Communication pursuant to Article 114(2) EPC issued Oct. 23, 2009 for EP 2801776.2, which claims priority to PCT/US02/33244 filed on Oct. 15, 2002 (Applicant—Molecular Staging, Inc.).
Response to Communication filed Dec. 5, 2007 for EP 2801776.2, which claims priority to PCT/US02/33244 filed on Oct. 15, 2002 (Applicant—Molecular Staging, Inc.).
Communication pursuant to Article 96(2) EPC issued Aug. 7, 2007 for EP 2801776.2, which claims priority to PCT/US02/33244filed on Oct. 15, 2002 (Applicant—Molecular Staging, Inc.).
Supplementary European Search Report issued Apr. 11, 2007 for EP 2801776.2, which claims priority to PCT/US02/33244 filed on Oct. 15, 2002 (Applicant—Molecular Staging, Inc.).
Response to Communication filed Dec. 6, 2006 for EP 2801776.2, which claims priority to PCT/US02/33244 filed on Oct. 15, 2002 (Applicant—Molecular Staging, Inc.).
Communication issued Nov. 7, 2006 for EP 2801776.2, which claims priority to PCT/US02/33244 filed on Oct. 15, 2002 (Applicant—Molecular Staging, Inc.).
International Preliminary Examination Report issued May 11, 2004 for PCT/US02/33244 filed on Oct. 15, 2002 (Applicant—Molecular Staging, Inc.).
Written Opinion issued Feb. 24, 2004 for PCT/US02/33244 filed on Oct. 15, 2002 (Applicant—Molecular Staging, Inc.).
International Search Report issued Oct. 17, 2003 for PCT/US02/33244 filed on Oct. 15, 2002 (Applicant—Molecular Staging, Inc.).
Notice of Acceptance issued Nov. 22, 1999 for AU 10240/97, which claims priority to PCT/US96/18812 filed on Nov. 21, 1996 (Applicant—Yale University).
First Statement of Proposed Amendments filed Oct. 15, 1999 for AU 10240/97, which claims priority to PCT/US96/18812 filed on Nov. 21, 1996 (Applicant—Yale University).
First Examination Report issued Apr. 30, 1999 for AU 10240/97, which claims priority to PCT/US96/18812 filed on Nov. 21, 1996 (Applicant—Yale University).
Notice of National Processing Completion issued Apr. 20, 2001 for BE 96940601.6, which claims priority to PCT/US96/18812 filed on Nov. 21, 1996 (Applicant—Yale University).
Notice of Allowance issued Jun. 13, 2007 for CA 2236161, which claims priority to PCT/US96/18812 filed on Nov. 21, 1996 (Applicant—Yale University).
Comments and Amendments after Examiner's Report filed Oct. 4, 2006 for CA 2236161, which claims priority to PCT/US96/18812 filed on Nov. 21, 1996 (Applicant—Yale University).
Examination Report issued Apr. 4, 2006 for CA 2236.61, which claims priority to PCT/US96/18812 filed on Nov. 21, 1996 (Applicant—Yale University).
Patent Granted issued Aug. 2, 2001 for DE 862652, which claims priority to PCT/US96/18812 filed on Nov. 21, 1996 (Applicant—Yale University).
Communication regarding Expiry of Opposition Time Period issued Jan. 15, 2002 for EP 862652, which claims priority to PCT/US96/18812 filed on Nov. 21, 1996 (Applicant—Yale University).
Decision to Grant issued Jan. 25, 2001 for EP 862652, which claims priority to PCT/US96/18812 filed on Nov. 21, 1996 (Applicant—Yale University).
Response to Communication under Rule 51(4) filed Dec. 21, 1999 for EP 862652, which claims priority to PCT/US96/18812 filed on Nov. 21, 1996 (Applicant—Yale University).
Communication under Rule 51(4) issued Jul. 1, 1999 for EP 862652, which claims priority to PCT/US96/18812 filed on Nov. 21, 1996 (Applicant—Yale University).

Notice of Allowance issued May 9, 2007 for JP 9-519942, which claims priority to PCT/US96/18812 filed on Nov. 21, 1996 (Applicant—Yale University).
Amended Claim Set filed Dec. 26, 2006 for JP 9-519942, which claims priority to PCT/US96/18812 filed on Nov. 21, 1996 (Applicant—Yale University).
Examination Report issued Jun. 27, 2006 for JP 9-519942, which claims priority to PCT/US96/18812 filed on Nov. 21, 1996 (Applicant—Yale University).
International Preliminary Examination Report issued Jan. 28, 1998 for PCT/US96/18812 filed on Nov. 21, 1996 (Applicant—Yale University).
Response to Written Opinion issued Nov. 18, 1997 for PCT/US96/18812 filed on Nov. 21, 1996 (Applicant—Yale University).
Written Opinion issued Aug. 21, 1997 for PCT/US96/18812 filed on Nov. 21, 1996 (Applicant—Yale University).
International Search Report issued Jun. 30, 1997 for PCT/US96/18812 filed on Nov. 21, 1996 (Applicant—Yale University).
International Search Report issued Apr. 28, 2003 for PCT/US03/00678 filed on Jan. 9, 2003 (Applicant—Molecular Staging, Inc.).
Notice of Acceptance issued May 12, 2005 for AU 27819/00, which claims prioity to PCT/AU99/01110 filed on Dec. 14, 1999 (Applicant—Molecular Staging, Inc.).
Response to Examination Report filed Apr. 15, 2005 for AU 27819/00, which claims prioity to PCT/AU99/01110 filed on Dec. 14, 1999 (Applicant—Molecular Staging, Inc.).
Examination Report issued Dec. 8, 2004 for AU 27819/00, which claims prioity to PCT/AU99/01110 filed on Dec. 14, 1999 (Applicant—Molecular Staging, Inc.).
Response to Examination Report filed Nov. 30, 2004 for AU 27819/00, which claims prioity to PCT/AU99/01110 filed on Dec. 14, 1999 (Applicant—Molecular Staging, Inc.).
Examination Report issued Oct. 13, 2004 for AU 27819/0, which claims prioity to PCT/AU99/01110 0 filed on Dec. 14, 1999 (Applicant—Molecular Staging, Inc.).
Response to Examination Report filed Sep. 22, 2004 for AU 27819/00, which claims prioity to PCT/AU99/01110 filed on Dec. 14, 1999 (Applicant—Molecular Staging, Inc.).
Examination Report issued Aug. 8, 2003 for AU 27819/00, which claims prioity to PCT/AU99/01110 filed on Dec. 14, 1999 (Applicant—Molecular Staging, Inc.).
Notice of Abandonment issued Feb. 11, 2008 for CA 2394800, which claims prioity to PCT/AU99/01110 filed on Dec. 14, 1999 (Applicant—Molecular Staging, Inc.).
Notice of Reinstatement issued Jan. 12, 2005 for CA 2394800, which claims prioity to PCT/AU99/01110 filed on Dec. 14, 1999 (Applicant—Molecular Staging, Inc.).
Notice of Abandonment issued Feb. 9, 2004 for CA 2394800, which claims prioity to PCT/AU99/01110 filed on Dec. 14, 1999 (Applicant—Molecular Staging, Inc.).
European Search Report issued Feb. 21, 2003 for EP 99969209.8, which claims prioity to PCT/AU99/01110 filed on Dec. 14, 1999 (Applicant—Molecular Staging, Inc.).
Notice of Allowance issued Jul. 22, 2008 for JP 2000-588388, which claims prioity to PCT/AU99/01110 filed on Dec. 14, 1999 (Applicant—Molecular Staging, Inc.).
Reasons for Appeal filed Jun. 19, 2008 for JP 2000-588388, which claims prioity to PCT/AU99/01110 filed on Dec. 14, 1999 (Applicant—Molecular Staging, Inc.).
Amendment filed May 20, 2008 for JP 2000-588388, which claims prioity to PCT/AU99/01110 filed on Dec. 14, 1999 (Applicant—Molecular Staging, Inc.).
Argument against Final Rejection filed Apr. 8, 2008, which claims prioity to PCT/AU99/01110 for JP 2000-588388 filed on Dec. 14, 1999 (Applicant—Molecular Staging, Inc.).
Examination Report issued Jan. 8, 2008 for JP 2000-588388, which claims prioity to PCT/AU99/01110 filed on Dec. 14, 1999 (Applicant—Molecular Staging, Inc.).
Amendment filed Nov. 26, 2007 for JP 2000-588388, which claims prioity to PCT/AU99/01110 filed on Dec. 14, 1999 (Applicant—Molecular Staging, Inc.).

(56) References Cited

OTHER PUBLICATIONS

Examination Report issued Jul. 24, 2007 for JP 2000-588388, which claims prioity to PCT/AU99/01110 filed on Dec. 14, 1999 (Applicant—Molecular Staging, Inc.).
Written Amendment filed Dec. 15, 2004 for JP 2000-588388, which claims prioity to PCT/AU99/01110 filed on Dec. 14, 1999 (Applicant—Molecular Staging, Inc.).
International Preliminary Examination Report issued Oct. 4, 2000 for PCT/AU99/01110 filed on Dec. 14, 1999 (Diatech Pty. Ltd.).
Written Opinion issued Jun. 28, 2000 for PCT/AU99/01110 filed on Dec. 14, 1999 (Diatech Pty. Ltd.).
International Search Report issued Mar. 7, 2000 for PCT/AU99/01110 filed on Dec. 14, 1999 (Diatech Pty. Ltd.).
Notice of Abandonment issued Feb. 5, 2008 for CA 2512196, which claims priority to PCT/US03/39430 filed on Dec. 11, 2003 (Applicant—Qiagen GMBH).
Notice of National Entry issued Oct. 3, 2005 for CA 2512196, which claims priority to PCT/US03/39430 filed on Dec. 11, 2003 (Applicant—Qiagen GMBH).
Communication re: Expiry of Time Period for Opposition issued Apr. 6, 2011 for EP 3796961.5, which claims priority to PCT/US03/39430 filed on Dec. 11, 2003 (Applicant—Qiagen GMBH).
Decision to Grant a European Patent issued May 7, 2010 for EP 3796961.5, which claims priority to PCT/US03/39430 filed on Dec. 11, 2003 (Applicant—Qiagen GMBH).
Response to Communication filed Apr. 1, 2010 for EP 3796961.5, which claims priority to PCT/US03/39430 filed on Dec. 11, 2003 (Applicant—Qiagen GMBH).
Amendment or Correction of the Text for Grant filed Mar. 4, 2010 for EP 3796961.5, which claims priority to PCT/US03/39430 filed on Dec. 11, 2003 (Applicant—Qiagen GMBH).
Response to Communication filed Dec. 10, 2009 for EP 3796961.5, which claims priority to PCT/US03/39430 filed on Dec. 11, 2003 (Applicant—Qiagen GMBH).
Communication under Rule 71(3) EPC issued Aug. 17, 2009 for EP 3796961.5, which claims priority to PCT/US03/39430 filed on Dec. 11, 2003 (Applicant—Qiagen GMBH).
Response to Communication filed Jul. 7, 2009 for EP 3796961.5, which claims priority to PCT/US03/39430 filed on Dec. 11, 2003 (Applicant—Qiagen GMBH).
Invitation pursuant to Article 94(3) and Rule 71(1) EPC issued Jun. 19, 2009 for EP 3796961.5, which claims priority to PCT/US03/39430 filed on Dec. 11, 2003 (Applicant—Qiagen GMBH).
Response to Communication filed Oct. 25, 2007 for EP 3796961.5, which claims priority to PCT/US03/39430 filed on Dec. 11, 2003 (Applicant—Qiagen GMBH).
Communication pursuant to Article 96(2) EPC issued Jun. 29, 2007 for EP 3796961.5, which claims priority to PCT/US03/39430 filed on Dec. 11, 2003 (Applicant—Qiagen GMBH).
Response to Communication filed Mar. 14, 2007 for EP 3796961.5, which claims priority to PCT/US03/39430 filed on Dec. 11, 2003 (Applicant—Qiagen GMBH).
Proceeding further with EP patent application pursuant to Article 96(1) and Rule 51(1) EPC issued Feb. 2, 2007 for EP 3796961.5, which claims priority to PCT/US03/39430 filed on Dec. 11, 2003 (Applicant—Qiagen GMBH).
Supplementary European Search Report issued Jan. 16, 2007 for EP 3796961.5, which claims priority to PCT/US03/39430 filed on Dec. 11, 2003 (Applicant—Qiagen GMBH).
Notice of Rejection issued Sep. 29, 2009 for JP 2004-565385, which claims priority to PCT/US03/39430 filed on Dec. 11, 2003 (Applicant—Qiagen GMBH).
Request for Examination filed Nov. 22, 2006 for JP 2004-565385, which claims priority to PCT/US03/39430 filed on Dec. 11, 2003 (Applicant—Qiagen GMBH).
International Search Report issued Aug. 23, 2004 for PCT/US03/39430 filed on Dec. 11, 2003 (Applicant—Qiagen GMBH).
Notice of Abandonment issued Feb. 13, 2008 for CA 2510587, which claims priority to PCT/US03/40364 filed on Dec. 19, 2003 (Applicant—Qiagen GMBH).

Reply to Rule 124(4) Communication filed Dec. 21, 2010 for EP 3799976, which claims priority to PCT/US03/40364 filed on Dec. 19, 2003 (Applicant—Qiagen GMBH).
Minutes of Oral Proceedings issued Oct. 18, 2010 for EP 3799976, which claims priority to PCT/US03/40364 filed on Dec. 19, 2003 (Applicant—Qiagen GMBH).
Brief Communication issued Sep. 10, 2010 for EP 3799976, which claims priority to PCT/US03/40364 filed on Dec. 19, 2003 (Applicant—Qiagen GMBH).
Requests including 1st-4th Auxiliary Requests filed Aug. 23, 2010 for EP 3799976, which claims priority to PCT/US03/40364 filed on Dec. 19, 2003 (Applicant—Qiagen GMBH).
Summons to Attend Oral Proceedings issued May 6, 2010 for EP 3799976, which claims priority to PCT/US03/40364 filed on Dec. 19, 2003 (Applicant—Qiagen GMBH).
Response to Art. 94(3) EPC Communication filed Aug. 13, 2009 for EP 3799976, which claims priority to PCT/US03/40364 filed on Dec. 19, 2003 (Applicant—Qiagen GMBH).
Art. 94(3) EPC Communication issued May 14, 2009 for EP 3799976, which claims priority to PCT/US03/40364 filed on Dec. 19, 2003 (Applicant—Qiagen GMBH).
Response to Art. 94(3) EPC Communication filed Jun. 2, 2008 for EP 3799976, which claims priority to PCT/US03/40364 filed on Dec. 19, 2003 (Applicant—Qiagen GMBH).
Art. 94(3) EPC Communication issued Apr. 18, 2008 for EP 3799976, which claims priority to PCT/US03/40364 filed on Dec. 19, 2003 (Applicant—Qiagen GMBH).
Response to Art. 96(2) EPC Communication filed Dec. 17, 2007 for EP 3799976, which claims priority to PCT/US03/40364 filed Dec. 19, 2003 (Applicant—.
Art. 96(2) EPC Communication issued Aug. 22, 2007 for EP 3799976, which claims priority to PCT/US03/40364 filed on Dec. 19, 2003 (Applicant—Qiagen GMBH).
Response to Art. 96(1) Communication filed Jun. 29, 2007 for EP 3799976, which claims priority to PCT/US03/40364 filed on Dec. 19, 2003 (Applicant—Qiagen GMBH).
Art. 96(1) EPC Communication issued May 7, 2007 for 3799976, which claims priority to PCT/US03/40364 filed on Dec. 19, 2003 (Applicant—Qiagen GMBH).
Supplementary EPO Search Report issued Apr. 18, 2007 for EP 3799976, which claims priority to PCT/US03/40364 filed on Dec. 19, 2003 (Applicant—Qiagen GMBH).
Claim Set filed Sep. 22, 2010 for EP 10178502, which claims priority to PCT/US03/40364 filed on Dec. 19, 2003 (Applicant—Qiagen GMBH).
Amendment and Response filed Jul. 21, 2010 for JP 2005510007, which claims priority to PCT/US03/40364 filed on Dec. 19, 2003 (Applicant—Qiagen GMBH).
Examination Report issued Mar. 23, 2010 for JP 2005510007, which claims priority to PCT/US03/40364 filed on Dec. 19, 2003 (Applicant—Qiagen GMBH).
Amendment and Response filed Feb. 26, 2010 for JP 2005510007, which claims priority to PCT/US03/40364 filed on Dec. 19, 2003 (Applicant—Qiagen GMBH).
Examination Report issued Nov. 4, 2009 for JP 2005510007, which claims priority to PCT/US03/40364 filed on Dec. 19, 2003 (Applicant—Qiagen GMBH).
Claim Set filed Feb. 26, 2010 for JP 2010042086, which claims priority to PCT/US03/40364 filed on Dec. 19, 2003 (Applicant—Qiagen GMBH).
International Search Report issued Apr. 4, 2005 for PCT/US03/40364 filed on Dec. 19, 2003 (Applicant—Qiagen GMBH).
Notice of Abandonment issued Feb. 4, 2008 for AU 2001268725, which claims priority to PCT/US01/20217 filed on Jun. 27, 2001 (Applicant—Qiagen GMBH).
Notice of Acceptance issued Jul. 20, 2006 for AU 2001268725, which claims priority to PCT/US01/20217 filed on Jun. 27, 2001 (Applicant—Qiagen GMBH).
Response to Examiner's First Report issued Jun. 23, 2006 for AU 2001268725, which claims priority to PCT/US01/20217 filed on Jun. 27, 2001 (Applicant—Qiagen GMBH).

(56) References Cited

OTHER PUBLICATIONS

Examination Report issued Jul. 18, 2005 for AU 2001268725, which claims priority to PCT/US01/20217 filed on Jun. 27, 2001 (Applicant—Qiagen GMBH).
Notification of Search Results issued May 5, 2004 for AU 2001268725, which claims priority to PCT/US01/20217 filed on Jun. 27, 2001 (Applicant—Qiagen GMBH).
Notice of Abandonment issued Aug. 22, 2007 for CA 2410951, which claims priority to PCT/US01/20217 filed on Jun. 27, 2001 (Applicant—Qiagen GMBH).
Notice of National Entry issued Jan. 14, 2003 for CA 2410951, which claims priority to PCT/US01/20217 filed on Jun. 27, 2001 (Applicant—Qiagen GMBH).
Expiry of Time Limit in which to file Notice of Opposition issued Aug. 22, 2007 for EP 1946712.5, which claims priority to PCT/US01/20217 filed on Jun. 27, 2001 (Applicant—Molecular Staging, Inc.).
Decision to Grant European Patent issued Sep. 21, 2006 for EP 1946712.5, which claims priority to PCT/US01/20217 filed on Jun. 27, 2001 (Applicant—Molecular Staging, Inc.).
Brief Communication re: Amendment issued Aug. 31, 2006 for EP 1946712.5, which claims priority to PCT/US01/20217filed on Jun. 27, 2001 (Applicant—Molecular Staging, Inc.).
Response to Communication under Rule 51(4) filed Aug. 18, 2006 for EP 1946712.5, which claims priority to PCT/US01/20217 filed on Jun. 27, 2001 (Applicant—Molecular Staging, Inc.).
Communication under Rule 51(4) issued Apr. 19, 2006 for EP 1946712.5, which claims priority to PCT/US01/20217 filed on Jun. 27, 2001 (Applicant—Molecular Staging, Inc.).
Response to Invitation pursuant to Article 96(2) EPC filed Feb. 6, 2006 for EP 1946712.5, which claims priority to PCT/US01/20217 filed on Jun. 27, 2001 (Applicant—Molecular Staging, Inc.).
Communication pursuant to Article 115(2) EPC issued Jan. 9, 2006 for EP 1946712.5, which claims priority to PCT/US01/20217 filed on Jun. 27, 2001 (Applicant—Molecular Staging, Inc.).
Transmittal of Third Party Observations issued Jan. 9, 2006 for EP 1946712.5, which claims priority to PCT/US01/20217 filed on Jun. 27, 2001 (Applicant—Molecular Staging, Inc.).
Observations by Third Party filed Dec. 22, 2005 for EP 1946712.5, which claims priority to PCT/US01/20217 filed on Jun. 27, 2001 (Applicant—Molecular Staging, Inc.).
Invitation pursuant to Article 96(2) and Rule 51(2) EPC issued Dec. 15, 2005 for EP 1946712.5, which claims priority to PCT/US01/20217 filed on Jun. 27, 2001 (Applicant—Molecular Staging, Inc.).
Brief Communication issued Dec. 6, 2005 for EP 1946712.5, which claims priority to PCT/US01/20217 filed on Jun. 27, 2001 (Applicant—Molecular Staging, Inc.).
Written Submissions with Requests filed Nov. 29, 2005 for EP 1946712.5, which claims priority to PCT/US01/20217 filed on Jun. 27, 2001 (Applicant—Molecular Staging, Inc.).
Result of Consultation issued Nov. 16, 2005 for EP 1946712.5, which claims priority to PCT/US01/20217 filed on Jun. 27, 2001 (Applicant—Molecular Staging, Inc.).
Response to Summons to Attend Oral Proceedings filed Oct. 31, 2005 for EP 1946712.5, which claims priority to PCT/US01/20217 filed on Jun. 27, 2001 (Applicant—Molecular Staging, Inc.).
Summons to attend Oral Proceedings issued Jul. 1, 2005 for EP 1946712.5, which claims priority to PCT/US01/20217 filed on Jun. 27, 2001 (Applicant—Molecular Staging, Inc.).
Response to Office Action filed Dec. 20, 2004 for EP 1946712.5, which claims priority to PCT/US01/20217 filed on Jun. 27, 2001 (Applicant—Molecular Staging, Inc.).
Communication pursuant to Article 96(2) EPC issued Nov. 11, 2004 for EP 1946712.5, which claims priority to PCT/US01/20217 filed on Jun. 27, 2001 (Applicant—Molecular Staging, Inc.).
Acknowledgment of Receipt of Third Party Observations issued Oct. 29, 2004 for EP 1946712.5, which claims priority to PCT/US01/20217 filed on Jun. 27, 2001 (Applicant—Molecular Staging, Inc.).
Communication pursuant to Article 115(2) EPC issued Oct. 29, 2004 for EP 1946712.5, which claims priority to PCT/US01/20217 filed on Jun. 27, 2001 (Applicant—Molecular Staging, Inc.).
Observations by Third Party filed Oct. 19, 2004 for 1946712.5, which claims priority to PCT/US01/20217 filed on Jun. 27, 2001 (Applicant—Molecular Staging, Inc.).
Response to Communication pursuant to Article 96(2) EPC filed Jul. 27, 2004 for EP 1946712.5, which claims priority to PCT/US01/20217 filed on Jun. 27, 2001 (Applicant—Molecular Staging, Inc.).
Communication pursuant to Article 96(2) EPC issued Mar. 19, 2004 for EP 1946712.5, which claims priority to PCT/US01/20217 filed on Jun. 27, 2001 (Applicant—Molecular Staging, Inc.).
Response to Communication pursuant to Article 96(2) EPC filed Jan. 30, 2004 for EP 1946712.5, which claims priority to PCT/US01/20217 filed on Jun. 27, 2001 (Applicant—Molecular Staging, Inc.).
Communication pursuant to Article 96(2) EPC issued Jul. 24, 2003 for EP 1946712.5, which claims priority to PCT/US01/20217 filed on Jun. 27, 2001 (Applicant—Molecular Staging, Inc.).
International Preliminary Examination Report issued Nov. 12, 2004 for PCT/US01/20217 filed on Jun. 27, 2001 (Applicant—Molecular Staging, Inc.).
Written Opinion issued Oct. 23, 2003 for PCT/US01/20217 filed on Jun. 27, 2001 (Applicant—Molecular Staging, Inc.).
International Search Report issued Dec. 20, 2002 for PCT/US01/20217 filed on Jun. 27, 2001 (Applicant—Molecular Staging, Inc.).
International Preliminary Examination Report issued Dec. 28, 2004 for PCT/US00/16130 filed on Jun. 12, 2000 (Applicant—Molecular Staging, Inc.).
International Search Report issued Mar. 13, 2003 for PCT/US00/16130 filed on Jun. 12, 2000 (Applicant—Molecular Staging, Inc.).
Acknowledgment of withdrawal of patent application issued Mar. 9, 2005 for EP 2705674.6, which claims priority to PCT/US02/00005 filed on Jan. 4, 2002 (Applicant—Molecular Staging, Inc.).
International Preliminary Examination Report issued May 12, 2003 for PCT/US02/00005 filed on Jan. 4, 2002 (Applicant—Molecular Staging, Inc.).
International Search Report issued Feb. 19, 2003 for PCT/US02/00005 filed on Jan. 4, 2002 (Applicant—Molecular Staging, Inc.).
Acknowledgement of Withdrawal issued Oct. 6, 2003 for EP 980827, which claims priority to PCT/US00/32370 filed on Nov. 28, 2000 (Applicant—Molecular Staging, Inc.).
Withdrawal of Application issued Sep. 10, 2003 for EP 980827, which claims priority to PCT/US00/32370 filed on Nov. 28, 2000 (Applicant—Molecular Staging, Inc.).
Response to Communication Pursuant to Rules 109 and 110 EPC filed Oct. 16, 2001 for EP 980827, which claims priority to PCT/US00/32370 filed on Nov. 28, 2000 (Applicant—Molecular Staging, Inc.).
International Search Report issued Apr. 12, 2000 for PCT/US00/32370 filed on Nov. 28, 2000 (Applicant—Molecular Staging, Inc.).
International Preliminary Examination Report issued Oct. 15, 2004 for PCT/US01/11151 filed on Apr. 5, 2001 (Applicant—Molecular Staging, Inc.).
International Search Report issued Oct. 18, 2002 for PCT/US01/11151 filed on Apr. 5, 2001 (Applicant—Molecular Staging, Inc.).
International Preliminary Examination Report issued Mar. 9, 2006 for PCT/US02/19443 filed on Jun. 19, 2002 (Applicant—Molecular Staging, Inc.).
International Search Report issued Oct. 10, 2003 for PCT/US02/19443 filed on Jun. 19, 2002 (Applicant—Molecular Staging, Inc.).
International Preliminary Examination Report issued Oct. 6, 2004 for PCT/US02/27097 filed on Aug. 14, 2002 (Applicant—Molecular Staging, Inc.).
International Search Report issued Jan. 29, 2003 for PCT/US02/27097 filed on Aug. 14, 2002 (Applicant—Molecular Staging, Inc.).
Response to Art. 94(3) EPC Communication filed Jan. 4, 2011 for EP 7118804.9 filed on Oct. 18, 2007 (Applicant—Qiagen GMBH).
Art. 94(3) EPC Communication issued Aug. 26, 2010 for EP 7118804.9 filed on Oct. 18, 2007 (Applicant—Qiagen GMBH).
Response to Art. 94(3) EPC Communication filed Sep. 29, 2008 for EP 7118804.9 filed on Oct. 18, 2007 (Applicant—Qiagen GMBH).

(56) References Cited

OTHER PUBLICATIONS

Art. 94(3) EPC Communication issued Aug. 7, 2008 for EP 7118804.9 filed on Oct. 18, 2007 (Applicant—Qiagen GMBH).
European Search Report issued Feb. 15, 2008 for EP 7118804.9 filed on Oct. 18, 2007 (Applicant—Qiagen GMBH).
Request for Examination filed Jul. 27, 2010 for JP 2007-276942 filed on Oct. 24, 2007(Applicant—Qiagen GmbH).
Notice of Sealing issued Oct. 10, 2002 for AU 97915/98, which claims priority to PCT/US98/21177 filed on Oct. 8, 1998 (Applicant—Yale University).
Notice of Acceptance issued May 20, 2002 for AU 97915/98, which claims priority to PCT/US98/21177 filed on Oct. 8, 1998 (Applicant—Yale University).
Request to Amend a Complete Specification filed Mar. 27, 2002 for AU 97915/98, which claims priority to PCT/US98/21177 filed on Oct. 8, 1998 (Applicant—Yale University).
First Statement of Proposed Amendments filed Mar. 27, 2002 for AU 97915/98, which claims priority to PCT/US98/21177 filed on Oct. 8, 1998 (Applicant—Yale University).
Examiner's First Report issued May 25, 2001 for AU 97915/98, which claims priority to PCT/US98/21177 filed on Oct. 8, 1998 (Applicant—Yale University).
Notice of Abandonment issued Dec. 4, 2007 for CA 2308004, which claims priority to PCT/US98/21177 filed on Oct. 8, 1998 (Applicant—Yale University).
Notice of Acceptance issued Oct. 16, 2006 for CA 2308004, which claims priority to PCT/US98/21177filed on Oct. 8, 1998 (Applicant—Yale University).
Response to Examination filed Dec. 23, 2004 for CA 2308004, which claims priority to PCT/US98/21177 filed on Oct. 8, 1998 (Applicant—Yale University).
Examination Report issued Jun. 30, 2004 for CA 2308004, which claims priority to PCT/US98/21177 filed on Oct. 8, 1998 (Applicant—Yale University).
Voluntary Amendments filed Oct. 12, 2000 for CA 2308004, which claims priority to PCT/US98/21177 filed on Oct. 8, 1998 (Applicant—Yale University).
Communication regarding Expiry of Opposition Time Period issued Nov. 5, 2008 for EP 98952147.1, which claims priority to PCT/US98/21177 filed on Oct. 8, 1998 (Applicant—Yale University).
Decision to Grant issued Dec. 6, 2007 for EP 98952147.1, which claims priority to PCT/US98/21177 filed on Oct. 8, 1998 (Applicant—Yale University).
Brief Communication re: Request for Amendment of Application issued Nov. 2, 2007 for EP 98952147.1, which claims priority to PCT/US98/21177 filed on Oct. 8, 1998 (Applicant—Yale University).
Response to Communication under Rule 51(4) filed Oct. 5, 2007 for EP 98952147.1, which claims priority to PCT/US98/21177 filed on Oct. 8, 1998 (Applicant—Yale University).
Communication under Rule 51(4) issued Jun. 6, 2007 for EP 98952147.1, which claims priority to PCT/US98/21177 filed on Oct. 8, 1998 (Applicant—Yale University).
Response to Article 96(2) EPC and Rule 51(2) EPC Communication filed May 14, 2007 for EP 98952147.1, which claims priority to PCT/US98/21177 filed on Oct. 8, 1998 (Applicant—Yale University).
Invitation pursuant to Article 96(2) EPC and Rule 51(2) EPC issued Apr. 16, 2007 for EP 98952147.1, which claims priority to PCT/US98/21177 filed on Oct. 8, 1998 (Applicant—Yale University).
Response to Examination Report filed Mar. 13, 2007 for EP 98952147.1, which claims priority to PCT/US98/21177 filed on Oct. 8, 1998 (Applicant—Yale University).
Invitation pursuant to Article 96(2) EPC and Rule 51(2) EPC issued Dec. 29, 2006 for 98952147.1, which claims priority to PCT/US98/21177 filed on Oct. 8, 1998 (Applicant—Yale University).
Response to Communication pursuant to Article 96(2) EPC filed Mar. 6, 2006 for EP 98952147.1, which claims priority to PCT/US98/21177 filed on Oct. 8, 1998 (Applicant—Yale University).
Examination Report issued Sep. 21, 2005 for EP 98952147.1, which claims priority to PCT/US98/21177 filed on Oct. 8, 1998 (Applicant—Yale University).
Favorable Decision regarding Notice of Appeal issued Feb. 3, 2009 for JP 2000515033, which claims priority to PCT/US98/21177 filed on Oct. 8, 1998 (Applicant—Yale University).
Amendment and Response to Official Action filed Dec. 22, 2008 for JP 2000515033, which claims priority to PCT/US98/21177 filed on Oct. 8, 1998 (Applicant—Yale University).
Official Action issued Dec. 2, 2008 for JP 2000-515033, which claims priority to PCT/US98/21177 filed on Oct. 8, 1998 (Applicant—Yale University).
Argument to Written Communication filed Apr. 2, 1008 for JP2000-515033, which claims priority to PCT/US98/21177 filed on Oct. 8, 1998 (Applicant—Yale University).
Report Concerning Reconsideration before Appeal issued Oct. 2, 2007 for JP 2000515033, which claims priority to PCT/US98/21177 filed on Oct. 8, 1998 (Applicant—Yale University).
Amendment and Response to Official Action filed Dec. 28, 2006 for JP 2000515033, which claims priority to PCT/US98/21177 filed on Oct. 8, 1998 (Applicant—Yale University).
Final Rejection issued Sep. 2, 2005 for JP 2000-515033, which claims priority to PCT/US98/21177 filed on Oct. 8, 1998 (Applicant—Yale University).
Response to Examination filed Nov. 11, 2004 for JP 2000-515033, which claims priority to PCT/US98/21177 filed on Oct. 8, 1998 (Applicant—Yale University).
Examination Report issued May 7, 2004 for JP 2000-515033, which claims priority to PCT/US98/21177 filed on Oct. 8, 1998 (Applicant—Yale University).
International Preliminary Examination Report issued Dec. 10, 1999 for PCT/US98/21177 filed on Oct. 8, 1998 (Applicant—Yale University).
Response to Written Opinion issued Oct. 18, 1999 for PCT/US98/21177 filed on Oct. 8, 1998 (Applicant—Yale University).
Written Opinion issued Jul. 20, 1999 for PCT/US98/21177 filed on Oct. 8, 1998 (Applicant—Yale University).
International Search Report issued Mar. 10, 1999 for PCT/US98/21177 filed on Oct. 8, 1998 (Applicant—Yale University).
Noting of Loss of Rights (69(1) EPC) issued Apr. 1, 2004 for EP 99935725.4, which claims priority to PCT/US99/16373 filed on Jul. 20, 1999 (Applicant—Yale University).
Examination Report issued Aug. 13, 2003 for EP 99935725.4, which claims priority to PCT/US99/16373 filed on Jul. 20, 1999 (Applicant—Yale University).
International Preliminary Examination Report issued Sep. 19, 2000 for PCT/US99/16373 filed on Jul. 20, 1999 (Applicant—Yale University).
Response to Written Opinion filed Aug. 18, 2000 for PCT/US99/16373 filed on Jul. 20, 1999 (Applicant—Yale University).
Written Opinion issued Jun. 20, 2000 for PCT/US99/16373 filed on Jul. 20, 1999 (Applicant—Yale University).
International Search Report issued Dec. 2, 1999 for PCT/US99/16373 filed on Jul. 20, 1999 (Applicant—Yale University) Applicant—.
International Search Report issued Aug. 8, 2006 for PCT Application No. PCT/EP2006/002771 filed on Mar. 27, 2006 (Applicant—Qiagen GMBH).
Written Opinion issued Oct. 2, 2007 for PCT Application No. PCT/EP2006/002771 filed on Mar. 27, 2006 (Applicant—Qiagen GMBH).
International Preliminary Opinion on Patentability issued Oct. 3, 2007 for PCT Application No. PCT/EP2006/002771 filed on Mar. 27, 2006 (Applicant—Qiagen GMBH).
Communication from the European Examining Division issued Jul. 17, 2009 for EP Application No. EP2006723749 filed on Oct. 24, 2007 (Applicant—Qiagen GMBH).
Reply to Communication from European Examining Division filed Aug. 20, 2009 for EP Application No. EP2006723749 filed on Oct. 24, 2007 (Applicant—Qiagen GMBH).

(56) References Cited

OTHER PUBLICATIONS

Communication from the European Examining Division issued Oct. 29, 2009 for EP Application No. EP2006723749 filed on Oct. 24, 2007 (Applicant—Qiagen GMBH).
Reply to Communication from European Examining Division filed Nov. 24, 2009 for EP Application No. EP2006723749 filed on Oct. 24, 2007 (Applicant—Qiagen GMBH).
Communication from the European Examining Division issued Dec. 23, 2009 for EP Application No. EP2006723749 filed on Oct. 24, 2007 (Applicant—Qiagen GMBH).
Reply to Communication from European Examining Division filed Apr. 9, 2010 for EP Application No. EP2006723749 filed on Oct. 24, 2007 (Applicant—Qiagen GMBH).
English Translation of Granted Claims issued Sep. 22, 2010 for EP Application No. EP2006723749 filed on Oct. 24, 2007 (Applicant—Qiagen GMBH).
Decision to Grant European Patent issued Oct. 21, 2010 for EP Application No. EP2006723749 filed on Oct. 24, 2007 (Applicant—Qiagen GMBH).
International Preliminary Report on Patentability and Written Opinion issued on Apr. 8, 2008 for International App. No. PCT/EP2006/06622, filed on Sep. 11, 2006 (Applicant—Qiagen GMBH).
International Search Report issued on Apr. 13, 2007 for International App. No. PCT/EP2006/06622, filed on Sep. 11, 2006 (Applicant—Qiagen GMBH).
Reply to Communication filed on Jan. 4, 2011 for EP Application No. EP07118804 filed on Oct. 18, 2007 (Applicant—Qiagen GMBH).
EPO Communication issued on Aug. 26, 2010 for EP Application No. EP07118804 filed on Oct. 18, 2007 (Applicant—Qiagen GMBH).
Reply to Communication from European Examining Division filed on Sep. 29, 2008 for EP Application No. EP07118804 filed on Oct. 18, 2007 (Applicant—Qiagen GMBH).
EPO Communication issued on Aug. 7, 2008 for EP Application No. EP07118804 filed on Oct. 18, 2007 (Applicant—Qiagen GMBH).
European Search Report issued on Feb. 15, 2008 for EP Application No. EP07118804 filed on Oct. 18, 2007 (Applicant—Qiagen GMBH).

* cited by examiner

NUCLEIC ACID AMPLIFICATION

FIELD OF THE INVENTION

The disclosed invention is generally in the field of nucleic acid amplification.

BACKGROUND OF THE INVENTION

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117-126 (1991); Landegren, *Trends Genetics* 9:199-202 (1993)).

Fundamental to most genetic analysis is availability of genomic DNA of adequate quality and quantity. Since DNA yield from human samples is frequently limiting, much effort has been invested in general methods for propagating and archiving genomic DNA. Methods include the creation of EBV-transformed cell lines or whole genome amplification (WGA) by random or degenerate oligonucleotide-primed PCR. Whole genome PCR, a variant of PCR amplification, involves the use of random or partially random primers to amplify the entire genome of an organism in the same PCR reaction. This technique relies on having a sufficient number of primers of random or partially random sequence such that pairs of primers will hybridize throughout the genomic DNA at moderate intervals. Replication initiated at the primers can then result in replicated strands overlapping sites where another primer can hybridize. By subjecting the genomic sample to multiple amplification cycles, the genomic sequences will be amplified. PCR based WGA methods and EBV-transformed cell lines suffer from high cost or insufficient coverage and inadequate average DNA size (Telenius et al., *Genomics*. 13:718-725 (1992); Cheung and Nelson, *Proc Natl Acad Sci USA*. 93:14676-14679 (1996); Zhang et al., *Proc Natl Acad Sci USA*. 89:5847-5851 (1992)).

Another form of nucleic acid amplification, involving strand displacement, has been described in U.S. Pat. No. 6,124,120 to Lizardi. In one form of the method, two sets of primers are used that are complementary to opposite strands of nucleotide sequences flanking a target sequence. Amplification proceeds by replication initiated at each primer and continuing through the target nucleic acid sequence, with the growing strands encountering and displacing previously replicated strands. In another form of the method a random set of primers is used to randomly prime a sample of genomic nucleic acid. The primers in the set are collectively, and randomly, complementary to nucleic acid sequences distributed throughout nucleic acid in the sample. Amplification proceeds by replication initiating at each primer and continuing so that the growing strands encounter and displace adjacent replicated strands. In another form of the method concatenated DNA is amplified by strand displacement synthesis with either a random set of primers or primers complementary to linker sequences between the concatenated DNA. Synthesis proceeds from the linkers, through a section of the concatenated DNA to the next linker, and continues beyond, with the growing strands encountering and displacing previously replicated strands.

BRIEF SUMMARY OF THE INVENTION

Disclosed are compositions and a method for amplification of nucleic acid sequences of interest. The method is based on strand displacement replication of the nucleic acid sequences by primers. The disclosed method is a form of multiple displacement amplification (MDA) useful for amplifying genomic nucleic acid samples and other nucleic acid samples of high complexity. The disclosed method can be used to amplify such highly complex nucleic acid samples using only one or a limited number of primers. It has been discovered that one or a small number of primers can effectively amplify whole genomes and other nucleic acid samples of high sequence complexity. The primers are specially selected or designed to be able to prime and efficiently amplify the broad range of sequences present in highly complex nucleic acid samples despite the limited amount of primer sequence represented in the primers. The disclosed method generally involves bringing into contact one, a few, or more primers having specific nucleic acid sequences, DNA polymerase, and a nucleic acid sample, and incubating the nucleic acid sample under conditions that promote replication of nucleic acid molecules in the nucleic acid sample. Replication of the nucleic acid molecules results in replicated strands such that, during replication, the replicated strands are displaced from the nucleic acid molecules by strand displacement replication of another replicated strand. The replication can result in amplification of all or a substantial fraction of the nucleic acid molecules in the nucleic acid sample. In one form of the disclosed method, which is a form of whole genome strand displacement amplification (WGSDA), one, a few, or more primers are used to prime a sample of genomic nucleic acid (or another sample of nucleic acid of high complexity).

It was discovered that highly complex nucleic acid samples can be efficiently amplified using only one or a few primers having specific nucleic acid sequences. The one or few primers are complementary to nucleic acid sequences distributed throughout nucleic acid molecules in the sample. For example, a single 6 base primer will be complementary to a sequence once every 4096 nucleotides, on average, and two 6 base primers collectively will be complementary to a sequence once every 2048 nucleotides, on average. It was discovered that such distributions of priming sites were sufficient to allow efficient multiple displacement amplification. It was also discovered that such distributions of priming sites result in amplification of nucleic acid samples with broad coverage of the sequences in the nucleic acid samples and in amplification products with high sequence and locus representation and low amplification bias. Thus, the disclosed method can result in replication of all or a substantial fraction of the nucleic acid molecules in a nucleic acid sample.

Amplification in the disclosed method proceeds by replication with a highly processive polymerase initiating at each primer and continuing until spontaneous termination. A key feature of the method is that as a DNA polymerase extends a primer, the polymerase displaces the replication products (that is, DNA strands) that resulted from extension of other primers. The polymerase is continuously extending new primers and displacing the replication products of previous priming events. In this way, multiple overlapping copies of all of the nucleic acid molecules and sequences in the sample (for example, an entire genome) can be synthesized in a short time. The method has advantages over prior amplification methods in that many fewer primers can be used. Further, the primers need not have a sequence specific for a given nucleic acid sample. Rather, the same primer or primers can be used to amplify a nucleic acid sample having unknown sequence. For example, a single primer as disclosed herein can be used to efficiently amplify any whole genome from any source, an entire cosmid library, artificial chromosomes, and so on, all without the need to know any sequence present in the sample.

The disclosed method can accurately and evenly amplify the various sequences in highly complex nucleic acid samples. This result can be quantified by references to, for example sequence representation, locus representation and amplification bias. For example, the replicated nucleic acid molecules produced in the disclosed method can have a sequence representation of at least 50% for at least 10 different target sequences. The amplification bias can be less than 10% for at least 10 different target sequences.

The method has advantages over the polymerase chain reaction since it can be carried out under isothermal conditions. Other advantages of whole genome strand displacement amplification include a higher level of amplification than whole genome PCR (up to five times higher), amplification is less sequence-dependent than PCR, and there are no re-annealing artifacts or gene shuffling artifacts as can occur with PCR (since there are no cycles of denaturation and re-annealing).

In some useful embodiments of WGSDA, the nucleic acid sample is not subjected to denaturing conditions, the primers are hexamer primers and contain modified nucleotides such that the primers are nuclease resistant, the DNA polymerase is $\phi$29 DNA polymerase, or any combination of these features. The genome can be any type of genome, such as a microbial genome, a viral genome, a eukayotic genome, a plant genome, an animal genome, a vertebrate genome, a mammalian genome, or a human genome.

In one embodiment of the disclosed method, the nucleic acid sample is not subjected to denaturing conditions. Nucleic acid molecules, genomic DNA, for example, need not be denatured for efficient multiple displacement amplification. Elimination of a denaturation step and denaturation conditions has additional advantages such as reducing sequence bias in the amplified products.

In another embodiment, the primers can be, for example, at least 8 bases long, at least 7 bases long, at least 6 bases long, 5 bases long, 4 bases long, at least 3 bases long, or at least 2 bases long. Such short primers can still prime multiple strand displacement replication efficiently. Such short primers are easier and less expensive to produce. The primers can have any sequence or can have particular sequences. For example, shorter primers, such as 6 nucleotide primers, will have complements in the nucleic acid sample at sufficiently short intervals to allow efficient and even amplification. Longer primers for use in the disclosed method generally will benefit from having sequences that are complementary to specific sequences that occur at intervals throughout the nucleic acid sample. For example, the primers can be complementary to sequence in a repeat sequence, such as a microsatellite sequence, a minisatellite sequence, a satellite sequence, a transposon sequence, a ribosomal RNA sequence, a short interspersed nuclear element (SINE), or a long interspersed nuclear element (LINE); a functional consensus sequence such as a promoter sequence, an enhancer sequence, a silencer sequence, an upstream regulatory element sequence, a transcription termination site sequence, a transposon regulatory sequence, a ribosomal RNA regulatory sequence, or a polyadenylation site sequence. Shorter primers can also includes such repeated sequences. When using repeated sequences in primers, more primers can be used in the reaction to improve the distribution of primer complement sequences in the nucleic acid sample. In particular, where some or all of the repeated sequences have uneven distributions in the nucleic acids of the nucleic acid sample, multiple primers complementary to different repeated sequences can be used.

In another embodiment, the primers can each contain at least one modified nucleotide such that the primers are nuclease resistant. In another embodiment, the primers can each contain at least one modified nucleotide such that the melting temperature of the primer is altered relative to a primer of the same sequence without the modified nucleotide(s). For these last two embodiments, it is preferred that the primers are modified RNA. In another embodiment, the DNA polymerase can be $\phi$29 DNA polymerase, or another suitable DNA polymerase. $\phi$29 DNA polymerase produces greater amplification in multiple displacement amplification. The combination of two or more of the above features also yields improved results in multiple displacement amplification. In a preferred embodiment, for example, the nucleic acid sample is not subjected to denaturing conditions, the primers are 6 base primers and contain modified nucleotides such that the primers are nuclease resistant, and the DNA polymerase is $\phi$29 DNA polymerase. The above features are especially useful in whole genome strand displacement amplification (WGSDA).

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. One form of labeling involves labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands. The replicated strands can also be labeled and/or detected using fluorescent change probes and/or primers.

In the disclosed method amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the disclosed strand displacement method.

Genetic analysis must frequently be carried out with DNA derived from biological samples, such as blood, tissue culture cells, buccal swabs, mouthwash, stool, tissues slices, biopsy aspiration, and archeological samples such as bone or mummified tissue. In some cases, the samples are too small to extract a sufficient amount of pure DNA and it is necessary to carry out DNA-based assays directly from the unprocessed sample. Furthermore, it is time consuming to isolate pure DNA, and so the disclosed method, which can amplify the genome directly from biological samples, is particularly useful.

The disclosed method has several distinct advantages over other methodologies. The genome can be amplified directly from whole blood or cultured cells with simple cell lysis techniques such as KOH treatment. PCR and other DNA amplification methods are severely inhibited by cellular contents and so purification of DNA is needed prior to amplification and assay. For example, heme present in lysed blood cells inhibits PCR. In contrast, the disclosed form of whole genome amplification can be carried out on crude lysates with no need to physically separate DNA by miniprep extraction and precipitation procedures, or with column or spin cartridge methods.

Bacteria, fungi, and viruses may all be involved in nosocomial infections. Identification of nosocomial pathogens at the sub-species level requires sophisticated discriminatory techniques. Such techniques utilize traditional as well as molecular methods for typing. Some traditional techniques are antimicrobial susceptibility testing, determination of the ability to utilize biochemical substrates, and serotyping. A major limitation of these techniques is that they take several days to complete, since they require pure bacterial cultures. Because such techniques are long, and the bacteria may even be non-viable in the clinical samples, there is a need to have a quick and reliable method for bacterial species identification.

Some of the DNA-based molecular methods for the identification of bacterial species are macrorestriction analysis (MRA) followed by pulsed-field gel electrophoresis (PFGE), amplified fragment length polymorphism (AFLP) analysis, and arbitrarily primed PCR (AP-PCR) (Tenover et al., J. Clin. Microbiol. 32:407-415 (1994), and Pruckler et al., J. Clin. Microbiol. 33:2872-2875 (1995)). These molecular techniques are labor-intensive and difficult to standardize among different laboratories.

The disclosed method provides a useful alternative method for the identification of bacterial strains by amplification of microbial DNA for analysis. Unlike PCR (Lantz et al., Biotechnol. Annu. Rev. 5:87-130 (2000)), the disclosed method is rapid, non-biased, reproducible, and capable of amplifying large DNA segments from bacterial, viral or fungal genomes.

The disclosed method can be used, for example, to obtain enough DNA from unculturable organisms for sequencing or other studies. Most microorganisms cannot be propagated outside their native environment, and therefore their nucleic acids cannot be sequenced. Many unculturable organisms live under extreme conditions, which makes their genetic complement of interest to investigators. Other microorganisms live in communities that play a vital role in certain ecosystems. Individual organisms or entire communities of organisms can be amplified and sequenced, individually or together.

Recombinant proteins may be purified from a large biomass grown up from bacterial or yeast strains harboring desired expression vectors. A high degree of purity may be desired for the isolated recombinant protein, requiring a sensitive procedure for the detection of trace levels of protein or DNA contaminants. The disclosed method is a DNA amplification reaction that is highly robust even in the presence of low levels of DNA template, and can be used to monitor preparations of recombinant protein for trace amounts of contaminating bacterial or yeast genomic DNA.

Amplification of forensic material for RFLP-based testing is one useful application for the disclosed method.

It is an object of the disclosed invention to provide a method of amplifying an entire genome or other highly complex nucleic acid sample in a continuous, isothermal reaction.

It is another object of the disclosed invention to provide a kit for amplifying an entire genome or other highly complex nucleic acid sample in a continuous, isothermal reaction.

DETAILED DESCRIPTION OF THE INVENTION

Figure 1:
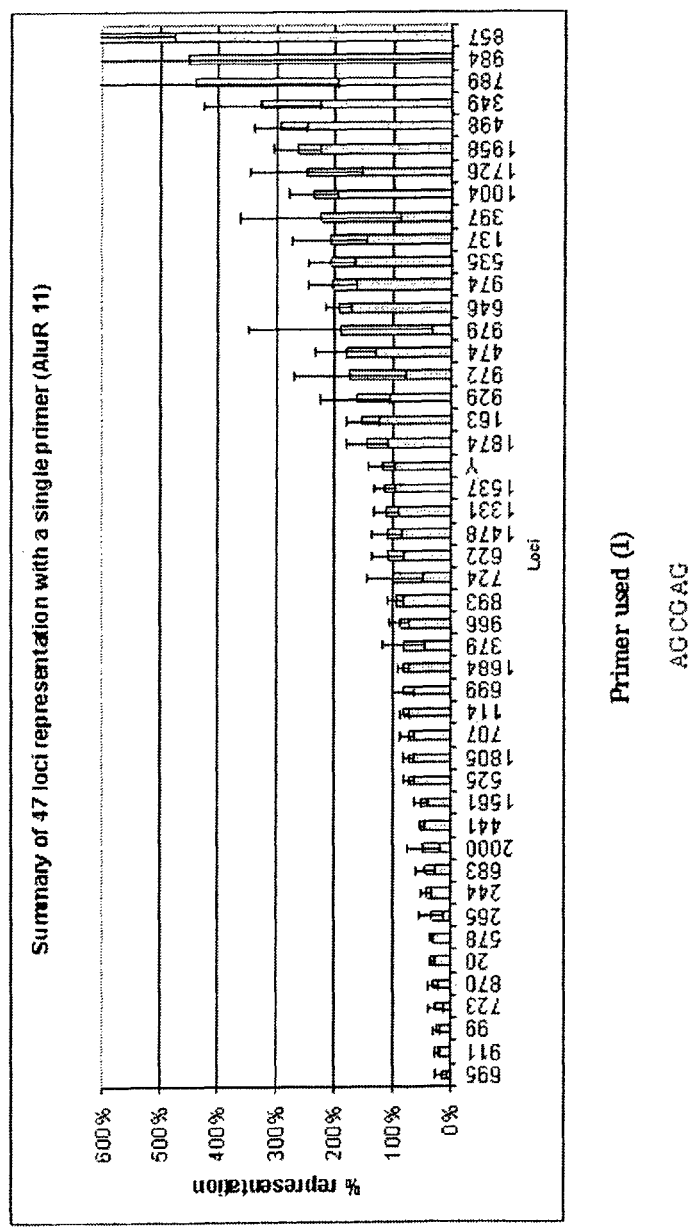
FIG. 1 is a graph of the locus representation (in percent) for 47 genetic loci (2 loci per chromosome, and one locus from the Y chromosome) in human genomic DNA amplified using a single six nucleotide primer of specific nucleotide sequence in an embodiment of the disclosed method.

The disclosed method makes use of certain materials and procedures which allow amplification of nucleic acid sequences and whole genomes or other highly complex nucleic acid samples. These materials and procedures are described in detail below.

Materials

A. Nucleic Acid Samples

Nucleic acid molecules, which are the object of amplification, can be any nucleic acid from any source. In general, the disclosed method is performed using a nucleic acid sample that contains (or is suspected of containing) nucleic acid molecules to be amplified. For whole genome amplification, the nucleic acid sample generally is all or a substantial portion of an entire genome. As used herein, a substantial portion of a genome refers to the presence of 90% or more of the sequences present in the entire genome. A nucleic acid sample or genomic nucleic acid sample including or comprising a substantial portion of a genome refers to a nucleic acid sample including 90% or more of the sequences present in the entire genome. A genomic nucleic acid sample refers to any nucleic acid sample derived from genomic nucleic acids and including or comprising a notable portion of the entire genome. As used herein, a notable portion of a genome refers to the presence of 20% or more of the sequences present in the entire genome. A nucleic acid sample or genomic nucleic acid sample including or comprising a notable portion of a genome refers to a nucleic acid sample including 20% or more of the sequences present in the entire genome. As used herein, a significant portion of a genome refers to the presence of 50% or more of the sequences present in the entire genome. A nucleic acid sample or genomic nucleic acid sample including or comprising a significant portion of a genome refers to a nucleic acid sample including 50% or more of the sequences present in the entire genome. A genomic nucleic acid sample is a form of nucleic acid sample. Reference herein to a nucleic acid sample encompasses genomic nucleic acid samples unless the context clearly indicates otherwise.

A nucleic acid sample can be any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful nucleic acid samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, a crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

For whole genome amplification, preferred nucleic acid samples are nucleic acid samples from a single cell. The nucleic acid samples for use in the disclosed method are preferably nucleic acid molecules and samples that are complex and non-repetitive. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome. The target genome is preferably pure or substantially pure, but this is not required. For example, an genomic sample from an animal source may include nucleic acid from contaminating or infecting organisms.

The nucleic acid sample can be, or can be derived from, for example, one or more whole genomes from the same or different organisms, tissues, cells or a combination; one or more partial genomes from the same or different organisms, tissues, cells or a combination; one or more whole chromosomes from the same or different organisms, tissues, cells or a combination; one or more partial chromosomes from the same or different organisms, tissues, cells or a combination; one or more chromosome fragments from the same or different organisms, tissues, cells or a combination; one or more artificial chromosomes; one or more yeast artificial chromosomes; one or more bacterial artificial chromosomes; one or more cosmids; or any combination of these.

Where the nucleic acid sample is a nucleic acid sample of high complexity, the nucleic acid molecules in the sample can be from any source or combination of sources that result in a highly complex sample. By high complexity or high sequence complexity is meant that the nucleic acid sample has a large number of unique (that is, non-repeated) sequences. The total number of nucleotides in the unique sequences is the sequence complexity of the nucleic acid sample. For example, the human genome has approximately $3 \times 10^9$ unique sequences and so has a sequence complexity of approximately $3 \times 10^9$ nucleotides. A nucleic acid sample of high sequence complexity has a sequence complexity of at least $1 \times 10^6$ nucleotides. Thus, a nucleic acid sample of high sequence complexity can have, for example, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

The nucleic acid sample can also be a nucleic acid sample of significant complexity. By significant complexity or significant sequence complexity is meant that the nucleic acid sample has a significant number of unique (that is, non-repeated) sequences. A nucleic acid sample of significant sequence complexity has a sequence complexity of at least $1 \times 10^5$ nucleotides. Thus, a nucleic acid sample of significant sequence complexity can have, for example, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides. The nucleic acid sample can also be a nucleic acid sample of notable complexity. By notable complexity or notable sequence complexity is meant that the nucleic acid sample has a notable number of unique (that is, non-repeated) sequences. A nucleic acid sample of notable sequence complexity has a sequence complexity of at least $1 \times 10^4$ nucleotides. Thus, a nucleic acid sample of significant sequence complexity can have, for example, a sequence complexity of at least $1 \times 10^4$ nucleotides, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

Nucleic acid samples and genomic nucleic acid samples can have, for example, a sequence complexity of at least $1 \times 10^3$ nucleotides, a sequence complexity of at least $1 \times 10^4$ nucleotides, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

B. Primers

Primers for use in the disclosed amplification method are oligonucleotides having specific sequences. The sequence in a primer intended to hybridize to nucleic acid molecules is referred to as the complementary portion of the primer. The complementary portion of a primer can be any length that supports specific and stable hybridization between the primer and the nucleic acid molecules under the reaction conditions. Generally, for reactions at 30° C., this can be, for example, 5 to 20 nucleotides long or 6 to 8 nucleotides long. For whole genome amplification, the primers can be, for example, from 2 to 60 nucleotides long, and in particular, can be 2, 3, 4, 5, 6, 7, 8, 9, 10, 11, 12, 13, 14, 15, 16, 17, 18, 19, and/or 20 nucleotides long. The primers also can be, for example, at least 2 nucleotides long, at least 3 nucleotides long, at least 4 nucleotides long, at least 5 nucleotides long, at least 6 nucleotides long, at least 7 nucleotides long, and/or at least 8 nucleotides long. The primers used in an amplification reaction need not be all of the same length, although this is preferred.

The primers can have, for example, a length of 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides. The primers can have, for example, a length of less than 4 nucleotides, less than 5 nucleotides, less than 6 nucleotides, less than 7 nucleotides, less than 8 nucleotides, less than 9 nucleotides, less than 10 nucleotides, less than 11 nucleotides, less than 12 nucleotides, less than 13 nucleotides, less than 14 nucleotides, less than 15 nucleotides, less than 16 nucleotides, less than 17 nucleotides, less than 18 nucleotides, less than 19 nucleotides, less than 20 nucleotides, less than 21 nucleotides, less than 22 nucleotides, less than 23 nucleotides, less than 24 nucleotides, less than 25 nucleotides, less than 26 nucleotides, less than 27 nucleotides, less than 28 nucleotides, less than 29 nucleotides, less than 30 nucleotides, or less than 31 nucleotides.

It is preferred that, when hybridized to nucleic acid molecules in a nucleic acid sample, the primers hybridize at intervals that allow efficient amplification. This generally can be accomplished by using a number of primers in the amplification reaction such that the primers collectively will be complementary to sequence in the nucleic acid sample at desired intervals. Thus, for example, a single 6 base primer will be complementary, on average, to a sequence once every 4096 nucleotides, two 6 base primers will be complementary, on average, to a sequence once every 2048 nucleotides, three 6 base primers will be complementary, on average, to a sequence once every 1024 nucleotides, four 6 base primers will be complementary, on average, to a sequence once every 512 nucleotides, five 6 base primers will be complementary, on average, to a sequence once every 256 nucleotides, six 6 base primers will be complementary, on average, to a sequence once every 128 nucleotides, seven 6 base primers will be complementary, on average, to a sequence once every 64 nucleotides, eight 6 base primers will be complementary, on average, to a sequence once every 32 nucleotides, nine 6 base primers will be complementary, on average, to a sequence once every 16 nucleotides, ten 6 base primers will be complementary, on average, to a sequence once every 8 nucleotides, and so on. Four 8 base primers will be complementary, on average, to a sequence once every 8192 nucleotides, five 8 base primers will be complementary, on average, to a sequence once every 4096 nucleotides, six 8 base primers will be complementary, on average, to a sequence once every 1024 nucleotides, seven 8 base primers will be complementary, on average, to a sequence once every 512 nucleotides, eight 8 base primers will be complementary, on average, to a sequence once every 256 nucleotides, nine 8 base primers will be complementary, on average, to a sequence once every 128 nucleotides, ten 8 base primers will be complementary, on average, to a sequence once every 64 nucleotides, eleven 8 base primers will be complementary, on average, to a sequence once every 32 nucleotides, twelve 8 base primers will be complementary, on average, to a sequence once every 16 nucleotides, thirteen 8 base primers will be complementary, on average, to a sequence once every 8 nucleotides, and so on.

The primers can also be complementary to a sequence that occurs, on average, every 5,000 nucleotides or less, every 4,000 nucleotides or less, every 3,000 nucleotides or less, every 2,500 nucleotides or less, every 2,000 nucleotides or less, every 1,500 nucleotides or less, every 1,000 nucleotides or less, every 900 nucleotides or less, every 800 nucleotides or less, every 700 nucleotides or less, every 600 nucleotides or less, every 500 nucleotides or less, every 400 nucleotides or less, every 300 nucleotides or less, every 200 nucleotides or less, every 100 nucleotides or less, or every 50 nucleotides or less, on average, in the nucleic acid molecules of the nucleic acid sample.

These distances assume a random distribution of sequences, which is approximately true for nucleic acid sample of high complexity, such as genomic nucleic acid samples. These distances are derived from the relationship $4^N$, where N is the number of bases in the primer. The distances can be affected by, for example, the G+C percentage of nucleotides in the nucleic acid sample since G+C percentages other than 50% will have altered distributions of specific nucleotides sequences. Further, the lower the sequence complexity of the nucleic acid sample, the more likely the distribution of specific nucleotide sequences will be altered. However, these effects should not greatly affect the amplification results. The use of shorter primers will minimize these effects. Where the G+C percentage of the nucleic acid sample is other than 50%, primers can be chosen and/or designed that have a similar G+C percentage, either in each primer or collectively among the primers used for amplification.

The optimal interval or separation distance between primer complementary sequences (and thus, the optimum number of primers) will not be the same for all DNA polymerases, because this parameter is dependent on the net polymerization rate. A processive DNA polymerase will have a characteristic polymerization rate which may range from 5 to 300 nucleotides per second, and may be influenced by the presence or absence of accessory ssDNA binding proteins and helicases. In the case of a non-processive polymerase, the net polymerization rate will depend on the enzyme concentration, because at higher concentrations there are more re-initiation events and thus the net polymerization rate will be increased. An example of a processive polymerase is φ29 DNA polymerase, which proceeds at 50 nucleotides per second. An example of a non-processive polymerase is Vent exo(−) DNA polymerase, which will give effective polymerization rates of 4 nucleotides per second at low concentration, or 16 nucleotides per second at higher concentrations.

To obtain an optimal yield in the disclosed method, the number of primers and their composition can be adjusted to suit the polymerase being used. Use of one or a few primers is preferred when using a polymerase with a rapid polymerization rate. Use of more primers is preferred when using a polymerase with a slower polymerization rate. The following assay can be used to determine optimal spacing with any polymerase. The assay uses some combination of one, two, three, four, five, six, seven, eight, nine, ten, eleven, twelve, thirteen, fourteen, fifteen, sixteen, seventeen, eighteen, nineteen, and twenty primers. Each new primer reduces the average distance between complementary sequences in the nucleic acids to be amplified. The number of primers can be varied systematically between a range of primer numbers (the average distance between priming sites varies with the number of primers used). A series of reactions can be performed in which the same nucleic acid sample is amplified using the different numbers of primers. The number of primers that produces the highest experimental yield of DNA and/or the highest quality of amplified product is the optimal primer number for the specific DNA polymerase, or DNA polymerase plus accessory protein combination being used.

DNA replication initiated at the sites in nucleic acid molecules where the primers hybridize will extend to and displace strands being replicated from primers hybridized at adjacent sites. Displacement of an adjacent strand makes it available for hybridization to another primer and subsequent initiation of another round of replication. This process is referred to herein as strand displacement replication.

Any desired number of primers of different nucleotide sequence can be used, but use of one or a few primers is preferred. The amplification reaction can be performed with, for example, one, two, three, four, five, six, seven, eight, nine, ten, eleven, twelve, thirteen, fourteen, fifteen, sixteen, or seventeen primers. More primers can be used. There is no fundamental upper limit to the number of primers that can be used. However, the use of fewer primers is preferred. When multiple primers are used, the primers should each have a different specific nucleotide sequence.

The amplification reaction can be performed with a single primer and, for example, with no additional primers, with 1 additional primer, with 2 additional primers, with 3 additional primers, with 4 additional primers, with 5 additional primers, with 6 additional primers, with 7 additional primers, with 8 additional primers, with 9 additional primers, with 10 additional primers, with 11 additional primers, with 12 additional primers, with 13 additional primers, with 14 additional primers, with 15 additional primers, with 16 additional primers, with 17 additional primers, with 18 additional primers, with 19 additional primers, with 20 additional primers, with 21 additional primers, with 22 additional primers, with 23 additional primers, with 24 additional primers, with 25 additional primers, with 26 additional primers, with 27 additional primers, with 28 additional primers, with 29 additional primers, with 30 additional primers, with 31 additional primers, with 32 additional primers, with 33 additional primers, with 34 additional primers, with 35 additional primers, with 36 additional primers, with 37 additional primers, with 38 additional primers, with 39 additional primers, with 40 additional primers, with 41 additional primers, with 42 additional primers, with 43 additional primers, with 44 additional primers, with 45 additional primers, with 46 additional primers, with 47 additional primers, with 48 additional primers, with 49 additional primers, with 50 additional primers, with 51 additional primers, with 52 additional primers, with 53 additional primers, with 54 additional primers, with 55 additional primers, with 56 additional primers, with 57 additional primers, with 58 additional primers, with 59 additional primers, with 60 additional primers, with 61 additional primers, with 62 additional primers, with 63 additional primers, with 64 additional primers, with 65 additional primers, with 66 additional primers, with 67 additional primers, with 68 additional primers, with 69 additional primers, with 70 additional primers, with 71 additional primers, with 72 additional primers, with 73 additional primers, with 74 additional primers, with 75 additional primers, with 76 additional primers, with 77 additional primers, with 78 additional primers, with 79 additional primers, with 80 additional primers, with 81 additional primers, with 82 additional primers, with 83 additional primers, with 84 additional primers, with 85 additional primers, with 86 additional primers, with 87 additional primers, with 88 additional primers, with 89 additional primers, with 90 additional primers, with 91 additional primers, with 92 additional primers, with 93 additional primers, with 94 additional primers, with 95 additional primers, with 96 additional primers, with 97 additional primers, with 98 additional primers, with 99 additional primers, with 100 additional primers, with 110 additional primers, with 120 additional primers, with 130 additional primers, with 140 additional primers, with 150 additional primers, with 160 additional primers, with 170 additional primers, with 180 additional primers, with 190 additional primers, with 200 additional primers, with 210 additional primers, with 220 additional primers, with 230 additional primers, with 240 additional primers, with 250 additional primers, with 260 additional primers, with 270 additional primers, with 280 additional primers, with 290 additional primers, with 300 additional primers, with 310 additional primers, with 320 additional primers, with 330 additional primers, with 340 additional primers, with 350 additional primers, with 360 additional primers, with 370 additional primers, with 380 additional primers, with 390 additional primers, with 400 additional primers, with 410 additional primers, with 420 additional primers, with 430 additional primers, with 440 additional primers, with 450 additional primers, with 460 additional primers, with 470 additional primers, with 480 additional primers, with 490 additional primers, with 400 additional primers, with 550 additional primers, with 600 additional primers, with 650 additional primers, with 700 additional primers, with 750 additional primers, with 800 additional primers, with 850 additional primers, with 900 additional primers, with 950 additional primers, with 1,000 additional primers, with 1,100 additional primers, with 1,200 additional primers, with 1,300 additional primers, with 1,400 additional primers, with 1,500 additional primers, with 1,600 additional primers, with 1,700 additional primers, with 1,800 additional primers, with 1,900 additional primers, with 2,000 additional primers, with 2,100 additional primers, with 2,200 additional primers, with 2,300 additional primers, with 2,400 additional primers, with 2,500 additional primers, with 2,600 additional primers, with 2,700 additional primers, with 2,800 additional primers, with 2,900 additional primers, with 3,000 additional primers, with 3,500 additional primers, or with 4,000 additional primers.

The amplification reaction can be performed with a single primer and, for example, with no additional primers, with fewer than 2 additional primers, with fewer than 3 additional primers, with fewer than 4 additional primers, with fewer than 5 additional primers, with fewer than 6 additional primers, with fewer than 7 additional primers, with fewer than 8 additional primers, with fewer than 9 additional primers, with fewer than 10 additional primers, with fewer than 11 additional primers, with fewer than 12 additional primers, with fewer than 13 additional primers, with fewer than 14 additional primers, with fewer than 15 additional primers, with fewer than 16 additional primers, with fewer than 17 additional primers, with fewer than 18 additional primers, with fewer than 19 additional primers, with fewer than 20 additional primers, with fewer than 21 additional primers, with fewer than 22 additional primers, with fewer than 23 additional primers, with fewer than 24 additional primers, with fewer than 25 additional primers, with fewer than 26 additional primers, with fewer than 27 additional primers, with fewer than 28 additional primers, with fewer than 29 additional primers, with fewer than 30 additional primers, with fewer than 31 additional primers, with fewer than 32 additional primers, with fewer than 33 additional primers, with fewer than 34 additional primers, with fewer than 35 additional primers, with fewer than 36 additional primers, with fewer than 37 additional primers, with fewer than 38 additional primers, with fewer than 39 additional primers, with fewer than 40 additional primers, with fewer than 41 additional primers, with fewer than 42 additional primers, with fewer than 43 additional primers, with fewer than 44 additional primers, with fewer than 45 additional primers, with fewer than 46 additional primers, with fewer than 47 additional primers, with fewer than 48 additional primers, with fewer than 49 additional primers, with fewer than 50 additional primers, with fewer than 51 additional primers, with fewer than 52 additional primers, with fewer than 53 additional primers, with fewer than 54 additional primers, with fewer than 55 additional primers, with fewer than 56 additional primers, with fewer than 57 additional primers, with fewer than 58 additional primers, with fewer than 59 additional primers, with fewer than 60 additional primers, with fewer than 61 additional primers, with fewer than 62 additional primers, with fewer than 63 additional primers, with fewer than 64 additional primers, with fewer than 65 additional primers, with fewer than 66 additional primers, with fewer than 67 additional primers, with fewer than 68 additional primers, with fewer than 69 additional primers, with fewer than 70 additional primers, with fewer than 71 additional primers, with fewer than 72 additional primers, with fewer than 73 additional primers, with fewer than 74 additional primers, with fewer than 75 additional primers, with fewer than 76 additional primers, with fewer than 77 additional primers, with fewer than 78 additional primers, with fewer than 79 additional primers, with fewer than 80 additional primers, with fewer than 81 additional primers, with fewer than 82 additional primers, with fewer than 83 additional primers, with fewer than 84 additional primers, with fewer than 85 additional primers, with fewer than 86 additional primers, with fewer than 87 additional primers, with fewer than 88 additional primers, with fewer than 89 additional primers, with fewer than 90 additional primers, with fewer than 91 additional primers, with fewer than 92 additional primers, with fewer than 93 additional primers, with fewer than 94 additional primers, with fewer than 95 additional primers, with fewer than 96 additional primers, with fewer than 97 additional primers, with fewer than 98 additional primers, with fewer than 99 additional primers, with fewer than 100 additional primers, with fewer than 110 additional primers, with fewer than 120 additional primers, with fewer than 130 additional primers, with fewer than 140 additional primers, with fewer than 150 additional primers, with fewer than 160 additional primers, with fewer than 170 additional primers, with fewer than 180 additional primers, with fewer than 190 additional primers, with fewer than 200 additional primers, with fewer than 210 additional primers, with fewer than 220 additional primers, with fewer than 230 additional primers, with fewer than 240 additional primers, with fewer than 250 additional primers, with fewer than 260 additional primers, with fewer than 270 additional primers, with fewer than 280 additional primers, with fewer than 290 additional primers, with fewer than 300 additional primers, with fewer than 310 additional primers, with fewer than 320 additional primers, with fewer than 330 additional primers, with fewer than 340 additional primers, with fewer than 350 additional primers, with fewer than 360 additional primers, with fewer than 370 additional primers, with fewer than 380 additional primers, with fewer than 390 additional primers, with fewer than 400 additional primers, with fewer than 410 additional primers, with fewer than 420 additional primers, with fewer than 430 additional primers, with fewer than 440 additional primers, with fewer than 450 additional primers, with fewer than 460 additional primers, with fewer than 470 additional primers, with fewer than 480 additional primers, with fewer than 490 additional primers, with fewer than 500 additional primers, with fewer than 550 additional primers, with fewer than 600 additional primers, with fewer than 650 additional primers, with fewer than 700 additional primers, with fewer than 750 additional primers, with fewer than 800 additional primers, with fewer than 850 additional primers, with fewer than 900 additional primers, with fewer than 950 additional primers, with fewer than 1,000 additional primers, with fewer than 1,100 additional primers, with fewer than 1,200 additional primers, with fewer than 1,300 additional primers, with fewer than fewer than 1,400 additional primers, with fewer than 1,500 additional primers, with fewer than 1,600 additional primers, with fewer than 1,700 additional primers, with fewer than 1,800 additional primers, with fewer than 1,900 additional primers, with fewer than 2,000 additional primers, with fewer than 2,100 additional primers, with fewer than 2,200 additional primers, with fewer than 2,300 additional primers, with fewer than 2,400 additional primers, with fewer than 2,500 additional primers, with fewer than 2,600 additional primers, with fewer than 2,700 additional primers, with fewer than 2,800 additional primers, with fewer than 2,900 additional primers, with fewer than 3,000 additional primers, with fewer than 3,500 additional primers, or with fewer than 4,000 additional primers.

The amplification reaction can be performed, for example, with fewer than 2 primers, with fewer than 3 primers, with fewer than 4 primers, with fewer than 5 primers, with fewer than 6 primers, with fewer than 7 primers, with fewer than 8 primers, with fewer than 9 primers, with fewer than 10 primers, with fewer than 11 primers, with fewer than 12 primers, with fewer than 13 primers, with fewer than 14 primers, with fewer than 15 primers, with fewer than 16 primers, with fewer than 17 primers, with fewer than 18 primers, with fewer than 19 primers, with fewer than 20 primers, with fewer than 21 primers, with fewer than 22 primers, with fewer than 23 primers, with fewer than 24 primers, with fewer than 25 primers, with fewer than 26 primers, with fewer than 27 primers, with fewer than 28 primers, with fewer than 29 primers, with fewer than 30 primers, with fewer than 31 primers, with fewer than 32 primers, with fewer than 33 primers, with fewer than 34 primers, with fewer than 35 primers, with fewer than 36 primers, with fewer than 37 primers, with fewer than 38 primers, with fewer than 39 primers, with fewer than 40 primers, with fewer than 41 primers, with fewer than 42 primers, with fewer than 43 primers, with fewer than 44 primers, with fewer than 45 primers, with fewer than 46 primers, with fewer than 47 primers, with fewer than 48 primers, with fewer than 49 primers, with fewer than 50 primers, with fewer than 51 primers, with fewer than 52 primers, with fewer than 53 primers, with fewer than 54 primers, with fewer than 55 primers, with fewer than 56 primers, with fewer than 57 primers, with fewer than 58 primers, with fewer than 59 primers, with fewer than 60 primers, with fewer than 61 primers, with fewer than 62 primers, with fewer than 63 primers, with fewer than 64 primers, with fewer than 65 primers, with fewer than 66 primers, with fewer than 67 primers, with fewer than 68 primers, with fewer than 69 primers, with fewer than 70 primers, with fewer than 71 primers, with fewer than 72 primers, with fewer than 73 primers, with fewer than 74 primers, with fewer than 75 primers, with fewer than 76 primers, with fewer than 77 primers, with fewer than 78 primers, with fewer than 79 primers, with fewer than 80 primers, with fewer than 81 primers, with fewer than 82 primers, with fewer than 83 primers, with fewer than 84 primers, with fewer than 85 primers, with fewer than 86 primers, with fewer than 87 primers, with fewer than 88 primers, with fewer than 89 primers, with fewer than 90 primers, with fewer than 91 primers, with fewer than 92 primers, with fewer than 93 primers, with fewer than 94 primers, with fewer than 95 primers, with fewer than 96 primers, with fewer than 97 primers, with fewer than 98 primers, with fewer than 99 primers, with fewer than 700 primers, with fewer than 110 primers, with fewer than 120 primers, with fewer than 130 primers, with fewer than 140 primers, with fewer than 150 primers, with fewer than 160 primers, with fewer than 170 primers, with fewer than 180 primers, with fewer than 190 primers, with fewer than 200 primers, with fewer than 210 primers, with fewer than 220 primers, with fewer than 230 primers, with fewer than 240 primers, with fewer than 250 primers, with fewer than 260 primers, with fewer than 270 primers, with fewer than 280 primers, with fewer than 290 primers, with fewer than 300 primers, with fewer than 310 primers, with fewer than 320 primers, with fewer than 330 primers, with fewer than 340 primers, with fewer than 350 primers, with fewer than 360 primers, with fewer than 370 primers, with fewer than 380 primers, with fewer than 390 primers, with fewer than 400 primers, with fewer than 410 primers, with fewer than 420 primers, with fewer than 430 primers, with fewer than 440 primers, with fewer than 450 primers, with fewer than 460 primers, with fewer than 470 primers, with fewer than 480 primers, with fewer than 490 primers, with fewer than 500 primers, with fewer than 550 primers, with fewer than 600 primers, with fewer than 650 primers, with fewer than 700 primers, with fewer than 750 primers, with fewer than 800 primers, with fewer than 850 primers, with fewer than 900 primers, with fewer than 950 primers, with fewer than 1,000 primers, with fewer than 1,000 primers, with fewer than 1,200 primers, with fewer than 1,300 primers, with fewer than fewer than 1,400 primers, with fewer than 1,500 primers, with fewer than 1,600 primers, with fewer than 1,700 primers, with fewer than 1,800 primers, with fewer than 1,900 primers, with fewer than 2,000 primers, with fewer than 2,100 primers, with fewer than 2,200 primers, with fewer than 2,300 primers, with fewer than 2,400 primers, with fewer than 2,500 primers, with fewer than 2,600 primers, with fewer than 2,700 primers, with fewer than 2,800 primers, with fewer than 2,900 primers, with fewer than 3,000 primers, with fewer than 3,500 primers, or with fewer than 4,000 primers.

The primers used in the disclosed method can be selected and/or designed to have certain desirable features and functional characteristics. The goal of primer selection and primer design can be obtaining better amplification results. For example, particular primers can be selected that result in the highest amplification yield (that is, the highest amount of increase in the amount of nucleic acid), the best locus or sequence representation in the amplified nucleic acid (that is, the closest to 100% locus or sequence representation for loci and sequences of interest), and/or the lowest amplification bias. This can be determined by testing particular primers in amplification reactions using a nucleic acid sample of interest. Different primers may produce optimal results for different nucleic acid samples. However, the primer number and primer composition principles described herein will generally produce good amplification results on nearly every nucleic acid sample. This broad-based usefulness of the disclosed primers and method is a useful feature of the disclosed primers and method.

Primers that produce amplification products of a desired quality are referred to herein as broad coverage primers. In general, a broad coverage primer (or primers, when used together) can produce a locus representation of at least 10% for at least 5 different loci, a sequence representation of at least 10% for at least 5 different target sequences, an amplification bias of less than 50-fold, an amplification bias of less than 50-fold for at least 5 different loci, and/or an amplification bias of less than 50-fold for at least 5 different target sequences. Primers can also produce, for example, a locus representation of at least 15%, at least 20%, at least 25%, at least 30%, at least 35%, at least 40%, at least 45%, at least 50%, at least 60%, at least 70%, at least 80%, at least 90%, or at least 100% for at least 5 different loci. Primers can also produce, for example, a locus representation of at least 10% for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

Primers can also produce, for example, a sequence representation of at least 15%, at least 20%, at least 25%, at least 30%, at least 35%, at least 40%, at least 45%, at least 50%, at least 60%, at least 70%, at least 80%, at least 90%, or at least 100% for at least 5 different target sequences. Primers can also produce, for example, a sequence representation of at least 10% for at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Primers can also produce, for example, an amplification bias of less than 45-fold, less than 40-fold, less than 35-fold, less than 30-fold, less than 25-fold, less than 20-fold, less than 19-fold, less than 18-fold, less than 17-fold, less than 16-fold, less than 15-fold, less than 14-fold, less than 13-fold, less than 12-fold, less than 11-fold, less than 10-fold, less than 9-fold, less than 8-fold, less than 7-fold, less than 6-fold, less than 5-fold, or less than 4-fold. Primers can also produce, for example, an amplification bias of less than 50-fold for at least 5 different loci, for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci. Primers can also produce, for example, an amplification bias of less than 50-fold for at least 5 different target sequences, for at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

These results can be over a variety of nucleic acid samples, for some selected types of nucleic acid samples, or for a specific type of nucleic acid sample. Thus, a broad coverage primer can be a broad coverage primer when used for, for example, a specific type of nucleic acid sample, when used for selected types of nucleic acid samples, or when used for a variety of nucleic acid samples or nucleic acid samples in general. Thus, the designation broad coverage primer is generally dependent on the nucleic acid sample involved and can also depend on the DNA polymerase used and the conditions used.

Regarding primer selection and design, as described above and elsewhere herein, the primers can be designed (in length and number of primers used) to hybridize at certain intervals, on average, in the nucleotide sequences in the nucleic acid sample. Distribution of primer complement sites can also be achieved by choosing primer sequences that are complementary to sequences that are repeated many times in the nucleic acid sample. Such sequences include classic repeat sequences, such as microsatellite sequences, minisatellite sequences, satellite sequences, transposon sequences, ribosomal RNA sequences, short interspersed nuclear elements (SINEs), or long interspersed nuclear elements (LINEs); and functional consensus sequences, such as promoter sequences, enhancer sequences, silencer sequences, upstream regulatory element sequences, transcription termination site sequences, transposon regulatory sequences, ribosomal RNA regulatory sequences, or polyadenylation site sequences. For example, the primer sequence can be chosen to be complementary to a sequence in an Alu repeat sequence. As a specific example, the primer can have one of the sequences AGTGGG or AGAGAG; one of the sequences AGCCGG, AGTAGG, or AGTTGG; one of the sequences AGGCGG, AGTGGG, AGGGAG, or AGTGAG; one of the sequences AGTGGG, AGCCAG, AGTTAG, AGTCAG, or AGACAG; one of the sequences AGAGGG, AGGCAG, AGCCAG, AGTCAG, or AGACAG; one of the sequences AGTAGG, AGGTGG, AGGCAG, AGACAG, or AGTGAG; AGGAGG, AGAGGG, AGGGAG, AGTCAG, or AGCGAG; or one of the sequences CGGTGG, TCACGC, CGAGCG, GCGTGG, ACTCGG, AATCGC, CGGAGG, CCGAGA, GATCGC, AGAGCG, AGCGAG, or ACTCCG. Multiple primers used in a reaction can have different sequences that are, for example, complementary to different sequences in an Alu repeat sequence. As a specific example, each primer has a different one of the sequences AGTGGG or AGAGAG; a different one of the sequences AGCCGG, AGTAGG, or AGTTGG; a different one of the sequences AGGCGG, AGTGGG, AGGGAG, or AGTGAG; a different one of the sequences AGTGGG, AGCCAG, AGTTAG, AGTCAG, or AGACAG; a different one of the sequences AGAGGG, AGGCAG, AGCCAG, AGTCAG, or AGACAG; a different one of the sequences AGTAGG, AGGTGG, AGGCAG, AGACAG, or AGTGAG; AGGAGG, AGAGGG, AGGGAG, AGTCAG, or AGCGAG; or a different one of the sequences CGGTGG, TCACGC, CGAGCG, GCGTGG, ACTCGG, AATCGC, CGGAGG, CCGAGA, GATCGC, AGAGCG, AGCGAG, or ACTCCG.

The nucleotide sequence and composition of the primers used can also be chosen to optimize amplification. For example, the G+C percentage of the primers can be chosen based on the G+C percentage of the nucleic acid sample to be amplified. The primer can have, for example, a G+C percentage within 20%, within 15%, within 10%, within 9%, within 8%, within 7%, within 6%, within 5%, within 4%, within 3%, within 2%, or within 1% of the G+C percentage of the nucleic acid sample. As used herein, G+C percentage refers to the percent of total nucleotides that are either guanosine (G) residues or cytidine (C) residues in a given nucleic acid molecule, nucleic acid sequence, nucleic acid sample, or other nucleic acid composition.

The primers can also have other characteristics that can, for example, increase amplification yield and reduce production of artifacts or artifactual amplification. For example, generation of primer dimer artifacts can be reduced by designing primers to avoid 3' end sequences that are complementary, either between primers or within the same primer. Such sequences to be avoided can be referred to as intercomplementary 3' ends. A useful measure of a primer's ability to avoid artifactual amplification is the lack or relative insignificance of amplification (that is, nucleic acid produced) when the primer is used in an amplification reaction without a nucleic acid sample.

The disclosed primers can have one or more modified nucleotides. Such primers are referred to herein as modified primers. Modified primers have several advantages. First, some forms of modified primers, such as RNA/2'-O-methyl RNA chimeric primers, have a higher melting temperature (Tm) than DNA primers. This increases the stability of primer hybridization and will increase strand invasion by the primers. This will lead to more efficient priming. Also, since the primers are made of RNA, they will be exonuclease resistant. Such primers, if tagged with minor groove binders at their 5' end, will also have better strand invasion of the template dsDNA.

Chimeric primers can also be used. Chimeric primers are primers having at least two types of nucleotides, such as both deoxyribonuucleotides and ribonucleotides, ribonucleotides and modified nucleotides, two or more types of modified nucleotides, deoxyribonucleotides and two or more different types of modified nucleotides, ribonucleotides and two or more different types of modified nucleotides, or deoxyribonucleotides, ribonucleotides and two or more different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. Other forms of chimeric primers are, for example, 5'-(2'-O-Methyl) RNA-RNA-3' or 5'-(2'-O-Methyl) RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. A primer having one or more universal bases is not considered to be a primer having a specific sequence.

Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)nO]m CH$_3$, —O(CH$_2$)nOCH$_3$, —O(CH$_2$)nNH$_2$, —O(CH$_2$)nCH$_3$, —O(CH$_2$)n—ONH$_2$, and —O(CH$_2$)nON[(CH$_2$)nCH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA).

Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate nucleic acid molecules.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can (and normally will) comprise different types of bases.

Primers may, but need not, also contain additional sequence at the 5' end of the primer that is not complementary to a target sequence. This sequence is referred to as the non-complementary portion of the primer. Primers for use in the disclosed method can include a non-complementary portion or can lack a non-complementary portion. The non-complementary portion of the primer, if present, serves to facilitate strand displacement during DNA replication. The non-complementary portion of the primer can also include a functional sequence such as a promoter for an RNA polymerase. The non-complementary portion of a primer may be any length, but is generally 1 to 100 nucleotides long, and preferably 4 to 8 nucleotides long. It is preferred that the complementary portion of each primer have a different sequence.

It is specifically contemplated that primers having random or degenerate sequence can be excluded from use in the disclosed method. It is also specifically contemplated that use of conditions that allow or are compatible with substantial, significant or notable mismatch hybridization of the primers to nucleic acid molecules being amplified can be excluded. As used herein, substantial mismatch hybridization of a primer refers to hybridization where 90% or more of the primer nucleotides are unpaired to nucleotides in the hybridization partner. Significant mismatch hybridization of a primer refers to hybridization where 50% or more of the primer nucleotides are unpaired to nucleotides in the hybridization partner. Notable mismatch hybridization of a primer refers to hybridization where 10% or more of the primer nucleotides are unpaired to nucleotides in the hybridization partner. Choosing conditions that avoid or that are not compatible with substantial or significant or notable mismatch hybridization of the primers emphasizes the use of specific or substantially specific hybridization of the primers in the disclosed method.

As used herein, conditions compatible with a given level of mismatch hybridization refer to conditions that would result in a notable fraction or more of hybridizations to be at the given level. Conditions that are not compatible with a given level of mismatch hybridization refer to conditions that would not result in a notable fraction of hybridizations to be at the given level. Conditions that allow a given level of mismatch hybridization refer to conditions that would result in a notable fraction or more of hybridizations to be at the given level. Conditions that do not allow a given level of mismatch hybridization refer to conditions that would not result in a notable fraction of hybridizations to be at the given level. In this regard, it is understood that conditions that theoretically would or would not produce a given level of hybridization will not prevent some transient or rare mismatch hybridizations.

An important factor for conditions that do or do not allow, or that are or are not compatible with, a given level of mismatch hybridization is the temperature at which the amplification is carried out. Thus, for example, a temperature significantly below the melting temperature of a primer generally would allow a higher level of mismatch hybridization by that primer than a temperature closer to its melting temperature because hybrids involving only some of the nucleotides in the primer would be stable at the lower temperature. In this way, the reaction temperature (that is, the temperature at which the nucleic acid sample, primer and DNA polymerase are incubated for amplification) affects the level of mismatch hybridization and the intervals at which primers will hybridize to nucleotide sequences in the nucleic acid sample.

To make use of primer specificity in the disclosed method, the primers can be designed (or, conversely, the incubation temperature can be chosen) to reduce the level of mismatch hybridization. In general, this can involve use of lower incubation temperatures for shorter primers and higher incubation temperatures for longer primers. As deemed suitable and desirable, the primers can be designed for use at, and/or the amplification reaction can be incubated at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53°

C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. The primers can be designed for use at, and/or the amplification reaction can be incubated at less than 21° C., less than 22° C., less than 23° C., less than 24° C., less than 25° C., less than 26° C., less than 27° C., less than 28° C., less than 29° C., less than 30° C., less than 31° C., less than 32° C., less than 33° C., less than 34° C., less than 35° C., less than 36° C., less than 37° C., less than 38° C., less than 39° C., less than 40° C., less than 41° C., less than 42° C., less than 43° C., less than 44° C., less than 45° C., less than 46° C., less than 47° C., less than 48° C., less than 49° C., less than 50° C., less than 51° C., less than 52° C., less than 53° C., less than 54° C., less than 55° C., less than 56° C., less than 57° C., less than 58° C., less than 59° C., less than 60° C., less than 61° C., less than 62° C., less than 63° C., less than 64° C., less than 65° C., less than 66° C., less than 67° C., less than 68° C., less than 69° C., less than 70° C., less than 71° C., less than 72° C., less than 73° C., less than 74° C., less than 75° C., less than 76° C., less than 77° C., less than 78° C., less than 79° C., or less than 80° C.

1. Detection Tags

The non-complementary portion of a primer can include sequences to be used to further manipulate or analyze amplified sequences. An example of such a sequence is a detection tag, which is a specific nucleotide sequence present in the non-complementary portion of a primer. Detection tags have sequences complementary to detection probes. Detection tags can be detected using their cognate detection probes. Detection tags become incorporated at the ends of amplified strands. The result is amplified DNA having detection tag sequences that are complementary to the complementary portion of detection probes. If present, there may be one, two, three, or more than three detection tags on a primer. It is preferred that a primer have one, two, three or four detection tags. Most preferably, a primer will have one detection tag. Generally, it is preferred that a primer have 10 detection tags or less. There is no fundamental limit to the number of detection tags that can be present on a primer except the size of the primer. When there are multiple detection tags, they may have the same sequence or they may have different sequences, with each different sequence complementary to a different detection probe. It is preferred that a primer contain detection tags that have the same sequence such that they are all complementary to a single detection probe. For some multiplex detection methods, it is preferable that primers contain up to six detection tags and that the detection tag portions have different sequences such that each of the detection tag portions is complementary to a different detection probe. A similar effect can be achieved by using multiple primers where each has a single different detection tag. The detection tags can each be any length that supports specific and stable hybridization between the detection tags and the detection probe. For this purpose, a length of 10 to 35 nucleotides is preferred, with a detection tag portion 15 to 20 nucleotides long being most preferred.

2. Address Tag

Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. It is preferred that a primer have one or two address tags. Most preferably, a primer will have one address tag. Generally, it is preferred that a primer have 10 address tags or less. There is no fundamental limit to the number of address tags that can be present on a primer except the size of the primer. When there are multiple address tags, they may have the same sequence or they may have different sequences, with each different sequence complementary to a different address probe. It is preferred that a primer contain address tags that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

C. Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers. The use of several types of fluorescent change probes and primers are reviewed in Schweitzer and Kingsmore, Curr. Opin. Biotech. 12:21-27 (2001). Hall et al., Proc. Natl. Acad. Sci. USA 97:8272-8277 (2000), describe the use of fluorescent change probes with Invader assays.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes (Holland et al., Proc. Natl. Acad. Sci. USA 88:7276-7280 (1991)) are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is, increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers (Nazerenko et al., Nucleic Acids Res. 25:2516-2521 (1997)) and scorpion primers (Thelwell et al., Nucleic Acids Res. 28(19):3752-3761 (2000)).

Cleavage activated primers are similar to cleavage activated probes except that they are primers that are incorporated into replicated strands and are then subsequently cleaved. Little et al., Clin. Chem. 45:777-784 (1999), describe the use of cleavage activated primers.

D. Nucleic Acid Fingerprints

The disclosed method can be used to produce replicated strands that serve as a nucleic acid fingerprint of a complex sample of nucleic acid. Such a nucleic acid fingerprint can be compared with other, similarly prepared nucleic acid fingerprints of other nucleic acid samples to allow convenient detection of differences between the samples. The nucleic acid fingerprints can be used both for detection of related nucleic acid samples and comparison of nucleic acid samples. For example, the presence or identity of specific organisms can be detected by producing a nucleic acid fingerprint of the test organism and comparing the resulting nucleic acid fingerprint with reference nucleic acid fingerprints prepared from known organisms. Changes and differences in gene expression patterns can also be detected by preparing nucleic acid fingerprints of mRNA from different cell samples and comparing the nucleic acid fingerprints. The replicated strands can also be used to produce a set of probes or primers that is specific for the source of a nucleic acid sample. The replicated strands can also be used as a library of nucleic acid sequences present in a sample. Nucleic acid fingerprints can be made up of, or derived from, whole genome amplification of a sample such that the entire relevant nucleic acid content of the sample is substantially represented, or from multiple strand displacement amplification of selected target sequences within a sample.

Nucleic acid fingerprints can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of nucleic acid fingerprints include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from nucleic acid fingerprints and replicated strands produced in the disclosed method can also be collected, used, saved, stored, and/or archived.

Nucleic acid fingerprints can also contain or be made up of other information derived from the information generated in the disclosed method, and can be combined with information obtained or generated from any other source. The informational nature of nucleic acid fingerprints produced using the disclosed method lends itself to combination and/or analysis using known bioinformatics systems and methods.

Nucleic acid fingerprints of nucleic acid samples can be compared to a similar nucleic acid fingerprint derived from any other sample to detect similarities and differences in the samples (which is indicative of similarities and differences in the nucleic acids in the samples). For example, a nucleic acid fingerprint of a first nucleic acid sample can be compared to a nucleic acid fingerprint of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same nucleic acid molecule, the same nucleic acid library, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and Salmonella. A different type of tissue refers to tissues of different types such as liver and kidney, or skin and brain. A different strain or species of organism refers to organisms differing in their species or strain designation as those terms are understood in the art.

E. Lysis Solution

In preparing nucleic acid samples for use in the disclosed method, cells can be exposed to alkaline conditions by mixing the cells with a lysis solution. A lysis solution is generally a solution that can raise the pH of a cell solution sufficiently to cause cell lysis. Denaturing solutions can be used as lysis solutions so long as the denaturing solution can have the effects required of lysis solutions. In some embodiments, the lysis solution can comprise a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of lysis solution include lysis solution comprising 400 mM KOH, lysis solution comprising 400 mM KOH, 100 mM dithiothreitol, and 10 mM EDTA, and lysis solution consisting of 400 mM KOH, 100 mM dithiothreitol, and 10 mM EDTA.

In some embodiments, the lysis solution can comprise a plurality of basic agents. As used herein, a basic agent is a compound, composition or solution that results in alkaline conditions. In some embodiments, the lysis solution can comprise a buffer. Useful buffers include phosphate buffers, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The lysis solution can comprise a plurality of buffering agents. As used herein, a buffering agent is a compound, composition or solution that acts as a buffer. An alkaline buffering agent is a buffering agent that results in alkaline conditions. In some embodiments, the lysis solution can comprise a combination of one or more bases, basic agents, buffers and buffering agents.

The amount of lysis solution mixed with the cells can be that amount that causes a substantial number of cells to lyse or those that cause a sufficient number of cells to lyse. Generally, this volume will be a function of the pH of the cell/lysis solution mixture. Thus, the amount of lysis solution to mix with cells can be determined generally from the volume of the cells and the alkaline concentration of the lysis buffer. For example, a smaller volume of a lysis solution with a stronger base and/or higher concentration of base would be needed to create sufficient alkaline conditions than the volume needed of a lysis solution with a weaker base and/or lower concentration of base. The lysis solution can be formulated such that the cells are mixed with an equal volume of the lysis solution (to produce the desired alkaline conditions).

For example, lysis solutions can be solutions that have a pH of from about 9.0 to about 13.0, from about 9.5 to about 13.0, from about 10.0 to about 13.0, from about 10.5 to about 13.0, from about 11.0 to about 13.0, from about 11.5 to about 13.0, from about 12.0 to about 13.0, from about 9.0 to about 12.0, from about 9.5 to about 12.0, from about 10.0 to about 12.0, from about 10.5 to about 12.0, from about 11.0 to about 12.0, from about 11.5 to about 12.0, from about 9.0 to about 11.5, from about 9.5 to about 11.5, from about 10.0 to about 11.5, from about 10.5 to about 11.5, from about 11.0 to about 11.5, from about 9.0 to about 11.0, from about 9.5 to about 11.0, from about 10.0 to about 11.0, from about 10.5 to about 11.0, from about 9.0 to about 10.5, from about 9.5 to about 10.5, from about 10.0 to about 10.5, from about 9.0 to about 10.0, from about 9.5 to about 10.0, from about 9.0 to about 9.5, about 9.0, about 9.5, about 10.0, about 10.5, about 11.0, about 11.5, about 12.0, about 12.5, or about 13.0.

Lysis solutions can have, for example, component concentrations of from about 10 mM to about 1 M, from about 10 mM to about 900 mM, from about 10 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 1 M, from about 20 mM to about 900 mM, from about 20 mM to about 800 mM, from about 20 mM to about 700 mM, from about 20 mM to about 600 mM, from about 20 mM to about 500 mM, from about 20 mM to about 400 mM, from about 20 mM to about 300 mM, from about 20 mM to about 200 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 30 mM to about 1 M, from about 30 mM to about 900 mM, from about 30 mM to about 800 mM, from about 30 mM to about 700 mM, from about 30 mM to about 600 mM, from about 30 mM to about 500 mM, from about 30 mM to about 400 mM, from about 30 mM to about 300 mM, from about 30 mM to about 200 mM, from about 30 mM to about 100 mM, from about 30 mM to about 90 mM, from about 30 mM to about 80 mM, from about 30 mM to about 70 mM, from about 30 mM to about 60 mM, from about 30 mM to about 50 mM, from about 30 mM to about 40 mM, from about 40 mM to about 1 M, from about 40 mM to about 900 mM, from about 40 mM to about 800 mM, from about 40 mM to about 700 mM, from about 40 mM to about 600 mM, from about 40 mM to about 500 mM, from about 40 mM to about 400 mM, from about 40 mM to about 300 mM, from about 40 mM to about 200 mM, from about 40 mM to about 100 mM, from about 40 mM to about 90 mM, from about 40 mM to about 80 mM, from about 40 mM to about 70 mM, from about 40 mM to about 60 mM, from about 40 mM to about 50 mM, from about 50 mM to about 1 M, from about 50 mM to about 900 mM, from about 50 mM to about 800 mM, from about 50 mM to about 700 mM, from about 50 mM to about 600 mM, from about 50 mM to about 500 mM, from about 50 mM to about 400 mM, from about 50 mM to about 300 mM, from about 50 mM to about 200 mM, from about 50 mM to about 100 mM, from about 50 mM to about 90 mM, from about 50 mM to about 80 mM, from about 50 mM to about 70 mM, from about 50 mM to about 60 mM, from about 60 mM to about 1 M, from about 60 mM to about 900 mM, from about 60 mM to about 800 mM, from about 60 mM to about 700 mM, from about 60 mM to about 600 mM, from about 60 mM to about 500 mM, from about 60 mM to about 400 mM, from about 60 mM to about 300 mM, from about 60 mM to about 200 mM, from about 60 mM to about 100 mM, from about 60 mM to about 90 mM, from about 60 mM to about 80 mM, from about 60 mM to about 70 mM, from about 70 mM to about 1 M, from about 70 mM to about 900 mM, from about 70 mM to about 800 mM, from about 70 mM to about 700 mM, from about 70 mM to about 600 mM, from about 70 mM to about 500 mM, from about 70 mM to about 400 mM, from about 70 mM to about 300 mM, from about 70 mM to about 200 mM, from about 70 mM to about 100 mM, from about 70 mM to about 90 mM, from about 70 mM to about 80 mM, from about 80 mM to about 1 M, from about 80 mM to about 900 mM, from about 80 mM to about 800 mM, from about 80 mM to about 700 mM, from about 80 mM to about 600 mM, from about 80 mM to about 500 mM, from about 80 mM to about 400 mM, from about 80 mM to about 300 mM, from about 80 mM to about 200 mM, from about 80 mM to about 100 mM, from about 80 mM to about 90 mM, from about 90 mM to about 1 M, from about 90 mM to about 900 mM, from about 90 mM to about 800 mM, from about 90 mM to about 700 mM, from about 90 mM to about 600 mM, from about 90 mM to about 500 mM, from about 90 mM to about 400 mM, from about 90 mM to about 300 mM, from about 90 mM to about 200 mM, from about 90 mM to about 100 mM, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The lysis solution can be composed of multiple solutions and/or components that can be added to cells separately or combined in different combinations prior to addition to cells. Thus, for example, a solution of 400 mM KOH and 10 mM EDTA and a solution of 100 mM dithiothreitol can be added to the cells separately. Similarly, the disclosed kits can be composed of multiple solutions and/or components to be combined to form a lysis solution prior to addition to cells or for separate addition to cells.

F. Stabilization Solution

In preparing nucleic acid samples for use in the disclosed method, the pH of the cell lysate can be reduced to form a stabilized cell lysate. A stabilization solution is generally a solution that can reduce the pH of a cell lysate exposed to alkaline conditions as described elsewhere herein. In some embodiments, the stabilization solution can comprise an acid. Useful acids include hydrochloric acid, sulfuric acid, phosphoric acid, acetic acid, acetylsalicylic acid, ascorbic acid, carbonic acid, citric acid, formic acid, nitric acid, perchloric acid, HF, HBr, HI, $H_2S$, HCN, HSCN, HClO, monochloroacetic acid, dichloroacetic acid, trichloroacetic acid, and any carboxylic acid (ethanoic, propanoic, butanoic, etc., including both linear or branched chain carboxylic acids). In some embodiments, the stabilization solution can comprise a buffer. Useful buffers include Tris-HCl, HEPES, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. Useful formulations of stabilization solutions include stabilization solution comprising 800 mM Tris-HCl; stabilization solution comprising 800 mM Tris-HCl at pH 4.1, and stabilization solution consisting of 800 mM Tris-HCl, pH 4.1.

In some embodiments, the stabilization solution can comprise a plurality of acidic agents. As used herein, an acidic agent is a compound, composition or solution that forms an acid in solution. In some embodiments, the stabilization solution can comprise a plurality of buffering agents. An acidic buffering agent is a buffering agent that forms an acid in solution. In some embodiments, the stabilization solution can comprise a combination of one or more acids, acidic agents, buffers and buffering agents.

A stabilized cell lysate is a cell lysate the pH of which is in the neutral range (from about pH 6.0 to about pH 9.0). Useful stabilized cell lysates have a pH that allows replication of nucleic acids in the cell lysate. For example, the pH of the stabilized cell lysate is usefully at a pH at which the DNA polymerase can function. The pH of the cell lysate can be reduced by mixing the cell lysate with a stabilization solution.

The amount of stabilization solution mixed with the cell lysate can be that amount that causes a reduction in pH to the neutral range (or other desired pH value). Generally, this volume will be a function of the pH of the cell lysate/ stabilization solution mixture. Thus, the amount of stabilization solution to mix with the cell lysate can be determined generally from the volume of the cell lysate, its pH and buffering capacity, and the acidic concentration of the stabilization buffer. For example, a smaller volume of a stabilization solution with a stronger acid and/or higher concentration of acid would be needed to reduce the pH sufficiently than the volume needed of a stabilization solution with a weaker acid and/or lower concentration of acid. The stabilization solution can be formulated such that the cell lysate is mixed with an equal volume of the stabilization solution (to produce the desired pH).

For example, stabilization solutions can be solutions that have a pH of from about 1.0 to about 6.0, from about 2.0 to about 6.0, from about 3.0 to about 6.0, from about 3.5 to about 6.0, from about 4.0 to about 6.0, from about 4.5 to about 6.0, from about 5.0 to about 6.0, from about 5.5 to about 6.0, from about 1.0 to about 5.5, from about 2.0 to about 5.5, from about 3.0 to about 5.5, from about 3.5 to about 5.5, from about 4.0 to about 5.5, from about 4.5 to about 5.5, from about 5.0 to about 5.5, from about 1.0 to about 5.0, from about 2.0 to about 5.0, from about 3.0 to about 5.0, from about 3.5 to about 5.0, from about 4.0 to about 5.0, from about 4.5 to about 5.0, from about 1.0 to about 4.5, from about 2.0 to about 4.5, from about 3.0 to about 4.5, from about 3.5 to about 4.5, from about 4.0 to about 4.5, from about 1.0 to about 4.0, from about 2.0 to about 4.0, from about 3.0 to about 4.0, from about 3.5 to about 4.0, from about 1.0 to about 3.5, from about 2.0 to about 3.5, from about 3.0 to about 3.5, from about 1.0 to about 3.0, from about 2.0 to about 3.0, from about 1.0 to about 2.5, from about 2.0 to about 2.5, from about 1.0 to about 2.0, about 1.0, about 2.0, about 2.5, about 3.0, about 3.5, about 4.0, about 4.5, about 5.0, about 5.5, or about 6.0.

Stabilization solutions can have, for example, component concentrations of from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 100 mM, about 200 mM, about 300 mM, about 400 mM, about 500 mM, about 600 mM, about 700 mM, about 800 mM, about 900 mM, or about 1 M.

The stabilization solution can be composed of multiple solutions and/or components that can be added to cell lysates separately or combined in different combinations prior to addition to cell lysates. Thus, for example, a solution of a buffer and a solution of an acid can be added to the cells separately. Similarly, the disclosed kits can be composed of multiple solutions and/or components to be combined to form a stabilization solution prior to addition to cell lysates or for separate addition to cell lysates.

G. Denaturing Solution

In some forms of the disclosed method, the nucleic acid samples can be exposed to denaturing conditions by mixing the sample with a denaturing solution. A denaturing solution is generally a solution that can raise the pH of a sample sufficiently to cause, in combination with other conditions such as heating, substantial denaturation of nucleic acid molecules in the nucleic acid sample. Substantial denaturation refers to denaturation of 90% or more of the nucleotides in 90% or more of the nucleic acid molecules in a sample. In this context, denaturation of nucleotides refers to unpaired nucleotides whether physically denatured by treatment or already unpaired in the sample. Lysis solutions can be used as denaturing solutions so long as the lysis solution has the effects required of denaturing solutions.

In some embodiments, the denaturing solution can comprises a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of denaturing solution include denaturing solution comprising about 150 mM to about 500 mM NaOH, denaturing solution comprising about 150 mM to about 500 mM NaOH, and denaturing solution consisting of about 150 mM to about 500 mM NaOH.

In some embodiments, the denaturing solution can comprise a plurality of basic agents. As used herein, a basic agent is a compound, composition or solution that results in denaturing conditions. In some embodiments, the denaturing solution can comprise a buffer. Useful buffers include phosphate buffers, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The denaturing solution can comprise a plurality of buffering agents. As used herein, a buffering agent is a compound, composition or solution that acts as a buffer. An alkaline buffering agent is a buffering agent that results in alkaline conditions. In some embodiments, the denaturing solution can comprise a combination of one or more bases, basic agents, buffers and buffering agents.

The amount of denaturing solution mixed with the nucleic acid samples can be that amount that causes, in combination with other conditions such as heating, substantial denaturation of nucleic acid molecules in the nucleic acid sample. Generally, this volume will be a function of the pH, ionic strength, and temperature of the sample/denaturing solution mixture. Thus, the amount of denaturing solution to mix with nucleic acid samples can be determined generally from the volume of the nucleic acid sample, the alkaline concentration of the denaturing buffer, and the temperature to which the resulting mixture will be heated. For example, at a given temperature, a smaller volume of a denaturing solution with a stronger base and/or higher concentration of base would be needed to create sufficient denaturing conditions than the volume needed of a denaturing solution with a weaker base and/or lower concentration of base. The denaturing solution can be formulated such that the nucleic acid samples are mixed with, for example, one tenth volume of the denaturing solution (to produce the desired denaturing conditions).

For example, denaturing solutions can be solutions that have a pH of from about 9.0 to about 13.0, from about 9.5 to about 13.0, from about 10.0 to about 13.0, from about 10.5 to about 13.0, from about 11.0 to about 13.0, from about 11.5 to about 13.0, from about 12.0 to about 13.0, from about 9.0 to about 12.0, from about 9.5 to about 12.0, from about 10.0 to about 12.0, from about 10.5 to about 12.0, from about 11.0 to about 12.0, from about 11.5 to about 12.0, from about 9.0 to about 11.5, from about 9.5 to about 11.5, from about 10.0 to about 11.5, from about 10.5 to about 11.5, from about 11.0 to about 11.5, from about 9.0 to about 11.0, from about 9.5 to about 11.0, from about 10.0 to about 11.0, from about 10.5 to about 11.0, from about 9.0 to about 10.5, from about 9.5 to about 10.5, from about 10.0 to about 10.5, from about 9.0 to about 10.0, from about 9.5 to about 10.0, from about 9.0 to about 9.5, about 9.0, about 9.5, about 10.0, about 10.5, about 11.0, about 11.5, about 12.0, about 12.5, or about 13.0.

Denaturing solutions can have, for example, component concentrations of from about 10 mM to about 1 M, from about 10 mM to about 900 mM, from about 10 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 1 M, from about 20 mM to about 900 mM, from about 20 mM to about 800 mM, from about 20 mM to about 700 mM, from about 20 mM to about 600 mM, from about 20 mM to about 500 mM, from about 20 mM to about 400 mM, from about 20 mM to about 300 mM, from about 20 mM to about 200 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 30 mM to about 1 M, from about 30 mM to about 900 mM, from about 30 mM to about 800 mM, from about 30 mM to about 700 mM, from about 30 mM to about 600 mM, from about 30 mM to about 500 mM, from about 30 mM to about 400 mM, from about 30 mM to about 300 mM, from about 30 mM to about 200 mM, from about 30 mM to about 100 mM, from about 30 mM to about 90 mM, from about 30 mM to about 80 mM, from about 30 mM to about 70 mM, from about 30 mM to about 60 mM, from about 30 mM to about 50 mM, from about 30 mM to about 40 mM, from about 40 mM to about 1 M, from about 40 mM to about 900 mM, from about 40 mM to about 800 mM, from about 40 mM to about 700 mM, from about 40 mM to about 600 mM, from about 40 mM to about 500 mM, from about 40 mM to about 400 mM, from about 40 mM to about 300 mM, from about 40 mM to about 200 mM, from about 40 mM to about 100 mM, from about 40 mM to about 90 mM, from about 40 mM to about 80 mM, from about 40 mM to about 70 mM, from about 40 mM to about 60 mM, from about 40 mM to about 50 mM, from about 50 mM to about 1 M, from about 50 mM to about 900 mM, from about 50 mM to about 800 mM, from about 50 mM to about 700 mM, from about 50 mM to about 600 mM, from about 50 mM to about 500 mM, from about 50 mM to about 400 mM, from about 50 mM to about 300 mM, from about 50 mM to about 200 mM, from about 50 mM to about 100 mM, from about 50 mM to about 90 mM, from about 50 mM to about 80 mM, from about 50 mM to about 70 mM, from about 50 mM to about 60 mM, from about 60 mM to about 1 M, from about 60 mM to about 900 mM, from about 60 mM to about 800 mM, from about 60 mM to about 700 mM, from about 60 mM to about 600 mM, from about 60 mM to about 500 mM, from about 60 mM to about 400 mM, from about 60 mM to about 300 mM, from about 60 mM to about 200 mM, from about 60 mM to about 100 mM, from about 60 mM to about 90 mM, from about 60 mM to about 80 mM, from about 60 mM to about 70 mM, from about 70 mM to about 1 M, from about 70 mM to about 900 mM, from about 70 mM to about 800 mM, from about 70 mM to about 700 mM, from about 70 mM to about 600 mM, from about 70 mM to about 500 mM, from about 70 mM to about 400 mM, from about 70 mM to about 300 mM, from about 70 mM to about 200 mM, from about 70 mM to about 100 mM, from about 70 mM to about 90 mM, from about 70 mM to about 80 mM, from about 80 mM to about 1 M, from about 80 mM to about 900 mM, from about 80 mM to about 800 mM, from about 80 mM to about 700 mM, from about 80 mM to about 600 mM, from about 80 mM to about 500 mM, from about 80 mM to about 400 mM, from about 80 mM to about 300 mM, from about 80 mM to about 200 mM, from about 80 mM to about 100 mM, from about 80 mM to about 90 mM, from about 90 mM to about 1 M, from about 90 mM to about 900 mM, from about 90 mM to about 800 mM, from about 90 mM to about 700 mM, from about 90 mM to about 600 mM, from about 90 mM to about 500 mM, from about 90 mM to about 400 mM, from about 90 mM to about 300 mM, from about 90 mM to about 200 mM, from about 90 mM to about 100 mM, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about, 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M; from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The denaturing solution can be composed of multiple solutions and/or components that can be added to nucleic acid samples separately or combined in different combinations prior to addition to nucleic acid samples. Thus, for example, a solution of a buffer and a solution of a base can be added to the samples separately. Similarly, the disclosed kits can be composed of multiple solutions and/or components to be combined to form a denaturing solution prior to addition to nucleic acid samples or for separate addition to samples.

H. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin films or membranes, beads, bottles, dishes, fibers, optical fibers, woven fibers, chips, compact disks, shaped polymers, particles and microparticles. A chip is a rectangular or square small piece of material. Preferred forms for solid-state substrates are thin films, beads, or chips.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a multiplex assay, address probes specific for numerous different amplified nucleic acids can be immobilized in an array, each in a different location. Capture and detection will occur only at those array locations corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (*Mosk*) (*USSR*) 25:718-730 (1991). A method for immobilization of 3'-amine oligonucleotides on casein-coated slides is described by Stimpson et al., *Proc. Natl. Acad. Sci. USA* 92:6379-6383 (1995). A preferred method of attaching oligonucleotides to solid-state substrates is described by Guo et al., *Nucleic Acids Res.* 22:5456-5465 (1994). Examples of nucleic acid chips and arrays, including methods of making and using such chips and arrays, are described in U.S. Pat. No. 6,287,768, U.S. Pat. No. 6,288,220, U.S. Pat. No. 6,287,776, U.S. Pat. No. 6,297,006, and U.S. Pat. No. 6,291,193.

I. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthamide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenoboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7', 1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule or sequence, where such labels include: "molecular beacons" as described in Tyagi & Kramer, Nature Biotechnology (1996) 14:303 and EP 0 070 685 B1, or other forms of fluorescent change probes. Other labels of interest include those described in U.S. Pat. No. 5,563,037; WO 97/17471 and WO 97/17076.

Labeled nucleotides are a useful form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.,* 22:3226-3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AAdUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [$3.3.1.1^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

J. Detection Probes

Detection probes are labeled oligonucleotides having sequence complementary to target sequences and/or detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnol.* 14:303-309 (1995)). The use of such probes eliminates the need for removal of unhybridized probes prior to label detection because the unhybridized detection probes will not produce a signal. This is especially useful in multiplex assays.

K. Address Probes

An address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

L. Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Tyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. No. 6,294,664 and U.S. Pat. No. 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. For the disclosed primers of specific sequence, specific nucleotide precursors would be added sequentially.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

So long as their relevant function is maintained, primers, detection probes, address probes, and any other oligonucleotides can be made up of or include modified nucleotides (nucleotide analogs). Many modified nucleotides are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[$(CH_2)_n$O]m $CH_3$, —O$(CH_2)_n$O$CH_3$, —O$(CH_2)_n$$NH_2$, —O$(CH_2)_n$$CH_3$, —O$(CH_2)_n$-O$NH_2$, and —O$(CH_2)_n$ON[$(CH_2)_n$$CH_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Oligonucleotides can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such oligonucleotides can be referred to as chimeric oligonucleotides.

M. DNA polymerases

DNA polymerases useful in multiple displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of nucleic acid molecules and sequences. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are bacteriophage φ29 DNA polymerase (U.S. Pat. Nos. 5,198,543 and 5,001,050 to Blanco et al.), Bst large fragment DNA polymerase (Exo(−) Bst; Aliotta et al., *Genet. Anal. (Netherlands)* 12:185-195 (1996)) and exo(−)Bca DNA polymerase (Walker and Linn, *Clinical Chemistry* 42:1604-1608 (1996)). Other useful polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)). φ29 DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648-7653 (1993)), adenovirus DNA-binding protein (Zijderveld and van der Vliet, *J. Virology* 68(2): 1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)); single-stranded DNA binding proteins (SSB; Rigler and Romano, *J. Biol. Chem.* 270:8910-8919 (1995)); phage T4 gene 32 protein (Villemain and Giedroc, *Biochemistry* 35:14395-14404 (1996); and calf thymus helicase (Siegel et al., *J. Biol. Chem.* 267:13629-13635 (1992)).

The ability of a polymerase to carry out strand displacement replication can be determined by using the polymerase in a strand displacement replication assay such as those described in Examples 1 and 5. The assay in the examples can be modified as appropriate. For example, a helicase can be used instead of SSB. Such assays should be performed at a temperature suitable for optimal activity for the enzyme being used, for example, 32° C. for φ29 DNA polymerase, from 46° C. to 64° C. for exo(−) Bst DNA polymerase, or from about 60° C. to 70° C. for an enzyme from a hyperthermophylic organism. For assays from 60° C. to 70° C., primer length may be increased to provide a melting temperature appropriate for the assay temperature. Another useful assay for selecting a polymerase is the primer-block assay described in Kong et al., *J. Biol. Chem.* 268:1965-1975 (1993). The assay consists of a primer extension assay using an M13 ssDNA template in the presence or absence of an oligonucleotide that is hybridized upstream of the extending primer to block its progress. Enzymes able to displace the blocking primer in this assay are expected to be useful for the disclosed method.

N. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for amplification of nucleic acid samples, the kit comprising a single primer and φ29 DNA polymerase. The kits also can contain nucleotides, buffers, detection probes, fluorescent change probes, lysis solutions, stabilization solutions, denaturation solutions, or a combination.

O. Mixtures

Disclosed are mixtures formed by performing or preparing to perform the disclosed method. For example, disclosed are mixtures comprising a single primer, a nucleic acid sample, and a DNA polymerase; a single primer, a genomic nucleic acid sample, and a DNA polymerase; one or more primers, one or more nucleic acid samples, and one or more DNA polymerases; a single primer, a nucleic acid sample, and one or more detection probes; a single primer, a nucleic acid sample, and one or more fluorescent change probes; a single primer, a nucleic acid sample, and replicated nucleic acid molecules; a single primer, a genomic nucleic acid sample, and replicated nucleic acid molecules; one or more primers, one or more nucleic acid samples, and replicated nucleic acid molecules; a single primer, a nucleic acid sample, replicated nucleic acid molecules, and one or more detection probes; a single primer, a nucleic acid sample, replicated nucleic acid molecules, and one or more fluorescent change probes.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps and each intermediate step regardless of how the steps were performed. The present disclosure contemplates these mixtures, obtained by the performance of the disclosed methods as well as mixtures containing any disclosed reagent, composition, or component, for example, disclosed herein.

P. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising solid supports and primers, nucleic acid samples, detection probes, fluorescent change probes, or a combination.

Q. Data Structures and Computer Control

Disclosed are data structures used in, generated by, or generated from, the disclosed method. Data structures generally are any form of data, information, and/or objects collected, organized, stored, and/or embodied in a composition or medium. A nucleic acid library stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Uses

The disclosed method and compositions are applicable to numerous areas including, but not limited to, analysis of nucleic acids present in cells (for example, analysis of genomic DNA in cells), disease detection, mutation detection, gene discovery, gene mapping (molecular haplotyping), and agricultural research. Particularly useful is whole genome amplification. Other uses include, for example, detection of nucleic acids in cells and on genomic DNA arrays; molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Method

The disclosed method is based on strand displacement replication of the nucleic acid sequences by one, a few, or more primers. The method can be used to amplify an nucleic acid sample and is particularly useful for amplifying nucleic acid samples having a high sequence complexity, such as entire genomes. The disclosed method can be used to amplify such highly complex nucleic acid samples using only one or a limited number of primers. It has been discovered that one or a small number of primers can effectively amplify whole genomes and other nucleic acid samples of high sequence complexity. The primers are specially selected or designed to be able to prime and efficiently amplify the broad range of sequences present in highly complex nucleic acid samples despite the limited amount of primer sequence represented in the primers. The disclosed method generally involves bringing into contact one, a few, or more primers having specific nucleic acid sequences, DNA polymerase, and a nucleic acid sample, and incubating the nucleic acid sample under conditions that promote replication of nucleic acid molecules in the nucleic acid sample. Replication of the nucleic acid molecules results in replicated strands such that, during replication, the replicated strands are displaced from the nucleic acid molecules by strand displacement replication of another replicated strand. The replication can result in amplification of all or a substantial fraction of the nucleic acid molecules in the nucleic acid sample. As used herein, a replicated strand is a nucleic acid strand resulting from elongation of a primer hybridized to a nucleic acid molecule or nucleic acid sequence or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of nucleic acid molecules or nucleic acid sequences to be made in a single, isothermic reaction.

In another form of the method, the primers can be 6 nucleotides in length. It was discovered that such short, 6 nucleotide primers can still prime multiple strand displacement replication efficiently. In another form of the method, the primers can each contain at least one modified nucleotide such that the primers are nuclease resistant. In another form of the method, the primers can each contain at least one modified nucleotide such that the melting temperature of the primer is altered relative to a primer of the same sequence without the modified nucleotide(s). In another form of the method, the DNA polymerase can be φ29 DNA polymerase. φ29 DNA polymerase produces greater amplification in multiple displacement amplification. The combination of two or more of the above features also yields improved results in multiple displacement amplification. In a preferred embodiment, for example, the nucleic acid sample is not subjected to denaturing conditions, the primers are 6 nucleotides long and contain modified nucleotides such that the primers are nuclease resistant, and the DNA polymerase is 429 DNA polymerase. The above features are especially useful in whole genome strand displacement amplification (WGSDA).

In another form of the disclosed method, the method includes labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

Some forms of the disclosed method provide amplified DNA of higher quality relative to previous methods due to the lack of a heat denaturation treatment of the nucleic acid molecules that are the target for amplification. Thus, the template DNA does not undergo the strand breakage events caused by heat treatment and the amplification that is accomplished by a single DNA polymerase extends farther along template strands of increased length.

A. Amplified Nucleic Acid Quality

The disclosed method can result in replication of all or a substantial fraction of the nucleic acid molecules in a nucleic acid sample. As used herein, a substantial fraction of the nucleic acid molecules in a nucleic acid sample refers to 90% or more of the nucleic acid molecules (or nucleic acid sequences) present in the nucleic acid sample. As used herein, a significant fraction of the nucleic acid molecules in a nucleic acid sample refers to 50% or more of the nucleic acid molecules (or nucleic acid sequences) present in the nucleic acid sample. As used herein, a notable fraction of the nucleic acid molecules in a nucleic acid sample refers to 20% or more of the nucleic acid molecules (or nucleic acid sequences) present in the nucleic acid sample.

Replication of the nucleic acid molecules in a nucleic acid sample can result replication of at least 0.01% of the nucleic acid sequences in the nucleic acid sample, at least 0.1% of the nucleic acid sequences in the nucleic acid sample, at least 1% of the nucleic acid sequences in the nucleic acid sample, at least 5% of the nucleic acid sequences in the nucleic acid sample, at least 10% of the nucleic acid sequences in the nucleic acid sample, at least 20% of the nucleic acid sequences in the nucleic acid sample, at least 30% of the nucleic acid sequences in the nucleic acid sample, at least 40% of the nucleic acid sequences in the nucleic acid sample, at least 50% of the nucleic acid sequences in the nucleic acid sample, at least 60% of the nucleic acid sequences in the nucleic acid sample, at least 70% of the nucleic acid sequences in the nucleic acid sample, at least 80% of the nucleic acid sequences in the nucleic acid sample, at least 90% of the nucleic acid sequences in the nucleic acid sample, at least 95% of the nucleic acid sequences in the nucleic acid sample, at least 96% of the nucleic acid sequences in the nucleic acid sample, at least 97% of the nucleic acid sequences in the nucleic acid sample, at least 98% of the nucleic acid sequences in the nucleic acid sample, or at least 99% of the nucleic acid sequences in the nucleic acid sample.

The fraction of the nucleic acid molecules in the nucleic acid sample that is replicated can vary with the sequence complexity of the nucleic acid sample (although higher fractions are preferred for all nucleic acid samples). For example, where the nucleic acid sample has a sequence complexity of at least $1 \times 10^9$ nucleotides, replication of nucleic acid molecules in the nucleic acid sample can result in replication of at least 0.01% of the nucleic acid sequences in the nucleic acid sample. Where the nucleic acid sample has a sequence complexity of at least $1 \times 10^8$ nucleotides, replication of nucleic acid molecules in the nucleic acid sample can result in replication of at least 0.1% of the nucleic acid sequences in the nucleic acid sample. Where the nucleic acid sample has a sequence complexity of at least $1 \times 10^7$ nucleotides, replication of nucleic acid molecules in the nucleic acid sample can result in replication of at least 1% of the nucleic acid sequences in the nucleic acid sample. Where the nucleic acid sample has a sequence complexity of at least $1 \times 10^6$ nucleotides, replication of nucleic acid molecules in the nucleic acid sample can result in replication of at least 10% of the nucleic acid sequences in the nucleic acid sample. Where the nucleic acid sample has a sequence complexity of at least $1 \times 10^5$ nucleotides, replication of nucleic acid molecules in the nucleic acid sample can result in replication of at least 80% of the nucleic acid sequences in the nucleic acid sample. Where the nucleic acid sample has a sequence complexity of at least $1 \times 10^4$ nucleotides, replication of nucleic acid molecules in the nucleic acid sample can result in replication of at least 90% of the nucleic acid sequences in the nucleic acid sample. Where the nucleic acid sample has a sequence complexity of at least $1 \times 10^3$ nucleotides, replication of nucleic acid molecules in the nucleic acid sample can result in replication of at least 96% of the nucleic acid sequences in the nucleic acid sample.

Where the nucleic acid sample has a sequence complexity of less than $1 \times 10^9$ nucleotides, replication of nucleic acid molecules in the nucleic acid sample can result in replication of at least 0.01% of the nucleic acid sequences in the nucleic acid sample. Where the nucleic acid sample has a sequence complexity of less than $1 \times 10^8$ nucleotides, replication of nucleic acid molecules in the nucleic acid sample can result in replication of at least 0.1% of the nucleic acid sequences in the nucleic acid sample. Where the nucleic acid sample has a sequence complexity of less than $1 \times 10^7$ nucleotides, replication of nucleic acid molecules in the nucleic acid sample can result in replication of at least 1% of the nucleic acid sequences in the nucleic acid sample. Where the nucleic acid sample has a sequence complexity of less than $1 \times 10^6$ nucleotides, replication of nucleic acid molecules in the nucleic acid sample can result in replication of at least 10% of the nucleic acid sequences in the nucleic acid sample. Where the nucleic acid sample has a sequence complexity of less than $1 \times 10^5$ nucleotides, replication of nucleic acid molecules in the nucleic acid sample can result in replication of at least 80% of the nucleic acid sequences in the nucleic acid sample. Where the nucleic acid sample has a sequence complexity of less than $1 \times 10^4$ nucleotides, replication of nucleic acid molecules in the nucleic acid sample can result in replication of at least 90% of the nucleic acid sequences in the nucleic acid sample. Where the nucleic acid sample has a sequence complexity of less than $1 \times 10^3$ nucleotides, replication of nucleic acid molecules in the nucleic acid sample can result in replication of at least 96% of the nucleic acid sequences in the nucleic acid sample.

One measure of the quality of the amplified nucleic acids can be the locus representation or sequence representation in the amplified nucleic acids. A locus representation or sequence representation the same as or close to the locus or sequence representation in the source nucleic acid sample indicates amplified nucleic acids of the highest quality. As used herein, locus representation refers to the ratio (usually expressed as a percentage) of the amount of a given locus in amplified nucleic acid to the amount of the same locus in the unamplified nucleic acid sample. In making this calculation, the measured amount of the locus in the amplified nucleic and the measured amount of the locus in the unamplified nucleic acid sample generally can be normalized to the total amount of nucleic acid present in the amplified nucleic acid and the unamplified nucleic acid sample, respectively. As used herein, sequence representation refers to the ratio (usually expressed as a percentage) of the amount of a given sequence in amplified nucleic acid to the amount of the same sequence in the unamplified nucleic acid sample. In making this calculation, the measured amount of the sequence in the amplified nucleic and the measured amount of the sequence in the unamplified nucleic acid sample generally can be normalized to the total amount of nucleic acid present in the amplified nucleic acid and the unamplified nucleic acid sample, respectively.

The locus or sequence representation can be, for example, 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350%, 400%, 450%, 500%, 600%, 700%, 800%, 900%, or 1000% for one, some, or all loci or sequences measured. The locus or sequence representation can be, for example, greater than 10%, greater than 20%, greater than 30%, greater than 40%, greater than 50%, greater than 60%, greater than 70%, greater than 80%, greater than 90%, greater than 100%, greater than 110%, greater than 120%, greater than 130%, greater than 140%, greater than 150%, greater than 160%, greater than 170%, greater than 180%, greater than 190%, greater than 200%, greater than 225%, greater than 250%, greater than 275%, greater than 300%, greater than 350%, greater than 400%, greater than 450%, greater than 500%, greater than 600%, greater than 700%, greater than 800%, greater than 900%, or greater than 1000% for one, some, or all loci or sequences measured. The locus or sequence representation can be, for example, less than 10%, less than 20%, less than 30%, less than 40%, less than 50%, less than 60%, less than 70%, less than 80%, less than 90%, less than 100%, less than 110%, less than 120%, less than 130%, less than 140%, less than 150%, less than 160%, less than 170%, less than 180%, less than 190%, less than 200%, less than 225%, less than 250%, less than 275%, less than 300%, less than 350%, less than 400%, less than 450%, less than 500%, less than 600%, less than 700%, less than 800%, less than 900%, or less than 1000% for one, some, or all loci or sequences measured.

The locus or sequence representation can be, for example, between 10% and 1000%, between 10% and 900%, between 10% and 800%, between 10% and 700%, between 10% and 600%, between 10% and 500%, between 10% and 400%, between 10% and 300%, between 10% and 250%, between 10% and 200%, between 10% and 150%, between 10% and 125%, between 10% and 100%, between 20% and 1000%, between 20% and 900%, between 20% and 800%, between 20% and 700%, between 20% and 600%, between 20% and 500%, between 20% and 400%, between 20% and 300%, between 20% and 250%, between 20% and 200%, between 20% and 150%, between 20% and 125%, between 20% and 100%, between 30% and 1000%, between 30% and 900%, between 30% and 800%, between 30% and 700%, between 30% and 600%, between 30% and 500%, between 30% and 400%, between 30% and 300%, between 30% and 250%, between 30% and 200%, between 30% and 150%, between 30% and 125%, between 30% and 100%, between 40% and 1000%, between 40% and 900%, between 40% and 800%, between 40% and 700%, between 40% and 600%, between 40% and 500%, between 40% and 400%, between 40% and 300%, between 40% and 250%, between 40% and 200%, between 40% and 150%, between 40% and 125%, between 40% and 100%, between 50% and 1000%, between 50% and 900%, between 50% and 800%, between 50% and 700%, between 50% and 600%, between 50% and 500%, between 50% and 400%, between 50% and 300%, between 50% and 250%, between 50% and 200%, between 50% and 150%, between 50% and 125%, between 50% and 100%, between 60% and 1000%, between 60% and 900%, between 60% and 800%, between 60% and 700%, between 60% and 600%, between 60% and 500%, between 60% and 400%, between 60% and 300%, between 60% and 250%, between 60% and 200%, between 60% and 150%, between 60% and 125%, between 60% and 100%, between 70% and 1000%, between 70% and 900%, between 70% and 800%, between 70% and 700%, between 70% and 600%, between 70% and 500%, between 70% and 400%, between 70% and 300%, between 70% and 250%, between 70% and 200%, between 70% and 150%, between 70% and 125%, between 70% and 100%, between 80% and 1000%, between 80% and 900%, between 80% and 800%, between 80% and 700%, between 80% and 600%, between 80% and 500%, between 80% and 400%, between 80% and 300%, between 80% and 250%, between 80% and 200%, between 80% and 150%, between 80% and 125%, between 80% and 100%, between 90% and 1000%, between 90% and 900%, between 90% and 800%, between 90% and 700%, between 90% and 600%, between 90% and 500%, between 90% and 400%, between 90% and 300%, between 90% and 250%, between 90% and 200%, between 90% and 150%, between 90% and 125%, between 90% and 100%, between 100% and 1000%, between 100% and 900%, between 100% and 800%, between 100% and 700%, between 100% and 600%, between 100% and 500%, between 100% and 400%, between 100% and 300%, between 100% and 250%, between 100% and 200%, between 100% and 150%, or between 100% and 125% for one, some, or all loci or sequences measured.

The various locus representations described above and elsewhere herein can be, for example, for 1 locus, 2 loci, 3 loci, 4 loci, 5 loci, 6 loci, 7 loci, 8 loci, 9 loci, 10 loci, 11 loci, 12 loci, 13 loci, 14 loci, 15 loci, 16 loci, 17 loci, 18 loci, 19 loci, 20 loci, 25 loci, 30 loci, 40 loci, 50 loci, 75 loci, or 100 loci. The locus representation can be, for example, for at least, 1 locus, at least 2 loci, at least 3 loci, at least 4 loci, at least 5 loci, at least 6 loci, at least 7 loci, at least 8 loci, at least 9 loci, at least 10 loci, at least 11 loci, at least 12 loci, at least 13 loci, at least 14 loci, at least 15 loci, at least 16 loci, at least 17 loci, at least 18 loci, at least 19 loci, at least 20 loci, at least 25 loci, at least 30 loci, at least 40 loci, at least 50 loci, at least 75 loci, or at least 100 loci.

The locus representation can be, for example, for 1 locus, 2 different loci, 3 different loci, 4 different loci, 5 different loci, 6 different loci, 7 different loci, 8 different loci, 9 different loci, 10 different loci, 11 different loci, 12 different loci, 13 different loci, 14 different loci, 15 different loci, 16 different loci, 17 different loci, 18 different loci, 19 different loci, 20 different loci, 25 different loci, 30 different loci, 40 different loci, 50 different loci, 75 different loci, or 100 different loci. The locus representation can be, for example, for at least 1 locus, at least 2 different loci, at least 3 different loci, at least 4 different loci, at least 5 different loci, at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

The various sequence representations described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The sequence representation can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The sequence representation can be, for example, for 1 target sequence, 2 different target sequences, 3 different target sequences, 4 different target sequences; 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The sequence representation can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Another measure of the quality of the amplified nucleic acids can be the amplification bias in the amplified nucleic acids. Amplification bias is the difference in the level of amplification of different sequences in a nucleic acid sample. A low amplification bias indicates amplified nucleic acids of the highest quality. Amplification bias can be calculated as the ratio (usually expressed as a fold difference) of the locus representation of the locus having the highest locus representation to the locus representation having the lowest locus representation in the amplified nucleic acid. If sequence representation is measured, then amplification bias can be calculated as the ratio (usually expressed as a fold difference) of the sequence representation of the sequence having the highest locus representation to the sequence representation having the lowest sequence representation in the amplified nucleic acid.

The amplification bias can be, for example, 1-fold, 2-fold, 3-fold, 4-fold, 5-fold, 6-fold, 7-fold, 8-fold, 9-fold, 10-fold, 11-fold, 12-fold, 14-fold, 16-fold, 20-fold, 24-fold, 30-fold, 35-fold, 40-fold, 50-fold, 60-fold, 70-fold, 80-fold, 90-fold, 100-fold, 150-fold, 200-fold, 250-fold, or 300-fold. The amplification bias can be, for example, about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, or about 300-fold. The amplification bias can be, for example, less than 2-fold, less than 3-fold, less than 4-fold, less than 5-fold, less than 6-fold, less than 7-fold, less than 8-fold, less than 9-fold, less than 10-fold, less than 11-fold, less than 12-fold, less than 14-fold, less than 16-fold, less than 20-fold, less than 24-fold, less than 30-fold, less than 35-fold, less than 40-fold, less than 50-fold, less than 60-fold, less than 70-fold, less than 80-fold, less than 90-fold, less than 100-fold, less than 150-fold, less than 200-fold, less than 250-fold, or less than 300-fold.

The amplification bias can be, for example, less than about 2-fold, less than about 3-fold, less than about 4-fold, less than about 5-fold, less than about 6-fold, less than about 7-fold, less than about 8-fold, less than about 9-fold, less than about 10-fold, less than about 11-fold, less than about 12-fold, less than about 14-fold, less than about 16-fold, less than about 20-fold, less than about 24-fold, less than about 30-fold, less than about 35-fold, less than about 40-fold, less than about 50-fold, less than about 60-fold, less than about 70-fold, less than about 80-fold, less than about 90-fold, less than about 100-fold, less than about 150-fold, less than about 200-fold, less than about 250-fold, or less than about 300-fold.

The amplification bias can be, for example, from 1-fold to 300-fold, from 2-fold to 300-fold, from 3-fold to 300-fold, from 4-fold to 300-fold, from 5-fold to 300-fold, from 6-fold to 300-fold, from 7-fold to 300-fold, from 8-fold to 300-fold, from 9-fold to 300-fold, from 10-fold to 300-fold, from 11-fold to 300-fold, from 12-fold to 300-fold, from 14-fold to 300-fold, from 16-fold to 300-fold, from 20-fold to 300-fold, from 24-fold to 300-fold, from 30-fold to 300-fold, from 35-fold to 300-fold, from 40-fold to 300-fold, from 50-fold to 300-fold, from 60-fold to 300-fold, from 70-fold to 300-fold, from 80-fold to 300-fold, from 90-fold to 300-fold, from 100-fold to 300-fold, from 150-fold to 300-fold, from 200-fold to 300-fold, or from 250-fold to 300-fold.

The amplification bias can be, for example, from 1-fold to 250-fold, from 2-fold to 250-fold, from 3-fold to 250-fold, from 4-fold to 250-fold, from 5-fold to 250-fold, from 6-fold to 250-fold, from 7-fold to 250-fold, from 8-fold to 250-fold, from 9-fold to 250-fold, from 10-fold to 250-fold, from 11-fold to 250-fold, from 12-fold to 250-fold, from 14-fold to 250-fold, from 16-fold to 250-fold, from 20-fold to 250-fold, from 24-fold to 250-fold, from 30-fold to 250-fold, from 35-fold to 250-fold, from 40-fold to 250-fold, from 50-fold to 250-fold, from 60-fold to 250-fold, from 70-fold to 250-fold, from 80-fold to 250-fold, from 90-fold to 250-fold, from 100-fold to 250-fold, from 150-fold to 250-fold, or from 200-fold to 250-fold.

The amplification bias can be, for example, from 1-fold to 200-fold, from 2-fold to 200-fold, from 3-fold to 200-fold, from 4-fold to 200-fold, from 5-fold to 200-fold, from 6-fold to 200-fold, from 7-fold to 200-fold, from 8-fold to 200-fold, from 9-fold to 200-fold, from 10-fold to 200-fold, from 11-fold to 200-fold, from 12-fold to 200-fold, from 14-fold to 200-fold, from 16-fold to 200-fold, from 20-fold to 200-fold, from 24-fold to 200-fold, from 30-fold to 200-fold, from 35-fold to 200-fold, from 40-fold to 200-fold, from 50-fold to 200-fold, from 60-fold to 200-fold, from 70-fold to 200-fold, from 80-fold to 200-fold, from 90-fold to 200-fold, from 100-fold to 200-fold, or from 150-fold to 200-fold.

The amplification bias can be, for example, from 1-fold to 150-fold, from 2-fold to 150-fold, from 3-fold to 150-fold, from 4-fold to 150-fold, from 5-fold to 150-fold, from 6-fold to 150-fold, from 7-fold to 150-fold, from 8-fold to 150-fold, from 9-fold to 150-fold, from 10-fold to 150-fold, from 11-fold to 150-fold, from 12-fold to 150-fold, from 14-fold to 150-fold, from 16-fold to 150-fold, from 20-fold to 150-fold, from 24-fold to 150-fold, from 30-fold to 150-fold, from 35-fold to 150-fold, from 40-fold to 150-fold, from 50-fold to 150-fold, from 60-fold to 150-fold, from 70-fold to 150-fold, from 80-fold to 150-fold, from 90-fold to 150-fold, or from 100-fold to 150-fold.

The amplification bias can be, for example, from 1-fold to 100-fold, from 2-fold to 100-fold, from 3-fold to 100-fold, from 4-fold to 100-fold, from 5-fold to 100-fold, from 6-fold to 100-fold, from 7-fold to 100-fold, from 8-fold to 100-fold, from 9-fold to 100-fold, from 10-fold to 100-fold, from 11-fold to 100-fold, from 12-fold to 100-fold, from 14-fold to 100-fold, from 16-fold to 100-fold, from 20-fold to 100-fold, from 24-fold to 100-fold, from 30-fold to 100-fold, from 35-fold to 100-fold, from 40-fold to 100-fold, from 50-fold to 100-fold, from 60-fold to 100-fold, from 70-fold to 100-fold, from 80-fold to 100-fold, or from 90-fold to 100-fold.

The amplification bias can be, for example, from 1-fold to 90-fold, from 2-fold to 90-fold, from 3-fold to 90-fold, from 4-fold to 90-fold, from 5-fold to 90-fold, from 6-fold to 90-fold, from 7-fold to 90-fold, from 8-fold to 90-fold, from 9-fold to 90-fold, from 10-fold to 90-fold, from 11-fold to 90-fold, from 12-fold to 90-fold, from 14-fold to 90-fold, from 16-fold to 90-fold, from 20-fold to 90-fold, from 24-fold to 90-fold, from 30-fold to 90-fold, from 35-fold to 90-fold, from 40-fold to 90-fold, from 50-fold to 90-fold, from 60-fold to 90-fold, from 70-fold to 90-fold, or from 80-fold to 90-fold.

The amplification bias can be, for example, from 1-fold to 80-fold, from 2-fold to 80-fold, from 3-fold to 80-fold, from 4-fold to 80-fold, from 5-fold to 80-fold, from 6-fold to 80-fold, from 7-fold to 80-fold, from 8-fold to 80-fold, from 9-fold to 80-fold, from 10-fold to 80-fold, from 11-fold to 80-fold, from 12-fold to 80-fold, from 14-fold to 80-fold, from 16-fold to 80-fold, from 20-fold to 80-fold, from 24-fold to 80-fold, from 30-fold to 80-fold, from 35-fold to 80-fold, from 40-fold to 80-fold, from 50-fold to 80-fold, from 60-fold to 80-fold, or from 70-fold to 80-fold.

The amplification bias can be, for example, from 1-fold to 70-fold, from 2-fold to 70-fold, from 3-fold to 70-fold, from 4-fold to 70-fold, from 5-fold to 70-fold, from 6-fold to 70-fold, from 7-fold to 70-fold, from 8-fold to 70-fold, from 9-fold to 70-fold, from 10-fold to 70-fold, from 11-fold to 70-fold, from 12-fold to 70-fold, from 14-fold to 70-fold, from 16-fold to 70-fold, from 20-fold to 70-fold, from 24-fold to 70-fold, from 30-fold to 70-fold, from 35-fold to 70-fold, from 40-fold to 70-fold, from 50-fold to 70-fold, or from 60-fold to 70-fold. The amplification bias can be, for example, from 1-fold to 60-fold, from 2-fold to 60-fold, from 3-fold to 60-fold, from 4-fold to 60-fold, from 5-fold to 60-fold, from 6-fold to 60-fold, from 7-fold to 60-fold, from 8-fold to 60-fold, from 9-fold to 60-fold, from 10-fold to 60-fold, from 11-fold to 60-fold, from 12-fold to 60-fold, from 14-fold to 60-fold, from 16-fold to 60-fold, from 20-fold to 60-fold, from 24-fold to 60-fold, from 30-fold to 60-fold, from 35-fold to 60-fold, from 40-fold to 60-fold, or from 50-fold to 60-fold.

The amplification bias can be, for example, from 1-fold to 50-fold, from 2-fold to 50-fold, from 3-fold to 50-fold, from 4-fold to 50-fold, from 5-fold to 50-fold, from 6-fold to 50-fold, from 7-fold to 50-fold, from 8-fold to 50-fold, from 9-fold to 50-fold, from 10-fold to 50-fold, from 11-fold to 50-fold, from 12-fold to 50-fold, from 14-fold to 50-fold, from 16-fold to 50-fold, from 20-fold to 50-fold, from 24-fold to 50-fold, from 30-fold to 50-fold, from 35-fold to 50-fold, or from 40-fold to 50-fold. The amplification bias can be, for example, from 1-fold to 40-fold, from 2-fold to 40-fold, from 3-fold to 40-fold, from 4-fold to 40-fold, from 5-fold to 40-fold, from 6-fold to 40-fold, from 7-fold to 40-fold, from 8-fold to 40-fold, from 9-fold to 40-fold, from 10-fold to 40-fold, from 11-fold to 40-fold, from 12-fold to 40-fold, from 14-fold to 40-fold, from 16-fold to 40-fold, from 20-fold to 40-fold, from 24-fold to 40-fold, from 30-fold to 40-fold, or from 35-fold to 40-fold.

The amplification bias can be, for example, from 1-fold to 30-fold, from 2-fold to 30-fold, from 3-fold to 30-fold, from 4-fold to 30-fold, from 5-fold to 30-fold, from 6-fold to 30-fold, from 7-fold to 30-fold, from 8-fold to 30-fold, from 9-fold to 30-fold, from 10-fold to 30-fold, from 11-fold to 30-fold, from 12-fold to 30-fold, from 14-fold to 30-fold, from 16-fold to 30-fold, from 20-fold to 30-fold, or from 24-fold to 30-fold. The amplification bias can be, for example, from 1-fold to 20-fold, from 2-fold to 20-fold, from 3-fold to 20-fold, from 4-fold to 20-fold, from 5-fold to 20-fold, from 6-fold to 20-fold, from 7-fold to 20-fold, from 8-fold to 20-fold, from 9-fold to 20-fold, from 10-fold to 20-fold, from 11-fold to 20-fold, from 12-fold to 20-fold, from 14-fold to 20-fold, from 16-fold to 20-fold, from 20-fold to 20-fold, or from 24-fold to 20-fold.

The amplification bias can be, for example, from 1-fold to 12-fold, from 2-fold to 12-fold, from 3-fold to 12-fold, from 4-fold to 12-fold, from 5-fold to 12-fold, from 6-fold to 12-fold, from 7-fold to 12-fold, from 8-fold to 12-fold, from 9-fold to 12-fold, from 10-fold to 12-fold, or from 11-fold to 12-fold. The amplification bias can be, for example, from 1-fold to 11-fold, from 2-fold to 11-fold, from 3-fold to 11-fold, from 4-fold to 11-fold, from 5-fold to 11-fold, from 6-fold to 11-fold, from 7-fold to 11-fold, from 8-fold to 11-fold, from 9-fold to 11-fold, or from 10-fold to 11-fold. The amplification bias can be, for example, from 1-fold to 10-fold, from 2-fold to 10-fold, from 3-fold to 10-fold, from 4-fold to 10-fold, from 5-fold to 10-fold, from 6-fold to 10-fold, from 7-fold to 10-fold, from 8-fold to 10-fold, or from 9-fold to 10-fold. The amplification bias can be, for example, from 1-fold to 9-fold, from 2-fold to 9-fold, from 3-fold to 9-fold, from 4-fold to 9-fold, from 5-fold to 9-fold, from 6-fold to 9-fold, from 7-fold to 9-fold, or from 8-fold to 9-fold.

The amplification bias can be, for example, from 1-fold to 8-fold, from 2-fold to 8-fold, from 3-fold to 8-fold, from 4-fold to 8-fold, from 5-fold to 8-fold, from 6-fold to 8-fold, or from 7-fold to 8-fold. The amplification bias can be, for example, from 1-fold to 7-fold, from 2-fold to 7-fold, from 3-fold to 7-fold, from 4-fold to 7-fold, from 5-fold to 7-fold, or from 6-fold to 7-fold. The amplification bias can be, for example, from 1-fold to 6-fold, from 2-fold to 6-fold, from 3-fold to 6-fold, from 4-fold to 6-fold, or from 5-fold to 6-fold. The amplification bias can be, for example, from 1-fold to 5-fold, from 2-fold to 5-fold, from 3-fold to 5-fold, from 4-fold to 5-fold, from 1-fold to 4-fold, from 2-fold to 4-fold, from 3-fold to 4-fold, from 1-fold to 3-fold, from 2-fold to 3-fold, or from 1-fold to 2-fold.

The amplification bias can be, for example, from about 1-fold to about 300-fold, from about 2-fold to about 300-fold, from about 3-fold to about 300-fold, from about 4-fold to about 300-fold, from about 5-fold to about 300-fold, from about 6-fold to about 300-fold, from about 7-fold to about 300-fold, from about 8-fold to about 300-fold, from about 9-fold to about 300-fold, from about 10-fold to about 300-fold, from about 11-fold to about 300-fold, from about 12-fold to about 300-fold, from about 14-fold to about 300-fold, from about 16-fold to about 300-fold, from about 20-fold to about 300-fold, from about 24-fold to about 300-fold, from about 30-fold to about 300-fold, from about 35-fold to about 300-fold, from about 40-fold to about 300-fold, from about 50-fold to about 300-fold, from about 60-fold to about 300-fold, from about 70-fold to about 300-fold, from about 80-fold to about 300-fold, from about 90-fold to about 300-fold, from about 100-fold to about 300-fold, from about 150-fold to about 300-fold, from about 200-fold to about 300-fold, or from about 250-fold to about 300-fold.

The amplification bias can be, for example, from about 1-fold to about 250-fold, from about 2-fold to about 250-fold, from about 3-fold to about 250-fold, from about 4-fold to about 250-fold, from about 5-fold to about 250-fold, from about 6-fold to about 250-fold, from about 7-fold to about 250-fold, from about 8-fold to about 250-fold, from about 9-fold to about 250-fold, from about 10-fold to about 250-fold, from about 11-fold to about 250-fold, from about 12-fold to about 250-fold, from about 14-fold to about 250-fold, from about 16-fold to about 250-fold, from about 20-fold to about 250-fold, from about 24-fold to about 250-fold, from about 30-fold to about 250-fold, from about 35-fold to about 250-fold, from about 40-fold to about 250-fold, from about 50-fold to about 250-fold, from about 60-fold to about 250-fold, from about 70-fold to about 250-fold, from about 80-fold to about 250-fold, from about 90-fold to about 250-fold, from about 100-fold to about 250-fold, from about 150-fold to about 250-fold, or from about 200-fold to about 250-fold.

The amplification bias can be, for example, from about 1-fold to about 200-fold, from about 2-fold to about 200-fold, from about 3-fold to about 200-fold, from about 4-fold to about 200-fold, from about 5-fold to about 200-fold, from about 6-fold to about 200-fold, from about 7-fold to about 200-fold, from about 8-fold to about 200-fold, from about 9-fold to about 200-fold, from about 10-fold to about 200-fold, from about 11-fold to about 200-fold, from about 12-fold to about 200-fold, from about 14-fold to about 200-fold, from about 16-fold to about 200-fold, from about 20-fold to about 200-fold, from about 24-fold to about 200-fold, from about 30-fold to about 200-fold, from about 35-fold to about 200-fold, from about 40-fold to about 200-fold, from about 50-fold to about 200-fold, from about 60-fold to about 200-fold, from about 70-fold to about 200-fold, from about 80-fold to about 200-fold, from about 90-fold to about 200-fold, from about 100-fold to about 200-fold, or from about 150-fold to about 200-fold.

The amplification bias can be, for example, from about 1-fold to about 150-fold, from about 2-fold to about 150-fold, from about 3-fold to about 150-fold, from about 4-fold to about 150-fold, from about 5-fold to about 150-fold, from about 6-fold to about 150-fold, from about 7-fold to about 150-fold, from about 8-fold to about 150-fold, from about 9-fold to about 150-fold, from about 10-fold to about 150-fold, from about 11-fold to about 150-fold, from about 12-fold to about 150-fold, from about 14-fold to about 150-fold, from about 16-fold to about 150-fold, from about 20-fold to about 150-fold, from about 24-fold to about 150-fold, from about 30-fold to about 150-fold, from about 35-fold to about 150-fold, from about 40-fold to about 150-fold, from about 50-fold to about 150-fold, from about 60-fold to about 150-fold, from about 70-fold to about 150-fold, from about 80-fold to about 150-fold, from about 90-fold to about 150-fold, or from about 100-fold to about 150-fold.

The amplification bias can be, for example, from about 1-fold to about 100-fold, from about 2-fold to about 100-fold, from about 3-fold to about 100-fold, from about 4-fold to about 100-fold, from about 5-fold to about 100-fold, from about 6-fold to about 100-fold, from about 7-fold to about 100-fold, from about 8-fold to about 100-fold, from about 9-fold to about 100-fold, from about 10-fold to about 100-fold, from about 11-fold to about 100-fold, from about 12-fold to about 100-fold, from about 14-fold to about 100-fold, from about 16-fold to about 100-fold, from about 20-fold to about 100-fold, from about 24-fold to about 100-fold, from about 30-fold to about 100-fold, from about 35-fold to about 100-fold, from about 40-fold to about 100-fold, from about 50-fold to about 100-fold, from about 60-fold to about 100-fold, from about 70-fold to about 100-fold, from about 80-fold to about 100-fold, or from about 90-fold to about 100-fold.

The amplification bias can be, for example, from about 1-fold to about 90-fold, from about 2-fold to about 90-fold, from about 3-fold to about 90-fold, from about 4-fold to about 90-fold, from about 5-fold to about 90-fold, from about 6-fold to about 90-fold, from about 7-fold to about 90-fold, from about 8-fold to about 90-fold, from about 9-fold to about 90-fold, from about 10-fold to about 90-fold, from about 11-fold to about 90-fold, from about 12-fold to about 90-fold, from about 14-fold to about 90-fold, from about 16-fold to about 90-fold, from about 20-fold to about 90-fold, from about 24-fold to about 90-fold, from about 30-fold to about 90-fold, from about 35-fold to about 90-fold, from about 40-fold to about 90-fold, from about 50-fold to about 90-fold, from about 60-fold to about 90-fold, from about 70-fold to about 90-fold, or from about 80-fold to about 90-fold.

The amplification bias can be, for example, from about 1-fold to about 80-fold, from about 2-fold to about 80-fold, from about 3-fold to about 80-fold, from about 4-fold to about 80-fold, from about 5-fold to about 80-fold, from about 6-fold to about 80-fold, from about 7-fold to about 80-fold, from about 8-fold to about 80-fold, from about 9-fold to about 80-fold, from about 10-fold to about 80-fold, from about 11-fold to about 80-fold, from about 12-fold to about 80-fold, from about 14-fold to about 80-fold, from about 16-fold to about 80-fold, from about 20-fold to about 80-fold, from about 24-fold to about 80-fold, from about 30-fold to about 80-fold, from about 35-fold to about 80-fold, from about 40-fold to about 80-fold, from about 50-fold to about 80-fold, from about 60-fold to about 80-fold, or from about 70-fold to about 80-fold.

The amplification bias can be, for example, from about 1-fold to about 70-fold, from about 2-fold to about 70-fold, from about 3-fold to about 70-fold, from about 4-fold to about 70-fold, from about 5-fold to about 70-fold, from about 6-fold to about 70-fold, from about 7-fold to about 70-fold, from about 8-fold to about 70-fold, from about 9-fold to about 70-fold, from about 10-fold to about 70-fold, from about 11-fold to about 70-fold, from about 12-fold to about 70-fold, from about 14-fold to about 70-fold, from about 16-fold to about 70-fold, from about 20-fold to about 70-fold, from about 24-fold to about 70-fold, from about 30-fold to about 70-fold, from about 35-fold to about 70-fold, from about 40-fold to about 70-fold, from about 50-fold to about 70-fold, or from about 60-fold to about 70-fold. The amplification bias can be, for example, from about 1-fold to about 60-fold, from about 2-fold to about 60-fold, from about 3-fold to about 60-fold, from about 4-fold to about 60-fold, from about 5-fold to about 60-fold, from about 6-fold to about 60-fold, from about 7-fold to about 60-fold, from about 8-fold to about 60-fold, from about 9-fold to about 60-fold, from about 10-fold to about 60-fold, from about 11-fold to about 60-fold, from about 12-fold to about 60-fold, from about 14-fold to about 60-fold, from about 16-fold to about 60-fold, from about 20-fold to about 60-fold, from about 24-fold to about 60-fold, from about 30-fold to about 60-fold, from about 35-fold to about 60-fold, from about 40-fold to about 60-fold, or from about 50-fold to about 60-fold.

The amplification bias can be, for example, from about 1-fold to about 50-fold, from about 2-fold to about 50-fold, from about 3-fold to about 50-fold, from about 4-fold to about 50-fold, from about 5-fold to about 50-fold, from about 6-fold to about 50-fold, from about 7-fold to about 50-fold, from about 8-fold to about 50-fold, from about 9-fold to about 50-fold, from about 10-fold to about 50-fold, from about 11-fold to about 50-fold, from about 12-fold to about 50-fold, from about 14-fold to about 50-fold, from about 16-fold to about 50-fold, from about 20-fold to about 50-fold, from about 24-fold to about 50-fold, from about 30-fold to about 50-fold, from about 35-fold to about 50-fold, or from about 40-fold to about 50-fold. The amplification bias can be, for example, from about 1-fold to about 40-fold, from about 2-fold to about 40-fold, from about 3-fold to about 40-fold, from about 4-fold to about 40-fold, from about 5-fold to about 40-fold, from about 6-fold to about 40-fold, from about 7-fold to about 40-fold, from about 8-fold to about 40-fold, from about 9-fold to about 40-fold, from about 10-fold to about 40-fold, from about 11-fold to about 40-fold, from about 12-fold to about 40-fold, from about 14-fold to about 40-fold, from about 16-fold to about 40-fold, from about 20-fold to about 40-fold, from about 24-fold to about 40-fold, from about 30-fold to about 40-fold, or from about 35-fold to about 40-fold.

The amplification bias can be, for example, from about 1-fold to about 30-fold, from about 2-fold to about 30-fold, from about 3-fold to about 30-fold, from about 4-fold to about 30-fold, from about 5-fold to about 30-fold, from about 6-fold to about 30-fold, from about 7-fold to about 30-fold, from about 8-fold to about 30-fold, from about 9-fold to about 30-fold, from about 10-fold to about 30-fold, from about 11-fold to about 30-fold, from about 12-fold to about 30-fold, from about 14-fold to about 30-fold, from about 16-fold to about 30-fold, from about 20-fold to about 30-fold, or from about 24-fold to about 30-fold. The amplification bias can be, for example, from about 1-fold to about 20-fold, from about 2-fold to about 20-fold, from about 3-fold to about 20-fold, from about 4-fold to about 20-fold, from about 5-fold to about 20-fold, from about 6-fold to about 20-fold, from about 7-fold to about 20-fold, from about 8-fold to about 20-fold, from about 9-fold to about 20-fold, from about 10-fold to about 20-fold, from about 11-fold to about 20-fold, from about 12-fold to about 20-fold, from about 14-fold to about 20-fold, from about 16-fold to about 20-fold, from about 20-fold to about 20-fold, or from about 24-fold to about 20-fold.

The amplification bias can be, for example, from about 1-fold to about 12-fold, from about 2-fold to about 12-fold, from about 3-fold to about 12-fold, from about 4-fold to about 12-fold, from about 5-fold to about 12-fold, from about 6-fold to about 12-fold, from about 7-fold to about 12-fold, from about 8-fold to about 12-fold, from about 9-fold to about 12-fold, from about 10-fold to about 12-fold, or from about 11-fold to about 12-fold. The amplification bias can be, for example, from about 1-fold to about 11-fold, from about 2-fold to about 11-fold, from about 3-fold to about 11-fold, from about 4-fold to about 11-fold, from about 5-fold to about 11-fold, from about 6-fold to about 11-fold, from about 7-fold to about 11-fold, from about 8-fold to about 11-fold, from about 9-fold to about 11-fold, or from about 10-fold to about 11-fold. The amplification bias can be, for example, from about 1-fold to about 10-fold, from about 2-fold to about 10-fold, from about 3-fold to about 10-fold, from about 4-fold to about 10-fold, from about 5-fold to about 10-fold, from about 6-fold to about 10-fold, from about 7-fold to about 10-fold, from about 8-fold to about 10-fold, or from about 9-fold to about 10-fold. The amplification bias can be, from about 1-fold to about 9-fold, from about 2-fold to about 9-fold, from about 3-fold to about 9-fold, from about 4-fold to about 9-fold, from about 5-fold to about 9-fold, from about 6-fold to about 9-fold, from about 7-fold to about 9-fold, or from about 8-fold to about 9-fold.

The amplification bias can be, for example, from about 1-fold to about 8-fold, from about 2-fold to about 8-fold, from about 3-fold to about 8-fold, from about 4-fold to about 8-fold, from about 5-fold to about 8-fold, from about 6-fold to about 8-fold, or from about 7-fold to about 8-fold. The amplification bias can be, for example, from about 1-fold to about 7-fold, from about 2-fold to about 7-fold, from about 3-fold to about 7-fold, from about 4-fold to about 7-fold, from about 5-fold to about 7-fold, or from about 6-fold to about 7-fold. The amplification bias can be, for example, from about 1-fold to about 6-fold, from about 2-fold to about 6-fold, from about 3-fold to about 6-fold, from about 4-fold to about 6-fold, or from about 5-fold to about 6-fold. The amplification bias can be, for example, from about 1-fold to about 5-fold, from about 2-fold to about 5-fold, from about 3-fold to about 5-fold, from about 4-fold to about 5-fold, from about 1-fold to about 4-fold, from about 2-fold to about 4-fold, from about 3-fold to about 4-fold, from about 1-fold to about 3-fold, from about 2-fold to about 3-fold, or from about 1-fold to about 2-fold.

The various amplification biases described above and elsewhere herein can be, for example, for 1 locus, 2 loci, 3 loci, 4 loci, 5 loci, 6 loci, 7 loci, 8 loci, 9 loci, 10 loci, 11 loci, 12 loci, 13 loci, 14 loci, 15 loci, 16 loci, 17 loci, 18 loci, 19 loci, 20 loci, 25 loci, 30 loci, 40 loci, 50 loci, 75 loci, or 100 loci. The amplification bias can be, for example, for at least 1 locus, at least 2 loci, at least 3 loci, at least 4 loci, at least 5 loci, at least 6 loci, at least 7 loci, at least 8 loci, at least 9 loci, at least 10 loci, at least 11 loci, at least 12 loci, at least 13 loci, at least 14 loci, at least 15 loci, at least 16 loci, at least 17 loci, at least 18 loci, at least 19 loci, at least 20 loci, at least 25 loci, at least 30 loci, at least 40 loci, at least 50 loci, at least 75 loci, or at least 100 loci.

The amplification bias can be, for example, for 1 locus, 2 different loci, 3 different loci, 4 different loci, 5 different loci, 6 different loci, 7 different loci, 8 different loci, 9 different loci, 10 different loci, 11 different loci, 12 different loci, 13 different loci, 14 different loci, 15 different loci, 16 different loci, 17 different loci, 18 different loci, 19 different loci, 20 different loci, 25 different loci, 30 different loci, 40 different loci, 50 different loci, 75 different loci, or 100 different loci. The amplification bias can be, for example, for at least 1 locus, at least 2 different loci, at least 3 different loci, at least 4 different loci, at least 5 different loci, at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

The various amplification biases described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The amplification bias can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The amplification bias can be, for example, for 1 target sequence, 2 different target sequences, 3 different target sequences, 4 different target sequences, 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The amplification bias can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

B. Amplification Level

The disclosed method can produce a high level of amplification. For example, the disclosed method can produce a 10,000-fold amplification or more. Fold amplification refers to the number of copies generated of the template being amplified. For example, if 1 ug of DNA is generated from 1 ng of template, the level of amplification is 1,000-fold. The disclosed method can produce, for example, amplification of about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, about 300-fold, about 400-fold, about 500-fold, about 600-fold, about 700-fold, about 800-fold, about 900-fold, about 1,000-fold, about 10,000-fold, about 100,000-fold, about 1,000,000-fold, about 10,000,000-fold, or about 100,000,000-fold.

The disclosed method can produce, for example, amplification of at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 14-fold, at least 16-fold, at least 20-fold, at least 24-fold, at least 30-fold, at least 35-fold, at least 40-fold, at least 50-fold, at least 60-fold, at least 70-fold, at least 80-fold, at least 90-fold, at least 100-fold, at least 150-fold, at least 200-fold, at least 250-fold, at least 300-fold, at least 400-fold, at least 500-fold, at least 600-fold, at least 700-fold, at least 800-fold, at least 900-fold, at least 1,000-fold, at least 10,000-fold, at least 100,000-fold, at least 1,000,000-fold, at least 10,000,000-fold, or at least 100,000,000-fold.

The disclosed method can produce, for example, amplification bias of at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 14-fold, at least about 16-fold, at least about 20-fold, at least about 24-fold, at least about 30-fold, at least about 35-fold, at least about 40-fold, at least about 50-fold, at least about 60-fold, at least about 70-fold, at least about 80-fold, at least about 90-fold, at least about 100-fold, at least about 150-fold, at least about 200-fold, at least about 250-fold, at least about 300-fold, at least about 400-fold, at least about 500-fold, at least about 600-fold, at least about 700-fold, at least about 800-fold, at least about 900-fold, at least about 1,000-fold, at least about 10,000-fold, at least about 100,000-fold, at least about 1,000,000-fold, at least about 10,000,000-fold, or at least about 100,000,000-fold.

The disclosed method can produce, for example, amplification of from about 1-fold to about 100,000,000-fold, from about 2-fold to about 100,000,000-fold, from about 3-fold to about 100,000,000-fold, from about 4-fold to about 100,000,000-fold, from about 5-fold to about 100,000,000-fold, from about 6-fold to about 100,000,000-fold, from about 7-fold to about 1100,000,000-fold, from about 8-fold to about 100,000,000-fold, from about 9-fold to about 100,000,000-fold, from about 10-fold to about 100,000,000-fold, from about 11-fold to about 100,000,000-fold, from about 12-fold to about 100,000,000-fold, from about 14-fold to about 100,000,000-fold, from about 16-fold to about 100,000,000-fold, from about 20-fold to about 100,000,000-fold, from about 24-fold to about 100,000,000-fold, from about 30-fold to about 100,000,000-fold, from about 35-fold to about 100,000,000-fold, from about 40-fold to about 100,000,000-fold, from about 50-fold to about 100,000,0000-fold, from about 60-fold to about 100,000,000-fold, from about 70-fold to about 100,000,000-fold, from about 80-fold to about 100,000,000-fold, from about 90-fold to about 100,000,000-fold, from about 800-fold to about 100,000,000-fold, from about 150-fold to about 100,000,000-fold, from about 200-fold to about 100,000,000-fold, from about 250-fold to about 100,000,000-fold, from about 300-fold to about 100,000,000-fold, from about 400-fold to about 100,000,000-fold, from about 500-fold to about 100,000,000-fold, from about 600-fold to about 100,000,000-fold, from about 700-fold to about 100,000,000-fold, from about 800-fold to about 100,000,000-fold, from about 900-fold to about 100,000,000-fold, from about 1,000-fold to about 100,000,000-fold, from about 10,000-fold to about 100,000,000-fold, from about 100,000-fold to about 100,000,000-fold, from about 1,000,000-fold to about 100,000,000-fold, or from about 10,000,000-fold to about 100,000,000-fold.

The disclosed method can produce, for example, amplification of from about 1-fold to about 10,000,000-fold, from about 2-fold to about 10,000,000-fold, from about 3-fold to about 10,000,000-fold, from about 4-fold to about 10,000,000-fold, from about 5-fold to about 10,000,000-fold, from about 6-fold to about 10,000,000-fold, from about 7-fold to about 10,000,000-fold, from about 8-fold to about 10,000,000-fold, from about 9-fold to about 10,000,000-fold, from about 10-fold to about 10,000,000-fold, from about 11-fold to about 10,000,000-fold, from about 12-fold to about 10,000,000-fold, from about 14-fold to about 10,000,000-fold, from about 16-fold to about 10,000,000-fold, from about 20-fold to about 10,000,000-fold, from about 24-fold to about 10,000,000-fold, from about 30-fold to about 10,000,000-fold, from about 35-fold to about 10,000,000-fold, from about 40-fold to about 10,000,000-fold, from about 50-fold to about 10,000,000-fold, from about 60-fold to about 10,000,000-fold, from about 70-fold to about 10,000,000-fold, from about 80-fold to about 10,000,000-fold, from about 90-fold to about 10,000,000-fold, from about 100-fold to about 10,000,000-fold, from about 150-fold to about 10,000,000-fold, from about 200-fold to about 10,000,000-fold, from about 250-fold to about 10,000,000-fold, from about 300-fold to about 10,000,000-fold, from about 400-fold to about 10,000,000-fold, from about 500-fold to about 10,000,000-fold, from about 600-fold to about 10,000,000-fold, from about 700-fold to about 10,000,000-fold, from about 800-fold to about 10,000,000-fold, from about 900-fold to about 10,000,000-fold, from about 1,000-fold to about 10,000,000-fold, from about 10,000-fold to about 10,000,000-fold, from about 100,000-fold to about 10,000,000-fold, or from about 1,000,000-fold to about 10,000,000-fold.

The disclosed method can produce, for example, amplification of from about 1-fold to about 1,000,000-fold, from about 2-fold to about 1,000,000-fold, from about 3-fold to about 1,000,000-fold, from about 4-fold to about 1,000,000-fold, from about 5-fold to about 1,000,000-fold, from about 6-fold to about 1,000,000-fold, from about 7-fold to about 1,000,000-fold, from about 8-fold to about 1,000,000-fold, from about 9-fold to about 1,000,000-fold, from about 10-fold to about 1,000,000-fold, from about 11-fold to about 1,000,000-fold, from about 12-fold to about 1,000,000-fold, from about 14-fold to about 1,000,000-fold, from about 16-fold to about 1,000,000-fold, from about 20-fold to about 1,000,000-fold, from about 24-fold to about 1,000,000-fold, from about 30-fold to about 1,000,000-fold, from about 35-fold to about 1,000,000-fold, from about 40-fold to about 1,000,000-fold, from about 50-fold to about 1,000,000-fold, from about 60-fold to about 1,000,000-fold, from about 70-fold to about 1,000,000-fold, from about 80-fold to about 1,000,000-fold, from about 90-fold to about 1,000,000-fold, from about 100-fold to about 1,000,000-fold, from about 150-fold to about 1,000,000-fold, from about 200-fold to about 1,000,000-fold, from about 250-fold to about 1,000,000-fold, from about 300-fold to about 1,000,000-fold, from about 400-fold to about 1,000,000-fold, from about 500-fold to about 1,000,000-fold, from about 600-fold to about 1,000,000-fold, from about 700-fold to about 1,000,000-fold, from about 800-fold to about 1,000,000-fold, from about 900-fold to about 1,000,000-fold, from about 1,000-fold to about 1,000,000-fold, from about 10,000-fold to about 1,000,000-fold, or from about 100,000-fold to about 1,000,000-fold.

The disclosed method can produce, for example, amplification of from about 1-fold to about 100,000-fold, from about 2-fold to about 100,000-fold, from about 3-fold to about 100,000-fold, from about 4-fold to about 100,000-fold, from about 5-fold to about 100,000-fold, from about 6-fold to about 100,000-fold, from about 7-fold to about 100,000-fold, from about 8-fold to about 100,000-fold, from about 9-fold to about 100,000-fold, from about 10-fold to about 100,000-fold, from about 11-fold to about 100,000-fold, from about 12-fold to about 100,000-fold, from about 14-fold to about 100,000-fold, from about 16-fold to about 100,000-fold, from about 20-fold to about 100,000-fold, from about 24-fold to about 100,000-fold, from about 30-fold to about 100,000-fold, from about 35-fold to about 100,000-fold, from about 40-fold to about 100,000-fold, from about 50-fold to about 100,000-fold, from about 60-fold to about 100,000-fold, from about 70-fold to about 100,000-fold, from about 80-fold to about 100,000-fold, from about 90-fold to about 100,000-fold, from about 100-fold to about 100,000-fold, from about 150-fold to about 100,000-fold, from about 200-fold to about 100,000-fold, from about 250-fold to about 100,000-fold, from about 300-fold to about 100,000-fold, from about 400-fold to about 100,000-fold, from about 500-fold to about 100,000-fold, from about 600-fold to about 100,000-fold, from about 700-fold to about 100,000-fold, from about 800-fold to about 100,000-fold, from about 900-fold to about 100,000-fold, from about 1,000-fold to about 100,000-fold, or from about 10,000-fold to about 100,000-fold.

The disclosed method can produce, for example, amplification of from about 1-fold to about 10,000-fold, from about 2-fold to about 10,000-fold, from about 3-fold to about 10,000-fold, from about 4-fold to about 10,000-fold, from about 5-fold to about 10,000-fold, from about 6-fold to about 10,000-fold, from about 7-fold to about 10,000-fold, from about 8-fold to about 10,000-fold, from about 9-fold to about 10,000-fold, from about 10-fold to about 10,000-fold, from about 11-fold to about 10,000-fold, from about 12-fold to about 10,000-fold, from about 14-fold to about 10,000-fold, from about 16-fold to about 10,000-fold, from about 20-fold to about 10,000-fold, from about 24-fold to about 10,000-fold, from about 30-fold to about 10,000-fold, from about 35-fold to about 10,000-fold, from about 40-fold to about 10,000-fold, from about 50-fold to about 10,000-fold, from about 60-fold to about 10,000-fold, from about 70-fold to about 10,000-fold, from about 80-fold to about 10,000-fold, from about 90-fold to about 10,000-fold, from about 100-fold to about 10,000-fold, from about 150-fold to about 10,000-fold, from about 200-fold to about 10,000-fold, from about 250-fold to about 10,000-fold, from about 300-fold to about 10,000-fold, from about 400-fold to about 10,000-fold, from about 500-fold to about 10,000-fold, from about 600-fold to about 10,000-fold, from about 700-fold to about 10,000-fold, from about 800-fold to about 10,000-fold, from about 900-fold to about 10,000-fold, or from about 1,000-fold to about 10,000-fold.

The disclosed method can produce, for example, amplification of from about 1-fold to about 1,000-fold, from about 2-fold to about 1,000-fold, from about 3-fold to about 1,000-fold, from about 4-fold to about 1,000-fold, from about 5-fold to about 1,000-fold, from about 6-fold to about 1,000-fold, from about 7-fold to about 1,000-fold, from about 8-fold to about 1,000-fold, from about 9-fold to about 1,000-fold, from about 10-fold to about 1,000-fold, from about 11-fold to about 1,000-fold, from about 12-fold to about 1,000-fold, from about 14-fold to about 1,000-fold, from about 16-fold to about 1,000-fold, from about 20-fold to about 1,000-fold, from about 24-fold to about 1,000-fold, from about 30-fold to about 1,000-fold, from about 35-fold to about 1,000-fold, from about 40-fold to about 1,000-fold, from about 50-fold to about 1,000-fold, from about 60-fold to about 1,000-fold, from about 70-fold to about 1,000-fold, from about 80-fold to about 1,000-fold, from about 90-fold to about 1,000-fold, from about 100-fold to about 1,000-fold, from about 150-fold to about 1,000-fold, from about 200-fold to about 1,000-fold, from about 250-fold to about 1,000-fold, from about 300-fold to about 1,000-fold, from about 400-fold to about 1,000-fold, from about 500-fold to about 1,000-fold, from about 600-fold to about 1,000-fold, from about 700-fold to about 1,000-fold, from about 800-fold to about 1,000-fold, or from about 900-fold to about 1,000-fold.

The disclosed method can produce, for example, amplification of from about 1-fold to about 900-fold, from about 2-fold to about 900-fold, from about 3-fold to about 900-fold, from about 4-fold to about 900-fold, from about 5-fold to about 900-fold, from about 6-fold to about 900-fold, from about 7-fold to about 900-fold, from about 8-fold to about 900-fold, from about 9-fold to about 900-fold, from about 10-fold to about 900-fold, from about 11-fold to about 900-fold, from about 12-fold to about 900-fold, from about 14-fold to about 900-fold, from about 16-fold to about 900-fold, from about 20-fold to about 900-fold, from about 24-fold to about 900-fold, from about 30-fold to about 900-fold, from about 35-fold to about 900-fold, from about 40-fold to about 900-fold, from about 50-fold to about 900-fold, from about 60-fold to about 900-fold, from about 70-fold to about 900-fold, from about 80-fold to about 900-fold, from about 90-fold to about 900-fold, from about 100-fold to about 900-fold, from about 150-fold to about 900-fold, from about 200-fold to about 900-fold, from about 250-fold to about 900-fold, from about 300-fold to about 900-fold, from about 400-fold to about 900-fold, from about 500-fold to about 900-fold, from about 600-fold to about 900-fold, from about 700-fold to about 900-fold, or from about 800-fold to about 900-fold.

The disclosed method can produce, for example, amplification of from about 1-fold to about 800-fold, from about 2-fold to about 800-fold, from about 3-fold to about 800-fold, from about 4-fold to about 800-fold, from about 5-fold to about 800-fold, from about 6-fold to about 800-fold, from about 7-fold to about 800-fold, from about 8-fold to about 800-fold, from about 9-fold to about 800-fold, from about 10-fold to about 800-fold, from about 11-fold to about 800-fold, from about 12-fold to about 800-fold, from about 14-fold to about 800-fold, from about 16-fold to about 800-fold, from about 20-fold to about 800-fold, from about 24-fold to about 800-fold, from about 30-fold to about 800-fold, from about 35-fold to about 800-fold, from about 40-fold to about 800-fold, from about 50-fold to about 800-fold, from about 60-fold to about 800-fold, from about 70-fold to about 800-fold, from about 80-fold to about 800-fold, from about 90-fold to about 800-fold, from about 100-fold to about 800-fold, from about 150-fold to about 800-fold, from about 200-fold to about 800-fold, from about 250-fold to about 800-fold, from about 300-fold to about 800-fold, from about 400-fold to about 800-fold, from about 500-fold to about 800-fold, from about 600-fold to about 800-fold, or from about 700-fold to about 800-fold.

The disclosed method can produce, for example, amplification of from about 1-fold to about 700-fold, from about 2-fold to about 700-fold, from about 3-fold to about 700-fold, from about 4-fold to about 700-fold, from about 5-fold to about 700-fold, from about 6-fold to about 700-fold, from about 7-fold to about 700-fold, from about 8-fold to about 700-fold, from about 9-fold to about 700-fold, from about 10-fold to about 700-fold, from about 11-fold to about 700-fold, from about 12-fold to about 700-fold, from about 14-fold to about 700-fold, from about 16-fold to about 700-fold, from about 20-fold to about 700-fold, from about 24-fold to about 700-fold, from about 30-fold to about 700-fold, from about 35-fold to about 700-fold, from about 40-fold to about 700-fold, from about 50-fold to about 700-fold, from about 60-fold to about 700-fold, from about 70-fold to about 700-fold, from about 80-fold to about 700-fold, from about 90-fold to about 700-fold, from about 100-fold to about 700-fold, from about 150-fold to about 700-fold, from about 200-fold to about 700-fold, from about 250-fold to about 700-fold, from about 300-fold to about 700-fold, from about 400-fold to about 700-fold, from about 500-fold to about 700-fold, or from about 600-fold to about 700-fold.

The disclosed method can produce, for example, amplification of from about 1-fold to about 600-fold, from about 2-fold to about 600-fold, from about 3-fold to about 600-fold, from about 4-fold to about 600-fold, from about 5-fold to about 600-fold, from about 6-fold to about 600-fold, from about 7-fold to about 600-fold, from about 8-fold to about 600-fold, from about 9-fold to about 600-fold, from about 10-fold to about 600-fold, from about 11-fold to about 600-fold, from about 12-fold to about 600-fold, from about 14-fold to about 600-fold, from about 16-fold to about 600-fold, from about 20-fold to about 600-fold, from about 24-fold to about 600-fold, from about 30-fold to about 600-fold, from about 35-fold to about 600-fold, from about 40-fold to about 600-fold, from about 50-fold to about 600-fold, from about 60-fold to about 600-fold, from about 70-fold to about 600-fold, from about 80-fold to about 600-fold, from about 90-fold to about 600-fold, from about 100-fold to about 600-fold, from about 150-fold to about 600-fold, from about 200-fold to about 600-fold, from about 250-fold to about 600-fold, from about 300-fold to about 600-fold, from about 400-fold to about 600-fold, or from about 500-fold to about 600-fold.

The disclosed method can produce, for example, amplification of from about 1-fold to about 500-fold, from about 2-fold to about 500-fold, from about 3-fold to about 500-fold, from about 4-fold to about 500-fold, from about 5-fold to about 500-fold, from about 6-fold to about 500-fold, from about 7-fold to about 500-fold, from about 8-fold to about 500-fold, from about 9-fold to about 500-fold, from about 10-fold to about 500-fold, from about 11-fold to about 500-fold, from about 12-fold to about 500-fold, from about 14-fold to about 500-fold, from about 16-fold to about 500-fold, from about 20-fold to about 500-fold, from about 24-fold to about 500-fold, from about 30-fold to about 500-fold, from about 35-fold to about 500-fold, from about 40-fold to about 500-fold, from about 50-fold to about 500-fold, from about 60-fold to about 500-fold, from about 70-fold to about 500-fold, from about 80-fold to about 500-fold, from about 90-fold to about 500-fold, from about 100-fold to about 500-fold, from about 150-fold to about 500-fold, from about 200-fold to about 500-fold, from about 250-fold to about 500-fold, from about 300-fold to about 500-fold, or from about 400-fold to about 500-fold.

The disclosed method can produce, for example, amplification of from about 1-fold to about 400-fold, from about 2-fold to about 400-fold, from about 3-fold to about 400-fold, from about 4-fold to about 400-fold, from about 5-fold to about 400-fold, from about 6-fold to about 400-fold, from about 7-fold to about 400-fold, from about 8-fold to about 400-fold, from about 9-fold to about 400-fold, from about 10-fold to about 400-fold, from about 11-fold to about 400-fold, from about 12-fold to about 400-fold, from about 14-fold to about 400-fold, from about 16-fold to about 400-fold, from about 20-fold to about 400-fold, from about 24-fold to about 400-fold, from about 30-fold to about 400-fold, from about 35-fold to about 400-fold, from about 40-fold to about 400-fold, from about 50-fold to about 400-fold, from about 60-fold to about 400-fold, from about 70-fold to about 400-fold, from about 80-fold to about 400-fold, from about 90-fold to about 400-fold, from about 100-fold to about 400-fold, from about 150-fold to about 400-fold, from about 200-fold to about 400-fold, from about 250-fold to about 400-fold, or from about 300-fold to about 400-fold.

The disclosed method can produce, for example, amplification of from about 1-fold to about 300-fold, from about 2-fold to about 300-fold, from about 3-fold to about 300-fold, from about 4-fold to about 300-fold, from about 5-fold to about 300-fold, from about 6-fold to about 300-fold, from about 7-fold to about 300-fold, from about 8-fold to about 300-fold, from about 9-fold to about 300-fold, from about 10-fold to about 300-fold, from about 11-fold to about 300-fold, from about 12-fold to about 300-fold, from about 14-fold to about 300-fold, from about 16-fold to about 300-fold, from about 20-fold to about 300-fold, from about 24-fold to about 300-fold, from about 30-fold to about 300-fold, from about 35-fold to about 300-fold, from about 40-fold to about 300-fold, from about 50-fold to about 300-fold, from about 60-fold to about 300-fold, from about 70-fold to about 300-fold, from about 80-fold to about 300-fold, from about 90-fold to about 300-fold, from about 100-fold to about 300-fold, from about 150-fold to about 300-fold, from about 200-fold to about 300-fold, or from about 250-fold to about 300-fold.

The disclosed method can produce, for example, amplification of from about 1-fold to about 200-fold, from about 2-fold to about 200-fold, from about 3-fold to about 200-fold, from about 4-fold to about 200-fold, from about 5-fold to about 200-fold, from about 6-fold to about 200-fold, from about 7-fold to about 200-fold, from about 8-fold to about 200-fold, from about 9-fold to about 200-fold, from about 10-fold to about 200-fold, from about 11-fold to about 200-fold, from about 12-fold to about 200-fold, from about 14-fold to about 200-fold, from about 16-fold to about 200-fold, from about 20-fold to about 200-fold, from about 24-fold to about 200-fold, from about 30-fold to about 200-fold, from about 35-fold to about 200-fold, from about 40-fold to about 200-fold, from about 50-fold to about 200-fold, from about 60-fold to about 200-fold, from about 70-fold to about 200-fold, from about 80-fold to about 200-fold, from about 90-fold to about 200-fold, from about 100-fold to about 200-fold, or from about 150-fold to about 200-fold.

The disclosed method can produce, for example, amplification of from about 1-fold to about 100-fold, from about 2-fold to about 100-fold, from about 3-fold to about 100-fold, from about 4-fold to about 100-fold, from about 5-fold to about 100-fold, from about 6-fold to about 100-fold, from about 7-fold to about 100-fold, from about 8-fold to about 100-fold, from about 9-fold to about 100-fold, from about 10-fold to about 100-fold, from about 11-fold to about 100-fold, from about 12-fold to about 100-fold, from about 14-fold to about 100-fold, from about 16-fold to about 100-fold, from about 20-fold to about 100-fold, from about 24-fold to about 100-fold, from about 30-fold to about 100-fold, from about 35-fold to about 100-fold, from about 40-fold to about 100-fold, from about 50-fold to about 100-fold, from about 60-fold to about 100-fold, from about 70-fold to about 100-fold, from about 80-fold to about 100-fold, or from about 90-fold to about 100-fold.

The disclosed method can produce, for example, amplification of from about 1-fold to about 90-fold, from about 2-fold to about 90-fold, from about 3-fold to about 90-fold, from about 4-fold to about 90-fold, from about 5-fold to about 90-fold, from about 6-fold to about 90-fold, from about 7-fold to about 90-fold, from about 8-fold to about 90-fold, from about 9-fold to about 90-fold, from about 10-fold to about 90-fold, from about 11-fold to about 90-fold, from about 12-fold to about 90-fold, from about 14-fold to about 90-fold, from about 16-fold to about 90-fold, from about 20-fold to about 90-fold, from about 24-fold to about 90-fold, from about 30-fold to about 90-fold, from about 35-fold to about 90-fold, from about 40-fold to about 90-fold, from about 50-fold to about 90-fold, from about 60-fold to about 90-fold, from about 70-fold to about 90-fold, or from about 80-fold to about 90-fold.

The disclosed method can produce, for example, amplification of from about 1-fold to about 80-fold, from about 2-fold to about 80-fold, from about 3-fold to about 80-fold, from about 4-fold to about 80-fold, from about 5-fold to about 80-fold, from about 6-fold to about 80-fold, from about 7-fold to about 80-fold, from about 8-fold to about 80-fold, from about 9-fold to about 80-fold, from about 10-fold to about 80-fold, from about 11-fold to about 80-fold, from about 12-fold to about 80-fold, from about 14-fold to about 80-fold, from about 16-fold to about 80-fold, from about 20-fold to about 80-fold, from about 24-fold to about 80-fold, from about 30-fold to about 80-fold, from about 35-fold to about 80-fold, from about 40-fold to about 80-fold, from about 50-fold to about 80-fold, from about 60-fold to about 80-fold, or from about 70-fold to about 80-fold.

The disclosed method can produce, for example, amplification of from about 1-fold to about 70-fold, from about 2-fold to about 70-fold, from about 3-fold to about 70-fold, from about 4-fold to about 70-fold, from about 5-fold to about 70-fold, from about 6-fold to about 70-fold, from about 7-fold to about 70-fold, from about 8-fold to about 70-fold, from about 9-fold to about 70-fold, from about 10-fold to about 70-fold, from about 11-fold to about 70-fold, from about 12-fold to about 70-fold, from about 14-fold to about 70-fold, from about 16-fold to about 70-fold, from about 20-fold to about 70-fold, from about 24-fold to about 70-fold, from about 30-fold to about 70-fold, from about 35-fold to about 70-fold, from about 40-fold to about 70-fold, from about 50-fold to about 70-fold, or from about 60-fold to about 70-fold.

The disclosed method can produce, for example, amplification of from about 1-fold to about 60-fold, from about 2-fold to about 60-fold, from about 3-fold to about 60-fold, from about 4-fold to about 60-fold, from about 5-fold to about 60-fold, from about 6-fold to about 60-fold, from about 7-fold to about 60-fold, from about 8-fold to about 60-fold, from about 9-fold to about 60-fold, from about 10-fold to about 60-fold, from about 11-fold to about 60-fold, from about 12-fold to about 60-fold, from about 14-fold to about 60-fold, from about 16-fold to about 60-fold, from about 20-fold to about 60-fold, from about 24-fold to about 60-fold, from about 30-fold to about 60-fold, from about 35-fold to about 60-fold, from about 40-fold to about 60-fold, or from about 50-fold to about 60-fold.

The disclosed method can produce, for example, amplification of from about 1-fold to about 50-fold, from about 2-fold to about 50-fold, from about 3-fold to about 50-fold, from about 4-fold to about 50-fold, from about 5-fold to about 50-fold, from about 6-fold to about 50-fold, from about 7-fold to about 50-fold, from about 8-fold to about 50-fold, from about 9-fold to about 50-fold, from about 10-fold to about 50-fold, from about 11-fold to about 50-fold, from about 12-fold to about 50-fold, from about 14-fold to about 50-fold, from about 16-fold to about 50-fold, from about 20-fold to about 50-fold, from about 24-fold to about 50-fold, from about 30-fold to about 50-fold, from about 35-fold to about 50-fold, or from about 40-fold to about 50-fold.

The disclosed method can produce, for example, amplification of from about 1-fold to about 40-fold, from about 2-fold to about 40-fold, from about 3-fold to about 40-fold, from about 4-fold to about 40-fold, from about 5-fold to about 40-fold, from about 6-fold to about 40-fold, from about 7-fold to about 40-fold, from about 8-fold to about 40-fold, from about 9-fold to about 40-fold, from about 10-fold to about 40-fold, from about 11-fold to about 40-fold, from about 12-fold to about 40-fold, from about 14-fold to about 40-fold, from about 16-fold to about 40-fold, from about 20-fold to about 40-fold, from about 24-fold to about 40-fold, from about 30-fold to about 40-fold, or from about 35-fold to about 40-fold.

The disclosed method can produce, for example, amplification of from about 1-fold to about 30-fold, from about 2-fold to about 30-fold, from about 3-fold to about 30-fold, from about 4-fold to about 30-fold, from about 5-fold to about 30-fold, from about 6-fold to about 30-fold, from about 7-fold to about 30-fold, from about 8-fold to about 30-fold, from about 9-fold to about 30-fold, from about 10-fold to about 30-fold, from about 11-fold to about 30-fold, from about 12-fold to about 30-fold, from about 14-fold to about 30-fold, from about 16-fold to about 30-fold, from about 20-fold to about 30-fold, or from about 24-fold to about 30-fold.

The disclosed method can produce, for example, amplification of from about 1-fold to about 20-fold, from about 2-fold to about 20-fold, from about 3-fold to about 20-fold, from about 4-fold to about 20-fold, from about 5-fold to about 20-fold, from about 6-fold to about 20-fold, from about 7-fold to about 20-fold, from about 8-fold to about 20-fold, from about 9-fold to about 20-fold, from about 10-fold to about 20-fold, from about 11-fold to about 20-fold, from about 12-fold to about 20-fold, from about 14-fold to about 20-fold, or from about 16-fold to about 20-fold. The disclosed method can produce, for example, amplification of from about 1-fold to about 10-fold, from about 2-fold to about 10-fold, from about 3-fold to about 10-fold, from about 4-fold to about 10-fold, from about 5-fold to about 10-fold, from about 6-fold to about 10-fold, from about 7-fold to about 10-fold, from about 8-fold to about 10-fold, or from about 9-fold to about 10-fold.

The disclosed method can produce, for example, amplification of from about 1-fold to about 9-fold, from about 2-fold to about 9-fold, from about 3-fold to about 9-fold, from about 4-fold to about 9-fold, from about 5-fold to about 9-fold, from about 6-fold to about 9-fold, from about 7-fold to about 9-fold, or from about 8-fold to about 9-fold. The disclosed method can produce, for example, amplification of from about 1-fold to about 8-fold, from about 2-fold to about 8-fold, from about 3-fold to about 8-fold, from about 4-fold to about 8-fold, from about 5-fold to about 8-fold, from about 6-fold to about 8-fold, or from about 7-fold to about 8-fold. The disclosed method can produce, for example, amplification of from about 1-fold to about 7-fold, from about 2-fold to about 7-fold, from about 3-fold to about 7-fold, from about 4-fold to about 7-fold, from about 5-fold to about 7-fold, or from about 6-fold to about 7-fold. The disclosed method can produce, for example, amplification of from about 1-fold to about 6-fold, from about 2-fold to about 6-fold, from about 3-fold to about 6-fold, from about 4-fold to about 6-fold, or from about 5-fold to about 6-fold. The disclosed method can produce, for example, amplification of from about 1-fold to about 5-fold, from about 2-fold to about 5-fold, from about 3-fold to about 5-fold, from about 4-fold to about 5-fold, from about 1-fold to about 4-fold, from about 2-fold to about 4-fold, from about 3-fold to about 4-fold, from about 1-fold to about 3-fold, from about 2-fold to about 3-fold, or from about 1-fold to about 2-fold.

C. Primer Selection

Primers for use in the disclosed method can be selected for their ability to produce high quality amplification products. Such primers are particularly useful in the disclosed method. Where more than one primer is used in the disclosed method, all of the primers can be selected primers or some of the primers can be selected primers. Any useful criteria can be used for primer selection. Useful criteria include the quality of amplification products, such as the locus representation, the sequence representation and the amplification bias, and a lack of negative characteristics, such as a lack or minimization of production of amplification artifacts. Primers that meet given selection criteria (or a selection criterion) are referred to herein as selected primers (for those selection criteria). Primers that do not meet the given selection criteria (or selection criterion) are referred to herein as non-selected primers (for those selection criteria). Both selected and non-selected primers can be used together in the disclosed method, although use of selected primers is preferred.

Selected primers meeting different selection criteria can be used together in the disclosed method. That is, the primers used in a given amplification reaction need not all have the same capabilities or meet the same criteria. Similarly, non-selected primers failing to meet different selection criteria can be included or excluded from use in the disclosed method. That is, primers not used (or used) need not lack the same capabilities or fail to meet the same criteria. Selected primers meeting a selection criterion, selection criteria, or a combination of different selection criteria, can be used with non-selected primers failing to meet the same or a different selection criterion, selection criteria, or a combination of the same or different selection criteria.

The disclosed method thus can be performed with one or more selected primers. The disclosed method can also be performed with one or more selected primers and one or more non-selected primers. Whether a primer is a selected primer or a non-selected primer can be determined by testing the primer for the selection criterion or criteria. Thus, for example, the primer can be tested in a form of the disclosed method. Such a method could use a nucleic acid sample of interest, such as a nucleic acid sample having relevant characteristics. A nucleic acid sample used for this purpose is referred to herein as a selection nucleic acid sample. Particularly useful selection nucleic acid samples are nucleic acid samples of the same type that the selected primers will be used to amplify. Thus, a human genomic nucleic acid sample can be used as the selection sample for selecting primers to be used to amplify human genomic DNA. Also useful as selection nucleic acid samples are nucleic acid samples that can be used as standards for selecting primers to be used to amplify a variety of different types of nucleic acid samples. For example, a yeast genomic nucleic acid sample can be used as a selection nucleic acid sample for selecting primers in general. Such a selection nucleic acid sample can set a benchmark for selection criteria. The sequence complexity of the selection nucleic acid sample can be important as, or an important factor in establishing, a selection criterion or selection criteria. Thus, for example, a certain quality of amplification product form a nucleic acid sample of a given sequence complexity can be required. The selection nucleic acid sample can have any level of sequence complexity. For example, the selection nucleic acid sample can have any of the sequence complexity levels described elsewhere herein. In general, the higher the sequence complexity of the selection nucleic acid sample, the lower the quality that can be required or allowed for the selection criteria.

For selection of primers, for example, the primer can be brought into contact with a DNA polymerase and a selection nucleic acid sample and incubated under conditions that promote replication of nucleic acid molecules in the selection nucleic acid sample. The results can then be compared to the selection criterion or criteria.

A primer can be selected based on producing a certain level or range of replication of nucleic acid sequences in a selection nucleic acid sample. Any replication level can be used. For example, any of the replication levels described elsewhere herein can be used as the selection criterion. A selected primer can produce, for example, replication of at least 0.01% of the nucleic acid sequences in the nucleic acid sample, at least 0.1% of the nucleic acid sequences in the nucleic acid sample, at least 1% of the nucleic acid sequences in the nucleic acid sample, at least 5% of the nucleic acid sequences in the nucleic acid sample, at least 10% of the nucleic acid sequences in the nucleic acid sample, at least 20% of the nucleic acid sequences in the nucleic acid sample, at least 30% of the nucleic acid sequences in the nucleic acid sample, at least 40% of the nucleic acid sequences in the nucleic acid sample, at least 50% of the nucleic acid sequences in the nucleic acid sample, at least 60% of the nucleic acid sequences in the nucleic acid sample, at least 70% of the nucleic acid sequences in the nucleic acid sample, at least 80% of the nucleic acid sequences in the nucleic acid sample, at least 90% of the nucleic acid sequences in the nucleic acid sample, at least 95% of the nucleic acid sequences in the nucleic acid sample, at least 96% of the nucleic acid sequences in the nucleic acid sample, at least 97% of the nucleic acid sequences in the nucleic acid sample, at least 98% of the nucleic acid sequences in the nucleic acid sample, or at least 99% of the nucleic acid sequences in the nucleic acid sample.

A primer can be selected based on producing a certain level or range of amplification of nucleic acid sequences in a selection nucleic acid sample. Any amplification level can be used. For example, any of the amplification levels described elsewhere herein can be used as the selection criterion. A selected primer can produce, for example, amplification of about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, about 300-fold, about 400-fold, about 500-fold, about 600-fold, about 700-fold, about 800-fold, about 900-fold, about 1,000-fold, about 10,000-fold, about 100,000-fold, about 1,000,000-fold, about 10,000,000-fold, or about 100,000,000-fold. Fold amplification refers to the number of copies generated of the template being amplified. For example, if 1 ug of DNA is generated from 1 ng of template, the level of amplification is 1,000-fold.

A selected primer can produce, for example, amplification of at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 14-fold, at least 16-fold, at least 20-fold, at least 24-fold, at least 30-fold, at least 35-fold, at least 40-fold, at least 50-fold, at least 60-fold, at least 70-fold, at least 80-fold, at least 90-fold, at least 100-fold, at least 150-fold, at least 200-fold, at least 250-fold, at least 300-fold, at least 400-fold, at least 500-fold, at least 600-fold, at least 700-fold, at least 800-fold, at least 900-fold, at least 1,000-fold, at least 10,000-fold, at least 100,000-fold, at least 1,000,000-fold, at least 10,000,000-fold, or at least 100,000,000-fold.

A selected primer can produce, for example, amplification bias of at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 14-fold, at least about 16-fold, at least about 20-fold, at least about 24-fold, at least about 30-fold, at least about 35-fold, at least about 40-fold, at least about 50-fold, at least about 60-fold, at least about 70-fold, at least about 80-fold, at least about 90-fold, at least about 100-fold, at least about 150-fold, at least about 200-fold, at least about 250-fold, at least about 300-fold, at least about 400-fold, at least about 500-fold, at least about 600-fold, at least about 700-fold, at least about 800-fold, at least about 900-fold, at least about 1,000-fold, at least about 10,000-fold, at least about 100,000-fold, at least about 1,000,000-fold, at least about 10,000,000-fold, or at least about 100,000,000-fold.

A primer can be selected based on producing a certain level or range of amplification bias. Any amplification bias can be used. For example, any of the amplification biases described elsewhere herein can be used as the selection criterion. A selected primer can produce, for example, an amplification bias of 1-fold, 2-fold, 3-fold, 4-fold, 5-fold, 6-fold, 7-fold, 8-fold, 9-fold, 10-fold, 11-fold, 12-fold, 14-fold, 16-fold, 20-fold, 24-fold, 30-fold, 35-fold, 40-fold, 50-fold, 60-fold, 70-fold, 80-fold, 90-fold, 100-fold, 150-fold, 200-fold, 250-fold, or 300-fold. A selected primer can produce, for example, an amplification bias of about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, or about 300-fold. A selected primer can produce, for example, an amplification bias of less than 2-fold, less than 3-fold, less than 4-fold, less than 5-fold, less than 6-fold, less than 7-fold, less than 8-fold, less than 9-fold, less than 10-fold, less than 11-fold, less than 12-fold, less than 14-fold, less than 16-fold, less than 20-fold, less than 24-fold, less than 30-fold, less than 35-fold, less than 40-fold, less than 50-fold, less than 60-fold, less than 70-fold, less than 80-fold, less than 90-fold, less than 100-fold, less than 150-fold, less than 200-fold, less than 250-fold, or less than 300-fold.

A selected primer can produce, for example, an amplification bias of less than about 2-fold, less than about 3-fold, less than about 4-fold, less than about 5-fold, less than about 6-fold, less than about 7-fold, less than about 8-fold, less than about 9-fold, less than about 10-fold, less than about 11-fold, less than about 12-fold, less than about 14-fold, less than about 16-fold, less than about 20-fold, less than about 24-fold, less than about 30-fold, less than about 35-fold, less than about 40-fold, less than about 50-fold, less than about 60-fold, less than about 70-fold, less than about 80-fold, less than about 90-fold, less than about 100-fold, less than about 150-fold, less than about 200-fold, less than about 250-fold, or less than about 300-fold. These amplification biases can be, for example, for any number of loci or target sequences, such as, for example, a number of loci and/or target sequences described elsewhere herein.

A primer can be selected based on producing a certain level or range of sequence representation. Any sequence representation can be used. For example, any of the sequence representations described elsewhere herein can be used as the selection criterion. A selected primer can produce, for example, a sequence representation of at least 10%, at least 20%, at least 30%, at least 40%, at least 50%, at least 60%, at least 70%, at least 80%, at least 90%, or at least 100%. A selected primer can produce, for example, a sequence representation of less than 500%, less than 400%, less than 300%, less than 250%, less than 200%, less than 190%, less than 180%, less than 170%, less than 160%, less than 150%, less than 140%, less than 130%, less than 120%, or less than 110%. These sequence representations can be, for example, for any number of target sequences, such as, for example, a number of target sequences described elsewhere herein.

A primer can be selected based on producing a certain level or range of locus representation. Any locus representation can be used. For example, any of the locus representations described elsewhere herein can be used as the selection criterion. A selected primer can produce, for example, a locus representation of at least 10%, at least 20%, at least 30%, at least 40%, at least 50%, at least 60%, at least 70%, at least 80%, at least 90%, or at least 100%. A selected primer can produce, for example, a locus representation of less than 500%, less than 400%, less than 300%, less than 250%, less than 200%, less than 190%, less than 180%, less than 170%, less than 160%, less than 150%, less than 140%, less than 130%, less than 120%, or less than 110%. These locus representations can be, for example, for any number of loci, such as, for example, a number of loci described elsewhere herein.

Primers can also be selected as groups of primers. That is, whether the group of primers, when used together, exhibit the selection criterion or criteria can be tested. This can be accomplished in all the ways described herein for selection of single primers. Thus, for example, the group of primers can be brought into contact with a DNA polymerase and a selection nucleic acid sample and incubated under conditions that promote replication of nucleic acid molecules in the selection nucleic acid sample.

Non-selected primers can be identified in the same way using similar criteria as selected primers are identified. The difference is that the non-selected primers fail to meet a selection criterion or selection criteria. It is understood however, that such failure to meet a criterion or criteria can be expressed as having a certain characteristic or feature, just as in the case of selected primers. Such criteria can be referred to as non-selection criteria.

A non-selected primer can be identified based on producing or failing to produce a certain level or range of replication of nucleic acid sequences in a selection nucleic acid sample. Any replication level can be used as the standard. For example, any of the replication levels described elsewhere herein can be used as the non-selection criterion. A non-selected primer can produce, for example, replication of less than 0.01% of the nucleic acid sequences in the nucleic acid sample, less than 0.1% of the nucleic acid sequences in the nucleic acid sample, less than 1% of the nucleic acid sequences in the nucleic acid sample, less than 5% of the nucleic acid sequences in the nucleic acid sample, less than 10% of the nucleic acid sequences in the nucleic acid sample, less than 20% of the nucleic acid sequences in the nucleic acid sample, less than 30% of the nucleic acid sequences in the nucleic acid sample, less than 40% of the nucleic acid sequences in the nucleic acid sample, less than 50% of the nucleic acid sequences in the nucleic acid sample, less than 60% of the nucleic acid sequences in the nucleic acid sample, less than 70% of the nucleic acid sequences in the nucleic acid sample, less than 80% of the nucleic acid sequences in the nucleic acid sample, less than 90% of the nucleic acid sequences in the nucleic acid sample, less than 95% of the nucleic acid sequences in the nucleic acid sample, less than 96% of the nucleic acid sequences in the nucleic acid sample, less than 97% of the nucleic acid sequences in the nucleic acid sample, less than 98% of the nucleic acid sequences in the nucleic acid sample, or less than 99% of the nucleic acid sequences in the nucleic acid sample.

A non-selected primer can be identified based on producing or failing to produce a certain level or range of amplification bias. Any amplification bias can be used as the standard. For example, any of the amplification biases described elsewhere herein can be used as the non-selection criterion. A non-selected primer can produce, for example, an amplification bias of 1-fold, 2-fold, 3-fold, 4-fold, 5-fold, 6-fold, 7-fold, 8-fold, 9-fold, 10-fold, 11-fold, 12-fold, 14-fold, 16-fold, 20-fold, 24-fold, 30-fold, 35-fold, 40-fold, 50-fold, 60-fold, 70-fold, 80-fold, 90-fold, 100-fold, 150-fold, 200-fold, 250-fold, or 300-fold. A non-selected primer can produce, for example, an amplification bias of about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, or about 300-fold. A non-selected primer can produce, for example, an amplification bias of more than 2-fold, more than 3-fold, more than 4-fold, more than 5-fold, more than 6-fold, more than 7-fold, more than 8-fold, more than 9-fold, more than 10-fold, more than 11-fold, more than 12-fold, more than 14-fold, more than 16-fold, more than 20-fold, more than 24-fold, more than 30-fold, more than 35-fold, more than 40-fold, more than 50-fold, more than 60-fold, more than 70-fold, more than 80-fold, more than 90-fold, more than 100-fold, more than 150-fold, more than 200-fold, more than 250-fold, or more than 300-fold.

A selected primer can produce, for example, an amplification bias of more than about 2-fold, more than about 3-fold, more than about 4-fold, more than about 5-fold, more than about 6-fold, more than about 7-fold, more than about 8-fold, more than about 9-fold, more than about 10-fold, more than about 11-fold, more than about 12-fold, more than about 14-fold, more than about 16-fold, more than about 20-fold, more than about 24-fold, more than about 30-fold, more than about 35-fold, more than about 40-fold, more than about 50-fold, more than about 60-fold, more than about 70-fold, more than about 80-fold, more than about 90-fold, more than about 100-fold, more than about 150-fold, more than about 200-fold, more than about 250-fold, or more than about 300-fold. These amplification biases can be, for example, for any number of loci or target sequences, such as, for example, a number of loci and/or target sequences described elsewhere herein.

A non-selected primer can be identified based on producing a certain level or range of sequence representation. Any sequence representation can be used as the standard. For example, any of the sequence representations described elsewhere herein can be used as the non-selection criterion. A non-selected primer can produce, for example, a sequence representation of less than 0.1%, less than 1%, less than 10%, less than 20%, less than 30%, less than 40%, less than 50%, less than 60%, less than 70%, less than 80%, less than 90%, or less than 100%. A selected primer can produce, for example, a sequence representation of more than 500%, more than 400%, more than 300%, more than 250%, more than 200%, more than 190%, more than 180%, more than 170%, more than 160%, more than 150%, more than 140%, more than 130%, more than 120%, or more than 110%. These sequence representations can be, for example, for any number of target sequences, such as, for example, a number of target sequences described elsewhere herein.

A non-selected primer can be identified based on producing a certain level or range of locus representation. Any locus representation can be used as the standard. For example, any of the locus representations described elsewhere herein can be used as the non-selection criterion. A non-selected primer can produce, for example, a locus representation of less than 0.1%, less than 1%, less than 10%, less than 20%, less than 30%, less than 40%, less than 50%, less than 60%, less than 70%, less than 80%, less than 90%, or less than 100%. A selected primer can produce, for example, a locus representation of more than 500%, more than 400%, more than 300%, more than 250%, more than 200%, more than 190%, more than 180%, more than 170%, more than 160%, more than 150%, more than 140%, more than 130%, more than 120%, or more than 110%. These locus representations can be, for example, for any number of loci, such as, for example, a number of loci described elsewhere herein.

For establishing potential for artifact production by a primer or group of primers, the primer or group of primers can be tested in a modified form of the disclosed method where no nucleic acid sample is used. If, when, and at what level amplification products are observed in such an assay is a measure of the potential of the primer or group of primers to produce amplification artifacts. One criterion for low potential for artifact production is a long delay before amplification products are first observed in a reaction performed in the absence of a nucleic acid sample (or other template nucleic acids). Delays can be, for example, to 125%, 150%, 175%, 200%, 225%, 250%, 275%, 300%, 325%, 350%, 375%, 400%, 425%, 450%, 475%, or 500% of the time where amplification products are first observed in a reaction having a nucleic acid sample. Delays can be, for example, to greater than 125%, greater than 150%, greater than 175%, greater than 200%, greater than 225%, greater than 250%, greater than 275%, greater than 300%, greater than 325%, greater than 350%, greater than 375%, greater than 400%, greater than 425%, greater than 450%, greater than 475%, or greater than 500% of the time where amplification products are first observed in a reaction having a nucleic acid sample.

D. Whole Genome Strand Displacement Amplification

In one form of the method, referred to as whole genome strand displacement amplification (WGSDA), one, a few, or more primers can be used to prime a sample of genomic nucleic acid (or another sample of nucleic acid of high complexity). It was discovered that one or a few primers can be used because the primers will be collectively complementary to nucleic acid sequences distributed throughout nucleic acid in the sample at sufficiently short intervals to allow effective strand displacement amplification. Amplification proceeds by replication with a processive polymerase initiated at each primer and continuing until spontaneous termination. A key feature of this method is the displacement of intervening primers and primer extension products during replication by the polymerase. In this way, multiple overlapping copies of the entire genome can be synthesized in a short time.

Whole genome strand displacement amplification can be performed by, for example, (a) mixing one or a few primers with a genomic nucleic acid sample (or other nucleic acid sample of high complexity), to produce a primer-nucleic acid sample mixture, and incubating the primer-nucleic acid sample mixture under conditions that promote hybridization between the primers and the genomic nucleic acids in the primer-nucleic acid sample mixture, and (b) mixing DNA polymerase with the primer-nucleic acid sample mixture, to produce a polymerase-nucleic acid sample mixture, and incubating the polymerase-nucleic acid sample mixture under conditions that promote replication of the genomic nucleic acids. Strand displacement replication is preferably accomplished by using a strand displacing DNA polymerase or a DNA polymerase in combination with a compatible strand displacement factor.

The method has advantages over the polymerase chain reaction since it can be carried out under isothermal conditions. Other advantages of whole genome strand displacement amplification include a higher level of amplification than whole genome PCR, amplification is less sequence-dependent than PCR, a lack of re-annealing artifacts or gene shuffling artifacts as can occur with PCR (since there are no cycles of denaturation and re-annealing), and a lower amplification bias than PCR-based genome amplification (bias of, for example, 3-fold for WGSDA versus 20- to 60-fold for PCR-based genome amplification).

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction.

It is preferred that the number of primers used for WGSDA allow the primers to hybridize at desired intervals within the nucleic acid sample. For example, by using a number of primers that allows them to hybridize, on average, every 4000 to 8000 bases, DNA replication initiated at these sites will extend to and displace strands being replicated from adjacent sites. It should be noted that the primers are not expected to hybridize to nucleic acid molecules in the nucleic acid sample at regular intervals. Rather, the average interval will be a general function of the number of primers (as described elsewhere herein).

Displacement of an adjacent strand makes it available for hybridization to another primer and subsequent initiation of another round of replication. The interval at which the primers hybridize to the nucleic acid molecules generally determines the level of amplification. For example, if the average interval is short, adjacent strands will be displaced quickly and frequently. If the average interval is long, adjacent strands will be displaced only after long runs of replication.

In the disclosed method, the DNA polymerase catalyzes primer extension and strand displacement in a processive strand displacement polymerization reaction that proceeds as long as desired. Preferred strand displacing DNA polymerases are bacteriophage φ29 DNA polymerase (U.S. Pat. Nos. 5,198,543 and 5,001,050 to Blanco et al.), large fragment Bst DNA polymerase (Exo(-) Bst), exo(-)Bca DNA polymerase, and Sequenase. During strand displacement replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al., *Proc. Natl. Acad. Sci. USA* 78:6633 (1981)).

Genome amplification using PCR, and uses for the amplified DNA, is described in Zhang et al., *Proc. Natl. Acad. Sci. USA* 89:5847-5851 (1992), Telenius et al., *Genomics* 13:718-725 (1992), Cheung et al., *Proc. Natl. Acad. Sci. USA* 93:14676-14679 (1996), and Kukasjaarvi et al., *Genes, Chromosomes and Cancer* 18:94-101 (1997). The uses of the amplified DNA described in these publications are also generally applicable to DNA amplified using the disclosed methods. Whole Genome Strand Displacement Amplification, unlike PCR-based whole genome amplification, is suitable for haplotype analysis since WGSDA yields longer fragments than PCR-based whole genome amplification. PCR-based whole genome amplification is also less suitable for haplotype analysis since each cycle in PCR creates an opportunity for priming events that result in the association of distant sequences (in the genome) to be put together in the same fragment.

Long nucleic acid segments can be amplified in the disclosed method since there is no cycling which could interrupt continuous synthesis or allow the formation of artifacts due to rehybridization of replicated strands.

E. Nucleic Acid Sample Preparation and Treatment

Nucleic acids for amplification are often obtained from cellular samples. This generally requires disruption of the cell (to make the nucleic acid accessible) and purification of the nucleic acids prior to amplification. It also generally requires the inactivation of protein factors such as nucleases that could degrade the DNA, or of factors such as histones that could bind to DNA strands and impede their use as a template for DNA synthesis by a polymerase. There are a variety of techniques used to break open cells, such as sonication, enzymatic digestion of cell walls, heating, and exposure to lytic conditions. Lytic conditions typically involve use of non-physiological pH and/or solvents. Many lytic techniques can result in damage to nucleic acids in cells, including, for example, breakage of genomic DNA. In particular, use of heating to lyse cells can damage genomic DNA and reduce the amount and quality of amplification products of genomic DNA. It has been discovered that alkaline lysis can cause less damage to genomic DNA and can thus result in higher quality amplification results. Alkaline lysis also inactivates protein factors such as nucleases, histones, or other factors that could impede the amplification of DNA within the sample. In addition, it is a useful property of alkaline lysis that reducing the pH does not reactivate the protein factors, but that such protein factors remain inactivated when the pH of the solution is brought back within a neutral range.

In some forms of the disclosed method, a genomic sample is prepared by exposing cells to alkaline conditions, thereby lysing the cells and resulting in a cell lysate; reducing the pH of the cell lysate to make the pH of the cell lysate compatible with DNA replication; and incubating the cell lysate under conditions that promote replication of the genome of the cells by multiple displacement amplification. Alkaline conditions are conditions where the pH is greater than 9.0. Particularly useful alkaline conditions for the disclosed method are conditions where the pH is greater than 10.0. The alkaline conditions can be, for example, those that cause a substantial number of cells to lyse, those that cause a significant number of cells to lyse, or those that cause a sufficient number of cells to lyse. The number of lysed cells can be considered sufficient if the genome can be sufficiently amplified in the disclosed method. The amplification is sufficient if enough amplification product is produced to permit some use of the amplification product, such as detection of sequences or other analysis. The reduction in pH is generally into the neutral range of pH 9.0 to pH 6.0.

The cells can be exposed to alkaline conditions by mixing the cells with a lysis solution. The amount of lysis solution mixed with the cells can be that amount that causes a substantial number of cells to lyse or those that cause a sufficient number of cells to lyse. Generally, this volume will be a function of the pH of the cell/lysis solution mixture. Thus, the amount of lysis solution to mix with cells can be determined generally from the volume of the cells and the alkaline concentration of the lysis buffer. For example, a smaller volume of a lysis solution with a stronger base and/or higher concentration of base would be needed to create sufficient alkaline conditions than the volume needed of a lysis solution with a weaker base and/or lower concentration of base. The lysis solution can be formulated such that the cells are mixed with an equal volume of the lysis solution (to produce the desired alkaline conditions).

In some embodiments, the lysis solution can comprise a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of lysis solution include lysis solution comprising 400 mM KOH, lysis solution comprising 400 mM KOH, 100 mM dithiothreitol, and 10 mM EDTA, and lysis solution consisting of 400 mM KOH, 100 mM dithiothreitol, and 10 mM EDTA.

In some embodiments, the lysis solution can comprise a plurality of basic agents. As used herein, a basic agent is a compound, composition or solution that results in alkaline conditions. In some embodiments, the lysis solution can comprise a buffer. Useful buffers include phosphate buffers, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The lysis solution can comprise a plurality of buffering agents. As used herein, a buffering agent is a compound, composition or solution that acts as a buffer. An alkaline buffering agent is a buffering agent that results in alkaline conditions. In some embodiments, the lysis solution can comprise a combination of one or more bases, basic agents, buffers and buffering agents.

The pH of the cell lysate can be reduced to form a stabilized cell lysate. A stabilized cell lysate is a cell lysate the pH of which is in the neutral range (from about pH 6.0 to about pH 9.0). Useful stabilized cell lysates have a pH that allows replication of nucleic acids in the cell lysate. For example, the pH of the stabilized cell lysate is usefully at a pH at which the DNA polymerase can function. The pH of the cell lysate can be reduced by mixing the cell lysate with a stabilization solution. The stabilization solution comprises a solution that can reduce the pH of a cell lysate exposed to alkaline conditions as described elsewhere herein.

The amount of stabilization solution mixed with the cell lysate can be that amount that causes a reduction in pH to the neutral range (or other desired pH value). Generally, this volume will be a function of the pH of the cell lysate/ stabilization solution mixture. Thus, the amount of stabilization solution to mix with the cell lysate can be determined generally from the volume of the cell lysate, its pH and buffering capacity, and the acidic concentration of the stabilization buffer. For example, a smaller volume of a stabilization solution with a stronger acid and/or higher concentration of acid would be needed to reduce the pH sufficiently than the volume needed of a stabilization solution with a weaker acid and/or lower concentration of acid. The stabilization solution can be formulated such that the cell lysate is mixed with an equal volume of the stabilization solution (to produce the desired pH).

In some embodiments, the stabilization solution can comprise an acid. Useful acids include hydrochloric acid, sulfuric acid, phosphoric acid, acetic acid, acetylsalicylic acid, ascorbic acid, carbonic acid, citric acid, formic acid, nitric acid, perchloric acid, HF, HBr, HI, $H_2S$, HCN, HSCN, HClO, monochloroacetic acid, dichloroacetic acid, trichloroacetic acid, and any carboxylic acid (ethanoic, propanoic, butanoic, etc., including both linear or branched chain carboxylic acids). In some embodiments, the stabilization solution can comprise a buffer. Useful buffers include Tris-HCl, HEPES, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. Useful formulations of stabilization solutions include stabilization solution comprising 800 mM Tris-HCl; stabilization solution comprising 800 mM Tris-HCl at pH 4.1; and stabilization solution consisting of 800 mM Tris-HCl, pH 4.1.

In some embodiments, the stabilization solution can comprise a plurality of acidic agents. As used herein, an acidic agent is a compound, composition or solution that forms an acid in solution. In some embodiments, the stabilization solution can comprise a plurality of buffering agents. An acidic buffering agent is a buffering agent that forms an acid in solution. In some embodiments, the stabilization solution can comprise a combination of one or more acids, acidic agents, buffers and buffering agents.

In some embodiments, the pH of the cell lysate can be reduced to about pH 9.0 or below, to about pH 8.5 or below, to about pH 8.0 or below, to about pH 7.5 or below, to about pH 7.2 or below, or to about pH 7.0 or below. In some embodiments, the pH of the cell lysate can be reduced to the range of about pH 9.0 to about pH 6.0, to the range of about pH 9.0 to about pH 6.5, to the range of about pH 9.0 to about pH 6.8, to the range of about pH 9.0 to about pH 7.0, to the range of about pH 9.0 to about pH 7.2, to the range of about pH 9.0 to about pH 7.5, to the range of about pH 9.0 to about pH 8.0, to the range of about pH 9.0 to about pH 8.5, to the range of about pH 8.5 to about pH 6.0, to the range of about pH 8.5 to about pH 6.5, to the range of about pH 8.5 to about pH 6.8, to the range of about pH 8.5 to about pH 7.0, to the range of about pH 8.5 to about pH 7.2, to the range of about pH 8.5 to about pH 7.5, to the range of about pH 8.5 to about pH 8.0, to the range of about pH 8.0 to about pH 6.0, to the range of about pH 8.0 to about pH 6.5, to the range of about pH 8.0 to about pH 6.8, to the range of about pH 8.0 to about pH 7.0, to the range of about pH 8.0 to about pH 7.2, to the range of about pH 8.0 to about pH 7.5, to the range of about pH 7.5 to about pH 6.0, to the range of about pH 7.5 to about pH 6.5, to the range of about pH 7.5 to about pH 6.8, to the range of about pH 7.5 to about pH 7.0, to the range of about pH 7.5 to about pH 7.2, to the range of about pH 7.2 to about pH 6.0, to the range of about pH 7.2 to about pH 6.5, to the range of about pH 7.2 to about pH 6.8, to the range of about pH 7.2 to about pH 7.0, to the range of about pH 7.0 to about pH 6.0, to the range of about pH 7.0 to about pH 6.5, to the range of about pH 7.0 to about pH 6.8, to the range of about pH 6.8 to about pH 6.0, to the range of about pH 6.8 to about pH 6.5, or to the range of about pH 6.5 to about pH 6.0. In some embodiments, the pH of the cell lysate can be reduced to any range having any combination of endpoints from about pH 6.0 to about pH 9.0 All such endpoints and ranges are specifically and separately contemplated.

In some embodiments, the cells are not lysed by heat. Those of skill in the art will understand that different cells under different conditions will be lysed at different temperatures and so can determine temperatures and times at which the cells will not be lysed by heat. In general, the cells are not subjected to heating above a temperature and for a time that would cause substantial cell lysis in the absence of the alkaline conditions used. As used herein, substantial cell lysis refers to lysis of 90% or greater of the cells exposed to the alkaline conditions. Significant cell lysis refers to lysis of 50% or more of the cells exposed to the alkaline conditions. Sufficient cell lysis refers to lysis of enough of the cells exposed to the alkaline conditions to allow synthesis of a detectable amount of amplification products by multiple strand displacement amplification. In general, the alkaline conditions used in the disclosed method need only cause sufficient cell lysis. It should be understood that alkaline conditions that could cause significant or substantial cell lysis need not result in significant or substantial cell lysis when the method is performed.

In some embodiments, the cells are not subjected to heating substantially or significantly above the temperature at which the cells grow. As used herein, the temperature at which the cells grow refers to the standard temperature, or highest of different standard temperatures, at which cells of the type involved are cultured. In the case of animal cells, the temperature at which the cells grow refers to the body temperature of the animal. In other embodiments, the cells are not subjected to heating substantially or significantly above the temperature of the amplification reaction (where the genome is replicated).

In some embodiments, the cell lysate is not subjected to purification prior to the amplification reaction. In the context of the disclosed method, purification generally refers to the separation of nucleic acids from other material in the cell lysate. It has been discovered that multiple displacement amplification can be performed on unpurified and partially purified samples. It is commonly thought that amplification reactions cannot be efficiently performed using unpurified nucleic acid. In particular, PCR is very sensitive to contaminants.

Forms of purification include centrifugation, extraction, chromatography, precipitation, filtration, and dialysis. Partially purified cell lysate includes cell lysates subjected to centrifugation, extraction, chromatography, precipitation, filtration, and dialysis. Partially purified cell lysate generally does not include cell lysates subjected to nucleic acid precipitation or dialysis. As used herein, separation of nucleic acid from other material refers to physical separation such that the nucleic acid to be amplified is in a different container or container from the material. Purification does not require separation of all nucleic acid from all other materials. Rather, what is required is separation of some nucleic acid from some other material. As used herein in the context of nucleic acids to be amplified, purification refers to separation of nucleic acid from other material. In the context of cell lysates, purification refers to separation of nucleic acid from other material in the cell lysate. As used herein, partial purification refers to separation of nucleic acid from some, but not all, of other material with which the nucleic acid is mixed. In the context of cell lysates, partial purification refers to separation of nucleic acid from some, but not all, of the other material in the cell lysate.

Unless the context clearly indicates otherwise, reference herein to a lack of purification, lack of one or more types of purification or separation operations or techniques, or exclusion of purification or one or more types of purification or separation operations or techniques does not encompass the exposure of cells to alkaline conditions (or the results thereof) the reduction of pH of a cell lysate (or the results thereof). That is, to the extent that the alkaline conditions and pH reduction of the disclosed method produce an effect that could be considered "purification" or "separation," such effects are excluded from the definition of purification and separation when those terms are used in the context of processing and manipulation of cell lysates and stabilized cell lysates (unless the context clearly indicates otherwise).

As used herein, substantial purification refers to separation of nucleic acid from at least a substantial portion of other material with which the nucleic acid is mixed. In the context of cell lysates, substantial purification refers to separation of nucleic acid from at least a substantial portion of the other material in the cell lysate. A substantial portion refers to 90% of the other material involved. Specific levels of purification can be referred to as a percent purification (such as 95% purification and 70% purification). A percent purification refers to purification that results in separation from nucleic acid of at least the designated percent of other material with which the nucleic acid is mixed.

Denaturation of nucleic acid molecules to be amplified is common in amplification techniques. This is especially true when amplifying genomic DNA. In particular, PCR uses multiple denaturation cycles. Denaturation is generally used to make nucleic acid strands accessible to primers. Nucleic acid molecules, genomic DNA, for example, need not be denatured for efficient multiple displacement amplification. Elimination of a denaturation step and denaturation conditions has additional advantages such as reducing sequence bias in the amplified products (that is, reducing the amplification bias). In preferred forms of the disclosed method, the nucleic acid sample or template nucleic acid is not subjected to denaturating conditions and/or no denaturation step is used.

In some forms of the disclosed method, the nucleic acid sample or template nucleic acid is not subjected to heat denaturating conditions and/or no heat denaturation step is used. In some forms of the disclosed method, the nucleic acid sample or template nucleic acid is not subjected to alkaline denaturating conditions and/or no alkaline denaturation step is used. It should be understood that while sample preparation (for example, cell lysis and processing of cell extracts) may involve conditions that might be considered denaturing (for example, treatment with alkali), the denaturation conditions or step eliminated in some forms of the disclosed method refers to denaturation steps or conditions intended and used to make nucleic acid strands accessible to primers. Such denaturation is commonly a heat denaturation, but can also be other forms of denaturation such as chemical denaturation. It should be understood that in the disclosed method where the nucleic acid sample or template nucleic acid is not subjected to denaturing conditions, the template strands are accessible to the primers (since amplification occurs). However, the template stands are not made accessible via general denaturation of the sample or template nucleic acids.

Alternatively, the nucleic acid sample or template nucleic acid can be subjected to denaturating conditions and/or a denaturation step can be used. In some forms of the disclosed method, the nucleic acid sample or template nucleic acid can be subjected to heat denaturating conditions and/or a heat denaturation step can be used. In some forms of the disclosed method, the nucleic acid sample or template nucleic acid can be subjected to alkaline denaturating conditions and/or an alkaline denaturation step can be used.

The efficiency of a DNA amplification procedure may be described for individual loci as the percent representation of that locus (that is, the locus representation), where the locus representation is 100% for a locus in genomic DNA as purified from cells. For 10,000-fold amplification, the average representation frequency was 141% for 8 loci in DNA amplified without heat denaturation of the template, and 37% for the 8 loci in DNA amplified with heat denaturation of the template. The omission of a heat denaturation step results in a 3.8-fold increase in the representation frequency for amplified loci. Amplification bias may be calculated between two samples of amplified DNA or between a sample of amplified DNA and the template DNA it was amplified from. The bias is the ratio between the values for percent representation for a particular locus (locus representation). The maximum bias is the ratio of the most highly represented locus to the least represented locus. For 10,000-fold amplification, the maximum amplification bias was 2.8 for DNA amplified without heat denaturation of the template, and 50.7 for DNA amplified with heat denaturation of the template. The omission of a heat denaturation step results in an 18-fold decrease in the maximum bias for amplified loci.

In one form of the disclosed method, a small amount of purified double-strand human genomic DNA (1 ng, for example) can be mixed with one or a few exonuclease-resistant primers 6 nucleotides long and 429 DNA polymerase under conditions that favor DNA synthesis. For example, the mixture can simply be incubated at 30° C. and multiple displacement amplification will take place. Thus, any single-stranded or duplex DNA may be used, without any additional treatment, making the disclosed method a simple, one-step procedure. Since so little DNA template is required, a major advantage of the disclosed method is that DNA template may be taken from preparations that contain levels of contaminants that would inhibit other DNA amplification procedures such as PCR. For MDA the sample may be diluted so that the contaminants fall below the concentration at which they would interfere with the reaction. The disclosed method can be performed (and the above advantages achieved) using any type of sample, including, for example, bodily fluids such as urine, semen, lymphatic fluid, cerebrospinal fluid, and amniotic fluid.

The need for only small amounts of DNA template in the disclosed method means that the method is useful for DNA amplification from very small samples. In particular, the disclosed method may be used to amplify DNA from a single cell. The ability to obtain analyzable amounts of nucleic acid from a single cell (or similarly small sample) has many applications in preparative, analytical, and diagnostic procedures such as prenatal diagnostics. Other examples of biological samples containing only small amounts of DNA for which amplification by the disclosed method would be useful are material excised from tumors or other archived medical samples, needle aspiration biopsies, clinical samples arising from infections, such as nosocomial infections, forensic samples, or museum specimens of extinct species.

More broadly, the disclosed method is useful for applications in which the amounts of DNA needed are greater than the supply. For example, procedures that analyze DNA by chip hybridization techniques are limited by the amounts of DNA that can be purified from typically sized blood samples. As a result many chip hybridization procedures utilize PCR to generate a sufficient supply of material for the high-throughput procedures. The disclosed method presents a useful technique for the generation of plentiful amounts of amplified DNA that faithfully reproduces the locus representation frequencies of the starting material.

The disclosed method can produce a DNA amplification product with improved performance in genetic assays compared to amplification performed with heat treatment of the template DNA. The longer DNA products produced without heat treatment of the template yield larger DNA fragments in Southern blotting and genetic analysis using RFLP. The disclosed method produces for a DNA amplification product with no loss of locus representation when used as a substrate in quantitative PCR assays compared to DNA amplified with heat treatment of the template. The disclosed method produces a DNA amplification product with a low amplification bias, with the variation in representation among eight different loci varying by less than 3.0. In contrast, the amplification bias of DNA products amplified by two PCR-based amplification methods, PEP and DOP-PCR, varies between two and six orders of magnitude.

Another specific form of the disclosed method involves amplification of genomic DNA the absence of a heat treatment step directly from whole blood or from tissue culture cells. Such amplification can be achieved with the same efficiency as from purified DNA. The DNA amplified directly from blood or cells can have substantially the same locus representation values as DNA amplified from purified human DNA template. This represents an advantage over other amplification procedures such as PCR, since components such as heme in whole blood inhibit PCR and necessitate a purification step before DNA from blood can be used as a PCR template.

F. Detection of Amplification Products

Products of amplification can be detected using any nucleic acid detection technique. For real-time detection, the amplification products and the progress of amplification are detected during amplification. Real-time detection is usefully accomplished using one or more or one or a combination of fluorescent change probes and fluorescent change primers. Other detection techniques can be used, either alone or in combination with real-timer detection and/or detection involving fluorescent change probes and primers. Many techniques are known for detecting nucleic acids. The nucleotide sequence of the amplified sequences also can be determined using any suitable technique.

1. Primary Labeling

Primary labeling consists of incorporating labeled moieties, such as fluorescent nucleotides, biotinylated nucleotides, digoxygenin-containing nucleotides, or bromodeoxyuridine, during amplification. For example, fluorescent labels can be incorporated into replicated nucleic acid by using fluorescently labeled primers, such as fluorescent change primers. In another example, one can incorporate cyanine dye UTP analogs (Yu et al. (1994)) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

Another method of labeling amplified nucleic acids is to incorporate 5-(3-aminoallyl)-dUTP (AAdUTP) in the nucleic acid during amplification followed by chemical labeling at the incorporated nucleotides. Incorporated 5-(3-aminoallyl)-deoxyuridine (AAdU) can be coupled to labels that have reactive groups that are capable of reacting with amine groups. AAdUTP can be prepared according to Langer et al. (1981). Proc. Natl. Acad. Sci. USA. 78: 6633-37. Other modified nucleotides can be used in analogous ways. That is, other modified nucleotides with minimal modification can be incorporated during replication and labeled after incorporation.

Examples of labels suitable for addition to AAdUTP are radioactive isotopes, fluorescent molecules, phosphorescent molecules, enzymes, antibodies, and ligands. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthamide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7', 1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

A useful form of primary labeling is the use of fluorescent change primers during amplification. Fluorescent change primers exhibit a change in fluorescence intensity or wavelength based on a change in the form or conformation of the primer and the amplified nucleic acid. Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers can be used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers and scorpion primers.

Cleavage activated primers are primers where fluorescence is increased by cleavage of the primer. Generally, cleavage activated primers are incorporated into replicated strands and are then subsequently cleaved. Cleavage activated primers can include a fluorescent label and a quenching moiety in proximity such that fluorescence from the label is quenched. When the primer is clipped or digested (typically by the 5'-3' exonuclease activity of a polymerase during amplification), the quenching moiety is no longer in proximity to the fluorescent label and fluorescence increases. Little et al., Clin. Chem. 45:777-784 (1999), describe the use of cleavage activated primers. Use of cleavage activated primers is not preferred in the disclosed method.

2. Secondary Labeling

Secondary labeling consists of using suitable molecular probes, referred to as detection probes, to detect the amplified nucleic acids. For example, a primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand. Detection probes can interact by hybridization or annealing via normal Watson-Crick base-pairing (or related alternatives) or can interact with double-stranded targets to form a triple helix. Such triplex-forming detection probes can be used in the same manner as other detection probes, such as in the form of fluorescent change probes.

A useful form of secondary labeling is the use of fluorescent change probes and primers in or following amplification. Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during or following amplification), the quenching moiety is no longer in proximity to the fluorescent label and fluorescence increases. TaqMan probes are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during or after amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity. Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends a the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes. Stem quenched primers (such as peptide nucleic acid quenched primers and hairpin quenched primers) can be used as secondary labels.

3. Multiplexing and Hybridization Array Detection

Detection of amplified nucleic acids can be multiplexed by, for example, using sets of different probes, each set designed for binding to different target sequences. Only those probes that are able to find their targets will associate signal with the amplified products. Amplified sequences can also be distinguished by sequence-specific capture on arrays or other solid-state substrates. There are at least two useful alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the amplified nucleic acid as an address tag. The disclosed method can be easily multiplexed by, for example, using sets of different detection probes directed to different target sequences. Use of different fluorescent labels with different detection probes allows specific detection of different target sequences.

4. Combinatorial Multicolor Coding

One form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided. Combinatorial labeling can be used with fluorescent change probes and primers.

The combinations of labels establish a code for identifying different detection probes and, by extension, different target molecules to which those detection probes are associated with. This labeling scheme is referred to as Combinatorial Multicolor Coding (CMC). Such coding is described by Speicher et al., *Nature Genetics* 12:368-375 (1996). Use of CMC is described in U.S. Pat. No. 6,143,495. Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, 5 labels form 31 label combinations, and 6 labels forms 63 label combinations.

For combinatorial multicolor coding, a group of different detection probes are used as a set. Each type of detection probe in the set is labeled with a specific and unique combination of fluorescent labels. For those detection probes assigned multiple labels, the labeling can be accomplished by labeling each detection probe molecule with all of the required labels. Alternatively, pools of detection probes of a given type can each be labeled with one of the required labels. By combining the pools, the detection probes will, as a group, contain the combination of labels required for that type of detection probe. Where each detection probe is labeled with a single label, label combinations can also be generated by using primers with coded combinations of detection tags complementary to the different detection probes. In this scheme, the primers will contain a combination of detection tags representing the combination of labels required for a specific label code. Further illustrations are described in U.S. Pat. No. 6,143,495. Use of pools of detection probes each probe with a single label is preferred when fluorescent change probes are used.

Speicher et al. describes a set of fluors and corresponding optical filters spaced across the spectral interval 350-770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 nm), FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm). The excitation and emission spectra, extinction coefficients and quantum yield of these fluors are described by Ernst et al., *Cytometry* 10:3-10 (1989), Mujumdar et al., *Cytometry* 10:11-19 (1989), Yu, *Nucleic Acids Res.* 22:3226-3232 (1994), and Waggoner, *Meth. Enzymology* 246:362-373 (1995). These fluors can all be excited with a 75W Xenon arc.

To attain selectivity, filters with bandwidths in the range of 5 to 16 nm are preferred. To increase signal discrimination, the fluors can be both excited and detected at wavelengths far from their spectral maxima. Emission bandwidths can be made as wide as possible. For low-noise detectors, such as cooled CCD cameras, restricting the excitation bandwidth has little effect on attainable signal to noise ratios. A list of preferred filters for use with the preferred fluor set is listed in Table 1 of Speicher et al. It is important to prevent infra-red light emitted by the arc lamp from reaching the detector; CCD chips are extremely sensitive in this region. For this purpose, appropriate IR blocking filters can be inserted in the image path immediately in front of the CCD window to minimize loss of image quality. Image analysis software can then be used to count and analyze the spectral signatures of fluorescent dots.

G. Enzyme-Linked Detection

Amplified nucleic acid labeled by incorporation of labeled nucleotides can be detected with established enzyme-linked detection systems. For example, amplified nucleic acid labeled by incorporation of biotin using biotin-16-UTP (Roche Molecular Biochemicals) can be detected as follows. The nucleic acid is immobilized on a solid glass surface by hybridization with a complementary DNA oligonucleotide (address probe) complementary to a target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

H. Reverse Transcription Multiple Displacement Amplification

Multiple displacement amplification can be performed on RNA or on DNA strands reverse transcribed from RNA. A useful form of the disclosed method, referred to as reverse transcription multiple displacement amplification (RT-MDA) involves reverse transcribing RNA, removal of the RNA (preferably by nuclease disgestion using an RNA-specific nuclease such as RNAse H), and multiple displacement amplification of the reverse transcribed DNA. RT-MDA can be performed using either double-stranded cDNA or using just the first cDNA strand. In the latter case, the second cDNA strand need not be, and preferably is not, synthesized. RT-MDA is useful for quantitative analysis of mRNA or general amplification of mRNA sequences for any other purpose.

I. Repeat Multiple Displacement Amplification

The disclosed multiple displacement amplification reactions can also be sequentially combined. For example, the product of MDA can itself be amplified in another multiple displacement amplification. This is referred to herein as repeat multiple displacement amplification (RMDA). This can be accomplished, for example, by diluting the replicated strands following MDA and subjecting them to a new MDA. This can be repeated one or more times. Each round of MDA will increase the amplification. Different forms of MDA, such as WGSDA and MSDA on particular target sequences can be combined. In general, repeat MDA can be accomplished by first bringing into contact one, a few, or more primers, DNA polymerase, and a nucleic acid sample, and incubating the nucleic acid sample under conditions that promote replication of nucleic acid molecules in the nucleic acid sample. Replication of the nucleic acid molecules results in replicated strands, wherein during replication at least one of the replicated strands is displaced from the nucleic acid molecules by strand displacement replication of another replicated strand; and then diluting the replicated strands, bringing into contact one, a few, or more primers, DNA polymerase, and the diluted replicated strands, and incubating the replicated strands under conditions that promote replication of the replicated strands. Replication of the replicated strands results in additional replicated strands, wherein during replication at least one of the additional replicated strands is displaced from the replicated strands by strand displacement replication of another additional replicated strand. This form of the method can be extended by performing the following operation one or more times: diluting the additional replicated strands, bringing into contact one, a few, or more primers, DNA polymerase, and the diluted replicated strands, and incubating the replicated strands under conditions that promote replication of the replicated strands. Replication of the replicated strands results in additional replicated strands, wherein during replication at least one of the additional replicated strands is displaced from the replicated strands by strand displacement replication of another additional replicated strand.

J. Using Products of Multiple Displacement Amplification

The nucleic acids produced using the disclosed method can be used for any purpose. For example, the amplified nucleic acids can be analyzed (such as by sequencing or probe hybridization) to determine characteristics of the amplified sequences or the presence or absence or certain sequences. The amplified nucleic acids can also be used as reagents for assays or other methods. For example, nucleic acids produced in the disclosed method can be coupled or adhered to a solid-state substrate. The resulting immobilized nucleic acids can be used as probes or indexes of sequences in a sample. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

Nucleic acids produced in the disclosed method also can be used as probes or hybridization partners. For example, sequences of interest can be amplified in the disclosed method and provide a ready source of probes. The replicated strands (produced in the disclosed method) can be cleaved prior to use as hybridization probes. For example, the replicated strands can be cleaved with DNAse I. The hybridization probes can be labeled as described elsewhere herein with respect to labeling of nucleic acids produce in the disclosed method.

Nucleic acids produced in the disclosed method also can be used for subtractive hybridization to identify sequences that are present in only one of a pair or set of samples. For example, amplified cDNA from different samples can be annealed and the resulting double-stranded material can be separated from single-stranded material. Unhybridized sequences would be indicative of sequences expressed in one of the samples but not others.

Specific Embodiments

Disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample. The primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample.

The genome can be a eukaryotic genome, a plant genome, an animal genome, a vertebrate genome, a fish genome, a mammalian genome, a human genome, a microbial genome or a viral genome. The amplification bias can be less than 20-fold for at least ten nucleic acid sequences in the genomic nucleic acid sample. The amplification bias can be less than 10-fold for at least ten nucleic acid sequences in the genomic nucleic acid sample. The primer has a length of 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

The primer can have a length of less than 4 nucleotides, less than 5 nucleotides, less than 6 nucleotides, less than 7 nucleotides, less than 8 nucleotides, less than 9 nucleotides, less than 10 nucleotides, less than 11 nucleotides, less than 12 nucleotides, less than 13 nucleotides, less than 14 nucleotides, less than 15 nucleotides, less than 16 nucleotides, less than 17 nucleotides, less than 18 nucleotides, less than 19 nucleotides, less than 20 nucleotides, less than 21 nucleotides, less than 22 nucleotides, less than 23 nucleotides, less than 24 nucleotides, less than 25 nucleotides, less than 26 nucleotides, less than 27 nucleotides, less than 28 nucleotides, less than 29 nucleotides, less than 30 nucleotides, or less than 31 nucleotides.

The genomic nucleic acid sample can be incubated at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C.

The genomic nucleic acid sample can be incubated at less than 21° C., less than 22° C., less than 23° C., less than 24° C., less than 25° C., less than 26° C., less than 27° C., less than 28° C., less than 29° C., less than 30° C., less than 31° C., less than 32° C., less than 33° C., less than 34° C., less than 35° C., less than 36° C., less than 37° C., less than 38° C., less than 39° C., less than 40° C., less than 41° C., less than 42° C., less than 43° C., less than 44° C., less than 45° C., less than 46° C., less than 47° C., less than 48° C., less than 49° C., less than 50° C., less than 51° C., less than 52° C., less than 53° C., less than 54° C., less than 55° C., less than 56° C., less than 57° C., less than 58° C., less than 59° C., less than 60° C., less than 61° C., less than 62° C., less than 63° C., less than 64° C., less than 65° C., less than 66° C., less than 67° C., less than 68° C., less than 69° C., less than 70° C., less than 71° C., less than 72° C., less than 73° C., less than 74° C., less than 75° C., less than 76° C., less than 77° C., less than 78° C., less than 79° C., or less than 80° C.

The genomic nucleic acid sample can have a sequence complexity of at least $1\times10^3$ nucleotides, the genomic nucleic acid sample can have a sequence complexity of at least $1\times10^4$ nucleotides, the genomic nucleic acid sample can have a sequence complexity of at least $1\times10^5$ nucleotides, the genomic nucleic acid sample can have a sequence complexity of at least $1\times10^6$ nucleotides, the genomic nucleic acid sample can have a sequence complexity of at least $1\times10^7$ nucleotides, the genomic nucleic acid sample can have a sequence complexity of at least $1\times10^8$ nucleotides, or the genomic nucleic acid sample can have a sequence complexity of at least $1\times10^9$ nucleotides.

The primer, DNA polymerase and genomic nucleic acid sample are brought into contact with 1 additional primer, with 2 additional primers, with 3 additional primers, with 4 additional primers, with 5 additional primers, with 6 additional primers, with 7 additional primers, with 8 additional primers, with 9 additional primers, with 10 additional primers, with 11 additional primers, with 12 additional primers, with 13 additional primers, with 14 additional primers, with 15 additional primers, with 16 additional primers, with 17 additional primers, with 18 additional primers, with 19 additional primers, with 20 additional primers, with 21 additional primers, with 22 additional primers, with 23 additional primers, with 24 additional primers, with 25 additional primers, with 26 additional primers, with 27 additional primers, with 28 additional primers, with 29 additional primers, with 30 additional primers, with 31 additional primers, with 32 additional primers, with 33 additional primers, with 34 additional primers, with 35 additional primers, with 36 additional primers, with 37 additional primers, with 38 additional primers, with 39 additional primers, with 40 additional primers, with 41 additional primers, with 42 additional primers, with 43 additional primers, with 44 additional primers, with 45 additional primers, with 46 additional primers, with 47 additional primers, with 48 additional primers, with 49 additional primers, with 50 additional primers, with 51 additional primers, with 52 additional primers, with 53 additional primers, with 54 additional primers, with 55 additional primers, with 56 additional primers, with 57 additional primers, with 58 additional primers, with 59 additional primers, with 60 additional primers, with 61 additional primers, with 62 additional primers, with 63 additional primers, with 75 additional primers, with 100 additional primers, with 150 additional primers, with 200 additional primers, with 300 additional primers, with 400 additional primers, with 500 additional primers, with 750 additional primers, or with 1,000 additional primers, wherein each primer can have a different specific nucleotide sequence.

The primers are all of the same length.

The primer, DNA polymerase and genomic nucleic acid sample are brought into contact with fewer than 2 additional primers, with fewer than 3 additional primers, with fewer than 4 additional primers, with fewer than 5 additional primers, with fewer than 6 additional primers, with fewer than 7 additional primers, with fewer than 8 additional primers, with fewer than 9 additional primers, with fewer than 10 additional primers, with fewer than 91 additional primers, with fewer than 12 additional primers, with fewer than 13 additional primers, with fewer than 14 additional primers, with fewer than 15 additional primers, with fewer than 16 additional primers, with fewer than 17 additional primers, with fewer than 18 additional primers, with fewer than 19 additional primers, with fewer than 20 additional primers, with fewer than 21 additional primers, with fewer than 22 additional primers, with fewer than 23 additional primers, with fewer than 24 additional primers, with fewer than 25 additional primers, with fewer than 26 additional primers, with fewer than 27 additional primers, with fewer than 28 additional primers, with fewer than 29 additional primers, with fewer than 30 additional primers, with fewer than 31 additional primers, with fewer than 32 additional primers, with fewer than 33 additional primers, with fewer than 34 additional primers, with fewer than 35 additional primers, with fewer than 36 additional primers, with fewer than 37 additional primers, with fewer than 38 additional primers, with fewer than 39 additional primers, with fewer than 40 additional primers, with fewer than 41 additional primers, with fewer than 42 additional primers, with fewer than 43 additional primers, with fewer than 44 additional primers, with fewer than 45 additional primers, with fewer than 46 additional primers, with fewer than 47 additional primers, with fewer than 48 additional primers, with fewer than 49 additional primers, with fewer than 50 additional primers, with fewer than 51 additional primers, with fewer than 52 additional primers, with fewer than 53 additional primers, with fewer than 54 additional primers, with fewer than 55 additional primers, with fewer than 56 additional primers, with fewer than 57 additional primers, with fewer than 58 additional primers, with fewer than 59 additional primers, with fewer than 60 additional primers, with fewer than 61 additional primers, with fewer than 62 additional primers, with fewer than 63 additional primers, with fewer than 64 additional primers, with fewer than 75 additional primers, with fewer than 100 additional primers, with fewer than 150 additional primers, with fewer than 200 additional primers, with fewer than 300 additional primers, with fewer than 400 additional primers, with fewer than 500 additional primers, with fewer than 750 additional primers, or with fewer than 1,000 additional primers, wherein each primer can have a different specific nucleotide sequence.

Each primer can have a different one of the sequences AGTGGG or AGAGAG. Each primer can have a different one of the sequences AGCCGG, AGTAGG, or AGTTGG. Each primer can have a different one of the sequences AGGCGG, AGTGGG, AGGGAG, or AGTGAG. Each primer can have a different one of the sequences AGTGGG, AGCCAG, AGTTAG, AGTCAG, or AGACAG. Each primer can have a different one of the sequences AGAGGG, AGGCAG, AGCCAG, AGTCAG, or AGACAG. Each primer can have a different one of the sequences AGTAGG, AGGTGG, AGGCAG, AGACAG, or AGTGAG. Each primer can have a different one of the sequences AGGAGG, AGAGGG, AGGGAG, AGTCAG, or AGCGAG. Each primer can have a different one of the sequences CGGTGG, TCACGC, CGAGCG, GCGTGG, ACTCGG, AATCGC, CGGAGG, CCGAGA, GATCGC, AGAGCG, AGCGAG, or ACTCCG.

Each primer can have one of the sequences AGTGGG or AGAGAG. Each primer can have one of the sequences AGCCGG, AGTAGG, or AGTTGG. Each primer can have one of the sequences AGGCGG, AGTGGG, AGGGAG, or AGTGAG. Each primer can have one of the sequences AGTGGG, AGCCAG, AGTTAG, AGTCAG, or AGACAG. Each primer can have one of the sequences AGAGGG, AGGCAG, AGCCAG, AGTCAG, or AGACAG. Each primer can have one of the sequences CGGTGG, TCACGC, CGAGCG, GCGTGG, ACTCGG, AATCGC, CGGAGG, CCGAGA, GATCGC, AGAGCG, AGCGAG, or ACTCCG.

The primer can be complementary to a sequence in a repeat sequence.

The repeat sequence can be a microsatellite sequence, a minisatellite sequence, a satellite sequence, a transposon sequence, a ribosomal RNA sequence, a short interspersed nuclear element (SINE), or a long interspersed nuclear element (LINE). The primer can be complementary to a sequence in a functional consensus sequence. The functional consensus sequence can be a promoter sequence, an enhancer sequence, a silencer sequence, an upstream regulatory element sequence, a transcription termination site sequence, a transposon regulatory sequence, a ribosomal RNA regulatory sequence, or a polyadenylation site sequence. The functional consensus sequence can be a microbial promoter sequence, a microbial enhancer sequence, a microbial silencer sequence, a microbial upstream regulatory element sequence, a microbial transcription termination site sequence, a microbial transposon regulatory sequence, a microbial ribosomal RNA regulatory sequence, or a microbial polyadenylation site sequence.

The primer can be a broad coverage primer. The primer can be complementary to a sequence that occurs every 5,000 nucleotides or less, every 4,000 nucleotides or less, every 3,000 nucleotides or less, every 2,500 nucleotides or less, every 2,000 nucleotides or less, every 1,500 nucleotides or less, every 1,000 nucleotides or less, every 900 nucleotides or less, every 800 nucleotides or less, every 700 nucleotides or less, every 600 nucleotides or less, every 500 nucleotides or less, every 400 nucleotides or less, every 300 nucleotides or less, every 200 nucleotides or less, every 100 nucleotides or less, or every 50 nucleotides or less, on average, in the nucleic acid molecules of the genomic nucleic acid sample.

The primer can have a G+C percentage within 20%, within 15%, within 10%, within 9%, within 8%, within 7%, within 6%, within 5%, within 4%, within 3%, within 2%, or within 1% of the G+C percentage of the genomic nucleic acid sample. The primer produces a locus representation of at least 10% for at least 5 different loci for the type of genomic nucleic acid sample used. The primer produces a locus representation of at least 15%, at least 20%, at least 25%, at least 30%, at least 35%, at least 40%, at least 45%, at least 50%, at least 60%, at least 70%, at least 80%, at least 90%, or at least 100% for at least 5 different loci for the type of genomic nucleic acid sample used. The primer produces a locus representation of at least 10% for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci for the type of genomic nucleic acid sample used.

The primer produces an amplification bias of less than 50-fold for the type of genomic nucleic acid sample used. The primer produces an amplification bias of less than 45-fold, less than 40-fold, less than 35-fold, less than 30-fold, less than 25-fold, less than 20-fold, less than 19-fold, less than 18-fold, less than 17-fold, less than 16-fold, less than 15-fold, less than 14-fold, less than 13-fold, less than 12-fold, less than 11-fold, less than 10-fold, less than 9-fold, less than 8-fold, less than 7-fold, less than 6-fold, less than 5-fold, or less than 4-fold for the type of genomic nucleic acid sample used. The primer produces an amplification bias of less than 50-fold for at least 5 different loci, for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci for the type of genomic nucleic acid sample used.

The primer does not have an inter-complementary 3' end. The primer does not produce significant replication products in the absence of a nucleic acid sample. The DNA polymerase can be φ29 DNA polymerase. The genomic nucleic acid sample need not be subjected to denaturing conditions. The genomic nucleic acid sample need not be subjected to heat denaturing conditions. The genomic nucleic acid sample need not be subjected to alkaline denaturing conditions. The genomic nucleic acid sample can be subjected to denaturing conditions. The genomic nucleic acid sample can be subjected to heat denaturing conditions. The genomic nucleic acid sample can be subjected to alkaline denaturing conditions.

Nucleic acids in the genomic nucleic acid sample are not separated from other material in the genomic nucleic acid sample. The genomic nucleic acid sample can be a crude cell lysate. The genomic nucleic acid sample can be produced by exposing cells to alkaline conditions to form a cell lysate, wherein the cell lysate can comprise a whole genome, and reducing the pH of the cell lysate to form a stabilized cell lysate. The cells are exposed to alkaline conditions by mixing the cells with a lysis solution. The lysis solution can comprise a base. The pH of the cell lysate can be reduced by mixing the cell lysate with a stabilization solution. The stabilization solution can comprise a buffer. The stabilization solution can comprise an acid.

Nucleic acids in the cell lysate and the stabilized cell lysate are not separated from other material in the cell lysate. The cell lysate and the stabilized cell lysate are not subjected to purification prior to the incubation. The cell lysate, stabilized cell lysate, or both are subjected to partial purification prior to the incubation. The cell lysate and the stabilized cell lysate are not subjected to substantial purification prior to the incubation. The incubation can be substantially isothermic. Neither the cell lysate nor the stabilized cell lysate can be heated substantially above the temperature of the incubation. Neither the cell lysate nor the stabilized cell lysate can be subjected to substantial heating above the temperature of the incubation. The cells are not heated substantially above the temperature of the incubation. The cells are not subjected to substantial heating above the temperature of the incubation. The cells are not heated substantially above the temperature at which the cells grow. The cells are not subjected to substantial heating above the temperature at which the cells grow.

Neither the cell lysate nor the stabilized cell lysate can be heated above a temperature and for a time that would cause notable denaturation of the genome. Neither the cell lysate nor the stabilized cell lysate can be subjected to heating above a temperature and for a time that would cause notable denaturation of the genome. The cells are not lysed by heat. The cells are not heated above a temperature and for a time that would cause substantial cell lysis in the absence of the alkaline conditions. The cells are not subjected to heating above a temperature and for a time that would cause substantial cell lysis in the absence of the alkaline conditions.

The method can further comprise, prior to bringing into contact the primer, the genomic nucleic acid sample and the DNA polymerase, exposing the genomic nucleic acid sample to conditions that promote substantial denaturation of the nucleic acid molecules in the genomic nucleic acid sample, thereby forming a denatured genomic nucleic acid sample, and altering the conditions to conditions that do not promote substantial denaturation of nucleic acid molecules in the genomic nucleic acid sample to form a denatured genomic nucleic acid sample.

Replication of the nucleic acid molecules in the genomic nucleic acid sample results in a longer average fragment length for the replicated nucleic acid molecules than the average fragment length in the genomic nucleic acid sample. The genomic nucleic acid sample, the denatured genomic nucleic acid sample, or both are exposed to ionic conditions. The genomic nucleic acid sample can be exposed to conditions that promote substantial denaturation by mixing the genomic nucleic acid sample with a denaturing solution and by heating the genomic nucleic acid sample to a temperature and for a length of time that substantially denatures the nucleic acid molecules in the genomic nucleic acid sample.

The primer contains at least one modified nucleotide such that the primer can be resistant to 3'-5' exonuclease. The primer can be 6 nucleotides long, wherein the primer contains at least one modified nucleotide such that the primer can be nuclease resistant, and wherein the DNA polymerase can be φ29 DNA polymerase. The conditions that promote replication of the nucleic acid molecules are substantially isothermic. The conditions that promote replication of the nucleic acid molecules do not involve thermal cycling. The conditions that promote replication of the nucleic acid molecules do not include thermal cycling. The primer can comprise nucleotides, wherein one or more of the nucleotides are ribonucleotides. From about 10% to about 50% of the nucleotides are ribonucleotides. About 50% or more of the nucleotides are ribonucleotides. All of the nucleotides are ribonucleotides.

The primer can comprise nucleotides, wherein one or more of the nucleotides are 2'-O-methyl ribonucleotides. From about 10% to about 50% of the nucleotides are 2'-O-methyl ribonucleotides. About 50% or more of the nucleotides are 2'-O-methyl ribonucleotides. All of the nucleotides are 2'-O-methyl ribonucleotides. The primer can comprise nucleotides, wherein the nucleotides are a mixture of ribonucleotides and 2'-O-methyl ribonucleotides. The primer can comprise nucleotides, wherein the nucleotides are a mixture of deoxyribonucleotides and 2'-O-methyl ribonucleotides. The genomic nucleic acid sample can be a blood sample, a urine sample, a semen sample, a lymphatic fluid sample, a cerebrospinal fluid sample, amniotic fluid sample, a biopsy sample, a needle aspiration biopsy sample, a cancer sample, a tumor sample, a tissue sample, a cell sample, a cell lysate sample, a crude cell lysate sample, a forensic sample, an archeological sample, an infection sample, a nosocomial infection sample, a production sample, a drug preparation sample, a biological molecule production sample, a protein preparation sample, a lipid preparation sample, a carbohydrate preparation sample, or a combination thereof.

The genomic nucleic acid sample can be a crude cell lysate. The genomic nucleic acid sample need not be processed beyond cell lysis. The replicated nucleic acid molecules are analyzed. The replicated nucleic acid molecules are analyzed using one or more DNA chips. The replicated nucleic acid molecules are analyzed by hybridization. The replicated nucleic acid molecules are analyzed by nucleic acid sequencing. The replicated nucleic acid molecules are stored prior to, following, or both prior to and following their analysis.

The method can further comprise bringing into contact the primer, DNA polymerase, and a second genomic nucleic acid sample, and incubating the second genomic nucleic acid sample under conditions that promote replication of nucleic acid molecules in the second genomic nucleic acid sample, wherein the second genomic nucleic acid sample can comprise all or a substantial portion of a genome, wherein replication of nucleic acid molecules in the second genomic nucleic acid sample proceeds by strand displacement replication, wherein replication of the nucleic acid molecules in the second genomic nucleic acid sample results in replication of all or a substantial fraction of the nucleic acid molecules in the second genomic nucleic acid sample.

The second genomic nucleic acid sample can be a sample from the same type of organism as the first genomic nucleic acid sample. The second genomic nucleic acid sample can be a sample from the same type of tissue as the first genomic nucleic acid sample. The second genomic nucleic acid sample can be a sample from the same organism as the first genomic nucleic acid sample. The second genomic nucleic acid sample can be obtained at a different time than the first genomic nucleic acid sample. The second genomic nucleic acid sample can be a sample from a different organism than the first genomic nucleic acid sample. The second genomic nucleic acid sample can be a sample from a different type of tissue than the first genomic nucleic acid sample.

The second genomic nucleic acid sample can be a sample from a different species of organism than the first genomic nucleic acid sample. The second genomic nucleic acid sample can be a sample from a different strain of organism than the first genomic nucleic acid sample. The second genomic nucleic acid sample can be a sample from a different cellular compartment than the first genomic nucleic acid sample.

Also disclosed is a method of amplifying genomes, the method comprising, bringing into contact fewer than 1,000 primers, DNA polymerase, and a genomic nucleic acid sample, and incubating the genomic nucleic acid sample under conditions that promote replication of nucleic acid molecules in the genomic nucleic acid sample, wherein each primer has a different specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample.

The DNA polymerase and genomic nucleic acid sample are brought into contact with fewer than 2 primers, with fewer than 3 primers, with fewer than 4 primers, with fewer than 5 primers, with fewer than 6 primers, with fewer than 7 primers, with fewer than 8 primers, with fewer than 9 primers, with fewer than 10 primers, with fewer than 11 primers, with fewer than 12 primers, with fewer than 13 primers, with fewer than 14 primers, with fewer than 15 primers, with fewer than 16 primers, with fewer than 17 primers, with fewer than 18 primers, with fewer than 19 primers, with fewer than 20 primers, with fewer than 21 primers, with fewer than 22 primers, with fewer than 23 primers, with fewer than 24 primers, with fewer than 25 primers, with fewer than 26 primers, with fewer than 27 primers, with fewer than 28 primers, with fewer than 29 primers, with fewer than 30 primers, with fewer than 31 primers, with fewer than 32 primers, with fewer than 33 primers, with fewer than 34 primers, with fewer than 35 primers, with fewer than 36 primers, with fewer than 37 primers, with fewer than 38 primers, with fewer than 39 primers, with fewer than 40 primers, with fewer than 41 primers, with fewer than 42 primers, with fewer than 43 primers, with fewer than 44 primers, with fewer than 45 primers, with fewer than 46 primers, with fewer than 47 primers, with fewer than 48 primers, with fewer than 49 primers, with fewer than 50 primers, with fewer than 51 primers, with fewer than 52 primers, with fewer than 53 primers, with fewer than 54 primers, with fewer than 55 primers, with fewer than 56 primers, with fewer than 57 primers, with fewer than 58 primers, with fewer than 59 primers, with fewer than 60 primers, with fewer than 61 primers, with fewer than 62 primers, with fewer than 63 primers, with fewer than 64 primers, with fewer than 75 primers, with fewer than 100 primers, with fewer than 150 primers, with fewer than 200 primers, with fewer than 300 primers, with fewer than 400 primers, with fewer than 500 primers, with fewer than 750 primers, or with fewer than 1,000 primers.

Also disclosed is a method of amplifying nucleic acid samples of notable sequence complexity, the method comprising, bringing into contact a single primer, DNA polymerase, and a nucleic acid sample, and incubating the nucleic acid sample under conditions that promote replication of nucleic acid molecules in the nucleic acid sample, wherein the primer has a specific nucleotide sequence, wherein the nucleic acid sample has a sequence complexity of at least $1 \times 10^4$ nucleotides, wherein replication of nucleic acid molecules in the nucleic acid sample proceeds by strand displacement replication, wherein replication of the nucleic acid molecules in the nucleic acid sample results in replication of all or a substantial fraction of the nucleic acid molecules in the nucleic acid sample.

The nucleic acid sample can have a sequence complexity of at least $1 \times 10^5$ nucleotides, the nucleic acid sample can have a sequence complexity of at least $1 \times 10^6$ nucleotides, the nucleic acid sample can have a sequence complexity of at least $1 \times 10^7$ nucleotides, the nucleic acid sample can have a sequence complexity of at least $1 \times 10^8$ nucleotides, or the nucleic acid sample can have a sequence complexity of at least $1 \times 10^9$ nucleotides. The nucleic acid sample is or is derived from a genome, a chromosome, a chromosome fragment, an artificial chromosome, a yeast artificial chromosome, a bacterial artificial chromosome, a cosmid, or a combination.

The nucleic acid sample is or is derived from a blood sample, a urine sample, a semen sample, a lymphatic fluid sample, a cerebrospinal fluid sample, amniotic fluid sample, a biopsy sample, a needle aspiration biopsy sample, a cancer sample, a tumor sample, a tissue sample, a cell sample, a cell lysate sample, a crude cell lysate sample, a forensic sample, an archeological sample, an infection sample, a nosocomial infection sample, a production sample, a drug preparation sample, a biological molecule production sample, a protein preparation sample, a lipid preparation sample, a carbohydrate preparation sample, or a combination thereof. The nucleic acid sample is or is derived from a eukaryote, a plant, and animal, a marine animal, a vertebrate, a mammal, or a human.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein the genomic nucleic acid sample has a sequence complexity of at least $1 \times 10^9$ nucleotides, wherein replication of the nucleic acid molecules in the genomic nucleic acid sample results in replication of at least 0.01% of the nucleic acid sequences in the genomic nucleic acid sample.

Replication of the nucleic acid molecules in the genomic nucleic acid sample results in replication of at least 0.1% of the nucleic acid sequences in the genomic nucleic acid sample, at least 1% of the nucleic acid sequences in the genomic nucleic acid sample, at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein the genomic nucleic acid sample has a sequence complexity of at least $1 \times 10^8$ nucleotides, wherein replication of the nucleic acid molecules in the genomic nucleic acid sample results in replication of at least 0.1% of the nucleic acid sequences in the genomic nucleic acid sample.

Replication of the nucleic acid molecules in the genomic nucleic acid sample results in replication of at least 1% of the nucleic acid sequences in the genomic nucleic acid sample, at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein the genomic nucleic acid sample has a sequence complexity of at least $1 \times 10^7$ nucleotides, wherein replication of the nucleic acid molecules in the genomic nucleic acid sample results in replication of at least 1% of the nucleic acid sequences in the genomic nucleic acid sample.

Replication of the nucleic acid molecules in the genomic nucleic acid sample results in replication of at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein the genomic nucleic acid sample has a sequence complexity of at least $1 \times 10^6$ nucleotides, wherein replication of the nucleic acid molecules in the genomic nucleic acid sample results in replication of at least 10% of the nucleic acid sequences in the genomic nucleic acid sample.

Replication of the nucleic acid molecules in the genomic nucleic acid sample results in replication of at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein the genomic nucleic acid sample has a sequence complexity of at least $1 \times 10^5$ nucleotides, wherein replication of the nucleic acid molecules in the genomic nucleic acid sample results in replication of at least 80% of the nucleic acid sequences in the genomic nucleic acid sample.

Replication of the nucleic acid molecules in the genomic nucleic acid sample results in replication of at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

Also disclosed is a method of amplifying genomes, the method comprising, bringing into contact a single primer, DNA polymerase, and a genomic nucleic acid sample, and incubating the genomic nucleic acid sample under conditions that promote replication of nucleic acid molecules in the genomic nucleic acid sample, wherein the primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in a locus representation of at least 10% for at least 5 different loci. Replication of the nucleic acid molecules in the genomic nucleic acid sample results in a locus representation of at least 15%, at least 20%, at least 25%, at least 30%, at least 35%, at least 40%, at least 45%, at least 50%, at least 60%, at least 70%, at least 80%, at least 90%, or at least 100% for at least 5 different loci.

Replication of the nucleic acid molecules in the genomic nucleic acid sample results in a locus representation of at least 10% for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

Replication of the nucleic acid molecules in the genomic nucleic acid sample results in an amplification bias of less than 50-fold. Replication of the nucleic acid molecules in the genomic nucleic acid sample results in an amplification bias of less than 45-fold, less than 40-fold, less than 35-fold, less than 30-fold, less than 25-fold, less than 20-fold, less than 19-fold, less than 18-fold, less than 17-fold, less than 16-fold, less than 15-fold, less than 14-fold, less than 13-fold, less than 12-fold, less than 11-fold, less than 10-fold, less than 9-fold, less than 8-fold, less than 7-fold, less than 6-fold, less than 5-fold, or less than 4-fold.

Replication of the nucleic acid molecules in the genomic nucleic acid sample results in an amplification bias of less than 50-fold for at least 5 different loci, for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

Also disclosed is a method of amplifying nucleic acid samples of high sequence complexity, the method comprising, bringing into contact a single primer, DNA polymerase, and a nucleic acid sample, and incubating the nucleic acid sample under conditions that promote replication of nucleic acid molecules in the nucleic acid sample, wherein the primer has a specific nucleotide sequence, wherein the nucleic acid sample has a sequence complexity of at least $1 \times 10^3$ nucleotides, wherein replication of nucleic acid molecules in the nucleic acid sample proceeds by strand displacement replication, wherein replication of the nucleic acid molecules in the nucleic acid sample results in a sequence representation of at least 10% for at least 5 different target sequences.

Replication of the nucleic acid molecules in the nucleic acid sample results in a sequence representation of at least 15%, at least 20%, at least 25%, at least 30%, at least 35%, at least 40%, at least 45%, at least 50%, at least 60%, at least 70%, at least 80%, at least 90%, or at least 100% for at least 5 different target sequences.

Replication of the nucleic acid molecules in the nucleic acid sample results in a sequence representation of at least 10% for at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Replication of the nucleic acid molecules in the nucleic acid sample results in an amplification bias of less than 50-fold. Replication of the nucleic acid molecules in the nucleic acid sample results in an amplification bias of less than 45-fold, less than 40-fold, less than 35-fold, less than 30-fold, less than 25-fold, less than 20-fold, less than 19-fold, less than 18-fold, less than 17-fold, less than 16-fold, less than 15-fold, less than 14-fold, less than 13-fold, less than 12-fold, less than 11-fold, less than 10-fold, less than 9-fold, less than 8-fold, less than 7-fold, less than 6-fold, less than 5-fold, or less than 4-fold.

Replication of the nucleic acid molecules in the nucleic acid sample results in an amplification bias of less than 50-fold for at least 5 different target sequences, for at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Also disclosed is a method of amplifying genomes, the method comprising, bringing into contact a set of primers, DNA polymerase, and a genomic nucleic acid sample, and incubating the genomic nucleic acid sample under conditions that promote replication of nucleic acid molecules in the genomic nucleic acid sample, wherein the set of primers comprises one or more selected primers, wherein each selected primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample, wherein each selected primer in the set can produce replication of at least 80% of the nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1\times10^8$ nucleotides.

The set of primers further can comprise at least one additional primer. The set of primers can further comprise at least one non-selected primer, wherein the non-selected primer produces replication of less than 80% of the nucleic acid sequences in a selection nucleic acid sample when the primer, DNA polymerase, and the selection nucleic acid sample are brought into contact and incubated under conditions that promote replication of nucleic acid molecules in the selection nucleic acid sample.

Also disclosed is a method of amplifying genomes, the method comprising, bringing into contact a set of primers, DNA polymerase, and a genomic nucleic acid sample, and incubating the genomic nucleic acid sample under conditions that promote replication of nucleic acid molecules in the genomic nucleic acid sample, wherein the set of primers comprises one or more selected primers, wherein each selected primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample, wherein each selected primer in the set can produce an amplification bias of less than 20-fold for at least 10 nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1\times10^8$ nucleotides.

Also disclosed is a method of amplifying genomes, the method comprising, bringing into contact a set of primers, DNA polymerase, and a genomic nucleic acid sample, and incubating the genomic nucleic acid sample under conditions that promote replication of nucleic acid molecules in the genomic nucleic acid sample, wherein the set of primers comprises one or more selected primers, wherein each selected primer has a specific nucleotide sequence, wherein the genomic nucleic acid sample comprises all or a substantial portion of a genome, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample, wherein each selected primer in the set can produce a sequence representation of at least 10% for at least 10 nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1\times10^8$ nucleotides.

Also disclosed is a method of amplifying nucleic acids, the method comprising, bringing into contact a set of primers, DNA polymerase, and a nucleic acid sample, and incubating the nucleic acid sample under conditions that promote replication of nucleic acid molecules in the nucleic acid sample, wherein the set of primers comprises one or more selected primers, wherein each selected primer has a specific nucleotide sequence, wherein replication of nucleic acid molecules in the nucleic acid sample proceeds by strand displacement replication, wherein replication of the nucleic acid molecules in the nucleic acid sample results in replication of all or a substantial fraction of the nucleic acid molecules in the nucleic acid sample, wherein each selected primer in the set can produce replication of at least 80% of the nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1 \times 10^8$ nucleotides.

The set of primers can further comprise at least one additional primer. The set of primers can further comprise at least one non-selected primer, wherein the non-selected primer produces replication of less than 80% of the nucleic acid sequences in a selection nucleic acid sample when the primer, DNA polymerase, and the selection nucleic acid sample are brought into contact and incubated under conditions that promote replication of nucleic acid molecules in the selection nucleic acid sample. The nucleic acid sample can have a sequence complexity of at least $1 \times 10^3$ nucleotides.

Also disclosed is a method of amplifying nucleic acids, the method comprising, bringing into contact a set of primers, DNA polymerase, and a nucleic acid sample, and incubating the nucleic acid sample under conditions that promote replication of nucleic acid molecules in the nucleic acid sample, wherein the set of primers comprises one or more selected primers, wherein each selected primer has a specific nucleotide sequence, wherein replication of nucleic acid molecules in the nucleic acid sample proceeds by strand displacement replication, wherein replication of the nucleic acid molecules in the nucleic acid sample results in replication of all or a substantial fraction of the nucleic acid molecules in the nucleic acid sample, wherein each selected primer in the set can produce an amplification bias of less than 20-fold for at least 10 nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1 \times 10^8$ nucleotides.

Also disclosed is a method of amplifying nucleic acids, the method comprising, bringing into contact a set of primers, DNA polymerase, and a nucleic acid sample, and incubating the nucleic acid sample under conditions that promote replication of nucleic acid molecules in the nucleic acid sample, wherein the set of primers comprises one or more selected primers, wherein each selected primer has a specific nucleotide sequence, wherein replication of nucleic acid molecules in the nucleic acid sample proceeds by strand displacement replication, wherein replication of the nucleic acid molecules in the nucleic acid sample results in replication of all or a substantial fraction of the nucleic acid molecules in the nucleic acid sample, wherein each selected primer in the set can produce a sequence representation of at least 10% for at least 10 nucleic acid sequences in a selection nucleic acid sample when the primer, DNA polymerase, and the selection nucleic acid sample are brought into contact and incubated under conditions that promote replication of nucleic acid molecules in the selection nucleic acid sample, wherein the selection nucleic acid sample has a sequence complexity of at least $1 \times 10^8$ nucleotides.

EXAMPLE

A. Example

Whole Genome Amplification Using Six Nucleotide Primers

This example describes a demonstration of several embodiments of the disclosed method and analysis and comparison of the results. The exemplified method is the disclosed multiple displacement amplification form of whole genome amplification using hexamer (six nucleotide) primers having specific sequences. Different primers, and different number of primers, were used in the various reactions. All of these examples use only one or a few primers of specific nucleotide sequence to efficiently amplify the whole human genome.

1. Amplification of Human Genomic DNA by Multiple Displacement Amplification (MDA)

In an example of an embodiment of the disclosed method, 100 μl reactions (in triplicates), assembled in 0.2 ml tubes, contained 10 ng human genomic DNA, 37 mM Tris-HCl, pH 7.5, 50 mM KCl, 10 mM MgCl$_2$, 5 mM (NH$_4$)$_2$SO$_4$, 1.0 mM dATP, dTTP, dCTP, and dGTP, 50 μM exonuclease resistant hexamer, and 800 units/ml Phi 29 DNA polymerase. Reactions were incubated for 16 hours at 30° C. and terminated by heating to 65° C. for 3 min. MDA reaction yield was determined via PicoGreen quantification using a lambda DNA standard curve (Molecular Probes, Eugene, Oreg.).

2. Quantitative PCR Analysis of Amplification Products

The quality of the amplified DNA was assessed using TaqMan analysis. TaqMan analysis was performed using both ABI 7700 and 7000 sequence detection systems according to the manufacturer's specifications (Applied Biosystems, Foster City, Calif.). The TaqMan reaction consists of 50 μl of 1× Platinum Taq Polymerase Buffer, 5 mM MgCl$_2$, 1 mM of each dNTPs, 1 μl of ROX Reference Dye (Invitrogen Life Technologies, Carlsbad, Calif.), 1 Unit of Platinum Taq Polymerase (Invitrogen Life Technologies, Carlsbad, Calif.), 0.3 μM each of forward and reverse PCR primers, 0.25 μM of FAM/TAMRA fluorescent/quencher probe, and 1 μg of MDA amplified DNA. Purified human genomic DNA (gDNA) (Promega, Madison, Wis.) was used to generate a standard curve of 0, 0.001, 0.01, 0.1, and 1 μg gDNA to quantify the MDA amplified DNA. Loci representation (MDA/gDNA) is reported as a percent and is derived as 100 (loci copy number/μg MDA product)/(loci copy number/μg gDNA). A value of 100% indicates that the loci copy number for the amplified DNA is equal to the loci copy number for the unamplified genomic DNA.

3. Single Primer

Human genomic DNA was amplified by Multiple Displacement Amplification followed by TaqMan loci analysis as described above. A single six nucleotide Alu-specific primer (that is, its sequence was derived from an Alu repeat sequence), AluR11 (AGCGAG), was used for the MDA reaction. A total of 47 genetic loci were analyzed (2 loci per chromosome, and one locus from the Y chromosome). As illustrated in FIG. 1, AluR11 efficiently amplified the whole human genome as indicated by locus representation.

4. Two Primers

Figure 2:
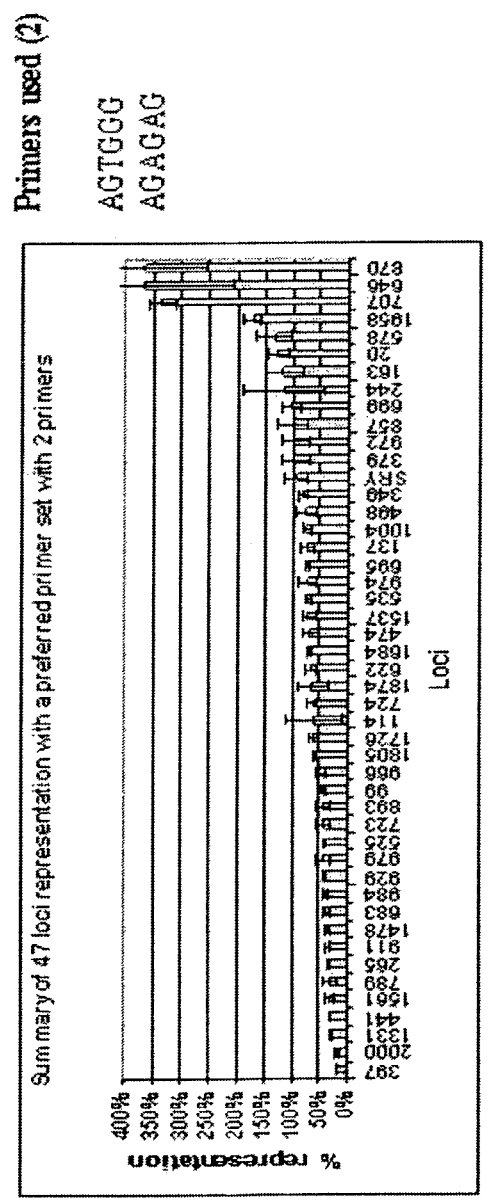
FIG. 2 is a graph of the locus representation (in percent) for 47 genetic loci (2 loci per chromosome, and one locus from the Y chromosome) in human genomic DNA amplified using two different six nucleotide primers of specific nucleotide sequence in an embodiment of the disclosed method.

Human genomic DNA was amplified by Multiple Displacement Amplification followed by TaqMan loci analysis as described above using two specific primers. The two primer sequences were AGTGGG and AGAGAG. A total of 47 genetic loci were analyzed (2 loci per chromosome, and one locus from the Y chromosome). As illustrated in FIG. 2, the two six nucleotide primers efficiently amplified the whole human genome as indicated by locus representation.

5. Three Primers

Figure 3:
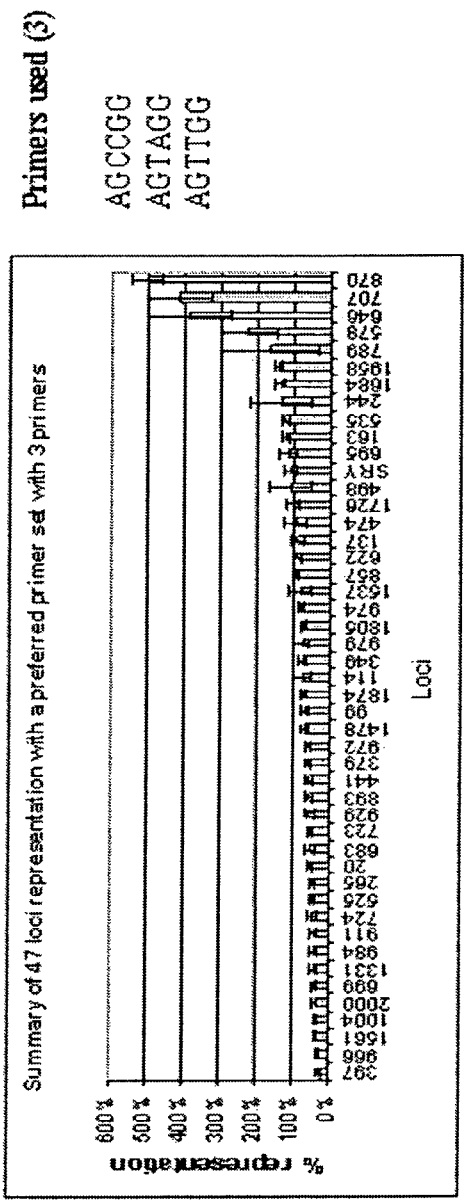
FIG. 3 is a graph of the locus representation (in percent) for 47 genetic loci (2 loci per chromosome, and one locus from the Y chromosome) in human genomic DNA amplified using three different six nucleotide primers of specific nucleotide sequence in an embodiment of the disclosed method.

Human genomic DNA was amplified by Multiple Displacement Amplification followed by TaqMan loci analysis as described above using three specific primers. The primers were six nucleotide non-Alu primers (that is, their sequence was not derived from an Alu repeat sequence) having the sequences AGCCGG, AGTAGG, and AGTTGG. A total of 47 genetic loci were analyzed (2 loci per chromosome, and one locus from the Y chromosome). As illustrated in FIG. 3, the three primers efficiently amplified the whole human genome as indicated by locus representation.

6. Four Primers

Figure 4:
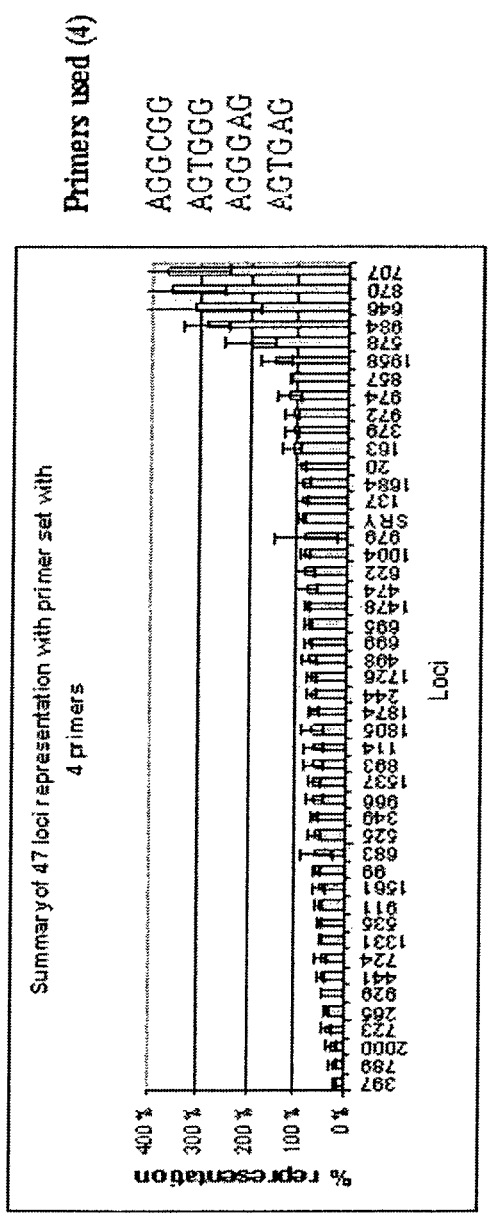
FIG. 4 is a graph of the locus representation (in percent) for 47 genetic loci (2 loci per chromosome, and one locus from the Y chromosome) in human genomic DNA amplified using four different six nucleotide primers of specific nucleotide sequence in an embodiment of the disclosed method.

Human genomic DNA was amplified by Multiple Displacement Amplification followed by TaqMan loci analysis as described above using four specific primers. The primers were six nucleotide primers having the sequences AGGCGG, AGTGGG, AGGGAG, and AGTGAG. A total of 47 genetic loci were analyzed (2 loci per chromosome, and one locus from the Y chromosome). As illustrated in FIG. 4, the four primer efficiently amplified the whole human genome as indicated by locus representation.

7. Five Primers

Figure 5:
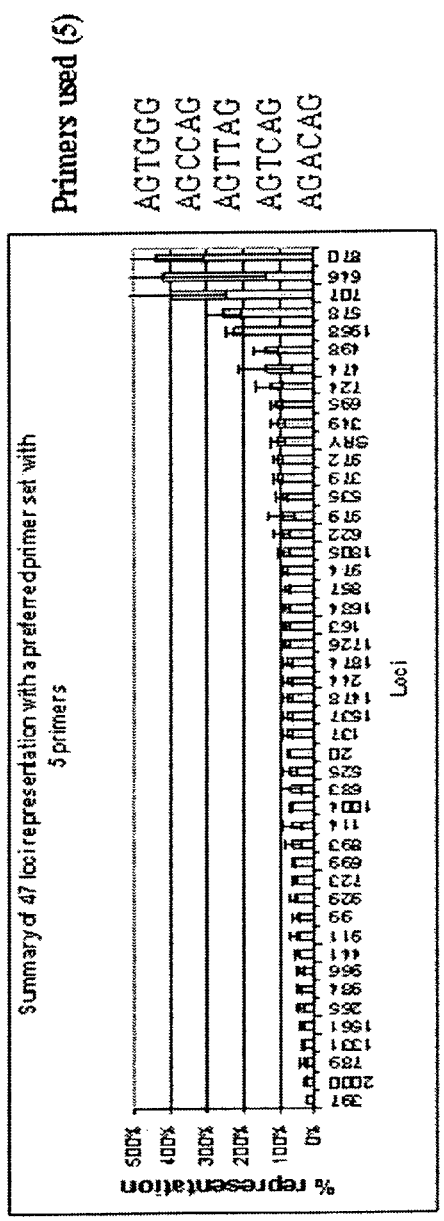
FIG. 5 is a graph of the locus representation (in percent) for 47 genetic loci (2 loci per chromosome, and one locus from the Y chromosome) in human genomic DNA amplified using five different six nucleotide primers of specific nucleotide sequence in an embodiment of the disclosed method.

Human genomic DNA was amplified by Multiple Displacement Amplification followed by TaqMan loci analysis as described above using five specific primers. In a first example, the primers were six nucleotide primers having the sequences AGTGGG, AGCCAG, AGTTAG, AGTCAG, and AGACAG. A total of 47 genetic loci were analyzed (2 loci per chromosome, and one locus from the Y chromosome). As illustrated in FIG. 5, these five primers efficiently amplified the whole human genome as indicated by locus representation.

Figure 6:
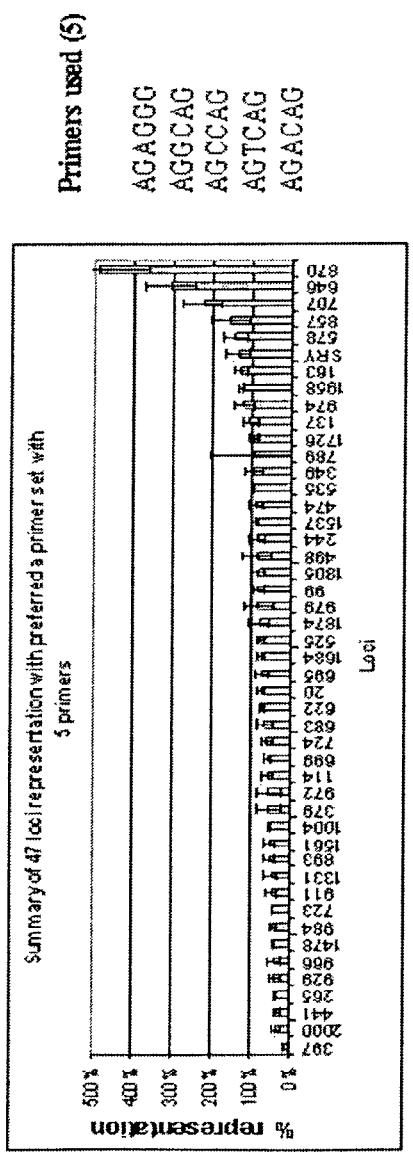
FIG. 6 is a graph of the locus representation (in percent) for 47 genetic loci (2 loci per chromosome, and one locus from the Y chromosome) in human genomic DNA amplified using five different six nucleotide primers of specific nucleotide sequence in an embodiment of the disclosed method.

In a second example, the primers were six nucleotide primers having the sequences AGAGGG, AGGCAG, AGCCAG, AGTCAG, and AGACAG. A total of 47 genetic loci were analyzed (2 loci per chromosome, and one locus from the Y chromosome). As illustrated in FIG. 6, these five primers efficiently amplified the whole human genome as indicated by locus representation.

Figure 7:
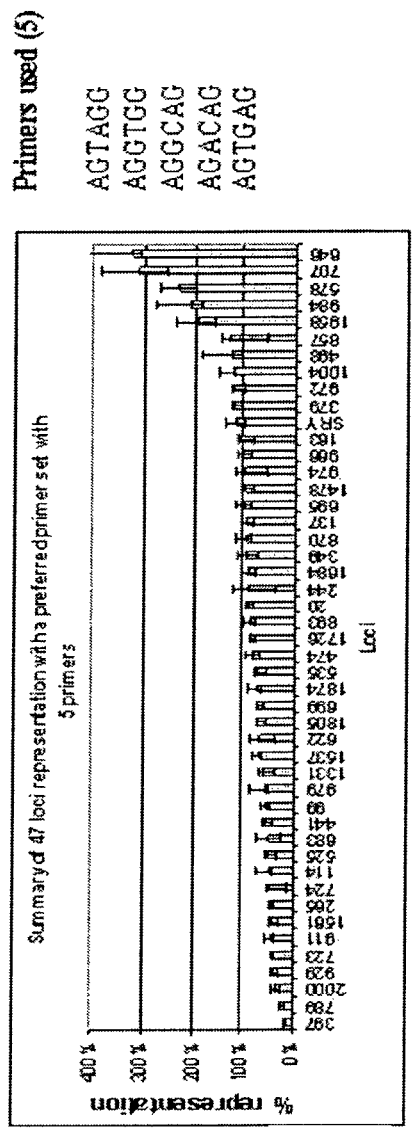
FIG. 7 is a graph of the locus representation (in percent) for 47 genetic loci (2 loci per chromosome, and one locus from the Y chromosome) in human genomic DNA amplified using five different six nucleotide primers of specific nucleotide sequence in an embodiment of the disclosed method.

In a third example, the primers were six nucleotide primers having the sequences AGTAGG, AGGTGG, AGGCAG, AGACAG, and AGTGAG. A total of 47 genetic loci were analyzed (2 loci per chromosome, and one locus from the Y chromosome). As illustrated in FIG. 7, these five primers efficiently amplified the whole human genome as indicated by locus representation.

Figure 8:
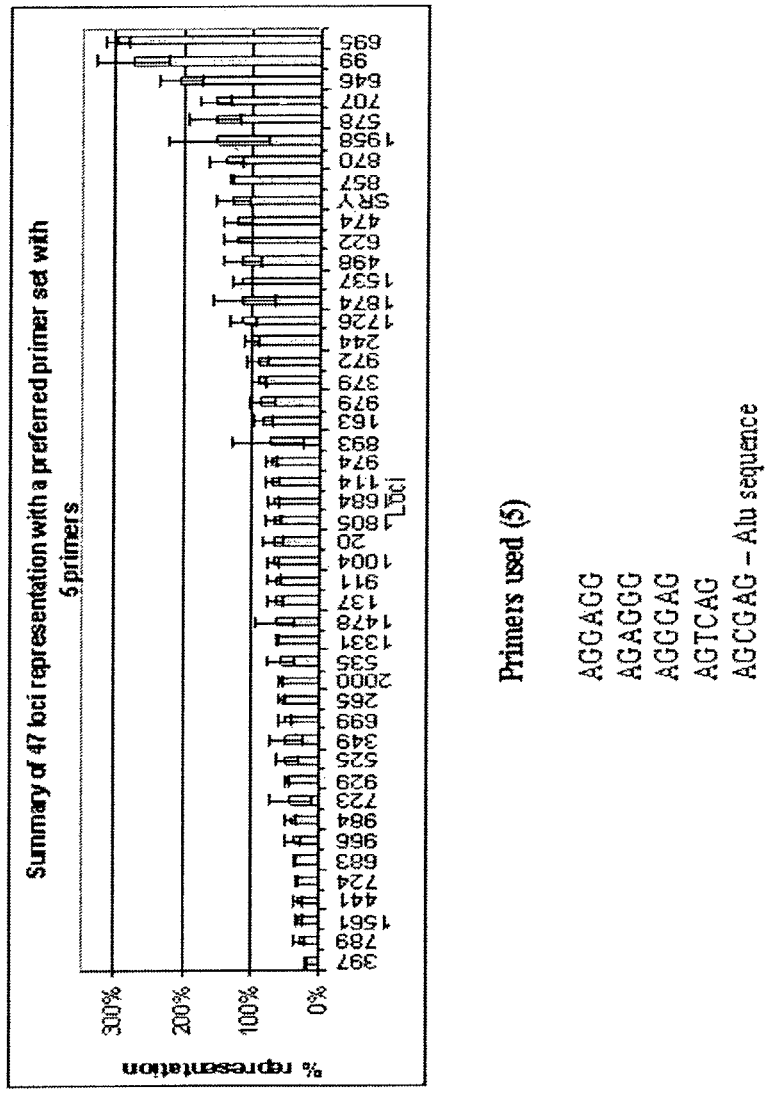
FIG. 8 is a graph of the locus representation (in percent) for 47 genetic loci (2 loci per chromosome, and one locus from the Y chromosome) in human genomic DNA amplified using five different six nucleotide primers of specific nucleotide sequence in an embodiment of the disclosed method.

In a fourth example, the primers were six nucleotide primers having the sequences AGCGAG, AGGAGG, AGAGGG, AGGGAG, and AGTGAG. One of the primers (AGCGAG) was specific for an Alu sequence. A total of 47 genetic loci were analyzed (2 loci per chromosome, and one locus from the Y chromosome). As illustrated in FIG. 8, these five primers efficiently amplified the whole human genome as indicated by locus representation.

8. Nine Primers

Figure 9:
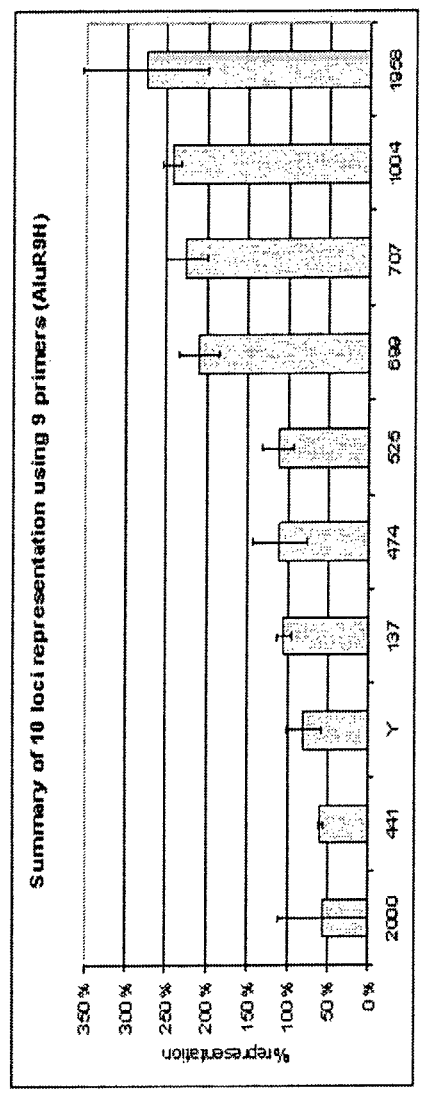
FIG. 9 is a graph of the locus representation (in percent) for 10 genetic loci in human genomic DNA amplified using nine different six nucleotide primers of specific nucleotide sequence in an embodiment of the disclosed method.

Human genomic DNA was amplified by Multiple Displacement Amplification followed by TaqMan loci analysis as described above using nine specific primers. The primers were six nucleotide Alu-specific primers, referred to as AluR9H. The name and sequence of all nine Alu-specific primers are shown in Table 1. The asterisks represent phosphothiolate linkages. A total of 10 genetic loci were analyzed. As illustrated in FIG. 9, the nine primers efficiently amplified the whole human genome as indicated by locus representation.

TABLE 1

| "AluR9H" mixture of 9 Alu-specific primers | |
|---|---|
| AluR1 | 5' CGG T*G*G 3' |
| AluR3 | 5' CGA G*G*C 3 |
| AluR4 | 5' GCG T*G*G 3' |
| AluR6 | 5' AAT C*G*C 3' |
| AluR8 | 5' CCG A*G*A 3' |
| AluR9 | 5' GAT C*G*C 3' |
| AluR10 | 5' AGA G*C*G 3' |
| AluR11 | 5' AGC G*A*G 3' |
| AluR12 | 5' ACT C*C*G 3' |

9. Twelve Primers

Figure 10:
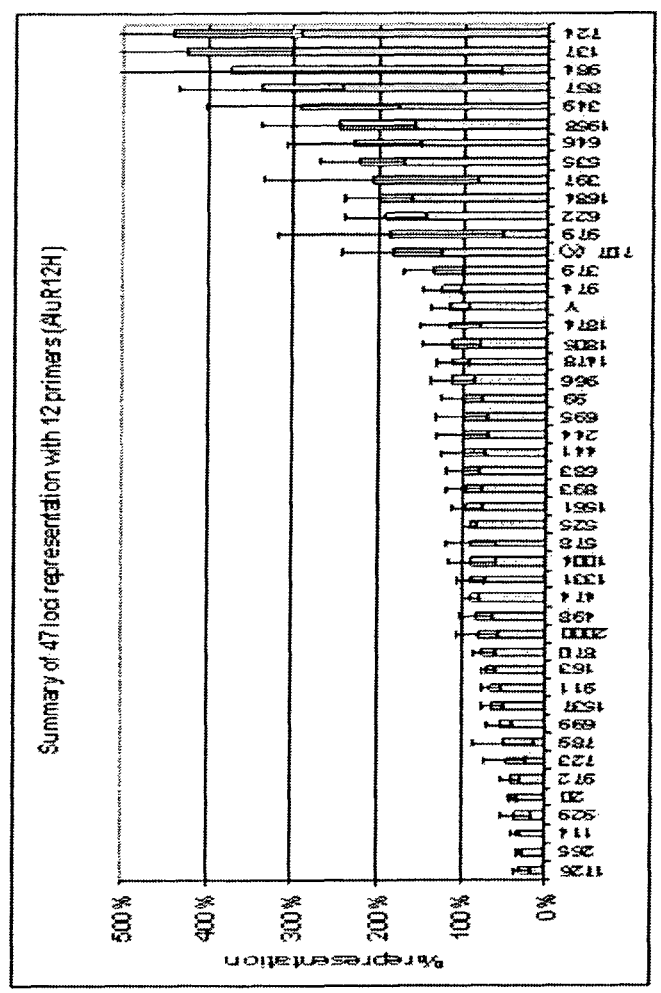
FIG. 10 is a graph of the locus representation (in percent) for 47 genetic loci (2 loci per chromosome, and one locus from the Y chromosome) in human genomic DNA amplified using twelve different six nucleotide primers of specific nucleotide sequence in an embodiment of the disclosed method.

Human genomic DNA was amplified by Multiple Displacement Amplification followed by TaqMan loci analysis as described above using twelve specific primers. The primers were six nucleotide Alu-specific primers, referred to as AluR12H. The name and sequence of all twelve Alu-specific primers are shown in Table 2. The asterisks represent phosphothiolate linkages. A total of 47 genetic loci were analyzed (2 loci per chromosome, and one locus from the Y chromosome). As illustrated in FIG. 10, the twelve primers efficiently amplified the whole human genome as indicated by locus representation.

TABLE 2

| "AluR12H" mixture of 12 Alu-specific primers | |
|---|---|
| AluR1 | 5' CGG T*G*G 3' |
| AluR2 | 5' TCA C*G*C 3' |
| AluR3 | 5' CGA G*G*C 3 |
| AluR4 | 5' GCG T*G*G 3' |
| AluR5 | 5' ACT C*G*G 3' |
| AluR6 | 5' AAT C*G*C 3' |
| AluR7 | 5' CGG A*G*G 3' |
| AluR8 | 5' CCG A*G*A 3' |
| AluR9 | 5' GAT C*G*C 3' |
| AluR10 | 5' AGA G*C*G 3' |
| AluR11 | 5' AGC G*A*G 3' |
| AluR12 | 5' ACT C*C*G 3' |

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a primer" includes a plurality of such primers, reference to "the primer" is a reference to one or more primers and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are specifically incorporated by reference. Nothing herein is to be construed as an admission that the present invention is not entitled to antedate such disclosure by virtue of prior invention.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of amplifying human genomes, the method comprising,
bringing in to contact a single DNA primer of at least 6 nucleotides in length which is non-degenerate and non-random, a non-human, strand displacement DNA polymerase, and a human genomic nucleic acid sample to form a mixture, and incubating the mixture under conditions that promote replication of nucleic acid molecules in the human genomic nucleic acid sample, wherein the primer hybridizes to nucleic acid molecules in the genomic nucleic acid sample, and wherein the primer has a specific nucleotide sequence, wherein the genomic nucleic acid sample comprises all or a substantial portion of a human genome,
replicating the nucleic acid molecules in the human genomic nucleic acid sample under isothermal conditions, wherein replication of nucleic acid molecules in the genomic nucleic acid sample proceeds by strand displacement replication, wherein replication of the nucleic acid molecules in the genomic nucleic acid sample results in replication of all or a substantial fraction of the nucleic acid molecules in the genomic nucleic acid sample.

2. The method of claim 1 wherein the primer has a length of 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides.

3. The method of claim 1 wherein the primer has one of the sequences AGTGGG or AGAGAG.

4. The method of claim 1 wherein the primer has one of the sequences AGCCGG, AGTAGG, or AGTTGG.

5. The method of claim 1 wherein the primer has one of the sequences AGGCGG, AGTGGG, AGGGAG, or AGTGAG.

6. The method of claim 1 wherein the primer has one of the sequences AGTGGG, AGCCAG, AGTTAG, AGTCAG, or AGACAG.

7. The method of claim 1 wherein the primer has one of the sequences AGAGGG, AGGCAG, AGCCAG, AGTCAG, or AGACAG.

8. The method of claim 1 wherein the primer has one of the sequences CGGTGG, TCACGC, CGAGCG, GCGTGG, ACTCGG, AATCGC, CGGAGG, CCGAGA, GATCGC, AGAGCG, AGCGAG, or ACTCCG.

9. The method of claim 1 wherein the primer is complementary to a sequence in a repeat sequence.

10. The method of claim 9 wherein the repeat sequence is a microsatellite sequence, a minisatellite sequence, a satellite sequence, a transposon sequence, a ribosomal RNA sequence, a short interspersed nuclear element (SINE), or a long interspersed nuclear element (LINE).

11. The method of claim 1 wherein the primer is complementary to a sequence in a functional consensus sequence.

12. The method of claim 11 wherein the functional consensus sequence is a promoter sequence, an enhancer sequence, a silencer sequence, an upstream regulatory element sequence, a transcription termination site sequence, a transposon regulatory sequence, a ribosomal RNA regulatory sequence, or a polyadenylation site sequence.

13. The method of claim 12 wherein the functional consensus sequence is a microbial promoter sequence, a microbial enhancer sequence, a microbial silencer sequence, a microbial upstream regulatory element sequence, a microbial transcription termination site sequence, a microbial transposon regulatory sequence, a microbial ribosomal RNA regulatory sequence, or a microbial polyadenylation site sequence.

14. The method of claim 1 wherein the primer is a broad coverage primer.

15. The method of claim 14 wherein the primer has a G+C percentage within 20%, within 15%, within 10%, within 9%, within 8%, within 7%, within 6%, within 5%, within 4%, within 3%, within 2%, or within 1% of the G+C percentage of the genomic nucleic acid sample.

16. The method of claim 14 wherein the primer produces a locus representation of at least 10% for at least 5 different loci for the type of genomic nucleic acid sample used.

17. The method of claim 16 wherein the primer produces a locus representation of at least 15%, at least 20%, at least 25%, at least 30%, at least 35%, at least 40%, at least 45%, at least 50%, at least 60%, at least 70%, at least 80%, at least 90%, or at least 100° A for at least 5 different loci for the type of genomic nucleic acid sample used.

18. The method of claim 16 wherein the primer produces a locus representation of at least 10% for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci for the type of genomic nucleic acid sample used.

19. The method of claim 1 wherein the primer does not have an inter-complementary 3' end.

20. The method of claim 1 wherein significant replication products are not produced in the absence of a nucleic acid sample.

21. The method of claim 1 wherein the DNA polymerase is φ29 DNA polymerase.

22. The method of claim 1 wherein the genomic nucleic acid sample is not subjected to denaturing conditions.

23. The method of claim 22 wherein the genomic nucleic acid sample is not subjected to heat denaturing conditions.

24. The method of claim 22 wherein the genomic nucleic acid sample is not subjected to alkaline denaturing conditions.

25. The method of claim 1 wherein the genomic nucleic acid sample is subjected to denaturing conditions.

26. The method of claim 25 wherein the genomic nucleic acid sample is subjected to heat denaturing conditions.

27. The method of claim 25 wherein the genomic nucleic acid sample is subjected to alkaline denaturing conditions.

28. The method of claim 1 wherein nucleic acids in the genomic nucleic acid sample are not separated from other material in the genomic nucleic acid sample.

29. The method of claim 1 wherein the genomic nucleic acid sample is a crude cell lysate.

30. The method of claim 1 wherein the genomic nucleic acid sample is a cell lysate, wherein the cell lysate is produced by exposing cells to alkaline conditions to form a cell lysate, wherein the cell lysate comprises a whole genome, and reducing the pH of the cell lysate to form a stabilized cell lysate.

31. The method of claim 30 wherein nucleic acids in the cell lysate and the stabilized cell lysate are not separated from other material in the cell lysate.

32. The method of claim 30 wherein the cell lysate and the stabilized cell lysate are not subjected to purification prior to incubating the mixture.

33. The method of claim 30 wherein the cell lysate, stabilized cell lysate, or both are subjected to partial purification prior to incubating the mixture.

34. The method of claim 30 wherein the cell lysate and the stabilized cell lysate are not subjected to substantial purification prior to incubating the mixture.

35. The method of claim 30 wherein neither the cell lysate nor the stabilized cell lysate is heated above the temperature of the incubation.

36. The method of claim 30 wherein the cells are not heated above the temperature of the incubation.

37. The method of claim 30 wherein the cells are not lysed by heat.

38. The method of claim 30 wherein the cells are not heated above a temperature and for a time that would cause substantial cell lysis in the absence of the alkaline conditions.

39. The method of claim 1 further comprising, prior to bringing into contact the primer, the genomic nucleic acid sample and the DNA polymerase,
exposing the genomic nucleic acid sample to conditions that promote substantial denaturation of the nucleic acid molecules in the genomic nucleic acid sample, thereby forming a denatured genomic nucleic acid sample, and altering the conditions to conditions that do not promote substantial denaturation of nucleic acid molecules in the genomic nucleic acid sample to form a denatured genomic nucleic acid sample.

40. The method of claim 39 wherein replication of the nucleic acid molecules in the genomic nucleic acid sample results in a longer average fragment length for the replicated nucleic acid molecules than the average fragment length in the genomic nucleic acid sample.

41. The method of claim 39 wherein the genomic nucleic acid sample, the denatured genomic nucleic acid sample, or both are exposed to ionic conditions.

42. The method of claim 39 wherein the genomic nucleic acid sample is exposed to conditions that promote substantial denaturation by mixing the genomic nucleic acid sample with a denaturing solution and by heating the genomic nucleic acid sample to a temperature and for a length of time that substantially denatures the nucleic acid molecules in the genomic nucleic acid sample.

43. The method of claim 1 wherein the primer contains at least one modified nucleotide such that the primer is resistant to 3'-5' exonuclease.

44. The method of claim 1 wherein the primer is 6 nucleotides long, wherein the primer contains at least one modified nucleotide such that the primer is nuclease resistant, and where in the DNA polymerase is φ29 DNA polymerase.

45. The method of claim 1 wherein the genomic nucleic acid sample is a blood sample, a urine sample, a semen sample, a lymphatic fluid sample, a cerebrospinal fluid sample, amniotic fluid sample, a biopsy sample, a needle aspiration biopsy sample, a cancer sample, a tumor sample, a tissue sample, a cell sample, a cell lysate sample, a crude cell lysate sample, a forensic sample, an archeological sample, an infection sample, a nosocomial infection sample, a production sample, a drug preparation sample, a biological molecule production sample, a protein preparation sample, a lipid preparation sample, a carbohydrate preparation sample, or a combination thereof.

46. The method of claim 1 wherein the replicated nucleic acid molecules are analyzed.

47. The method of claim 46 wherein the replicated nucleic acid molecules are analyzed using one or more DNA chips.

48. The method of claim 46 wherein the replicated nucleic acid molecules are analyzed by hybridization.

49. The method of claim 46 wherein the replicated nucleic acid molecules are analyzed by nucleic acid sequencing.

50. The method of claim 46 wherein the replicated nucleic acid molecules are stored prior to, following, or both prior to and following their analysis.

51. The method of claim 1 further comprising
bringing into contact the primer, DNA polymerase, and a second genomic nucleic acid sample, and incubating the second genomic nucleic acid sample under conditions that promote replication of nucleic acid molecules in the second genomic nucleic acid sample,
wherein the second genomic nucleic acid sample comprises all or a substantial portion of a genome, wherein replication of nucleic acid molecules in the second genomic nucleic acid sample proceeds by strand displacement replication, wherein replication of the nucleic acid molecules in the second genomic nucleic acid sample results in replication of all or a substantial fraction of the nucleic acid molecules in the second genomic nucleic acid sample.

52. The method of claim 51 wherein the second genomic nucleic acid sample is a sample from the same type of organism as the first genomic nucleic acid sample.

53. The method of claim 51 wherein the second genomic nucleic acid sample is a sample from the same type of tissue as the first genomic nucleic acid sample.

54. The method of claim 51 wherein the second genomic nucleic acid sample is obtained at a different time than the first genomic nucleic acid sample.

55. The method of claim 51 wherein the second genomic nucleic acid sample is a sample from a different organism than the first genomic nucleic acid sample.

56. The method of claim 51 wherein the second genomic nucleic acid sample is a sample from a different type of tissue than the first genomic nucleic acid sample.

57. The method of claim 51 wherein the second genomic nucleic acid sample is a sample from a different species of organism than the first genomic nucleic acid sample.

58. The method of claim 51 wherein the second genomic nucleic acid sample is a sample from a different strain of organism than the first genomic nucleic acid sample.

59. The method of claim 51 wherein the second genomic nucleic acid sample is a sample from a different cellular compartment than the first genomic nucleic acid sample.

60. A method of amplifying human nucleic acid samples of notable sequence complexity, the method comprising,
bringing into contact a single, non-random, non-degenerate, DNA primer, a non-human, strand displacement DNA polymerase, and a human nucleic acid sample to form a mixture, and incubating the mixture under conditions that promote replication of nucleic acid molecules in the nucleic acid sample,
wherein the primer hybridizes to the nucleic acid sample of notable sequence complexity, and wherein the primer has a specific nucleotide sequence, wherein the nucleic acid sample has a sequence complexity of at least $1 \times 10^4$ nucleotides,
replicating the nucleic acid molecules in the human genomic nucleic acid sample, wherein replication of nucleic acid molecules in the nucleic acid sample proceeds by strand displacement replication, wherein replication of the nucleic acid molecules in the nucleic acid sample results in replication of all or a substantial fraction of the nucleic acid molecules in the nucleic acid sample, and wherein the primer is 6 or more nucleotides in length.

61. The method of claim 60 wherein the nucleic acid sample has a sequence complexity of at least $1 \times 10^5$ nucleotides, the nucleic acid sample has a sequence complexity of at least $1 \times 10^6$ nucleotides, the nucleic acid sample has a sequence complexity of at least $1 \times 10^7$ nucleotides, the nucleic acid sample has a sequence complexity of at least $1 \times 10^8$ nucleotides, or the nucleic acid sample has a sequence complexity of at least $1 \times 10^9$ nucleotides.

62. The method of claim 60 wherein the nucleic acid sample is or is derived from a genome, a chromosome, a chromosome fragment, or a combination.

63. The method of claim 60 wherein the nucleic acid sample is or is derived from a blood sample, a urine sample, a semen sample, a lymphatic fluid sample, a cerebrospinal fluid sample, amniotic fluid sample, a biopsy sample, a needle aspiration biopsy sample, a cancer sample, a tumor sample, a tissue sample, a cell sample, a cell lysate sample, a crude cell lysate sample, a forensic sample, an archeological sample, an infection sample, a nosocomial infection sample, a production sample, a drug preparation sample, a biological molecule production sample, a protein preparation sample, a lipid preparation sample, a carbohydrate preparation sample, or a combination thereof.

64. A method of amplifying human genomes, the method comprising,
bringing in to contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein the genomic nucleic acid sample has a sequence complexity of at least $1 \times 10^9$ nucleotides, wherein replication of the nucleic acid molecules in the genomic nucleic acid sample results in replication of at least 0.01% of the nucleic acid sequences in the genomic nucleic acid sample, and wherein the primer is 6 or more nucleotides in length.

65. The method of claim 64 wherein replication of the nucleic acid molecules in the genomic nucleic acid sample results in replication of at least 0.1% of the nucleic acid sequences in the genomic nucleic acid sample, at least 1% of the nucleic acid sequences in the genomic nucleic acid sample, at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

66. A method of amplifying human genomes, the method comprising,
bringing into contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein the genomic nucleic acid sample has a sequence complexity of at least $1 \times 10^8$ nucleotides, wherein replication of the nucleic acid molecules in the genomic nucleic acid sample results in replication of at least 0.1% of the nucleic acid sequences in the genomic nucleic acid sample, and wherein the primer is 6 or more nucleotides in length.

67. The method of claim 66 wherein replication of the nucleic acid molecules in the genomic nucleic acid sample results in replication of at least 1% of the nucleic acid sequences in the genomic nucleic acid sample, at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

68. A method of amplifying human genomes, the method comprising,
bringing into contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein the genomic nucleic acid sample has a sequence complexity of at least $1 \times 10^7$ nucleotides, wherein replication of the nucleic acid molecules in the genomic nucleic acid sample results in replication of at least 1% of the nucleic acid sequences in the genomic nucleic acid sample, and wherein the primer is 6 or more nucleotides in length.

69. The method of claim 68 wherein replication of the nucleic acid molecules in the genomic nucleic acid sample results in replication of at least 5% of the nucleic acid sequences in the genomic nucleic acid sample, at least 10% of the nucleic acid sequences in the genomic nucleic acid sample, at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

70. A method of amplifying human genomes, the method comprising,
bringing into contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein the genomic nucleic acid sample has a sequence complexity of at least $1 \times 10^6$ nucleotides, wherein replication of the nucleic acid molecules in the genomic nucleic acid sample results in replication of at least 10% of the nucleic acid sequences in the genomic nucleic acid sample, and wherein the primer is 6 or more nucleotides in length.

71. The method of claim 70 wherein replication of the nucleic acid molecules in the genomic nucleic acid sample results in replication of at least 20% of the nucleic acid sequences in the genomic nucleic acid sample, at least 30% of the nucleic acid sequences in the genomic nucleic acid sample, at least 40% of the nucleic acid sequences in the genomic nucleic acid sample, at least 50% of the nucleic acid sequences in the genomic nucleic acid sample, at least 60% of the nucleic acid sequences in the genomic nucleic acid sample, at least 70% of the nucleic acid sequences in the genomic nucleic acid sample, at least 80% of the nucleic acid sequences in the genomic nucleic acid sample, at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

72. A method of amplifying human genomes, the method comprising,
bringing into contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein the genomic nucleic acid sample has a sequence complexity of at least $1 \times 10^5$ nucleotides, wherein replication of the nucleic acid molecules in the genomic nucleic acid sample results in replication of at least 80% of the nucleic acid sequences in the genomic nucleic acid sample, and wherein the primer is 6 or more nucleotides in length.

73. The method of claim 72 wherein replication of the nucleic acid molecules in the genomic nucleic acid sample results in replication of at least 90% of the nucleic acid sequences in the genomic nucleic acid sample, at least 95% of the nucleic acid sequences in the genomic nucleic acid sample, at least 96% of the nucleic acid sequences in the genomic nucleic acid sample, at least 97% of the nucleic acid sequences in the genomic nucleic acid sample, at least 98% of the nucleic acid sequences in the genomic nucleic acid sample, or at least 99% of the nucleic acid sequences in the genomic nucleic acid sample.

74. A method of amplifying human genomes, the method comprising,
bringing into contact a single, non-random, non-degenerate, DNA primer, a non-human, strand displacement DNA polymerase, and a human genomic nucleic acid sample to form a mixture, and incubating the mixture under conditions that promote replication of nucleic acid molecules in the genomic nucleic acid sample,
wherein the primer hybridizes to nucleic acid molecules in the genomic nucleic acid sample, and wherein the primer has a specific nucleotide sequence, wherein the genomic nucleic acid sample comprises all or a substantial portion of a genome,
replicating the nucleic acid molecules in the human genomic nucleic acid sample, wherein replication of nucleic acid molecules in the genomic nucleic acid sample proceeds by strand displacement replication, wherein replication of the nucleic acid molecules in the genomic nucleic acid sample results in a locus representation of at least 10% for at least 5 different loci, and wherein the primer is 6 or more nucleotides in length.

75. The method of claim 74 wherein replication of the nucleic acid molecules in the genomic nucleic acid sample results in a locus representation of at least 15%, at least 20%, at least 25%, at least 30%, at least 35%, at least 40%, at least 45%, at least 50%, at least 60%, at least 70%, at least 80%, at least 90%, or at least 100% for at least 5 different loci.

76. The method of claim 74 wherein replication of the nucleic acid molecules in the genomic nucleic acid sample results in a locus representation of at least 10% for at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

77. A method of amplifying human nucleic acid samples of high sequence complexity, the method comprising,
bringing into contact a single, non-random, non-degenerate, DNA primer, a non-human, strand displacement DNA polymerase, and a human nucleic acid sample to form a mixture, and incubating the mixture under conditions that promote replication of nucleic acid molecules in the nucleic acid sample,
wherein the primer hybridizes to the nucleic acid sample of high sequence complexity, and wherein the primer has a specific nucleotide sequence, wherein the nucleic acid sample has a sequence complexity of at least $1 \times 10^3$ nucleotides,
replicating the nucleic acid molecules in the human genomic nucleic acid sample, wherein replication of nucleic acid molecules in the nucleic acid sample proceeds by strand displacement replication, wherein replication of the nucleic acid molecules in the nucleic acid sample results in a sequence representation of at least 10% for at least 5 different target sequences, and wherein the primer is 6 or more nucleotides in length.

78. The method of claim 77 wherein replication of the nucleic acid molecules in the nucleic acid sample results in a sequence representation of at least 15%, at least 20%, at least 25%, at least 30%, at least 35%, at least 40%, at least 45%, at least 50%, at least 60%, at least 70%, at least 80%, at least 90%, or at least 100% for at least 5 different target sequences.

79. The method of claim 77 wherein replication of the nucleic acid molecules in the nucleic acid sample results in a sequence representation of at least 10% for at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

80. The method of claim 1, wherein the genomic nucleic acid sample is substantially pure.

81. The method of claim 60, wherein the nucleic acid sample is substantially pure.

82. The method of claim 64, wherein the genomic nucleic acid sample is substantially pure.

83. The method of claim 66, wherein the genomic nucleic acid sample is substantially pure.

84. The method of claim 68, wherein the genomic nucleic acid sample is substantially pure.

85. The method of claim 70, wherein the genomic nucleic acid sample is substantially pure.

86. The method of claim 72, wherein the genomic nucleic acid sample is substantially pure.

87. The method of claim 74, wherein the genomic nucleic acid sample is substantially pure.

88. The method of claim 77, wherein the nucleic acid sample is substantially pure.

89. The method of claim 1, wherein the genomic nucleic acid sample is incubated at a temperature of 23° C. to 40° C.

90. The method of claim 60, wherein the genomic nucleic acid sample is incubated at a temperature of 23° C. to 40° C.

91. The method of claim 64, wherein the genomic nucleic acid sample is incubated at a temperature of 23° C. to 40° C.

92. The method of claim 66, wherein the genomic nucleic acid sample is incubated at a temperature of 23° C. to 40° C.

93. The method of claim 68, wherein the genomic nucleic acid sample is incubated at a temperature of 23° C. to 40° C.

94. The method of claim 70, wherein the genomic nucleic acid sample is incubated at a temperature of 23° C. to 40° C.

95. The method of claim 72, wherein the genomic nucleic acid sample is incubated at a temperature of 23° C. to 40° C.

96. The method of claim 74, wherein the genomic nucleic acid sample is incubated at a temperature of 23° C. to 40° C.

97. The method of claim 77, wherein the genomic nucleic acid sample is incubated at a temperature of 23° C. to 40° C.

98. The method of claim 1, wherein the DNA polymerase is bacteriophage φ29 DNA polymerase, Bst large fragment DNA polymerase, Bca DNA polymerase, phage M2 DNA polymerase, phage φPRD1 DNA polymerase, exo(−) VENT® DNA polymerase, Klenow fragment of DNA polymerase I, T5 DNA polymerase, Sequenase, PRD1 DNA polymerase, or T4 DNA polymerase holoenzyme.

* * * * *